(12) United States Patent
Smith et al.

(10) Patent No.: US 12,268,275 B2
(45) Date of Patent: Apr. 8, 2025

(54) CROSS-LINKED ELASTOMERIC PROTEINS IN POLAR NONAQUEOUS SOLVENTS AND USES THEREOF

(71) Applicant: Bolt Threads, Inc., Emeryville, CA (US)

(72) Inventors: Matthew Jordan Smith, Emeryville, CA (US); Michael Eun-Suk Lee, Berkeley, CA (US); Mitchell Joseph Heinrich, Oakland, CA (US); Paul James Jehlen, Richmond, CA (US)

(73) Assignee: BOLT THREADS, INC., Emeryville, CA (US)

(*) Notice: Subject to any disclaimer, the term of this patent is extended or adjusted under 35 U.S.C. 154(b) by 896 days.

(21) Appl. No.: 16/515,577

(22) Filed: Jul. 18, 2019

(65) Prior Publication Data

US 2020/0102429 A1   Apr. 2, 2020

Related U.S. Application Data

(60) Provisional application No. 62/700,197, filed on Jul. 18, 2018.

(51) Int. Cl.

| | |
|---|---|
| *A43B 13/04* | (2006.01) |
| *A43B 3/10* | (2006.01) |
| *A43B 3/12* | (2006.01) |
| *A43B 13/02* | (2022.01) |
| *A43B 13/12* | (2006.01) |
| *A43B 13/14* | (2006.01) |
| *A43B 13/16* | (2006.01) |
| *A43B 13/18* | (2006.01) |
| *A43B 17/00* | (2006.01) |
| *A43B 23/08* | (2006.01) |
| *B29C 39/00* | (2006.01) |
| *B29D 35/12* | (2010.01) |
| *C07K 1/02* | (2006.01) |
| *C07K 1/14* | (2006.01) |
| *C07K 14/435* | (2006.01) |
| *C07K 14/78* | (2006.01) |
| *C08J 3/24* | (2006.01) |
| *C08J 9/00* | (2006.01) |
| *C08J 9/04* | (2006.01) |
| *C08J 9/08* | (2006.01) |
| *C08J 9/12* | (2006.01) |
| *B29L 31/50* | (2006.01) |

(52) U.S. Cl.
CPC .............. *A43B 13/04* (2013.01); *A43B 3/101* (2013.01); *A43B 3/108* (2013.01); *A43B 3/128* (2013.01); *A43B 13/02* (2013.01); *A43B 13/122* (2013.01); *A43B 13/125* (2013.01); *A43B 13/127* (2013.01); *A43B 13/14* (2013.01); *A43B 13/16* (2013.01); *A43B 13/186* (2013.01); *A43B 13/187* (2013.01); *A43B 13/188* (2013.01); *A43B 17/003* (2013.01); *A43B 23/088* (2013.01); *B29C 39/003* (2013.01); *B29D 35/122* (2013.01); *C07K 1/02* (2013.01); *C07K 1/14* (2013.01); *C07K 14/43563* (2013.01); *C07K 14/78* (2013.01); *C08J 3/247* (2013.01); *C08J 9/0066* (2013.01); *C08J 9/04* (2013.01); *C08J 9/08* (2013.01); *C08J 9/122* (2013.01); *B29K 2089/00* (2013.01); *B29L 2031/504* (2013.01); *B29L 2031/507* (2013.01); *C08J 2389/00* (2013.01)

(58) Field of Classification Search
CPC ....... A43B 13/04; A43B 3/128; A43B 13/188; A43B 13/127; A43B 17/003; A43B 13/186; A43B 3/108; A43B 13/02; A43B 13/122; A43B 13/125; A43B 13/14; A43B 13/16; A43B 13/187; A43B 23/088; A43B 3/101; C07K 14/43563; C07K 1/02; C07K 1/14; C08J 3/247; C08J 9/0066; C08J 9/04; C08J 9/08; C08J 9/122; C08J 2389/00; B29C 39/003; B29D 35/122; B29K 2089/00; B29L 2031/504; B29L 2031/507

See application file for complete search history.

(56) References Cited

U.S. PATENT DOCUMENTS

| | | |
|---|---|---|
| 4,016,661 A | 4/1977 | Tibbitts |
| 4,439,937 A | 4/1984 | Daswick |
| RE33,066 E | 9/1989 | Stubblefield |
| 7,421,808 B2 | 9/2008 | Baier et al. |
| 7,810,252 B2 | 10/2010 | Stone et al. |
| 8,302,330 B2 | 11/2012 | Doran |

(Continued)

FOREIGN PATENT DOCUMENTS

| | | |
|---|---|---|
| CN | 1332189 A | 1/2002 |
| CN | 101316862 A | 12/2008 |

(Continued)

OTHER PUBLICATIONS

Machine English translation of JP 2010-275496, Ikenaga et al., Dec. 9, 2010.*

(Continued)

*Primary Examiner* — Patrick D Niland

(74) *Attorney, Agent, or Firm* — MARSHALL, GERSTEIN & BORUN LLP

(57) ABSTRACT

Disclosed herein are improved cross-linked resilin compositions and methods of making these improved compositions. These include new methods of cross-linking resilin compositions, use of polar nonaqueous solvents for adjusting material properties of cross-linked resilin solid compositions, and resilin foam compositions and methods of making the same.

23 Claims, 15 Drawing Sheets

Specification includes a Sequence Listing.

(56) References Cited

U.S. PATENT DOCUMENTS

| | | | |
|---|---|---|---|
| 9,074,098 | B2 | 7/2015 | Tew et al. |
| 10,231,510 | B2 | 3/2019 | Wawrousek et al. |
| 10,799,616 | B2 | 10/2020 | Shoseyov et al. |
| 10,806,213 | B2 | 10/2020 | Wawrousek et al. |
| 2004/0136977 | A1 | 7/2004 | Miyamoto |
| 2004/0211089 | A1 | 10/2004 | Boncutter et al. |
| 2005/0091881 | A1 | 5/2005 | Burgess |
| 2005/0282454 | A1 | 12/2005 | Meschter et al. |
| 2006/0026863 | A1 | 2/2006 | Liu |
| 2006/0277795 | A1 | 12/2006 | Baier et al. |
| 2007/0099231 | A1 | 5/2007 | Elvin |
| 2007/0275408 | A1 | 11/2007 | Elvin |
| 2008/0256828 | A1 | 10/2008 | Doran |
| 2008/0264867 | A1 | 10/2008 | Mika et al. |
| 2010/0242306 | A1 | 9/2010 | Fu |
| 2010/0263228 | A1 | 10/2010 | Kang |
| 2011/0229698 | A1* | 9/2011 | Rasmussen ............. C08L 91/06 156/267 |
| 2012/0090077 | A1 | 4/2012 | Brown |
| 2012/0141609 | A1* | 6/2012 | Topolkaraev ............. C08K 5/09 424/725 |
| 2014/0206022 | A1 | 7/2014 | Nuti et al. |
| 2014/0296425 | A1 | 10/2014 | Tew et al. |
| 2014/0360053 | A1 | 12/2014 | Morris |
| 2015/0133593 | A1 | 5/2015 | Kissell et al. |
| 2015/0223560 | A1 | 8/2015 | Wawrousek et al. |
| 2015/0344542 | A1* | 12/2015 | Osawa ................... C07K 14/78 530/412 |
| 2016/0114075 | A1 | 4/2016 | Brownlee et al. |
| 2016/0135537 | A1 | 5/2016 | Wawrousek et al. |
| 2016/0175794 | A1* | 6/2016 | Domaske ................ C08L 89/00 516/16 |
| 2016/0222174 | A1 | 8/2016 | Widmaier et al. |
| 2016/0252505 | A1 | 9/2016 | Braun et al. |
| 2019/0125030 | A1 | 5/2019 | Brown et al. |
| 2020/0022451 | A1 | 1/2020 | Smith et al. |
| 2020/0354416 | A1 | 11/2020 | Lim et al. |

FOREIGN PATENT DOCUMENTS

| | | |
|---|---|---|
| CN | 101855239 A | 10/2010 |
| CN | 103351470 A | 10/2013 |
| CN | 104710635 A | 6/2015 |
| CN | 104884463 A | 9/2015 |
| CN | 108025082 A | 5/2018 |
| EP | 2668962 A1 | 12/2013 |
| JP | 2007-531506 A | 11/2007 |
| JP | 2010-275496 * | 12/2010 |
| JP | 2020-503882 | 2/2020 |
| KR | 10-2017-0113209 A | 10/2017 |
| WO | 2004/104043 A1 | 12/2004 |
| WO | WO 2004/104042 * | 12/2004 |
| WO | 2006/026325 A2 | 3/2006 |
| WO | WO-2007/057207 A1 | 5/2007 |
| WO | 2008/019183 A2 | 2/2008 |
| WO | WO-2008/155304 A1 | 12/2008 |
| WO | WO 2013/030840 * | 3/2013 |
| WO | WO-2013/178627 A2 | 12/2013 |
| WO | WO-2014/103846 A1 | 7/2014 |
| WO | 2015/068160 A1 | 5/2015 |
| WO | WO-2017/019841 A1 | 2/2017 |
| WO | WO-2018/092156 A1 | 5/2018 |
| WO | 2018/132821 A2 | 7/2018 |

OTHER PUBLICATIONS

Azam, A., et al., "Type III Secretion as a Generalizable Strategy for the Production of Full-Lenth Biopolymer-Forming Proteins", Biotechnology and Bioenginering 113: 2313-2320 (Year: 2016).

Qin, G., et al., "Mechanism of resilin elasticity", Nature Commnications, published Aug. 14, 2012, 9 pages.

Elvin, C., et al., "Synthesis and properties of crosslinked recombinant pro-resilin", Nature, vol. 437, Oct. 13, 2015, 4 pages.

UniProtKB—Q9V7U0 (Resil_Drome): ORF Names: CG15920, 5 pages.

Kim, M., et al., "High yield expression of recombinant pro-resilin: Lactose-induced fermentation in E. coli and facile purification", Elsevier, 2006, 7 pages.

Charati, M., et al., "Hydophilic elastomeric biomaterials based on reilin-like polypeptides", Soft Matter. 2009; 5(18): 3412-3416.

International Search Report and the Written Opinion for PCT/US2018/013829, 24 pages.

Ghazinezhad, M., et al., "Preparation of Hydrogels via Cross-Linking of Partially Hydrolyzed Polyacrylamides with Potassium Persulfate at Moderate Temperatures", Der Chemica Sinica. 2014, vol. 5, No. 5, pp. 19-26.

International Search Report and the Written Opinion for PCT/US19/42387, 30 pages.

Khandaker et al., "Expression, crosslinking, and developing modulus master curves of recombinant resilin", Journal of the Mechanical Behavior of Biomedical Materials, Elsevier, Amsterdam, NL, vol. 69, pp. 385-394 (Jan. 11, 2017).

Qin et al., "Recombinant exon-encoded resilins for elastomeric biomaterials", Biomaterial, Elsevier, Amsterdam, NL, vol. 32, No. 35, pp. 9231-9243 (Jun. 6, 2011).

Zhiguang Yao, Polymer Chemistry, Beijing Institute of Technology Press, p. 70, Section 3 (Jan. 2013).

Zhang, "Research progress and application prospect of insect cuticular proteins", Guandong Canye, vol. 40(3):38-42 (2006).

Altschul et al., Basic local alignment search tool, J. Mol. Biol., 215(3):403-410 (1990).

Altschul et al., Gapped BLAST and PSI-BLAST: a new generation of protein database search programs, Nucleic Acids Res., 25(17):3389-3402 (1997).

Degtyar et al., Recombinant engineering of reversible cross-links into a resilient biopolymer, Polymer, 69(9):255-263 (2015).

European Application No. 19838411.7, Supplementary European search report and Opinion, mailed Apr. 12, 2022.

European Application No. 19838656.7, Supplementary European search report mailed Mar. 21, 2022.

Gish et al., Identification of protein coding regions by database similarity search, Nature Genet., 3:266-272 (1993).

Huang et al., A proteomic analysis of the Pichia pastoris secretome in methanol-induced cultures, Appl. Microbiol. Biotechnol., 90(1):235-247 (2011).

Idiris et al., Engineering of protein secretion in yeast: strategies and impact on protein production, Appl. Microbiol. Biotechnol., 86:403-417 (2010).

International Application No. PCT/IB2019/056125, International Preliminary Report on Patentability, mailed Jan. 28, 2021.

International Application No. PCT/IB2019/056125, International Search Report and Written Opinion, mailed Dec. 20, 2019.

International Application No. PCT/US2019/042387, International Preliminary Report on Patentability, mailed Jan. 28, 2021.

International Application No. PCT/US2019/042387, International Search Report and Written Opinion, mailed Oct. 22, 2019.

Kim et al., Enzymatic Cross-Linking of Resilin-Based Proteins for Vascular Tissue Engineering Applications, Biomacromolecules, 17(8):2530-2539 (2016).

Li et al., Cell culture processes for monoclonal antibody production, Mabs, 2(5):466-477 (2010).

Madden et al., Applications of network BLAST server, Meth. Enzymol., 266:131-141 (1996).

McGann et al., Resilin-Based Hybrid Hydrogels for Cardiovascular Tissue Engineering, Macromol. Chem Phys., 214(2):203-213 (2013).

McGann et al., Resilin-PEG Hybrid Hydrogels Yield Degradable Elastomeric Scaffolds with Heterogeneous Microstructure, Biomacromolecules, 17(1):128-140 (2016).

Pearson, Rapid and sensitive sequence comparison with FASTP and FASTA, Methods Enzymol., 183:63-98 (1990).

Rebers et al., A conserved domain in arthropod cuticular proteins binds chitin, Insect Biochem Mol. Biol., 31(11):1083-1093 (2001).

Whittaker et al., Fabrication of highly elastic resilin/silk fibroin based hydrogel by rapid photo-crosslinking reaction, Journal of Materials Chemistry B., 3(32):6576-6579 (2015).

(56) References Cited

OTHER PUBLICATIONS

Zhang et al., Fermentation strategies for recombinant protein expression in the methylotrophic yeast *Pichia pastoris*, Biotechnol. Bioprocess. Eng., 5:275-287 (2000).

Zhang et al., PowerBLAST: a new network BLAST application for interactive or automated sequence analysis and annotation, Genome Res., 7:649-656 (1997).

Zhu, Mammalian cell protein expression for biopharmaceutical production, Biotechnol. Adv., 30:1158-1170 (2012).

Harnessing flea power to create near-perfect rubber, downloaded from the Internet at: <https://phys.org/news/2005-10-harnessing-flea-power-near-perfect-rubber.html> (Oct. 17, 2005).

Needles, Crosslinking of Gelatin by Aqueous Peroxydisulfote, J. Pol. Scien., Part A-1., 5:1-13 (1967).

\* cited by examiner

CROSS-LINKED ELASTOMERIC PROTEINS IN POLAR NONAQUEOUS SOLVENTS AND USES THEREOF

CROSS-REFERENCE TO RELATED APPLICATIONS

This application claims the benefit of U.S. Provisional Application No. 62/700,197, filed Jul. 18, 2018, the contents of which are incorporated by reference in their entirety.

SEQUENCE LISTING

The instant application contains a Sequence Listing which has been filed electronically in ASCII format and is hereby incorporated by reference in its entirety. Said ASCII copy, created on Aug. 28, 2019, is named BTT-027US_SL.txt and is 340,115 bytes in size.

BACKGROUND

Elastomeric proteins are polypeptides that exhibit viscoelastic mechanical properties, and include elastin, resilin, abductin, and octopus arterial elastomers. Resilin is a particularly interesting elastomeric protein because it dissipates very little energy during loading and unloading. Resilin is found in many insects, and the low energy dissipation enables the extraordinary ability of many insect species to jump or pivot their wings very efficiently. The unique properties of resilin make it an interesting elastomeric material that could have many industrial applications. What is needed, therefore, are new resilin compositions and methods of making the same that have desirable mechanical properties and are suitable for large-scale, efficient production.

Variations of natural resilins and resilin-like proteins (based on resilin sequences) have been recombinantly produced by a number of groups in *E. coli* cultures, and have been isolated by lysing the cells to extract recombinantly expressed proteins, and using affinity chromatography techniques to purify (Elvin et al., 2005; Charati et al.; 2009, McGann et al., 2013). The recombinantly produced resilin and resilin-like proteins have been cross-linked targeting the tyrosine residues that also form the cross-links in natural resilin (see, for example, Elvin et al., 2005; Qin et al., 2011). Recombinantly produced resilin has also been cross-linked targeting lysine residues (Li et al., 2011) or cysteine residues (McGann et al., 2013). Cross-linking methods have included enzymatically catalyzed cross-linking and photoactivated cross-linking. Enzymes for enzymatic catalysis of cross-linking can be hard to remove from the final composition, while photoactivated cross-linking may suffer from inefficiency due to only the surface being exposed to light, while also leaving impurities. The enzymatic impurities can degrade the resilin, while impurities from either enzymes or photocatalysts left in the final solid cross-linked composition can result in undesirable mechanical properties. What is needed, therefore, are new methods of cross-linking recombinant resilin proteins that do not leave behind degradation causing impurities and can be performed efficiently at a large scale.

SUMMARY OF THE INVENTION

Disclosed herein are improved cross-linked resilin compositions and methods of making these improved compositions. These include new methods of cross-linking resilin compositions and the use of polar nonaqueous solvents for adjusting material properties of cross-linked resilin solid compositions.

In some embodiments, provided herein is a method of cross-linking recombinant resilin, comprising: providing a composition comprising purified recombinant resilin; placing said recombinant resilin in a cross-linking solution comprising ammonium persulfate; and incubating said recombinant resilin in said cross-linking solution at a temperature of at least 60° C., thereby generating a cross-linked recombinant resilin solid composition.

In some embodiments, the incubation is performed for at least 15 minutes, at least 30 minutes, at least 45 minutes, at least 60 minutes, at least 90 minutes, or at least 2 hours.

In some embodiments, the recombinant resilin in said cross-linking solution is incubated at a temperature of from 60° C. to 85° C., from 70° C. to 85° C., or from 75° C. to 85° C.

In some embodiments, the incubation is performed for at least 2 hours.

In some embodiments, the cross-linking solution does not comprise a photocatalyst or a cross-linking enzyme.

In some embodiments, the cross-linked recombinant resilin solid composition is stable at room temperature for more than 5 days, more than 10 days, more than 20 days, or more than 40 days.

In some embodiments, the purified recombinant resilin is prepared by recombinantly expressing a gene encoding said recombinant resilin in a modified organism in a culture, and purifying expressed recombinant resilin from said culture.

Also provided herein, according to some embodiments, is a composition comprising cross-linked recombinant resilin, wherein said recombinant resilin has been cross-linked by exposure of said resilin to ammonium persulfate and heat. In some embodiments, the composition does not comprise a cross-linking enzyme. In some embodiments, the composition does not comprise a photocatalyst.

In some embodiments, provided herein is a recombinant resilin composition comprising a cross-linked recombinant resilin in a polar nonaqueous solvent.

In some embodiments, the polar nonaqueous solvent is a protic solvent. In some embodiments, the protic solvent is selected from the group consisting of: glycerol, propylene glycol, and ethylene glycol. In some embodiments, the polar nonaqueous solvent is an aprotic solvent. In some embodiments, the aprotic solvent is DMSO.

In some embodiments, the composition comprises from 20-40% resilin by weight.

In some embodiments, the resilin is at least 20%, at least 50%, at least 70%, or at least 80% full length resilin as a portion of all resilin as measured by size exclusion chromatography.

In some embodiments, the polar nonaqueous solvent is at least 60%, at least 70%, at least 80%, at least 90%, at least 95%, at least 98%, or at least 99% by volume of said solvent.

In some embodiments, the recombinant resilin composition has an elastic modulus greater than a similar cross-linked recombinant resilin in an aqueous solvent.

In some embodiments, the recombinant resilin composition comprises a hardness of at least 10 as measured using a Shore 00 Durometer via ASTM D2240.

In some embodiments, the recombinant resilin composition comprises a hardness of from about 10 to about 50 as measured using a Shore 00 Durometer via ASTM D2240.

In some embodiments, the recombinant resilin composition comprises a rebound resilience from about 40% to about 60% as measured by ASTM D7121.

In some embodiments, the recombinant resilin composition comprises a compressive stress at 25% of about 6 to about 8 psi as measured by ASTM D575.

In some embodiments, the recombinant resilin composition does not undergo an elastic to plastic transition below 2 kN of compressive force as measured by a Zwick compression test. In some embodiments, the recombinant resilin composition is a foam material.

Also provided herein, according to some embodiments, is a method of preparing a recombinant resilin solid, comprising: providing a cross-linked recombinant resilin solid composition in an aqueous solvent; and exchanging said aqueous solvent with a polar nonaqueous solvent.

In some embodiments, the polar nonaqueous solvent is a protic solvent. In some embodiments, the protic solvent is selected from the group consisting of: glycerol, propylene glycol, and ethylene glycol. In some embodiments, the polar nonaqueous solvent is an aprotic solvent. In some embodiments, the aprotic solvent is DMSO.

In some embodiments, the solvent exchange is performed for at least 8 hours, at least 16 hours, at least 24 hours, or at least 48 hours.

In some embodiments, the solvent exchange is performed at about 60° C.

In some embodiments, the cross-linked recombinant resilin solid composition comprises at least 20%, at least 50%, at least 70%, or at least 80% full length resilin as a portion of all resilin as measured by size exclusion chromatography.

In some embodiments, the cross-linked recombinant solid composition is prepared by the ammonium persulfate and heat method described herein.

Also provided herein, according to some embodiments, is a method of tuning material properties of a solid composition comprising cross-linked recombinant resilin solid, comprising: providing a cross-linked recombinant resilin solid composition comprising an aqueous solvent; and performing a solvent exchange to replace said aqueous solvent with a polar nonaqueous solvent. In some embodiments, replacing said solvent changes the elastic modulus, the resilience, the hardness, the maximum elastic compressive load, or the material lifetime of the cross-linked recombinant resilin solid composition.

Also provided herein, according to some embodiments, is a method of preparing a recombinant cross-linked resilin solid, comprising: providing a composition comprising purified recombinant resilin; placing said recombinant resilin in an aqueous solvent comprising ammonium persulfate; incubating said recombinant resilin in said aqueous solvent at a temperature of at least 60° C., thereby generating a cross-linked recombinant resilin solid composition; and exchanging said aqueous solvent with a polar nonaqueous solvent selected from the group consisting of: glycerol, propylene glycol, ethylene glycol, and DMSO.

Also provided herein, according to some embodiments, is a method of preparing a recombinant resilin foam, comprising: providing a cross-linked recombinant resilin solid composition in an aqueous solvent; exchanging said aqueous solvent with a polar nonaqueous solvent; and introducing one or more bubbles to the cross-linked recombinant resilin solid composition.

In some embodiments, the polar nonaqueous solvent is a protic solvent. In some embodiments, the protic solvent is selected from the group consisting of: glycerol, propylene glycol, and ethylene glycol. In some embodiments, the polar nonaqueous solvent is an aprotic solvent. In some embodiments, the aprotic solvent is DMSO.

In some embodiments, the solvent exchange is performed for at least 8 hours, at least 16 hours, at least 24 hours, or at least 48 hours.

In some embodiments, the solvent exchange is performed at about 60° C.

In some embodiments, the cross-linked recombinant resilin solid composition comprises at least 20%, at least 50%, at least 70%, or at least 80% full length resilin as a portion of all resilin as measured by size exclusion chromatography.

In some embodiments, the cross-linked recombinant solid composition is prepared by the ammonium persulfate and heat method described herein.

In some embodiments, the introducing comprises adding a blowing agent to the cross-linked recombinant resilin solid composition.

In some embodiments, the blowing agent comprises a chemical blowing agent. In some embodiments, the chemical blowing agent comprises sodium bicarbonate, potassium bicarbonate, ammonium, azodicarbonamide, isocyanate, hydrazine, isopropanol, 5-phenyltetrazole, triazole, 4,4'oxybis(benzenesulfonyl hydrazide) (OBSH), trihydrazine triazine (THT), hydrogen phosphate, tartaric acid, citric acid, and toluenesulphonyl semicarbazide (TSS). In some embodiments, the chemical blowing agent comprises sodium bicarbonate.

In some embodiments, the blowing agent comprises a physical blowing agent. In some embodiments, the physical blowing agent comprises chlorofluorocarbon (CFC), dissolved nitrogen, $N_2$, $CH_4$, $H_2$, $CO_2$, Ar, pentane, isopentane, hexane, methylene dichloride, and dichlorotetra-fluoroethane. In some embodiments, the physical blowing agent comprises dissolved nitrogen.

According to some embodiments, provided herein is a method for producing a composition comprising a recombinant resilin protein, the method comprising: culturing a population of recombinant host cells in a fermentation, wherein said recombinant host cells comprise a vector comprising a secreted resilin coding sequence, and wherein said recombinant host cells secrete a recombinant resilin protein encoded by said secreted resilin coding sequence; and purifying said recombinant resilin protein from said fermentation.

In some embodiments, the recombinant resilin protein is a full-length or truncated native resilin. In some embodiments, the native resilin is from an organism selected from the group consisting of: *Drosophila sechellia, Acromyrmex echinatior, Aeshna, Haematobia irritans, Ctenocephalides fells, Bombus terrestris, Tribolium castaneum, Apis mellifera, Nasonia vitripennis, Pediculus humanus corporis, Anopheles gambiae, Glossina morsitans, Atta cephalotes, Anopheles darlingi, Acyrthosiphon pisum, Drosophila virilis, Drosophila erecta, Lutzomyia longipalpis, Rhodnius prolixus, Solenopsis invicta, Culex quinquefasciatus, Bactrocera cucurbitae*, and *Trichogramma pretiosum*. In some embodiments, the recombinant resilin protein comprises SEQ ID NO: 1. In some embodiments, the recombinant resilin protein comprises SEQ ID NO: 4.

In some embodiments, the recombinant resilin protein comprises an alpha mating factor secretion signal. In some embodiments, the recombinant resilin protein comprises a FLAG-tag. In some embodiments, the vector comprises more than one secreted resilin coding sequence.

In some embodiments, the recombinant host cells are yeast cells. In some embodiments, the yeast cells are methylotrophic yeast cells. In some embodiments, the recombinant host cells are a species selected from the group consisting of: *Pichia (Komagataella) pastoris, Hansenula*

*polymorpha, Arxula adeninivorans, Yarrowia lipolytica, Pichia (Scheffersomyces) stipitis, Pichia methanolica, Saccharomyces cerevisiae*, and *Kluyveromyces lactis*.

In some embodiments, the recombinant host cells produce the recombinant resilin at a rate of greater than 2 mg resilin/g dry cell weight/hour. In some embodiments, the recombinant host cells produce a secreted fraction of the recombinant resilin that is greater than 50% as compared to the total recombinant resilin protein expressed by the recombinant host cells. In some embodiments, the recombinant host cells secrete the recombinant resilin at a rate of greater than 2 mg resilin/g dry cell weight/hour. In some embodiments, greater than 80% of the recombinant resilin is outside of the recombinant host cells in said fermentation. In some embodiments, the fermentation comprises at least 2 g recombinant resilin/L.

In some embodiments, purifying said recombinant resilin protein comprises: generating a first pellet fraction and a first supernatant fraction by centrifuging the fermentation; and isolating the recombinant resilin protein from the first pellet fraction. In some embodiments, purifying said recombinant resilin protein further comprises: adding a chaotrope to the first pellet fraction to generate a solution in which the recombinant resilin protein is soluble; generating a second supernatant fraction and a second pellet fraction by centrifuging the first pellet fraction comprising said chaotrope; and isolating the soluble full-length resilin from the second supernatant fraction.

In some embodiments, provided herein is a vector comprising a secreted resilin coding sequence. In some embodiments, the secreted resilin coding sequence encodes a full-length or truncated native resilin. In some embodiments, the secreted resilin coding sequence encodes a modified full-length or truncated native resilin. In some embodiments, the modified resilin comprises an addition, subtraction, replacement, or change in position of an amino acid residue capable of cross-linking to another resilin.

In some embodiments, the full-length or truncated native resilin is from an organism selected from the group consisting of: *Drosophila sechellia, Acromyrmex echinatior, Aeshna, Haematobia irritans, Ctenocephalides fells, Bombus terrestris, Tribolium castaneum, Apis mellifera, Nasonia vitripennis, Pediculus humanus corporis, Anopheles gambiae, Glossina morsitans, Atta cephalotes, Anopheles darlingi, Acyrthosiphon pisum, Drosophila virilis, Drosophila erecta, Lutzomyia longipalpis, Rhodnius prolixus, Solenopsis invicta, Culex quinquefasciatus, Bactrocera cucurbitae*, and *Trichogramma pretiosum*.

In some embodiments, the secreted resilin coding sequences encodes a polypeptide comprising SEQ ID NO: 1. In some embodiments, the secreted resilin coding sequence encodes a polypeptide comprising SEQ ID NO: 4. In some embodiments, the secreted resilin coding sequence encodes a recombinant resilin comprising one or more A-repeats or quasi-A-repeats. In some embodiments, the secreted resilin coding sequence encodes a recombinant resilin comprising one or more B-repeats or quasi-B-repeats. In some embodiments, the secreted resilin coding sequence encodes a recombinant resilin comprising either one or more A-repeats or quasi-A-repeats or one or more B-repeats or quasi-B repeats but not both. In some embodiments, the secreted resilin coding sequence encodes a recombinant resilin comprising one or more A-repeats or quasi-A-repeats and one or more B-repeats or quasi-B-repeats.

In some embodiments, the recombinant resilin further comprises a chitin binding domain. In some embodiments, the secreted resilin coding sequence encodes a polypeptide comprising an alpha mating factor secretion signal. In some embodiments, the secreted resilin coding sequence comprises a FLAG-tag.

In some embodiments, the vector comprises more than one secreted resilin coding sequence. In some embodiments, the vector comprises 3 secreted resilin coding sequences. In some embodiments, the secreted resilin coding sequence is operatively linked to a constitutive or inducible promoter.

Also provided herein, according to some embodiments, is a recombinant host cell comprising one or more vectors comprising a secreted resilin coding sequence. In some embodiments, the recombinant host cell is a yeast cell. In some embodiments, the yeast cell is a methylotrophic yeast cell. In some embodiments, the recombinant host cell is a species selected from the group consisting of: *Pichia (Komagataella) pastoris, Hansenula polymorpha, Arxula adeninivorans, Yarrowia lipolytica, Pichia (Scheffersomyces) stipitis, Pichia methanolica, Saccharomyces cerevisiae*, and *Kluyveromyces lactis*.

In some embodiments, the recombinant host cell comprises 3 vectors comprising a secreted resilin coding sequence.

In some embodiments, the recombinant host cell produces recombinant resilin at a rate of greater than 2 mg resilin/g dry cell weight/hour. In some embodiments, the recombinant host cell has a secreted fraction of recombinant resilin that is greater than 50%. In some embodiments, the recombinant host cell secretes resilin at a rate of greater than 2 mg resilin/g dry cell weight/hour.

Also provided herein, according to some embodiments, is a fermentation comprising a recombinant host cell comprising one or more vectors comprising a secreted resilin coding sequence and a culture medium suitable for growing the recombinant host cell.

In some embodiments, the fermentation comprises at least 2 g recombinant resilin/L.

In some embodiments of the fermentation, greater than 80% of recombinant resilin is outside of the recombinant host cells.

In some embodiments of the fermentation, the recombinant resilin is full-length recombinant resilin.

Also provided herein, according to some embodiments, is a composition comprising recombinant resilin derived from a fermentation comprising a recombinant host cell comprising one or more vectors comprising a secreted resilin coding sequence and a culture medium suitable for growing the recombinant host cell. In some embodiments, the composition comprises at least 60% by weight of recombinant resilin.

In some embodiments, the composition has similar properties compared to compositions comprising similar amounts of native resilins. In some embodiments, the composition has different properties compared to compositions comprising similar amounts of native resilins.

In some embodiments, the composition comprises a resilience of greater than 50%. In some embodiments, the composition comprises has a compressive elastic modulus of less than 10 MPa. In some embodiments, the composition has a tensile elastic modulus of less than 10 MPa. In some embodiments, the composition has a shear modulus of less than 1 MPa. In some embodiments, the composition has an extension to break of greater than 1%. In some embodiments, the composition has a maximum tensile strength of greater than 0.1 kPa. In some embodiments, the composition has a Shore 00 Hardness of less than 90. In some embodiments, the composition comprises full-length resilin.

Also provided herein, according to some embodiments, is a method for producing a composition comprising recombinant resilin, the method comprising the step of culturing a recombinant host cell comprising one or more vectors comprising a secreted resilin coding sequence to produce a fermentation under conditions that promote secretion of recombinant resilin from the recombinant host cell.

In some embodiments, the method for producing a composition comprising recombinant resilin further comprises the step of purifying said recombinant resilin to produce full-length native resilin. In some embodiments, purifying said recombinant resilin to produce full-length native resilin comprises: generating a first pellet fraction and a first supernatant fraction by centrifuging the fermentation; and isolating the recombinant resilin protein from the first pellet fraction. In some embodiments, isolating the recombinant resilin protein from the first pellet fraction comprises: adding a chaotrope to the first pellet fraction to generate a solution in which the recombinant resilin protein is soluble; generating a second supernatant fraction and a second pellet fraction by centrifuging the first pellet fraction comprising said chaotrope; and isolating the recombinant resilin protein from the second supernatant fraction.

In some embodiments, the method for producing a composition comprising recombinant resilin further comprises the step of cross-linking a plurality of said recombinant resilins. In some embodiments, said cross-linking is enzymatic cross-linking. In some embodiments, said cross-linking is photochemical cross-linking. In some embodiments, the recombinant resilin protein comprises a full-length resilin protein.

Also provided herein, according to some embodiments, is a fermentation comprising a culture medium and a recombinant host cell, wherein the recombinant host cell comprises a vector, wherein the vector comprises a secreted resilin coding sequence, and wherein the recombinant host cell secretes recombinant resilin at a rate of at least 2 mg/g dry cell weight/hour.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

Figure 1:
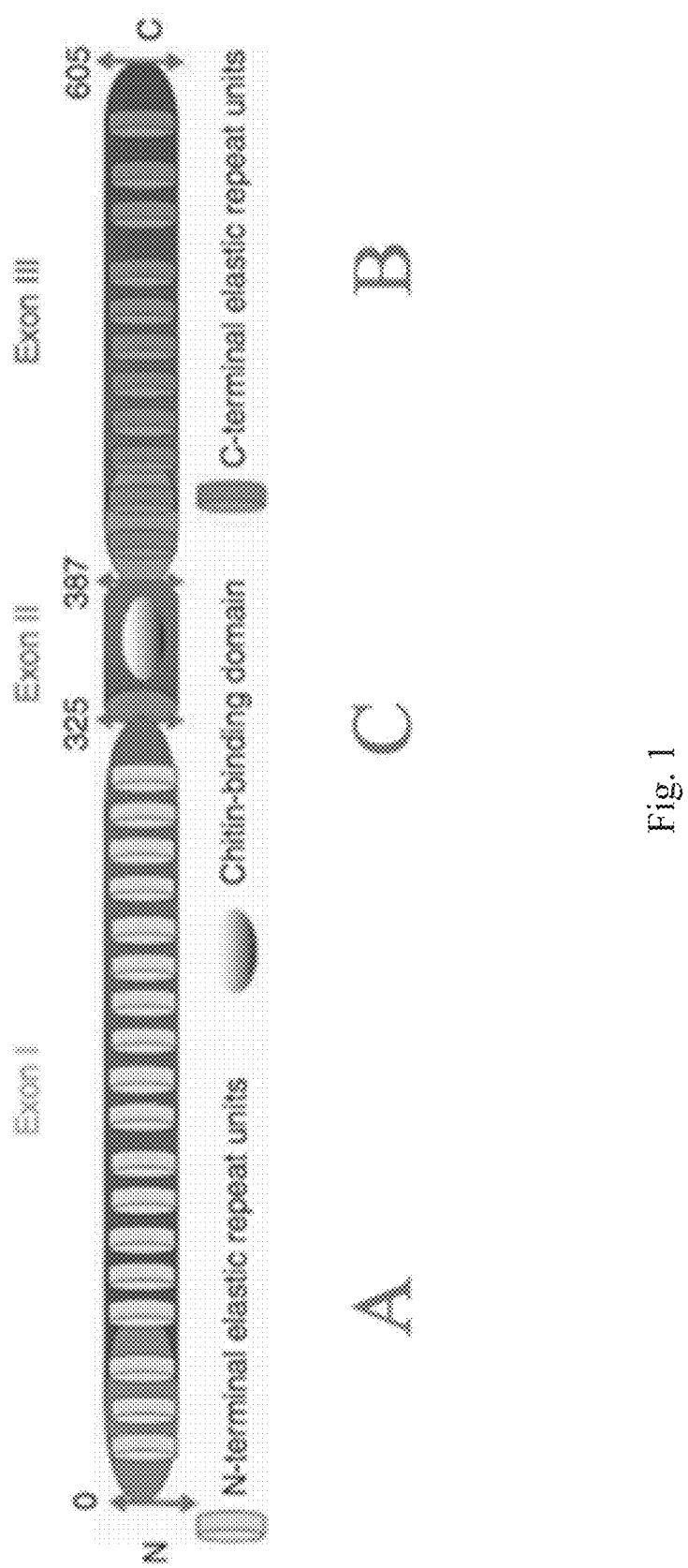
FIG. 1 schematically illustrates the structure of an exemplary resilin.

The figures depict various embodiments of the present disclosure for purposes of illustration only. One skilled in the art will readily recognize from the following discussion that alternative embodiments of the structures and methods illustrated herein may be employed without departing from the principles described herein.

DETAILED DESCRIPTION

The details of various embodiments of the invention are set forth in the description below. Other features, objects, and advantages of the invention will be apparent from the description and the drawings, and from the claims.

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

The terms "including," "includes," "having," "has," "with," or variants thereof are intended to be inclusive in a manner similar to the term "comprising."

The term "microbe" as used herein refers to a microorganism, and refers to a unicellular organism. As used herein, the term includes all bacteria, all archaea, unicellular protista, unicellular animals, unicellular plants, unicellular fungi, unicellular algae, all protozoa, and all chromista.

The term "native" as used herein refers to compositions found in nature in their natural, unmodified state.

The terms "optional" or "optionally" mean that the feature or structure may or may not be present, or that an event or circumstance may or may not occur, and that the description includes instances where a particular feature or structure is present and instances where the feature or structure is absent, or instances where the event or circumstance occurs and instances where the event or circumstance does not occur.

The term "secreted fraction" as used herein refers to the fraction of recombinant resilins that are secreted from cells compared to the total resilins produced by the cells.

The term "secretion signal" as used herein refers to a short peptide that when fused to a polypeptide mediates the secretion of that polypeptide from a cell.

The term "secreted resilin coding sequence" as used herein refers to a nucleotide sequence that encodes a resilin as provided herein fused at its N-terminus to a secretion signal and optionally at its C-terminus to a tag peptide or polypeptide.

The term "recombinant" as used herein in reference to a polypeptide (e.g., resilin) refers to a polypeptide that is produced in a recombinant host cell, or to a polypeptide that is synthesized from a recombinant nucleic acid.

The term "recombinant host cell" as used herein refers to a host cell that comprises a recombinant nucleic acid.

The term "recombinant nucleic acid" as used herein refers to a nucleic acid that is removed from its naturally occurring environment, or a nucleic acid that is not associated with all or a portion of a nucleic acid abutting or proximal to the nucleic acid when it is found in nature, or a nucleic acid that is operatively linked to a nucleic acid that it is not linked to in nature, or a nucleic acid that does not occur in nature, or a nucleic acid that contains a modification that is not found in that nucleic acid in nature (e.g., insertion, deletion, or point mutation introduced artificially, e.g., by human intervention), or a nucleic acid that is integrated into a chromosome at a heterologous site. The term includes cloned DNA isolates and nucleic acids that comprise chemically-synthesized nucleotide analog.

The term "vector" as used herein refers to a nucleic acid molecule capable of transporting another nucleic acid to which it has been linked. One type of vector is a "plasmid," which generally refers to a circular double stranded DNA loop into which additional DNA segments can be ligated, but also includes linear double-stranded molecules such as those resulting from amplification by the polymerase chain reaction (PCR) or from treatment of a circular plasmid with a restriction enzyme. Other vectors include bacteriophages, cosmids, bacterial artificial chromosomes (BAC), and yeast artificial chromosomes (YAC). Another type of vector is a viral vector, wherein additional DNA segments can be ligated into the viral genome. Certain vectors are capable of autonomous replication in a cell into which they are introduced (e.g., vectors having an origin of replication that functions in the cell). Other vectors can be integrated into the genome of a cell upon introduction into the cell, and are thereby replicated along with the cell genome.

The term "repeat" as used herein, in reference to an amino acid or nucleic acid sequence, refers to a sub-sequence that is present more than once in a polynucleotide or polypeptide (e.g., a concatenated sequence). A polynucleotide or polypeptide can have a direct repetition of the repeat sequence without any intervening sequence, or can have non-consecutive repetition of the repeat sequence with intervening sequences. The term "quasi-repeat" as used herein, in reference to amino acid or nucleic acid sequences, is a sub-sequence that is inexactly repeated (i.e., wherein some portion of the quasi-repeat subsequence is variable between quasi-repeats) across a polynucleotide or polypeptide. Repeating polypeptides and DNA molecules (or portions of polypeptides or DNA molecules) can be made up of either repeat sub-sequences (i.e., exact repeats) or quasi-repeat sub-sequences (i.e., inexact repeats).

The term "native resilin" as used herein refers to an elastomeric polypeptide or protein produced by insects. GenBank Accession Nos. of non-limiting examples of native resilin includes the following NCBI sequence numbers: NP 995860 (*Drosophila melanogaster*), NP 611157 (*Drosophila melanogaster*), Q9V7U0 (*Drosophila melanogaster*), AAS64829, AAF57953 (*Drosophila melanogaster*), XP 001817028 (*Tribolium castaneum*) and XP001947408 (*Acyrthosiphon pisum*).

The term "modified" as used herein refers to a protein or polypeptide sequence that differs in composition from a native protein or polypeptide sequence, where the functional properties are preserved to within 10% of the native protein or polypeptide properties. In some embodiments, the difference between the modified protein or polypeptide and the native protein or polypeptide can be in primary sequence (e.g., one or more amino acids are removed, inserted or substituted) or post-translation modifications (e.g., glycosylation, phosphorylation). Amino acid deletion refers to removal of one or more amino acids from a protein. Amino acid insertion refers to one or more amino acid residues being introduced in a protein or polypeptide. Amino acid insertions may comprise N-terminal and/or C-terminal fusions as well as intra-sequence insertions of single or multiple amino acids. Amino acid substitution includes non-conservative or conservative substitution, where conservative amino acid substitution tables are well known in the art (see for example Creighton (1984) Proteins. W. H. Freeman and Company (Eds)). In some embodiments, the modified protein or polypeptide and the native protein or polypeptide amino acid or nucleotide sequence identity is at least 60%, at least 65%, at least 70%, at least 75%, at least 80%, at least 85%, at least 90%, at least 95%, or at least 98% of the amino acids or nucleotide bases.

The term "truncated" as used herein refers to a protein or polypeptide sequence that is shorter in length than a native protein or polypeptide. In some embodiments, the truncated protein or polypeptide can be greater than 10%, or greater than 20%, or greater than 30%, or greater than 40%, or greater than 50%, or greater than 60%, or greater than 70%, or greater than 80%, or greater than 90% of the length of the native protein or polypeptide.

The term "homolog" or "substantial similarity," as used herein, when referring to a polypeptide, nucleic acid or fragment thereof, indicates that, when optimally aligned with appropriate amino acid or nucleotide insertions or deletions with another amino acid or nucleic acid (or its complementary strand), there is amino acid or nucleotide sequence identity in at least 60%, at least 65%, at least 70%, at least 75%, at least 80%, at least 85%, at least 90%, at least 95%, or at least 98% of the amino acids or nucleotide bases, as measured by any well-known algorithm of sequence identity, such as FASTA, BLAST or Gap, as discussed above.

The term "resilin" as used herein refers to a protein or a polypeptide, capable of cross-linking to form an elastomer, where the protein or polypeptide is a native resilin, or a native resilin that is modified, or a native resilin that is truncated. Resilins of the present invention are preferably recombinant resilins. In some embodiments, recombinant resilins comprise a natural or modified (e.g., truncated or concatenated) nucleotide sequence coding for resilin or resilin fragments (e.g., isolated from insects), heterologously expressed and secreted from a host cell. In preferred embodiments, the secreted recombinant resilin protein is collected from a solution extracellular to the host cell. In some embodiments, resilin is in a form of a foam material, e.g., a solid foam.

As used herein, the term "elastomer" refers to a polymer with viscoelasticity and typically weak inter-molecular forces (except for covalent cross-links between molecules, if they are present). Viscoelasticity is a property of materials that exhibit both viscous and elastic characteristics when undergoing deformation, and therefore exhibit time-dependent strain. Elasticity is associated with bond stretching along crystallographic planes in an ordered solid, and viscosity is the result of the diffusion of atoms or molecules inside an amorphous material. Elastomers that are viscoelastic, therefore, generally have low Young's modulus and high failure strain compared with other materials. Due to the viscous component of the material, viscoelastic materials dissipate energy when a load is applied and then removed. This phenomenon is observed as hysteresis in the stress-strain curve of viscoelastic materials. As a load is applied there is a particular stress-strain curve, and as the load is removed the stress-strain curve upon unloading is different than that of the curve during loading. The energy dissipated is the area between the loading and unloading curves.

As used herein, the term "nonaqueous" refers to a solvent that predominantly comprises one or more compounds that are not water. This includes compositions that have undergone a solvent exchange process with a solvent that results in an overall decrease in the proportion of water present as a solvent, i.e., water has been replaced by non-water molecules as a solvent. In some embodiments, a nonaqueous solvent is one that comprises less than 50% water. A polar nonaqueous solvent, as used herein with respect to solvents for cross-linked resilin compositions, refers to any nonaqueous solvent that is capable of dissolving resilin.

Recitation of ranges of values herein are merely intended to serve as a shorthand method of referring individually to each separate value inclusively falling within the range, unless otherwise indicated herein, and each separate value is incorporated into the specification as if it were individually recited herein.

Resilin Compositions

Provided herein are compositions comprising recombinant resilins, and methods for their production.

Resilins have many unique properties compared to petroleum-based elastomers. Most notably, resilin has an extreme elastic efficiency (i.e., resilience), where very little of the energy input into deformation is lost as heat. Other desirable properties of resilin include, for example, compressive elastic modulus, tensile elastic modulus, shear modulus, hardness, rebound, and compression set. Moreover, resilin is a protein, and therefore can be biodegraded, which makes it more environmentally friendly than petroleum-based polymers. Also, resilin is biocompatible and can therefore be used in applications that involve contact with humans or animals. Lastly, the mechanical properties of recombinant resilins can be tuned through varying protein sequence, protein structure, amount of intermolecular cross-linking and processing variables to produce elastomers designed for a universe of specific applications.

In some embodiments, provided herein are cross-linked resilin compositions with desirable mechanical properties and methods of producing them. In some embodiments, provided herein are methods of cross-linking resilin compositions to form a cross-linked resilin solid that can be performed efficiently in large batches and is not susceptible to degradation from impurities left over from the cross-linking reaction. In some embodiments, the cross-linking reaction comprises exposure of the resilin to a persulfate, such as ammonium persulfate. Heat can be applied to initiate a cross-linking reaction catalyzed by persulfate. This type of cross-linking reaction does not leave any photoactive or enzymatic compounds in the composition. Furthermore, this cross-linking reaction does not require photoactivation, so large batches can be produced efficiently without the requirement for light to reach all parts of the cross-linking solution. In some embodiments, cross-linking occurs in vessels or molds such that the recombinant resilin compositions obtained have specific shapes or forms.

The cross-linked resilin solid compositions provided herein also include cross-linked resilin compositions comprising a polar nonaqueous solvent to provide desired mechanical properties, such as elastic modulus, hardness, maximum elastic compressive load, resilience, and material lifetime/fatigue that are preferred in certain applications. In some embodiments, the compositions are made by performing a solvent exchange with a resilin composition to replace an aqueous solvent with a nonaqueous solvent. Solvents that are capable of doing solvent exchange with cross-linked resilin include solvents that dissolve resilin in its non-crosslinked form.

In preferred embodiments, the nonaqueous solvent is non-volatile and water soluble or polar. In some embodiments, the molecular weight of the solvent is about 100 or less. In some embodiments, the polar nonaqueous solvent comprises glycerol, propylene glycol, ethylene glycol, or DMSO. In some embodiments, the solvent exchange is done using a polar nonaqueous solvent gradient (e.g., from 60% to 100% glycerol).

In some embodiments, the cross-linked resilin compositions described herein can be used to provide a composition having improved physical properties, including, e.g., for absorption of energy from an applied force as desired. In some embodiments, the cross-linked resilin compositions described herein can be used to improve existing products containing rubber. In particular, some of the cross-linked resilin compositions provided herein can absorb a large amount of force, while not transitioning to an inelastic material.

In some embodiments, the cross-linked resilin compositions provided herein can be used as a mid-sole. In some embodiments, the cross-linked resilin compositions provided herein can be used as part of a core for a golf ball. In other embodiments, the cross-linked resilin compositions provided herein can be used in handles or grips, e.g., for sports equipment such as golf clubs or tennis rackets, as bicycle grips or motorcycle grips, or as groups for tools and industrial uses such as hammers, nail guns, jackhammers, and any other tools where it is preferable to absorb and return energy. In some embodiments, the cross-linked resilin compositions provided herein can be used in brushings or dampenings, e.g., skate board trucks or hard drive platter vibration dampener. In some embodiments, the cross-linked resilin compositions can be used as superior material for wheels, such as for skate boards, roller blades, or scooters. In some embodiments, the cross-linked resilin compositions provided herein can be used for safety and protective gear, such as padding for protective equipment such as helmets, elbow or knee pads, or hard hats, or as a protective outer layer to protect the skin from abrasions.

In some embodiments, the cross-linked resilin compositions provided herein can be used for automotive parts, e.g., suspension components such as bushings or shock absorbers, or for interior cushioning such as seat bolsters and lumbar support. In some embodiments, the cross-linked resilin compositions provided herein can be used for tires and inner tubes. In some embodiments, the cross-linked resilin compositions provided herein can be used for superballs. In some embodiments, the cross-linked resilin compositions provided herein can be used for shoe insoles, midsoles, and outsoles. In some embodiments, the cross-linked resilin compositions provided herein can be used in a padded mat. In some embodiments, the cross-linked resilin compositions provided herein can be used for several types of gaskets or O-rings. In some embodiments, the cross-linked resilin compositions provided herein can be added to plastic items to increase their impact resistance. In some embodiments, the cross-linked resilin compositions provided herein can be used for protective cases, such as phone or tablet cases. In some embodiments, the cross-linked resilin compositions provided herein can be used for rubber stamps. In some embodiments, the cross-linked resilin compositions provided herein can be used for rollers. In some embodiments, the cross-linked resilin compositions provided herein can be used for rubber bands.

In some embodiments, the cross-linked resilin compositions provided herein can be used for shoe soles, basement flooring, noise protection for sound studios, car bumpers, cushion pads, door mats, yoga mats, drum pads, window wipers, car tires, fire hoses, electrical wiring insulation, rubber bands, rubber ducks, elastic gloves, cooking utensils, rain boots, teething toys, bicycle tires, watches, jars, gaskets, hair ties, flip-flops, phone cases, medicine balls, bouncy balls, seals for electronic devices to prevent contamination from water or dust, refrigerator or freezer door seals, seals to prevent air flow in or out of a chamber, trampolines, pacifiers, window seals, halloween masks, garden hoses, table tennis rackets, conveyer belts, ducting, stamps, balloons, cosmetic compositions for the care and protection of skin and hair, nail compositions, or preparations for decorative cosmetics.

Suitable skin cosmetic compositions are, for example, face tonics, facial masks, e.g., sheet masks, deodorants, and other cosmetic lotions. Compositions for use in decorative cosmetics include, for example, concealing sticks, stage make-up, mascara and eye shadows, lipsticks, kohl pencils, eyeliners, blushers, powders, and eyebrow pencils.

Depending on the field of use, the compositions described herein can be applied in a form suitable for skincare, such as, for example, as cream, foam, gel, stick, mousse, milk, spray (pump spray or propellant-containing spray) or lotion.

FIG. 1 illustrates an example of a native resilin, which contains an N-terminal A-domain comprising a plurality of repeat units comprising the consensus amino acid sequence YGXP ("A-repeat"), where X is any amino acid; a chitin-binding type RR-2 (C) domain (Pfam reference PF00379; Rebers J E & Willis, JI-1. A conserved domain in anthropod cuticular proteins binds chitin. Insect Biochem Mol Biol 31:1083-1093); and a C-terminal B-domain comprising a plurality of repeat units comprising the consensus amino acid sequence UYZXZ ("B-repeat"), where U is glycine or serine; Z is serine, glycine, arginine, or proline; and X is any amino acid. Not all naturally occurring resilins have A-, C-, and B-domains. Native resilins produced by various insects typically have inexact repeats (i.e., quasi-repeats) within the A- and/or B-domains with some amino acid variation between the quasi-repeats.

In some embodiments, the recombinant resilins provided herein comprise one or more A-repeats. In some embodiments, the recombinant resilins comprise N-terminal A-domains comprising a plurality of blocks of A-repeat and/or quasi-A-repeat amino acid sub-sequences each with the consensus sequence SXXYGXP (SEQ ID NO: 50), where S is serine, X is an amino acid, Y is tyrosine, G is glycine, and P is proline.

In some embodiments, the recombinant resilins provided herein comprise one or more B-repeats. In some embodiments, the recombinant resilins comprise a C-terminal B-domain comprising a plurality of blocks of B-repeat and/or quasi-B-repeat amino acid sub-sequences each with the consensus sequence GYZXZZX and/or SYZXZZX, where G is glycine; Y is tyrosine; Z is serine, glycine, proline, or arginine; S is serine; and X is any amino acid.

In some embodiments, the recombinant resilins provided herein comprise one or more A-repeats. In some such embodiments, the recombinant resilins comprise between 1 and 100 A-repeats, or from 2 to 50 A-repeats, or from 5 to 50 A-repeats, or from 5 to 20 A-repeats.

In some embodiments, the recombinant resilins comprise one or more consensus sequences described by the formula, $$(X_1-X_2-X_3-X_4)_n \qquad (1) \text{ (SEQ ID NO: 64)}$$

wherein the brackets delineate a repeat or quasi-repeat of the consensus sequence;

wherein n describes the number of A-repeats or quasi-A-repeats, and is from 1 to 100, or from 2 to 50, or from 5 to 50, or from 5 to 20;

wherein $X_1$ is a motif that is 4 amino acids in length, wherein the first amino acid of $X_1$ is Y, and wherein the remaining amino acids of $X_1$ are GAP, GLP, GPP, GTP, or GVP;

wherein $X_2$ is a motif that is from 3 to 20 amino acids in length;

wherein $X_2$ comprises GGG, GGGG (SEQ ID NO: 51), N, NG, NN, NGN, NGNG (SEQ ID NO: 52), GQGG (SEQ ID NO: 53), GQGN (SEQ ID NO: 54), GQGQ (SEQ ID NO: 55), GQGQG (SEQ ID NO: 56), or 3 or more glycine residues, or wherein 50% or more of the residues of $X_2$ are either glycine or asparagine, or wherein 60% or more of the residues of $X_2$ are either glycine or asparagine, or wherein 70% or more of the residues of $X_2$ are either glycine or asparagine, or wherein 80% or more of the residues of $X_2$ are either glycine or asparagine;

wherein $X_3$ is a motif that is from 2 to 4 amino acids in length, wherein $X_3$ is GG, LS, APS, GAG, GGG, KPS, RPS, or GGGG (SEQ ID NO: 51); and wherein $X_4$ is a motif that is from 1 to 2 amino acids in length, wherein $X_4$ is S, D, T, N, L, DS, DT, LS, SS, ST, TN, or TS.

In some such embodiments, the recombinant resilins comprise motifs $X_1$, $X_2$, $X_3$, and $X_4$ whereas in other embodiments, the recombinant resilins comprise motifs $X_1$, $X_2$, $X_3$, or $X_4$, or combinations thereof.

In some embodiments, the recombinant resilins provided herein comprise one or more B-repeats. In some such embodiments, the recombinant resilins comprise between 1 and 100 B-repeats, or from 2 to 50 A-repeats, or from 5 to 50 A-repeats, or from 5 to 20 A-repeats.

In some embodiments, the recombinant resilins comprise one or more consensus sequences described by the formula, $$(X_{11}-X_{12}-X_{13})_m \quad (2) \text{ (SEQ ID NO: 65)}$$

wherein the brackets delineate a repeat or quasi-repeat of the consensus sequence;

wherein m describes the number of B-repeats or quasi-B-repeats, and is from 1 to 100;

wherein $X_{11}$ is a motif that is from 1 to 5 amino acids in length, the first amino acid is Y, and where the remaining amino acids can comprise GAP, GPP, SSG, or SGG;

wherein $X_{12}$ is a motif that is from 2 to 5 amino acids in length and comprises GQ, GN, RPG, RPGGQ (SEQ ID NO: 57), RPGGN (SEQ ID NO: 58), SSS, SKG, or SN; and wherein $X_{13}$ is a motif that is from 4 to 30 amino acids in length and comprises GG, DLG, GFG, GGG, RDG, SGG, SSS, GGSF (SEQ ID NO: 59), GNGG (SEQ ID NO: 60), GGAGG (SEQ ID NO: 61), or 3 or more glycine residues, or 30% or more of the residues are glycine, or 40% or more of the residues are glycine, or 50% or more of the residues are glycine, or 60% or more of the residues are glycine.

In some such embodiments, the recombinant resilins comprise motifs $X_{11}$, $X_{12}$, and $X_{13}$ whereas in other such embodiments, the recombinant resilins comprise motifs $X_{11}$, $X_{12}$, or $X_{13}$, or combinations thereof.

In some embodiments, the recombinant resilins provided herein comprise one or more A-repeats, one or more B-repeats, and/or one or more C-domain. In some embodiments, the recombinant resilins comprise one or more A-repeats or one or more B-repeats but not both. In some embodiments, the recombinant resilins comprise one or more A-repeats but not B-repeats or C-domains. In some embodiments, the recombinant resilins comprise one or more B-repeats but not A-repeats or C-domains. In embodiments in which the recombinant resilins comprise a C-domain, the C-domain can be situated either on the N-terminal or the C-terminal sides of the A-repeats or B-repeats, or between the A-repeats and the B-repeats.

In some embodiments, the recombinant resilins further comprise the sequence XXEPPVSYLPPS (SEQ ID NO: 62), where X is any amino acid. In some such embodiments, the sequence is located on the N-terminal side of an A-repeat or B-repeat.

In some embodiments, the recombinant resilins are full-length native resilins expressed in a non-native environment. In some embodiments, the recombinant resilins comprise a truncated version of native resilins. In some embodiments, the truncated native resilins comprise at least one A-repeat. In some embodiments, the truncated native resilins comprise at least one B-repeat. Non-limiting examples of full-length and truncated native resilins are provided as SEQ ID NOs: 1 through 44. In some embodiments, the recombinant resilins are full-length *Drosophila sechellia* resilin (SEQ ID NO: 1). In some embodiments, the recombinant resilins are truncated *Acromyrmex echinatior* resilin (SEQ ID NO: 4). In some embodiments, the recombinant resilins are full-length or truncated native resilins that are cross-linked in a non-native manner (e.g., less or more cross-linking, cross-linking via different amino acid residues).

In some embodiments, the recombinant resilins are modified full-length or truncated native resilins. In some embodiments, the recombinant resilins are at least 60%, at least 65%, at least 70%, at least 75%, at least 80%, at least 85%, at least 90%, at least 95%, or at least 98% identical to a full-length or truncated native resilin. In some embodiments, the recombinant resilins are at least 60%, at least 65%, at least 70%, at least 75%, at least 80%, at least 85%, at least 90%, at least 95%, or at least 98% identical to full-length *Drosophila sechellia* resilin (SEQ ID NO: 1). In some embodiments, the recombinant resilins are at least 60%, at least 65%, at least 70%, at least 75%, at least 80%, at least 85%, at least 90%, at least 95%, or at least 98% identical to truncated *Acromyrmex echinatior* resilin (SEQ ID NO: 4).

There are a number of different algorithms known in the art which can be used to measure nucleotide sequence or protein sequence identity. For instance, polynucleotide sequences can be compared using FASTA, Gap, or Bestfit, which are programs in Wisconsin Package Version 10.0, Genetics Computer Group (GCG), Madison, Wis. FASTA provides alignments and percent sequence identity of the regions of the best overlap between the query and search sequences. See, e.g., Pearson, Methods Enzymol. 183:63-98, 1990 (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410, 1990; Gish and States, Nature Genet. 3:266-272, 1993; Madden et al., Meth. Enzymol. 266:131-141, 1996; Altschul et al., Nucleic Acids Res. 25:3389-3402, 1997; Zhang and Madden, Genome Res. 7:649-656, 1997, especially blastp or tblastn (Altschul et al., Nucleic Acids Res. 25:3389-3402, 1997.

In some embodiments, the modified resilins differ from full-length or truncated native resilins in amino acid residues that are post-translationally modified (e.g., glycosylated, phosphorylated) such that the modified resilins have one or more different locations and/or different amounts and/or different types of post-translational modifications than the full-length or truncated native resilins. In some embodiments, the modified resilins differ from full-length or truncated native resilins in amino acid residues that are involved in cross-linking such that the modified resilins have one or more different locations and/or different amounts and/or different types of amino acids that are involved in cross-linking than full-length or truncated native resilins. In some such embodiments, the modified resilins differ from the full-length or truncated native resilin in comprising one or more additional or fewer tyrosine residues, one or more additional or fewer lysine residues, and/or one or more additional or fewer cysteine residues.

In some embodiments, the recombinant resilins comprise concatenated native or truncated native resilins or concatenated modified resilins. In some embodiments, the concatenated native or truncated native resilins or concatenated modified resilins comprise at least 2 A-repeats (e.g., 2, 3, 4, 5, 6, 7, 8, 9, 10, or more). In some embodiments, the concatenated truncated native resilins or concatenated modified resilins comprise at least 2 B-repeats (e.g., 2, 3, 4, 5, 6, 7, 8, 9, 10, or more).

Protein Quantification and Purity Analysis

In some embodiments, the total amount of full length resilin in a composition is determined by size exclusion chromatography (SEC), Reverse Phase High Performance Liquid Chromatography or other methods as known in the art (e.g. quantitative Western blots). In various embodiments, the same or similar assays may be used to assess the relative amount of full length resilin in its monomeric and aggregate forms.

As described herein, in a specific embodiment, data characterizing the relative amount of the predominant species of resilin (i.e. monomeric full length resilin) in a resilin composition is determined from Size Exclusion Chromatography (SEC) as follows: resilin powder is dissolved in 5M Guanidine Thiocyanate and injected onto a Yarra SEC-3000 SEC-HPLC column to separate constituents on the basis of molecular weight. Refractive index is used as the detection modality. BSA is used as a general protein standard with the assumption that >90% of all proteins demonstrate do/dc values (the response factor of refractive index) within ~7% of each other. Poly(ethylene oxide) is used as a retention time standard, and a BSA calibrator is used as a check standard to ensure consistent performance of the method. A range corresponding to monomeric full length resilin is assessed from 60-40 kDa; higher peaks observed which may correspond to aggregate or polymerized full length resilin are not included in this quantification. The relative percentage of this resilin peak is reported as mass % and area % to determine the amount of full length resilin in a composition as a portion of total resilin.

Cross-Linking

Figure 2:
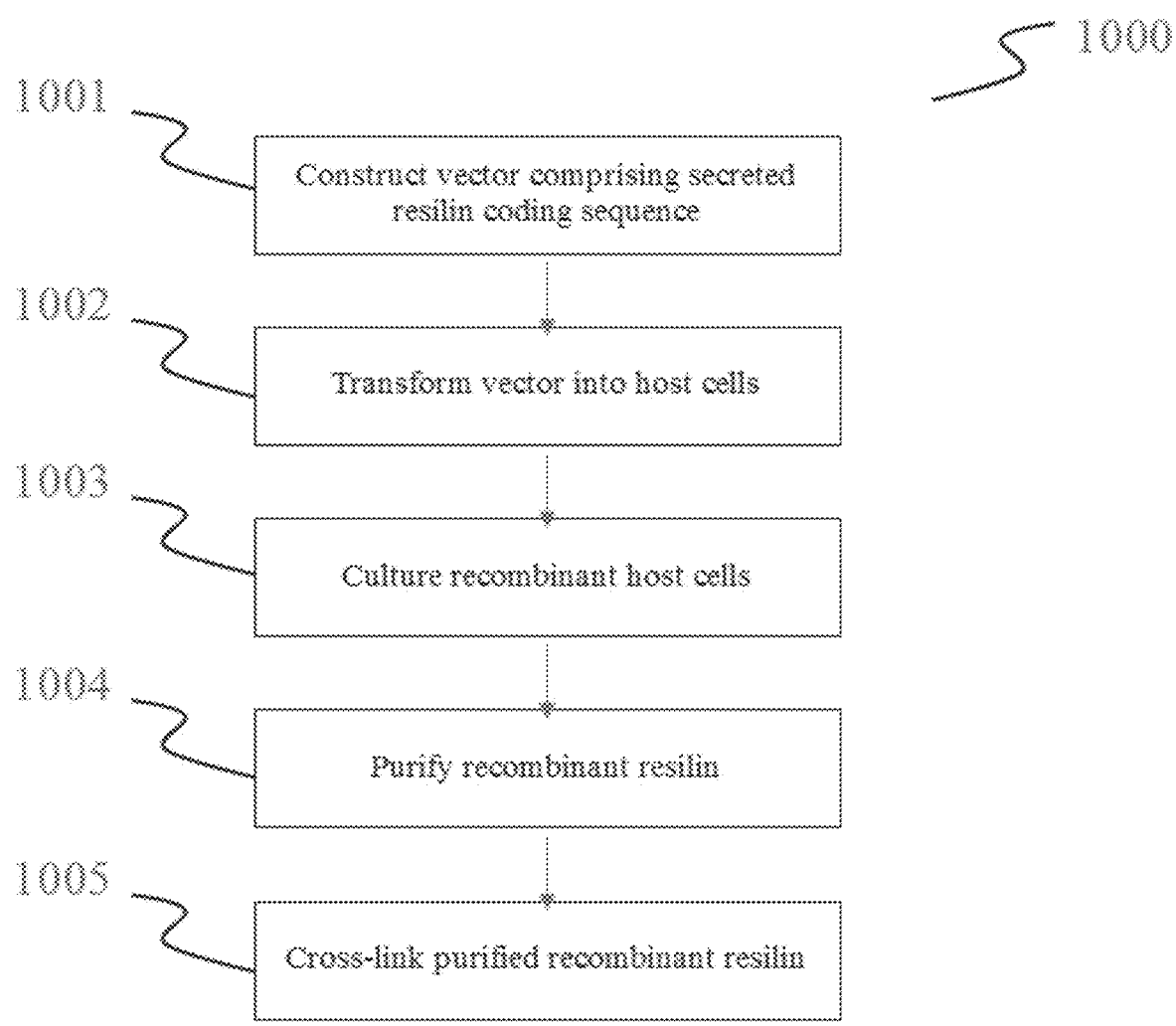
FIG. 2 is a flow diagram of methods for the production of compositions comprising recombinant resilins.
Figure 4:
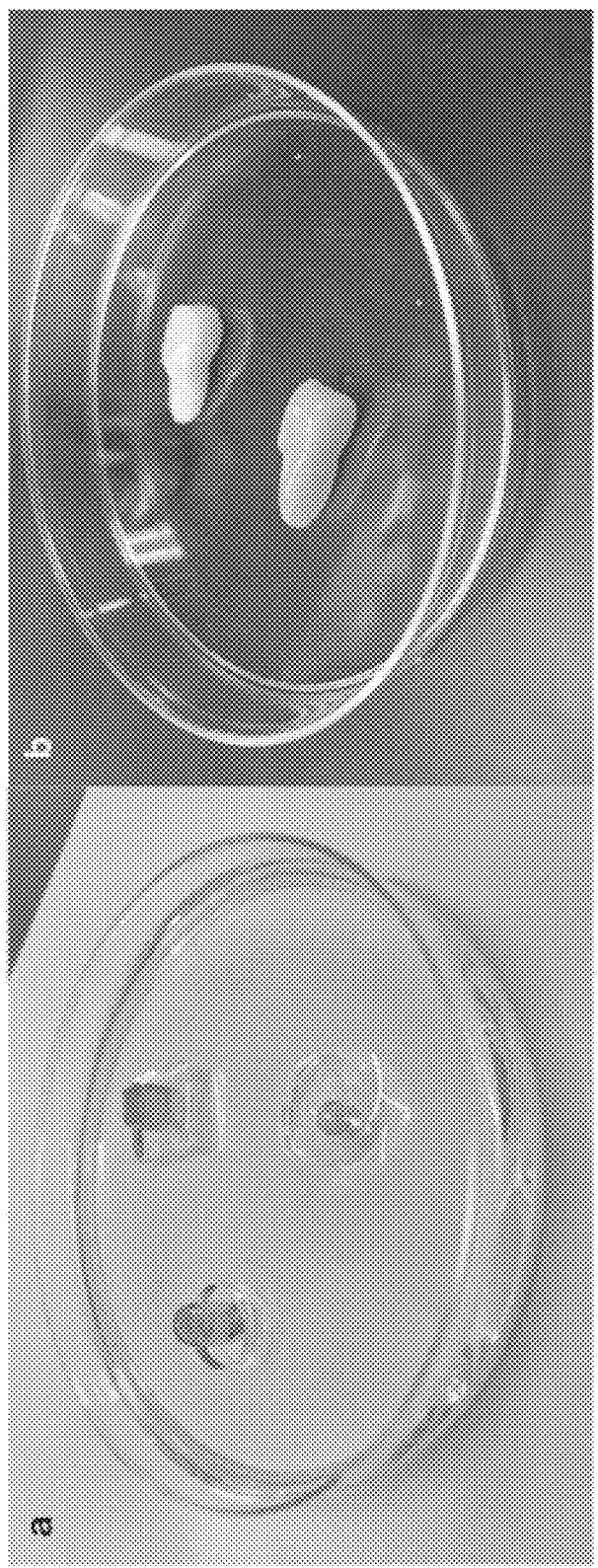
FIG. 4 shows photographs of proteinaceous block co-polymers comprising cross-linked purified recombinant resilins in various shapes and forms.

In some embodiments, the methods provided herein further comprise the step of cross-linking the recombinant resilins to obtain the recombinant resilin compositions provided herein (step 1005 in FIG. 2). The recombinant resilin in the desired solvent with cross-linking agents can be filled into small shaped molds to control the shape of the resulting solid after cross-linking. Examples of resulting recombinant resilin solids are shown in FIG. 4.

In some embodiments, cross-linking is achieved via tyrosine residues. Resilin has a tyrosine residue every 15-24 amino acids throughout most of its length. In some embodiments, cross-linking of resilin creates di- and tri-tyrosine crosslinking in resilin to form a resilin solid.

In other embodiments, cross linking is achieved via lysine residues. In some embodiments, cross linking is achieved via cysteine residues. In some embodiments, cross-linking employs transglutaminase (see, for example, Kim Y, Gill E E, Liu J C. Enzymatic Cross-Linking of Resilin-Based Proteins for Vascular Tissue Engineering Applications. Biomacromolecules. 17(8):2530-9). In some embodiments, cross-linking employs poly(ethylene glycol) (PEG) (McGann C L, Levenson E A, Kiick K L. Macromol. Chem. Phys. 2013, 214, 203-13; McGann C L, Akins R E, Kiick K L. Resilin-PEG Hybrid Hydrogels Yield Degradable Elastomeric Scaffolds with Heterogeneous Microstructure. Biomacromolecules. 2016; 17(1):128-40).

In some embodiments, recombinant resilin is cross-linked via enzymatic cross-linking (e.g., using horseradish peroxidase). While this method can efficiently cross-link large solutions of resilin, the resulting cross-linked product comprises covalently incorporated active enzyme in the cross-linked resilin solid. This yields radical chain reactions that degrade the protein backbone of the resilin.

In other embodiments, recombinant resilin is cross-linked via photochemical cross-linking (see, for example, Elvin C M, Carr A G, Huson M G, Maxwell J M, Pearson R D, Vuocolo T, Liyou N E, Wong D C C, Merritt D J, Dixon N E. Nature 2005, 437, 999-1002; Whittaker J L, Duna N K, Elvin C M, Choudhury N R. Journal of Materials Chemistry B 2015, 3, 6576-79; Degtyar E, Mlynarczyk B, Fratzl P, Harrington M J. Polymer 2015, 69, 255-63).

This cross-linking reaction also results in the incorporation of an active catalyst into the resilin solid that is difficult to completely dialyze out of the material, uses relatively high catalyst loading, and is not efficient for reactions where photoactivation throughout the mold may be difficult.

Provided herein are new recombinant resilin cross-linking chemistries that prevent degradation and make solid substances with some mechanical properties preferred for certain applications where the amount and form of energy absorption is important.

In preferred embodiments, recombinant resilin is cross-linked via a solvent comprising ammonium persulfate and application of heat (e.g., incubation at a temperature of about 80° C. for about 2.5 hours). This cross-linking reaction is efficient and does not leave an active catalyst behind in the resilin solid, resulting in a composition with less degraded protein.

In some embodiments, the final concentration of ammonium persulfate for the resilin cross-linking reaction is about 30 to 40 mM. In some embodiments, the cross-linking solution with ammonium persulfate and resilin is incubated (i.e., exposed to heat) for at least 15 minutes, at least 30 minutes, at least 60 minutes, at least 90 minutes, or at least 2 hours to facilitate sufficient cross-linking to form a solid with desirable mechanical properties. In some embodiments, other persulfates are used.

In some embodiments, the heat applied to the ammonium persulfate and resilin composition solution is at least 40° C., at least 45° C., at least 50° C., at least 55° C., at least 60° C., at least 65° C., at least 70° C., at least 75° C., or at least 80° C. In some embodiments, the heat applied to the cross-linking solution of ammonium persulfate and resilin is from 50° C.-90° C. or from 60° C.-90° C. or from 70° C.-90° C. or from 75° C. to 85° C. or from 70° C. to 80° C. In some embodiments, the cross-linking solution does not comprise an enzymatic catalyst. In some embodiments, the cross-linking solution does not comprise a photoactive catalyst.

In some embodiments, the cross-linking solution comprises at least 1%, 5%, 10%, 20%, 25%, 30%, 35%, 40%, 45%, or 50% resilin, from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%; from 60% to 100%, 90%, 80%, or 70%; from 70% to 100%, 90%, or 80%; from 80% to 100%, or 90%; or from 90% to 100% by weight of the total cross-linking solution. In preferred embodiments, resilin is dissolved in a cross-linking solution to a concentration of between 20% to 30% by weight resilin. In some embodiments the total resilin comprises at least 10%, at least 20%, at least 30%, at least 40%, at least 50%, at least 60%, at least 70%, at least 80%, or at least 90% full length resilin as measured by size exclusion chromatography (SEC).

Solvent-Exchanged Resilin Solids

Cross-linked resilin can be formed in an aqueous solvent resulting in a composition that has a low hardness and elastic modulus that is less suitable for certain applications where energy absorption and stiffness are desired. In some embodiments, a solvent exchange is performed on cross-linked resilin compositions to replace an aqueous solvent with a polar nonaqueous solvent to provide desired material properties. In some embodiments, the polar nonaqueous solvent comprises glycerol, propylene glycol, ethylene glycol, or DMSO. In some embodiments, the nonaqueous solvents are water-miscible. In some embodiments the nonaqueous solvents are non-volatile solvents. In some embodiments, the nonaqueous solvents comprise molecules with a plurality of alcohol functional groups. In some embodiments the nonaqueous solvent comprises at least 50%, at least 60%, at least 70%, at least 80%, at least 90%, or 100% of a molecule or molecules with a molecular weight less than about 100 g/mol. As described herein, material properties of cross-linked resilin compositions, including elastic modulus, hardness, maximum elastic compressive load, resilience, and material lifetime/fatigue, can be tuned using solvent exchange. Solvents that are capable of doing solvent exchange with cross-linked resilin include solvents that dissolve resilin in its non-crosslinked form.

In some embodiments, a solvent exchange to replace an aqueous solvent of resilin with a polar nonaqueous solvent is performed in the presence of heat, e.g., at a temperature of about 60° C. In some embodiments the solvent exchange process is performed in a solution containing at least 1×, at least 2×, at least 5×, at least 10×, or at least 20× the volume of exchange solvent relative to the resilin solid. In some embodiments, the solvent exchange is performed for at least 1 hour, at least 2 hours, at least 4 hours, at least 8 hours, at least 16 hours, at least 24 hours, or at least 48 hours. In some embodiments, glycerol, propylene glycol, ethylene glycol, or DMSO are used as exchange solvents for cross-linked resilin solid compositions.

In some embodiments, the choice of exchange solvent and the concentration used is selected to achieve a desired tunable mechanical property, such as stiffness, from the solvent design. This can be selected depending on the desired application (e.g., shoe soles, golf balls, etc.).

In some embodiments, the cross-linked resilin composition formed by the above solvent exchange process and in a nonaqueous solvent is stable at room temperature for at least 10 days, at least 20 days, at least 30 days, at least 40 days, or at least 50 days. In some embodiments, the cross-linked resilin composition formed by the above solvent exchange process and in a nonaqueous solvent is resistant to mold growth for at least 10 days, at least 20 days, at least 30 days, at least 40 days, or at least 50 days. In some embodiments, the cross-linked resilin composition formed by the above solvent exchange process and in a nonaqueous solvent is resistant to dehydration for at least 7 days or at least 14 days. By contrast, water-based cross-linked resilin solids were observed to dehydrate completely within 2 weeks and to grow mold within 5-14 days when stored in an open environment under ambient conditions. In addition, a 10 mm by 5 mm disc of water-based resilin solid breaks when 220 lbs of force is applied whereas a 10 mm by 5 mm disc of a glycerol-based resilin solid does not break under 220 lbs of force.

Figure 5:
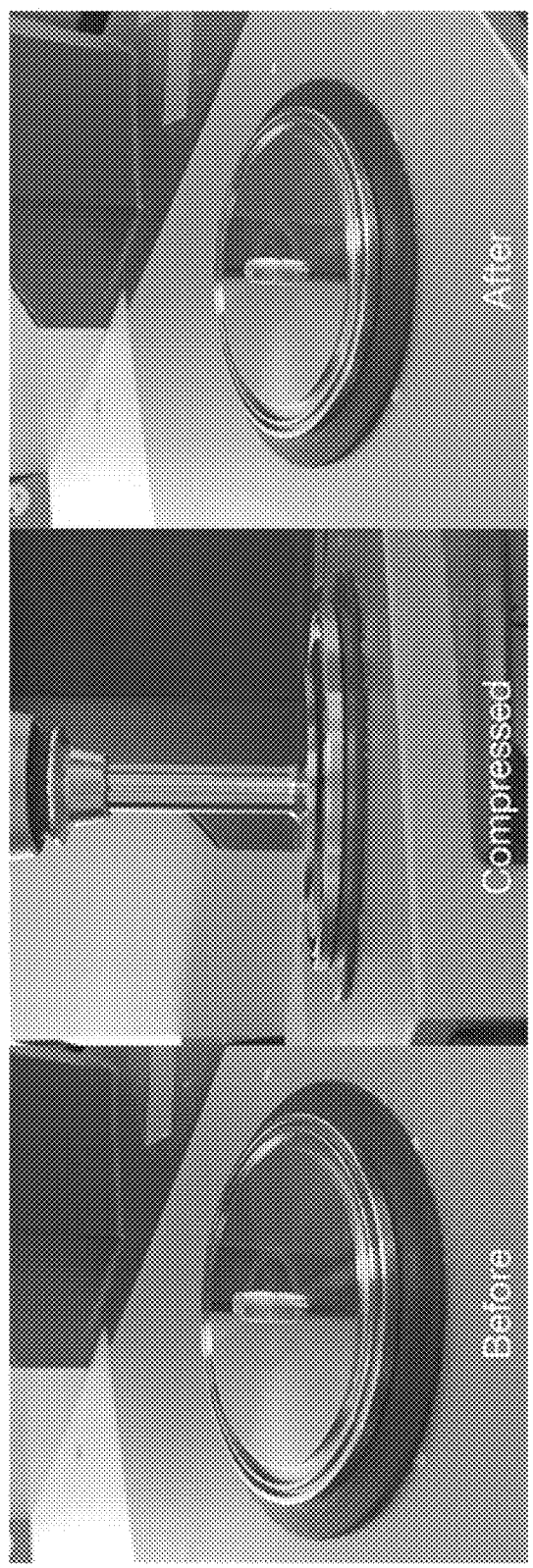
FIG. 5 shows photographs of the compression of a proteinaceous block co-polymer comprising cross-linked recombinant resilin.

In some embodiments, relative material properties between consecutively tested materials can be tested using a rheometer. For example, a cross-linked resilin composition may be formed in a cylinder mold, and the resulting resilin cylinder is subjected to compression test using a rheometer. A recombinant resilin cylinder could be compressed from an initial height of 7.3 mm (avg width 5.4 mm) to less than 0.66 mm without any breakage. As shown in FIG. 5, the cylinder returned to a height of 6.7 mm (avg width 5.6 mm) upon release of the compressive load.

In some embodiments, the polar nonaqueous solvent comprises at least 50%, at least 60%, at least 70%, at least 80%, at least 90%, at least 95%, at least 98%, or at least 99% of a polar nonaqueous composition by volume of said solvent. In some embodiments, the solvent comprises at least 50%, at least 60%, at least 70%, at least 80%, at least 90%, at least 95%, at least 98%, or at least 99% of glycerol, propylene glycol, ethylene glycol, or DMSO by volume of said solvent.

In some embodiments, the recombinant resilin composition provided herein has an elastic modulus greater than cross-linked recombinant resilin in an aqueous solvent.

In some embodiments, the cross-linked resilin compositions provided herein have a Shore OO Hardness of 50 or more, 40 or more, 30 or more, 20 or more, 10 or more, from 10 to 50, 40, 30, or 20; from 20 to 50, 40, or 30; from 30 to 50 or 40; or from 40 to 50; In some embodiments, hardness measurements in resilin are performed according to ASTM D2240. In some embodiments, the recombinant resilin composition comprises a hardness of at least 10 as measured using a Shore OO Durometer via ASTM D2240. In some embodiments, the recombinant resilin composition comprises a hardness of at least 30 as measured using a Shore OO Durometer via ASTM D2240. In some embodiments, the recombinant resilin composition comprises a hardness of from about 10 to about 50 as measured using a Shore OO Durometer via ASTM D2240. In some embodiments, the hardness of the cross-linked resilin composition is comparable to an orthopedic sole.

In some embodiments, the recombinant resilin composition comprises a rebound resilience from about 40% to about 60% as measured by ASTM D7121.

In some embodiments, the recombinant resilin composition comprises a compressive stress at 25% of about 6 psi to about 8 psi as measured by ASTM D575.

In some embodiments, the recombinant resilin composition does not undergo an elastic to plastic transition below 2 kN of compressive force as measured by a Zwick compression test.

In some embodiments, resilin solid material properties, such as resilience, compressive elastic modulus, tensile elastic modulus, shear modulus, extension to break, maximum tensile strength, hardness, stiffness, and rebound can be tuned based on the solvent used and how the solvent exchange is performed. For example, glycerol can be exchanged into the resilin solid either with a gradient or without, result in different resulting material properties. The concentration of resilin in the resilin solid and the amount of full length resilin as a portion of total resilin can also be adjusted to affect the material properties of the cross-linked resilin solid composition.

In some embodiments, solvent exchange to replace the water-based resilin composition (i.e, a cross-linked resilin composition in an aqueous solvent) with a polar nonaqueous-based resilin composition (i.e., a cross-linked resilin composition in a polar nonaqueous solvent) as described herein resulting in a stiffer material with a similar resilience and a similar elasticity.

In some embodiments, the compositions provided herein comprise at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%; between 10% and 100%, 90%, 80%, 70%, 60%, 50%, 40%, 30%, or 20%; between 20% and 100%, 90%, 80%, 70%, 60%, 50%, 40%, or 30%; between 30% and 100%, 90%, 80%, 70%, 60%, 50%, or 40%; between 40% and 100%, 90%, 80%, 70%, 60%, or 50%; between 50% and 100%, 90%, 80%, 70%, or 60%; between 60% and 100%, 90%, 80%, or 70%; between 70% and 100%, 90%, or 80%; between 80% and 100%, or 90%; or between 90% and 100% by weight of recombinant resilins. The recombinant resilins can be identical recombinant resilins or mixtures of recombinant resilins having at least 2 different amino acid sequences.

In some embodiments, the compositions provided herein comprise at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%; between 10% and 100%, 90%, 80%, 70%, 60%, 50%, 40%, 30%, or 20%; between 20% and 100%, 90%, 80%, 70%, 60%, 50%, 40%, or 30%; between 30% and 100%, 90%, 80%, 70%, 60%, 50%, or 40%; between 40% and 100%, 90%, 80%, 70%, 60%, or 50%; between 50% and 100%, 90%, 80%, 70%, or 60%; between 60% and 100%, 90%, 80%, or 70%; between 70% and 100%, 90%, or 80%; between 80% and 100%, or 90%; or between 90% and 100% by weight of full length recombinant resilins as a portion of total resilin in each composition.

In some embodiments, a recombinant resilin composition is a foam material. In some embodiments, a cross-linked resilin composition is a foam material, e.g., a foamed solid. In some embodiments, the foam material comprises at least 50%, at least 60%, at least 70%, at least 80%, at least 90%, at least 95%, at least 98%, or at least 99% porosity. As described herein, porosity refers to the percentage of the volume of interstices of a material to the volume of its mass. In some embodiments, density of the foam material as described herein is at least ⅓rd the density of a non-foam material, e.g., at least ½, at least ¾th, or at least twice the density of a non-foam cross-linked resilin composition. In some embodiments, average diameter of the bubbles in the foam material as described herein is about 0.01 mm to about 3 mm, e.g., about 0.02 mm to about 1 mm, about 0.05 mm to about 2 mm, about 0.1 mm to about 3 mm, about 0.2 mm to about 4 mm, about 0.5 mm to about 5 mm, about 1 mm to about 1.5 mm, or about 1.5 mm to about 2 mm.

In some embodiments, a recombinant resilin composition comprises one or more layers of foam material. In some embodiments, the one or more layers of foam material are configured in a desired order, e.g. a sequential or alternate configuration, wherein a supporting layer is positioned in between two layers of foam material. The one or more layers of foam material may be positioned in any manner known in the art, e.g., spray drying, injection molding. In some embodiments, the one or more layers of foam material includes one or more void spaces. The topography of each layer and the propensity of the one or more layers of foam material to nest together may differ. In some embodiments, the void spaces may provide flow channels on one or more sides to help guide air flow and provide additional absorbent capacity.

Mechanical Properties

In other embodiments, the compositions provided herein have different properties compared to compositions comprising cross-linked resilins. In some embodiments, the compositions provided herein have similar properties compared to synthetic elastic materials. Non-limited examples of such properties include resilience, compressive elastic modulus, tensile elastic modulus, shear modulus, hardness, rebound, and compression set. Parameters that can be modified to obtain compositions with specific mechanical properties include, for example, the length and/or sequence of the recombinant resilins, the extent and/or type of post-translational modifications of the recombinant resilins, the extent and/or type of cross-linking of the recombinant resilins and the nature of the solvent of the cross-linked resilin composition.

In some embodiments, mechanical properties such as maximum tensile strength, compressive elastic modulus, tensile elastic modulus, shear modulus, extension to break and resilience can be measured using many different types of tensile and compression systems that conduct stress-strain measurements on elastomeric samples. The resulting stress-strain curves, including curves with hysteresis, can be measured in tension or compression. In some embodiments, tension and compression test systems can apply a strain to a sample and measure the resulting force using a load cell. In some embodiments, the mechanical properties can be measured at the macroscopic scale (e.g., using macroscopic compression testers), microscopic, or nanoscopic scale (e.g., using atomic-force microscopy (AFM) or nanoindentation measurements). In some embodiments, the compressive mechanical properties of elastomers can be measured according to the standard ASTM D575-91(2012) Standard Test Methods for Rubber Properties in Compression. Mechanical measurements of elastomers in tension can be performed using ASTM D412-15a Standard Test Methods for Vulcanized Rubber and Thermoplastic Elastomers-Tension. In some embodiments, tear strength of elastomers can be performed using ASTM D624-00 Standard Test Method for Tear Strength of Conventional Vulcanized Rubber and Thermoplastic Elastomers. In some embodiments, mechanical properties of slab, bonded, and molded elastomers can be performed using ASTM D3574-11 Standard Test Methods for Flexible Cellular Materials—Slab, Bonded, and Molded Urethane Foams. In some embodiments, the mechanical properties of elastomers can be measured using ASTM D5992-96(2011) Standard Guide for Dynamic Testing of Vulcanized Rubber and Rubber-Like Materials Using Vibratory Methods.

In some embodiments, the compositions provided herein have a resilience of greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%.

In some embodiments, the compositions provided herein have a compressive elastic modulus of less than 10 MPa, less than 7 MPa, less than 5 MPa, less than 2 MPa, less than 1 MPa, less than 0.5 MPa, or less than 0.1 MPa; from 0.01 MPa to 10 MPa, 7 MPa, 5 MPa, 2 MPa, 1 MPa, 0.5 MPa, or 0.1 MPa; from 0.1 MPa to 10 MPa, 7 MPa, 5 MPa, 2 MPa, 1 MPa, or 0.5 MPa; from 0.5 MPa to 10 MPa, 7 MPa, 5 MPa, 2 MPa, or 1 MPa; from 1 MPa to 10 MPa, 7 MPa, 5 MPa, or 2 MPa; from 2 MPa to 10 MPa, 7 MPa, or 5 MPa; from 5 MPa to 10 MPa, or 7 MPa; or from 7 MPa to 10 MPa. In some embodiments, the compressive elastic modulus of a composition can be measured as defined by the ASTM D575-91(2012) Standard Test Methods for Rubber Properties in Compression.

In some embodiments, the compositions provided herein have a tensile elastic modulus of less than 10 MPa, less than 7 MPa, less than 5 MPa, less than 2 MPa, less than 1 MPa, less than 0.5 MPa, or less than 0.1 MPa; from 0.01 MPa to 10 MPa, 7 MPa, 5 MPa, 2 MPa, 1 MPa, or 0.5 MPa; from 0.5 MPa to 10 MPa, 7 MPa, 5 MPa, 2 MPa, or 1 MPa; from 1 MPa to 10 MPa, 7 MPa, 5 MPa, or 2 MPa; from 2 MPa to 10 MPa, 7 MPa, or 5 MPa; from 5 MPa to 10 MPa, or 7 MPa; or from 7 MPa to 10 MPa.

In some embodiments, the compositions provided herein have a shear modulus of less than 1 MPa, less than 100 kPa, less than 50 kPa, less than 20 kPa, less than 10 kPa, or less than 1 kPa; from 0.1 kPa to 1 MPa, 100 kPa, 50 kPa, 20 kPa, 10 kPa, or 1 kPa; from 1 kPa to 1 MPa, 100 kPa, 50 kPa, 20 kPa, or 10 kPa; from 10 kPa to 1 MPa, 100 kPa, 50 kPa, or 20 kPa; from 20 kPa to 1 MPa, 100 kPa, or 50 kPa; from 50 kPa to 1 MPa, or 100 kPa; or from 100 kPa to 1 MPa.

In some embodiments, the compositions provided herein have an extension to break of greater than 1%, greater than 10%, greater than 50%, greater than 100%, greater than 300%, or greater than 500%; from 1% to 500%, 300%, 100%, 50%, or 10%; from 10% to 500%, 300%, 100%, or 50%; from 50% to 500%, 300%, or 100%; from 100% to 500%, or 300%; or from 300% to 500%.

In some embodiments, the compositions provided herein have a maximum tensile strength of greater than 0.1 kPa, greater than 1 kPa, greater than 2 kPa, greater than 5 kPa, or greater than 10 kPa; from 0.1 kPa to 100 kPa, 10 kPa, 5 kPa, 2 kPa, or 1 kPa; from 1 kPa to 100 kPa, 10 kPa, 5 kPa, or 2 kPa; from 2 kPa to 100 kPa, 10 kPa, or 5 kPa; from 5 kPa to 100 kPa, or 10 kPa; or from 10 kPa to 100 kPa.

In some embodiments, mechanical properties such as hardness and compressive elastic modulus can be measured using indentation and nanoindentation measurement systems. In some embodiments, indentation measurements utilizing a tip to indent the sample to a given amount of strain are used to measure the hardness and compressive elastic modulus of resilin, and the resulting force is measured using a load cell. In some embodiments, different tip shapes can be used including Vickers and Berkovich shaped tips. In some embodiments, the hardness measured by indentation techniques is characterized by the relation, Hardness=(Peak Force)/(Contact Area).

In some embodiments, the hardness in polymers, elastomers, and rubbers can be measured using a durometer. In some embodiments the hardness of an elastomer can be measured using the standard ASTM D2240, which recognizes twelve different durometer scales using combinations of specific spring forces and indentor configurations. The most common scales are the Shore 00, A and D Hardness Scales. Hardness scales range from 0 to 100, where 0 is softer material and 100 is harder material.

In some embodiments, the compositions provided herein have a Shore 00 Hardness of less than 90, less than 80, less than 70, less than 60, less than 50, less than 40, less than 30, or less than 20; from 10 to 90, 80, 70, 60, 50, 40, 30, or 20; from 20 to 90, 80, 70, 60, 50, 40, or 30; from 30 to 90, 80, 70, 60, 50, or 40; from 40 to 90, 80, 70, 60, or 50; from 50 to 90, 80, 70, or 60; from 60 to 90, 80, or 70; from 70 to 90, or 80; or from 80 to 90. In some embodiments, hardness measurements in resilin are performed according to ASTM D2240.

As used here, the term "rebound" refers to a particular measure of resilience. In some embodiments, rebound can be measured with a number of different tools including pendulum tools and dropped balls. In the pendulum type measurements, RB, commonly called percentage rebound, is determined from the equation:

$$RB = \frac{[1 - \cos(\text{angle of rebound})]}{[1 - \cos(\text{originial angle})]} \times 100$$

The rebound resilience can be calculated as:

$$R = \frac{h}{H}$$

where h=apex height of the rebound, and H=initial height. The rebound resilience can also be determined by the measurement of the angle of rebound. Some examples of test methods for determining rebound in elastomers are ASTM D2632-15 and ASTM D7121-05(2012).

In some embodiments, the compositions provided herein have a rebound greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%. In some embodiments, rebound measurements in resilin are performed according to ASTM D2632-15, or ASTM D7121-05(2012).

As used herein, the term "compression set" refers to a measure of the permanent deformation remaining after an applied force is removed. In some embodiments, compression set can be measured in different ways, including compression set under constant force in air (referred to as Compression Set A), compression set under constant deflection in air (referred to as Compression Set B), and compression set under constant deflection in air considering material hardness (referred to as Compression Set C). Compression Set A ($C_A$) is calculated by the following expression: $C_A = [(t_o - t_i)/t_o] \times 100$, where to is the original specimen thickness, and $t_i$ is the specimen thickness after testing). Compression set B ($C_B$) is given by $C_B = [(t_o - t_i)/(t_o - t_n)] \times 100$, where $t_o$ is the original specimen thickness, $t_i$ is the specimen thickness after testing, and $t_o$ is the spacer thickness or the specimen thickness during the test. Some examples of test methods for determining compression set in elastomers are ASTM D3574-11 and ASTM D395-16.

In some embodiments, the compositions provided herein have a Compression Set A or a Compression Set B of greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%. In some embodiments, compression set measurements in resilin are performed according to ASTM D3574-11 and ASTM D395-16.

The processing and forming of resilin into products can take many forms for different applications. Accordingly, the compositions provided herein can have any shape and form, including but not limited to gels, porous sponges, films, machinable solids, cast forms, molded forms, and composites.

As used herein, the term "density" refers to the mass of the sample divided by the volume. In some embodiments, the density of an elastomer can be determined using a pycnometer with alcohol in place of water to eliminate air bubbles. In some embodiments, the density of an elastomer can be determined using a hydrostatic method. As used herein, the term "compressed volume density" refers to the ratio of the sample mass to the compressed volume of the sample, where the "compressed volume" is defined as the final equilibrium volume attained by an elastomeric sample when it is subjected to a compressive force sufficient to cause it to flow until it fully conforms to the surrounding shape of the piston-cylinder test chamber enclosure. In some embodiments, the compressed volume density of an elastomer can be determined using a compressed volume densimeter.

In some embodiments, the compositions provided herein have a density or a compressed volume density are from 0.5 $mg/cm^3$ to 2.0 $mg/cm^3$, or from 1.0 $mg/cm^3$ to 1.5 $mg/cm^3$, or from 1.1 $mg/cm^3$ to 1.4 $mg/cm^3$, or from 1.2 $mg/cm^3$ to 1.35 $mg/cm^3$. In some embodiments, the determination of the density or the compressed volume density of elastomers can be performed using ASTM D297-15 Standard Test Methods for Rubber Products—Chemical Analysis.

The compositions provided herein have a number of uses, including but not limited to applications in aerospace, automotive, sporting equipment, vibration isolation, footwear, and clothing among others. Some applications from these categories are listed as non-limiting examples. Due to the desirable elastic efficiency, resilin can be used as an energy storage device (e.g., a rubber band) for storing and recovering mechanical energy. Automobile suspension systems can be improved by application of resilin bushings to keep more tire contact on the road when going over bumps and through potholes at speed. Additionally, there are a number of sporting equipment applications for resilin with differently tuned mechanical properties including cores of golf balls, tennis racket grips, golf club grips, and table tennis paddles.

An application of particular interest is footwear due to the unique properties of resilin compositions provided herein. As an insole or midsole, resilin can improve the comfort and bioefficiency of shoes by cushioning the foot strike and restoring more of the energy from that footstrike as forward momentum. As a midsole, resilin can make up the entire midsole or be encapsulated within another material to complement its properties (e.g., an abrasion or wear resistant material, or a material tuned for traction). The resilin midsole can also contain a plurality of resilin materials with differently tuned mechanical properties that work in concert to provide enhanced performance (e.g., softer heel strike area and firmer arch support).

Vectors, Host Cells, and Fermentations

Further provided herein are vectors encoding recombinant resilins, recombinant host cells comprising such vectors, and fermentations comprising such recombinant host cells and recombinant resilins.

In some embodiments, the vectors provided herein comprise secreted resilin coding sequences, which encode a resilin polypeptide fused at its N-terminus to a secretion signal and optionally at its C-terminus to a tag peptide or polypeptide. In some embodiments, the vectors comprise secreted resilin coding sequences that are codon-optimized for expression in a particular host cell.

Suitable secretion signals are secretion signals that mediate secretion of polypeptides in the recombinant host cells provided herein. Non-limiting examples of suitable secretion signals are the secretion signals of the alpha mating factor (α-MF) of *Saccharomyces cerevisiae*, acid phosphatase (PH01) of *Pichia pastoris*, and phytohemagglutinin (PHA-E) from the common bean *Phaseolus vulgaris*. Additional secretion signals are known in the art, or can be identified by identification of proteins secreted by a host cell followed by genomic analysis of the secreted proteins and identification of the non-translated N-terminal sequences (see, for example, Huang et al. A proteomic analysis of the *Pichia pastoris* secretome in methanol-induced cultures. Appl Microbiol Biotechnol. 2011 April; 90(1):235-47).

The resilins encoded by the secreted resilin coding sequences can be further fused to tag peptides or polypeptides. Non-limiting examples of tag peptides or polypeptides include affinity tags (i.e., peptides or polypeptides that bind to certain agents or matrices), solubilization tags (i.e., peptides or polypeptides that assist in proper folding of proteins and prevent precipitation), chromatography tags (i.e., peptides or polypeptides that alter the chromatographic properties of a protein to afford different resolution across a particular separation techniques), epitope tags (i.e., peptides or polypeptides that are bound by antibodies), fluorescence tags (i.e., peptides or polypeptides that upon excitation with short-wavelength light emit high-wavelength light), chromogenic tags (i.e., peptides or polypeptides that absorb specific segments of the visible light spectrum), enzyme substrate tags (i.e., peptides or polypeptides that are the substrates for specific enzymatic reactions), chemical substrate tags (i.e., peptides or polypeptides that are the substrates for specific chemical modifications), or combinations thereof. Non-limiting examples of suitable affinity tags include maltose binding protein (MBP), glutathione-S-transferase (GST), poly(His) tag, SBP-tag, Strep-tag, and calmodulin-tag. Non-limiting examples of suitable solubility tags include thioredoxin (TRX), poly(NANP), MBP, and GST. Non-limiting examples of chromatography tags include polyanionic amino acids (e.g., FLAG-tag [GDYKDDDDKDYKDDDDKDYKDDDDK (SEQ ID NO: 45)]) and polyglutamate tag. Non-limiting examples of epitope tags include V5-tag, VSV-tag, Myc-tag, HA-tag, E-tag, NE-tag, and FLAG-tag. Non-limiting examples of fluorescence tags include green fluorescent protein (GFP), blue fluorescent protein (BFP), cyan fluorescent protein (CFP), yellow fluorescent protein (YFP), orange fluorescent protein (OFP), red fluorescent protein (RFP), and derivatives thereof. Non-limiting examples of chromogenic tags include non-fluorescent members of the GFP-like family of proteins (e.g., BlitzenBlue, DonnerMagenta; DNA2.0, Neward, CA). Non-limiting examples of enzyme substrate tags include peptides or polypeptides comprising a lysine within a sequence suitable for biotinilation (e.g., AviTag, Biotin Carboxyl Carrier Protein [BCCP]). Non-limiting examples of chemical substrate tags include substrates suitable for reaction with FlAsH-EDT2. The fusion of the C-terminal peptide or polypeptide to the resilin can be cleavable (e.g., by TEV protease, thrombin, factor Xa, or enteropeptidase) on non-cleavable.

In some embodiments, the vectors comprise single secreted resilin coding sequences. In other embodiments, the vectors comprise 2 or more (e.g., 3, 4, or 5) secreted resilin coding sequences. In some such embodiments, the secreted resilin coding sequences are identical. In other such embodiments, at least 2 of the secreted resilin coding sequences are not identical. In embodiments in which at least 2 of the secreted resilin coding sequences are not identical, the at least 2 secreted resilin coding sequences can differ from each other in the resilins and/or in the secretion signals and/or the optional tag peptides or polypeptides they encode.

In some embodiments, the vectors comprise promoters that are operably linked to the secreted resilin coding sequences such that they drive the expression of the secreted resilin coding sequences. The promotors can be constitutive promoters or inducible promoters. In some embodiments, induction of the inducible promoter occurs via glucose repression, galactose induction, sucrose induction, phosphate repression, thiamine repression, or methanol induction. Suitable promoters include promoters that mediate expression of proteins in the recombinant host cells provided herein. Non-limiting examples of suitable promoters include the AOX1 promoter, GAP promoter, LAC4-PBI promoter, T7 promoter, TAC promoter, GCW14 promoter, GAL1 promoter, πPL promoter, πPR promoter, beta-lactamase promoter, spa promoter, CYC1 promoter, TDH3 promoter, GPD promoter, TEF1 promoter, ENO2 promoter, PGL1 promoter, SUC2 promoter, ADH1 promoter, ADH2 promoter, HXT7 promoter, PHO5 promoter, and CLB1 promoter. Additional promoters that can be used to facilitate expression of the secreted resilin coding sequences are known in the art.

In some embodiments, the vectors comprise terminators that are operably linked to the secreted resilin coding sequences such that they effect termination of transcription of the secreted resilin coding sequences. Suitable terminators include terminators that terminate transcription in the recombinant host cells provided herein. Non-limiting examples of suitable terminators include the AOX1 terminator, PGK1 terminator, and TPS1 terminator. Additional terminators that effect termination of transcription of the secreted resilin coding sequences are known in the art.

In embodiments in which the vectors comprise 2 or more resilin coding sequences, the 2 or more resilin coding sequences can be operably linked to the same promoters and/or terminators or to 2 or more different promoters and/or terminators.

The vectors provided herein can further comprise elements suitable for propagation of the vectors in recombinant host cells. Non-limiting examples of such elements include bacterial origins of replication and selection markers (e.g., antibiotic resistance genes, auxotrophic markers). Bacterial origins of replication and selection markers are known in the art. In some embodiments, the selection marker is a drug resistant marker. A drug resistant maker enables cells to detoxify an exogenously added drug that would otherwise kill the cell. Illustrative examples of drug resistant markers include but are not limited to those for resistance to antibiotics such as ampicillin, tetracycline, kanamycin, bleomycin, streptomycin, hygromycin, neomycin, Zeocin™, and the like. In some embodiments, the selection marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine-free media in the presence of histidinol. Other selection markers suitable for the vectors of the present invention include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, and a xanthine-guanine phosphoribosyltransferase gene.

The vectors of the present invention can further comprise targeting sequences that direct integration of the secreted resilin coding sequences to specific locations in the genome of host cells. Non-limiting examples of such targeting sequences include nucleotide sequences that are identical to nucleotide sequences present in the genome of a host cell. In some embodiments, the targeting sequences are identical to repetitive elements in the genome of host cells. In some embodiments, the targeting sequences are identical to transposable elements in the genome of host cells.

In some embodiments, recombinant host cells are provided herein that comprise the vectors described herein. In some embodiments, the vectors are stably integrated within the genome (e.g., a chromosome) of the recombinant host cells, e.g., via homologous recombination or targeted integration. Non-limiting examples of suitable sites for genomic integration include the Ty1 loci in the *Saccharomyces cerevisiae* genome, the rDNA and HSP82 loci in the *Pichia pastoris* genome, and transposable elements that have copies scattered throughout the genome of the recombinant host cells. In other embodiments, the vectors are not stably integrated within the genome of the recombinant host cells but rather are extrachromosomal.

Recombinant host cells can be of mammalian, plant, algae, fungi, or microbe origin. Non-limiting examples of suitable fungi include methylotrophic yeast, filamentous yeast, *Arxula adeninivorans, Aspergillus niger, Aspergillus niger* var. *awamori, Aspergillus oryzae, Candida etchellsii, Candida guilliermondii, Candida humilis, Candida lipolytica, Candida pseudotropicalis, Candida utilis, Candida versatilis, Debaryomyces hansenii, Endothia parasitica, Eremothecium ashbyii, Fusarium moniliforme, Hansenula polymorpha, Kluyveromyces lactis, Kluyveromyces marxianus, Kluyveromyces thermotolerans, Morteirella vinaceae* var. *raffinoseutilizer, Mucor miehei, Mucor miehei* var. *Cooney et Emerson, Mucor pusillus Lindt, Penicillium roquefortii, Pichia methanolica, Pichia pastoris (Komagataella phaffii), Pichia (Scheffersomyces) stipitis, Rhizopus niveus, Rhodotorula* sp., *Saccharomyces bayanus, Saccharomyces beticus, Saccharomyces cerevisiae, Saccharomyces chevaliers, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma reesi, Xanthophyllomyces dendrorhous, Yarrowia lipolytica, Zygosaccharomyces rouxii,* and derivatives and crosses thereof.

Non-limiting examples of suitable microbes include *Acetobacter suboxydans, Acetobacter xylinum, Actinoplane missouriensis, Arthrospira platensis, Arthrospira maxima, Bacillus cereus, Bacillus coagulans, Bacillus licheniformis, Bacillusstearothermophilus, Bacillus subtilis, Escherichia coli, Lactobacillus acidophilus, Lactobacillus bulgaricus, Lactobacillus reuteri, Lactococcus lactis, Lactococcus lactis* Lancefield Group N, *Leuconostoc citrovorum, Leuconostoc dextranicum, Leuconostoc mesenteroides* strain NRRL B-512(F), *Micrococcus lysodeikticus, Spirulina, Streptococcus cremoris, Streptococcus lactis, Streptococcus lactis* subspecies *diacetylactis, Streptococcus thermophilus, Streptomyces chattanoogensis, Streptomyces griseus, Streptomyces natalensis, Streptomyces olivaceus, Streptomyces olivochromogenes, Streptomyces rubiginosus, Xanthomonas campestris,* and derivatives and crosses thereof. Additional strains that can be used as recombinant host cells are known in the art. It should be understood that the term "recombinant host cell" is intended to refer not only to the particular subject cell but to the progeny of such a cell. Because certain modifications may occur in succeeding generations due to either mutation or environmental influences, such progeny may not, in fact, be identical to the parent cell, but is still included within the scope of the term "recombinant host cell" as used herein.

In some embodiments, the recombinant host cells comprise genetic modifications that improve production of the recombinant resilins provided herein. Non-limiting examples of such genetic modifications include altered promoters, altered kinase activities, altered protein folding activities, altered protein secretion activities, altered gene expression induction pathways, and altered protease activities.

The recombinant host cells provided herein are generated by transforming cells of suitable origin with vectors provided herein. For such transformation, the vectors can be circularized or be linear. Recombinant host cell transformants comprising the vectors can be readily identified, e.g., by virtue of expressing drug resistance or auxotrophic markers encoded by the vectors that permit selection for or against growth of cells, or by other means (e.g., detection of light emitting peptide comprised in vectors, molecular analysis of individual recombinant host cell colonies, e.g., by restriction enzyme mapping, PCR amplification, or sequence analysis of isolated extrachromosomal vectors or chromosomal integration sites).

In some embodiments, the recombinant host cells provided herein can produce high titers of the recombinant resilins provided herein. In some such embodiments, the recombinant host cells produce the recombinant resilins at a rate of greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. In other such embodiments, the recombinant host cells secrete the recombinant resilins at a rate of greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. The identities of the recombinant resilins produced can be confirmed by HPLC quantification, Western blot analysis, polyacrylamide gel electrophoresis, and 2-dimensional mass spectroscopy (2D-MS/MS) sequence identification.

In some embodiments, the recombinant host cells provided herein have high secreted fractions of the recombinant resilins provided herein. In some such embodiments, the recombinant host cells have secreted fractions of recombinant resilient that is greater than 50%, 60%, 70%, 80%, or 90%; from 50% to 100%, 90%, 80%, 70%, or 60%; from 60% to 100%, 90%, 80%, or 70%; from 70% to 100%, 90%, or 80%; from 90% to 100%, or 90%; or from 90% to 100%.

Production and secretion of recombinant resilins can be influenced by the number of copies of the secreted resilin coding sequences comprised in the recombinant host cells and/or the rate of transcription of the secreted resilin coding sequences comprised in the recombinant host cells. In some embodiments, the recombinant host cells comprise a single secreted resilin coding sequence. In other embodiments, the recombinant host cells comprise 2 or more (e.g., 3, 4, 5, or more) secreted resilin coding sequences. In some embodiments, the recombinant host cells comprise secreted resilin coding sequences that are operably linked to strong promoters. Non-limiting examples of strong promoters include the pGCW14 promoter of *Pichia pastoris*. In some embodiments, the recombinant host cells comprise secreted resilin coding sequences that are operably linked to medium promoters. Non-limiting examples of such medium promoters include the pGAP promoter of *Pichia pastoris*. In some embodiments, the recombinant host cells comprise coding sequences encoding resilins under the control of weak promoters.

The fermentations provided herein comprise recombinant host cells described herein and a culture medium suitable for growing the recombinant host cells.

The fermentations are obtained by culturing the recombinant host cells in culture media that provide nutrients needed by the recombinant host cells for cell survival and/or growth, and for secretion of the recombinant resilins. Such culture media typically contain an excess carbon source. Non-limiting examples of suitable carbon sources include monosaccharides, disaccharides, polysaccharides, and combinations thereof. Non-limiting examples of suitable monosaccharides include glucose, galactose, mannose, fructose, ribose, xylose, arabinose, ribose, and combinations thereof. Non-limiting examples of suitable disaccharides include sucrose, lactose, maltose, trehalose, cellobiose, and combinations thereof. Non-limiting examples of suitable polysaccharides include raffinose, starch, glycogen, glycan, cellulose, chitin, and combinations thereof.

In some embodiments, the fermentations comprise recombinant resilins in amounts of at least 1%, 5%, 10%, 20%, or 30%; from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%; from 60% to 100%, 90%, 80%, or 70%; from 70% to 100%, 90%, or 80%; from 80% to 100%, or 90%; or from 90% to 100% by weight of the total fermentation.

In some embodiments, the fermentations comprise recombinant resilin in an amount of at least 2 g/L, 5 g/L, 10 g/L, 15 g/L, 20 g/L, 25 g/L, or 30 g/L; from 2 g/L to 300 g/L, 200 g/L, 100 g/L, 90 g/L, 80 g/L, 70 g/L, 60 g/L, 50 g/L, 40 g/L, 30 g/L, 20 g/L, or 10 g/L; from 10 g/L to 300 g/L, 200 g/L, 100 g/L, 90 g/L, 80 g/L, 70 g/L, 60 g/L, 50 g/L, 40 g/L, 30 g/L, or 20 g/L; from 20 g/L to 300 g/L, 200 g/L, 100 g/L, 90 g/L, 80 g/L, 70 g/L, 60 g/L, 50 g/L, 40 g/L, or 30 g/L; from 30 g/L to 300 g/L, 200 g/L, 100 g/L, 90 g/L, 80 g/L, 70 g/L, 60 g/L, 50 g/L, or 40 g/L; from 40 g/L to 300 g/L, 200 g/L, 100 g/L, 90 g/L, 80 g/L, 70 g/L, 60 g/L, or 50 g/L; from 50 g/L to 300 g/L, 200 g/L, 100 g/L, 90 g/L, 80 g/L, 70 g/L, or 60 g/L; from 60 g/L to 300 g/L, 200 g/L, 100 g/L, 90 g/L, 80 g/L, or 70 g/L; from 70 g/L to 300 g/L, 200 g/L, 100 g/L, 90 g/L, or 80 g/L; from 80 g/L to 300 g/L, 200 g/L, 100 g/L, or 90 g/L; from 90 g/L to 300 g/L, 200 g/L, or 100 g/L; from 100 g/L to 300 g/L, or 200 g/L; or from 200 g/L to 300 g/L.

Methods of Producing Recombinant Resilin

Further provided herein are methods for the production of the recombinant resilins described herein.

The methods are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y., 1989; Ausubel et al., Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

In some embodiments, a novel method is utilized to secrete resilin extracellularly from a host cell. In some embodiments, the method comprises constructing a vector comprising a secreted resilin coding sequence (step 1001 in FIG. 2), transforming the vector into a host cell (step 1002 in FIG. 2), and then culturing the recombinant host cells to secrete resilin extracellularly (step 1003 in FIG. 2). In some embodiments, the method includes secreting the resilin extracellularly at a rate greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. In some embodiments, the secreted resilin is then purified (step 1004 in FIG. 2), and the purified resilin is cross-linked to form an elastomer (step 1005 in FIG. 2). In some embodiments, the methods provided herein comprise the step of transforming cells with vectors provided herein to obtain recombinant host cells provided herein (step 1002 in FIG. 2). Methods for transforming cells with vectors are well-known in the art. Non-limiting examples of such methods include calcium phosphate transfection, dendrimer transfection, liposome transfection (e.g., cationic liposome transfection), cationic polymer transfection, electroporation, cell squeezing, sonoporation, optical transfection, protoplast fusion, impalefection, hyrodynamic delivery, gene gun, magnetofection, and viral transduction. One skilled in the art is able to select one or more suitable methods for transforming cells with vectors provided herein based on the knowledge in the art that certain techniques for introducing vectors work better for certain types of cells.

In some embodiments, the methods further comprise the step of culturing the recombinant host cells provided herein in culture media under conditions suitable for obtaining the fermentations provided herein (step 1003 in FIG. 2). In some embodiments, the conditions and culture media are suitable to facilitate secretion of the recombinant proteins from the recombinant host cells into the culture media. Suitable culture media for use in these methods are known in the art, as are suitable culture conditions. Exemplary details of culturing yeast host cells are described in Idiris et al., Appl. Microbiol. Biotechnol. 86:403-417, 2010; Zhang et al., Biotechnol. Bioprocess. Eng. 5:275-287, 2000; Zhu, Biotechnol. Adv. 30:1158-1170, 2012; Li et al., MAbs 2:466-477, 2010.

In some embodiments, the methods further comprise the step of purifying secreted recombinant resilins from the fermentations provided herein to obtain the recombinant resilins provided herein (step 1004 in FIG. 2). Purification can occur by a variety of methods known in the art for purifying secreted proteins from fermentations. Common steps in such methods include centrifugation (to remove cells) followed by precipitation of the proteins using precipitants or other suitable cosmotropes (e.g., ammonium sulfate). The precipitated protein can then be separated from the supernatant by centrifugation, and resuspended in a solvent (e.g., phosphate buffered saline [PBS]). The suspended protein can be dialyzed to remove the dissolved salts. Additionally, the dialyzed protein can be heated to denature other proteins, and the denatured proteins can be removed by centrifugation. Optionally, the purified recombinant resilins can be coacervated.

In various embodiments, methods of purifying the secreted recombinant proteins from the fermentation can include various centrifugation steps in conjunction with solubilizing protein in a whole cell broth or cell pellet with known chaotropes such as urea or guanidine thiocyanate.

In some embodiments, recombinant resilin protein can be purified by centrifuging a whole cell broth to produce a first pellet of cells and a first supernatant, and extracting the first supernatant to produce a clear cell broth. The first supernatant is then precipitated using ammonium sulfate and centrifuged to produce a second pellet and second supernatant which was discarded. The second pellet is then re-suspended in PBS for dialysis. In some embodiments, the dialyzed solution is then subject to high temperature to denature proteins that are less stable than the target recombinant protein. Then, denatured proteins are removed by centrifuging the dialyzed and denatured solution to produce a third pellet and third supernatant. The third supernatant is retained from the denatured solution, then coacervated by chilling the third supernatant to induce a phase separation into a dense lower layer containing the target recombinant resilin protein and an upper layer. Samples purified by this method can be referred to as "CCB" samples. In some embodiments, multiple coacervations are performed by retaining the lower layer and incubating the lower layer at a lower temperature to induce further phase separation.

In some embodiments, recombinant resilin protein can be purified by centrifuging a whole cell broth to produce a first pellet of cells and protein proximal to the cells (e.g. adherent to the cells, on the surface of the cells) and/or insoluble protein (e.g. protein aggregates) and first supernatant, then discarding the first supernatant to obtain the first pellet. The first pellet can then be re-suspended in guanidine thiocyanate to solubilize recombinant resilin protein. The re-suspension is then centrifuged again produce a second pellet and a second supernatant. The second supernatant is then dialyzed against PBS and subject to high temperature in order to denature proteins other than recombinant resilin and centrifuged to produce a third pellet and third supernatant. In some embodiments, the third supernatant is then subject to coacervation by chilling to yield phase separation into a dense lower layer containing recombinant resilin and an upper layer. Samples purified by this method can be referred to as "gel layer" samples. In some embodiments, multiple coacervations are performed by retaining the lower layer and incubating the lower layer at a lower temperature to induce further phase separation.

In some embodiments, recombinant resilin protein can be purified by centrifuging a whole cell broth to produce a pellet and supernatant, then discarding the supernatant to obtain a pellet of cells and protein proximal to the cells (e.g. adherent to the cells, on the surface of the cells) and/or insoluble protein (e.g. protein aggregates). The pellet of cells is then re-suspended in guanidine thiocyanate to solubilize the protein that was proximal to the cells. The re-suspension is centrifuged again produce a second pellet of cells and a second supernatant. The second supernatant is then precipitated with ammonium sulfate and centrifuged to produce a third pellet and third supernatant. The third pellet is then suspended in guanidine thiocyanate, then dialyzed against PBS and subject to high temperature to denature proteins other than recombinant resilin and centrifuged to produce a fourth supernatant and fourth pellet. The fourth supernatant is then subject to coacervation by chilling to yield phase separation. Samples purified by this method can be referred to as "gel layer precipitated" samples.

In some embodiments, recombinant resilin protein can be purified by adding urea to a whole cell broth to solubilize the protein, then centrifuging the whole cell broth to produce a first pellet and first supernatant. The first supernatant is then precipitated using ammonium sulfate and centrifuged to produce a second pellet and second supernatant. The second supernatant is discarded and the second pellet is then re-suspended in guanidine thiocyanate and dialyzed against PBS, then subject to high temperature in order to denature proteins other than recombinant resilin and centrifuged again to produce a third pellet and a third supernatant. The third supernatant is then coacervated by chilling the third supernatant to induce a phase separation into a dense lower layer containing recombinant resilin and an upper layer. Samples purified by this method can be referred to as "Urea WCBE" samples.

In some embodiments, recombinant resilin protein can be purified by centrifuging a whole cell broth to produce a first pellet and first supernatant, then discarding the first supernatant to obtain a first pellet of cells and protein proximal to the cells (e.g. adherent to the cells, on the surface of the cells) and/or insoluble protein (e.g. protein aggregates). The first pellet of cells is then re-suspended in guanidine thiocyanate to solubilize the protein. The re-suspension is centrifuged again to produce a second pellet of cells and a second supernatant. The second supernatant is then dialyzed against PBS and then centrifuged to produce a heavy phase of protein, a light phase of supernatant and a film separating the heavy phase from the light phase. The heavy phase of protein is then isolated by discarding the light phase and the film. Samples purified by this method can be referred to as "Dense layer" samples.

In some embodiments, the recombinant resilin composition is a foam material. In some embodiments, a method of preparing the recombinant resilin foam, comprises: providing a cross-linked recombinant resilin solid composition in an aqueous solvent; exchanging said aqueous solvent with a polar nonaqueous solvent; and introducing one or more bubbles to the cross-linked recombinant resilin solid composition. Any method of introducing bubbles known in the art may be used herein. For instance, methods of introducing bubbles include, but are not limited to, vortexing, mixing, adding yeast, and chemical reactions. In some embodiments, the introducing the one or more bubbles may occur at the same time the cross-linked recombinant resilin solid composition is provided. In some embodiments, the introducing the one or more bubbles may occur after the cross-linked recombinant resilin solid composition is provided.

Blowing agents typically are introduced into polymeric material to make polymer foams. According to one embodiment, a chemical blowing agent is mixed with a polymer. The chemical blowing agent undergoes a chemical reaction in the polymeric material, typically under conditions in which the polymer is molten, causing formation of a gas.

Chemical blowing agents generally are low molecular weight organic compounds that decompose at a particular temperature and release a gas such as nitrogen, carbon dioxide, or carbon monoxide.

Exemplary chemical blowing agents include, but are not limited to, sodium bicarbonate, potassium bicarbonate, ammonium, azodicarbonamide, isocyanate, hydrazine, isopropanol, 5-phenyltetrazole, triazole, 4,4'oxybis(benzenesulfonyl hydrazide) (OBSH), trihydrazine triazine (THT), hydrogen phosphate, tartaric acid, citric acid, and toluenesulphonyl semicarbazide (TSS).

In some embodiments, foaming agents, thickeners, and/or hardeners are added to the recombinant resilin solid. Exemplary foaming agents include, but are not limited to, xanthan gum, sodium dodecyl sulfate, ammonium lauryl sulfate, bovine serum albumin. Exemplary thickeners include, but are not limited to, fumed silica and xanthan gum. Exemplary hardeners include, but are not limited to, aliphatic polyamine, fatty polyamides, aromatic polyamine hardeners, anhydride hardeners, boron trifluoride hardeners, and curing agents (dicyandiamide).

According to another embodiment, a physical blowing agent, i.e., a fluid that is a gas under ambient conditions, is injected into a molten polymeric stream to form a mixture. The mixture is subjected to a pressure drop, causing the blowing agent to expand and form bubbles (cells) in the polymer. In some embodiments, the pressure required is about 500 psi to about 2000 psi, e.g., about 600 psi to about 1000 psi, about 700 psi to about 1500 psi, and about 800 psi to about 2000 psi. In some embodiments, the pressure required is about 500 psi.

Exemplary physical blowing agents include, but are not limited to, chlorofluorocarbon (CFC), dissolved nitrogen, $N_2$, $CH_4$, $H_2$, $CO_2$, Ar, pentane, isopentane, hexane, methylene dichloride, and dichlorotetra-fluoroethane.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Production of Recombinant Resilin

*Pichia pastoris* recombinant host cells that secrete recombinant resilin were generated by transforming a HIS+ derivative of GS115 (NRRL Y15851) *Pichia pastoris* (*Komagataella phaffii*) with vectors comprising secreted resilin coding sequences.

Figure 3:
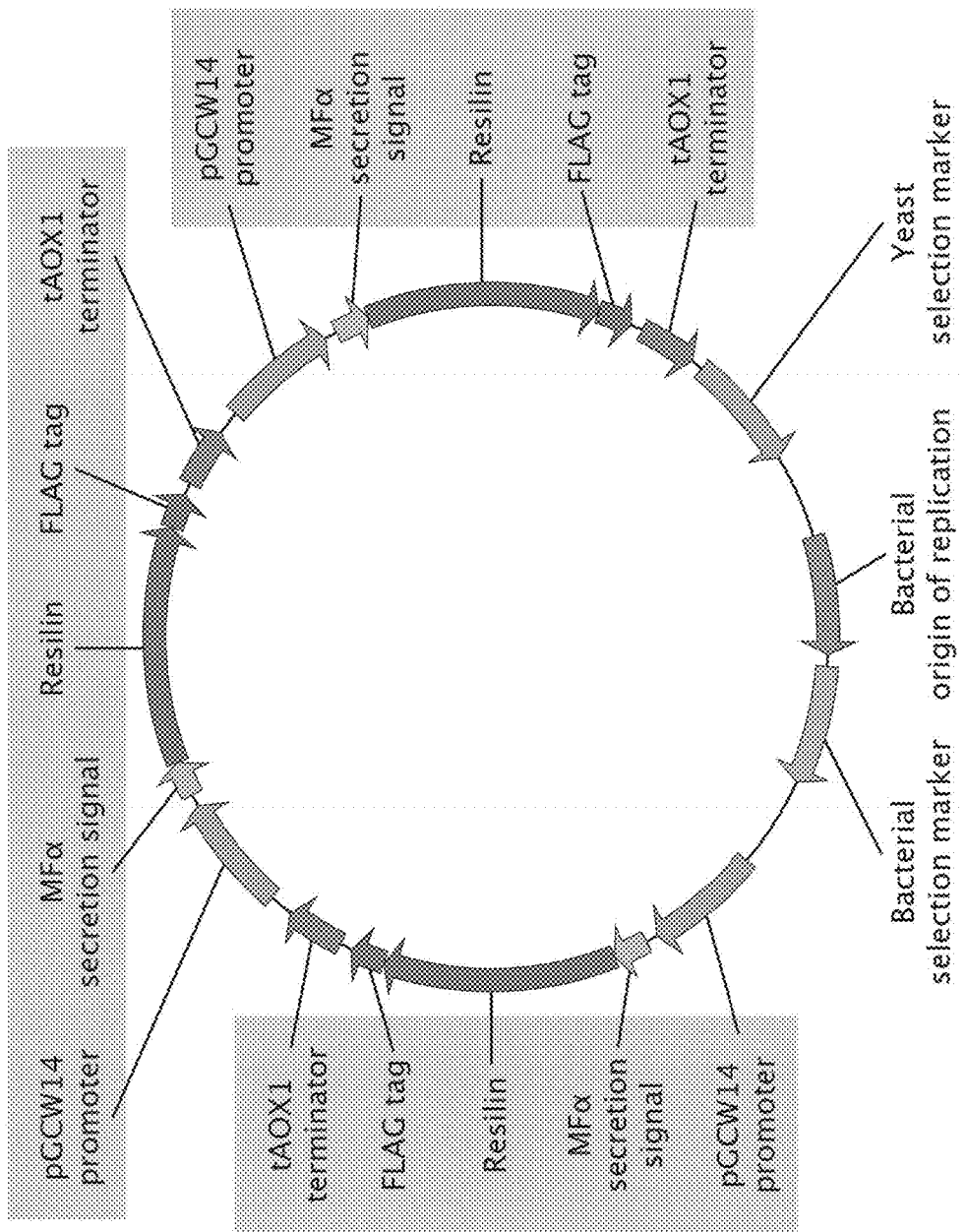
FIG. 3 is an illustrative map of a vector that comprises 3 secreted resilin coding sequences.

The vectors each comprised 3 resilin coding sequences fused in frame to an N-terminal secretion signal (alpha mating factor leader and pro sequence), and in some instances a C-terminal 3×FLAG tag (SEQ ID NO: 45) (see FIG. 3). Each of the secreted resilin coding sequences was flanked by a promoter (pGCW14) and a terminator (tAOX1 pA signal). The vectors further comprised a targeting region that can direct integration of the 3 secreted resilin coding sequences to the HSP82 locus of the *Pichia pastoris* genome, dominant resistance markers for selection of bacterial and yeast transformants, as well as a bacterial origin of replication.

The resilin coding sequences were obtained from scientific literature and from searching public sequence databases. The nucleotide sequences were translated into amino acid sequences and then codon-optimized. Both full length and truncated resilin sequences were chosen. Selected secreted resilin coding sequences are listed in Table 1.

TABLE 1

Exemplary full-length and truncated resilin amino acid sequences and recombinant host strains

| Species | Type | Short Name | Amino Acid SEQ ID NO: | With FLAG tag | | Without FLAG tag | |
|---|---|---|---|---|---|---|---|
| | | | | Plasmid | Strain | Plasmid | Strain |
| *Drosophila sechellia* | Full length | Ds_ACB | 1 | RMp4830 | RMs1209 | RMp4842 | RMs1221 |
| *Drosophila sechellia* | A repeats + Chitin binding domain | Ds_AC | 2 | RMp4831 | RMs1210 | RMp4843 | RMsl222 |
| *Drosophila sechellia* | A repeats only | Ds_A | 3 | RMp4832 | RMs1211 | RMp4844 | RMs1223 |
| *Acromyrmex echinatior* | A repeats only | Ae_A | 4 | RMp4833 | RMS1212 | RMp4845 | RMs1224 |
| *Aeshna* sp. | B repeats only | As_B | 5 | RMp4834 | RMs1213 | RMp4846 | RMs1225 |
| *Aeshna* sp. | Full length | As_ACB | 6 | RMp4835 | RMs1214 | RMp4847 | RMS1226 |
| *Haematobia irritans* | A repeats only | Hi_A | 7 | RMp4836 | RMs1215 | RMp4848 | RMS1227 |
| *Haematobia irritans* | Full length | Hi_ACB | 8 | RMp4837 | RMs1216 | RMp4849 | RMS1228 |
| *Ctenocephalides felis* | A repeats only | Cf_A | 9 | RMp4838 | RMs1217 | RMp4850 | RMs1229 |
| *Ctenocephalides felis* | B repeats only | Cf_B | 10 | RMp4839 | RMs1218 | RMp4851 | RMs1230 |
| *Bombus terrestris* | A repeats only | Bt_A | 11 | RMp4840 | RMs1219 | RMp4852 | RMs1231 |
| *Tribolium castaneum* | A repeats only | Tc_A | 12 | RMp4841 | RMs1220 | RMp4853 | RMs1232 |

The vectors were transformed into *Pichia pastoris* using electroporation to generate host strains comprising 3 integrated copies of each secreted resilin coding sequence. Transformants were plated on YPD agar plates supplemented with an antibiotic, and incubated for 48 hours at 30° C.

Clones from each final transformation were inoculated into 400 µL of Buffered Glycerol-complex Medium (BMGY) in 96-well blocks, and incubated for 24 hours at 30° C. with agitation at 1,000 rpm. A sample was removed, the recombinant host cells were pelleted via centrifugation, and the supernatant was recovered and run on a SDS-PAGE gel for analysis of resilin content via Coomassie gel and Western blot analysis (for polypeptides comprising the 3×FLAG tag). For FLAG-tagged proteins, the remaining cultures were used to inoculate minimal media cultures in duplicate for ELISA measurements. One duplicate was pelleted and the supernatant was measured directly. The second duplicate was extracted with guanidine thiocyanate and both the intra- and extra-cellular fractions were measured.

Recombinant resilin from numerous species expressed successfully in the *Pichia pastoris* recombinant host cells. Recombinant host cells secreted up to 90% of the recombinant resilin produced.

SEQ ID NO: 49 of the sequence listing provides the full-length *Drosophila sechellia* resilin sequence (Ds_ACB) that is expressed along with signal sequences that are later cleaved. The first sequence (italics), is an alpha mating factor precursor protein signal sequence (SEQ ID NO: 46) that is cleaved twice after transcription by a signal peptidase followed by cleavage with Kex2. The second sequence (bold) is an EAEA repeat (SEQ ID NO: 47) that is cleaved by Ste13 (SEQ ID NO: 47). The third sequence (lower case) corresponds to *Drosophila sechellia* full-length resilin (SEQ ID NO 1). The fourth sequence (bold and italicized) corresponds to a linker sequence (SEQ ID NO: 46). The fifth sequence (underlined) corresponds to the 3×FLAG tag (SEQ ID NO: 45).

Edman sequencing confirmed that the N-terminus of the protein sequences at the approximately 110 kDa band corresponded to the full-length length *Drosophila sechellia* resilin sequence. Specifically, the N-terminus sequencing showed that the N-terminus either corresponded to "EAEA" (SEQ ID NO: 47) or "GRPE" (SEQ ID NO: 63), respectively the full-length *Drosophila sechellia* resilin sequence with or without the EAEA repeat (SEQ ID NO: 47).

Example 2: Purification of Recombinant Resilin

Non-FLAG-tagged Ds_ACB and Ae_A recombinant resilin polypeptides were purified as follows: Strains RMs1221 (expressing Ds_ACB) and RMs1224 (expressing Ae_A) were grown in 500 mL of BMGY in flasks for 48 hours at 30° C. with agitation at 300 rpm.

The protocol for purification was adapted from Lyons et al. (2007). Cells were pelleted by centrifugation, and supernatants were collected. Proteins were precipitated by addition of ammonium sulfate. The precipitated proteins were resuspended in a small volume of phosphate buffered saline (PBS), and the resuspended samples were dialyzed against PBS to remove salts. The dialyzed samples were then heated to denature native proteins, and denatured proteins were removed by centrifugation. The retained supernatants contained the purified resilin polypeptides. Optionally, the retained supernatants were chilled, which caused coacervation, resulting in a concentrated lower phase and dilute upper phase.

A second set of samples was prepared by centrifuging a whole cell broth to produce a first pellet of cells and protein proximal to the cells (e.g. adherent to the cells, on the surface of the cells) and/or insoluble protein (e.g. protein aggregates) and first supernatant, then discarding the first supernatant to obtain the first pellet. The first pellet was re-suspended in guanidine thiocyanate to solubilize Ds_ACB. The re-suspension was centrifuged again produce a second pellet and a second supernatant. The second supernatant was then dialyzed against PBS and subject to high temperature in order to denature proteins other than Ds_ACB and centrifuged to produce a third pellet and third supernatant. The third supernatant was subject to coacervation by chilling to yield phase separation into a dense lower layer containing Ds_ACB and an upper layer. This is also referred to herein as gel layer separation, or coacervation samples. In some gel layer samples, multiple coacervations were performed by retaining the lower layer and incubating the lower layer at a lower temperature to induce further phase separation.

TABLE 2

Stability of Cross-linked Resilin

| Sample | 110 kDa band? | Degradation | Time as solid |
|---|---|---|---|
| A | Yes | Substantial | 13 days |
| B | No | Substantial | 8 days |
| C | No | Substantial | 6 days |
| D | No | Substantial | 6 days |
| E | Yes | Minimal | N/A |
| F | Yes | Minimal | 27 days |
| G | No | Substantial | 8 days |
| H | Yes | Minimal | 15 days |
| I | Yes | Substantial | 15 days |
| J | No | Substantial | 6 days |
| K | Yes | Minimal | 13 days |
| L | Yes | Minimal | 13 days |

Example 3: Cross-Linking of Purified, Secreted, Recombinant Resilin

Purified resilin was cross-linked via one of three methods: photo cross-linking (adapted from Elvin et al. 2005), enzymatic cross-linking (adapted from Qin et al. 2009), or the method described herein (i.e., exposure to ammonium persulfate and heat).

Photo Cross-Linking

For photo cross-linking, resilin protein was mixed with ammonium persulfate and tris (bipyridine) ruthenium (II) ([Ru(bpy)3]2+). The mixture was exposed to bright white light, after which the mixture formed a rubbery solid.

Specifically, a 10 mM Ru (II) photocatalyst (CAS 50525-27-4) in water and 100 mM ammonium persulfate in water stock solutions were prepared. Purified resilin powder was dissolved in phosphate buffered saline to a concentration between 20-30 wt % resilin to prepare the resilin stock solution.

2 µL of the 10 mM Ru (II) photocatalyst solution and 2 µL of the 100 mM ammonium persulfate was added to and mixed with 10 µL of resilin stock solution to form the photo cross-linking solution. Bubbles were removed from the photo cross-linking solution by centrifugation, and the photo cross-linking solution was poured into a mold.

The photo cross-linking solution was then exposed to white light (White LED floodlight, Zochlon USPT100W 110V) for 30 seconds to 1 minute.

Enzymatic Cross-Linking

For enzymatic cross-linking, resilin protein was mixed with horseradish peroxidase (HRP) and hydrogen peroxide. The mixture was incubated at 37° C., after which the mixture formed a rubbery solid.

Specifically, a 10 mg/mL stock of horse radish peroxidase (type 1, P8125 Sigma) in water (HRP stock) and a 100 mM $H_2O_2$ stock in water. Purified resilin powder was dissolved in phosphate buffered saline to a concentration between 20-30 wt % resilin to prepare the resilin stock solution.

6 μL of HRP stock was added to and mixed with 21 μL of the resilin stock solution. 3 uL $H_2O_2$ stock was then added and mixed by vortexing to form the enzymatic cross-linking solution. Bubbles were removed from the enzymatic cross-linking solution by centrifugation, and the enzymatic cross-linking solution was poured into a mold while maintaining the solution at 4° C. To perform cross-linking, the enzymatic cross-linking solution was incubated for 15 minutes at 37° C. The resulting cross-linked resilin composition includes an active enzyme covalently bound to the resilin solid.

Persulfate and Heat Cross-Linking

Purified resilin was cross-linked using ammonium persulfate and heat.

Specifically, purified resilin powder was dissolved in phosphate buffered saline to a concentration between 20-30 wt % resilin to prepare the resilin stock solution. 4 μL of n 200 mM ammonium persulfate in water was mixed with 18 μL of the resilin stock solution to a final concentration of 36 mM ammonium persulfate. Bubbles were removed from the persulfate cross-linking solution by centrifugation, and the persulfate cross-linking solution was poured into a mold.

To perform cross-linking, the persulfate cross-linking solution was incubated at 80° C. for 2.5 hours in a sealed humid environment. The resulting cross-linked resilin composition does not leave an active catalyst behind in the resilin solid and results in a composition with a less degraded protein.

Degradation of HRP Cross-Linked Compositions

The stability of the cross-linked samples was assessed over time by determining the duration each cross-linked samples remained a solid through daily observation. Table 3 shows the time as a solid for each cross-linked sample prepared via photo cross-linking (Ru+hv), enzymatic cross-linking (HRP), and cross-linking via ammonium persulfate and heat (AP+heat). As shown in Table 3, at room temperature, the resilin compositions cross-linked via photo cross-linking or via ammonium persulfate had a much longer duration of stability than resilin compositions cross-linked via enzymatic cross-linking.

TABLE 3

Degradation of resilin compositions cross-linked by different cross-linking procedures

| Resilin # | Crosslinking | Washing? | Incubation Temp. (° C.) | Observed Melt Time (days) |
|---|---|---|---|---|
| 1967 I-8 | HRP | N | RT | 8 |
| 1967 I-8 | HRP | N | RT | 8 |
| 1729 I-10 | HRP | N | RT | 8 |
| 1729 I-10 | HRP | N | RT | 10 |
| 1967 I-8 | Ru + hv | N | RT | >92 |
| 1967 I-8 | Ru + hv | N | RT | >92 |

TABLE 3-continued

Degradation of resilin compositions cross-linked by different cross-linking procedures

| Resilin # | Crosslinking | Washing? | Incubation Temp. (° C.) | Observed Melt Time (days) |
|---|---|---|---|---|
| 1729 I-10 | AP + heat | N | RT | >91 |
| 1967 I-8 | AP + heat | N | RT | >91 |

Figure 6:
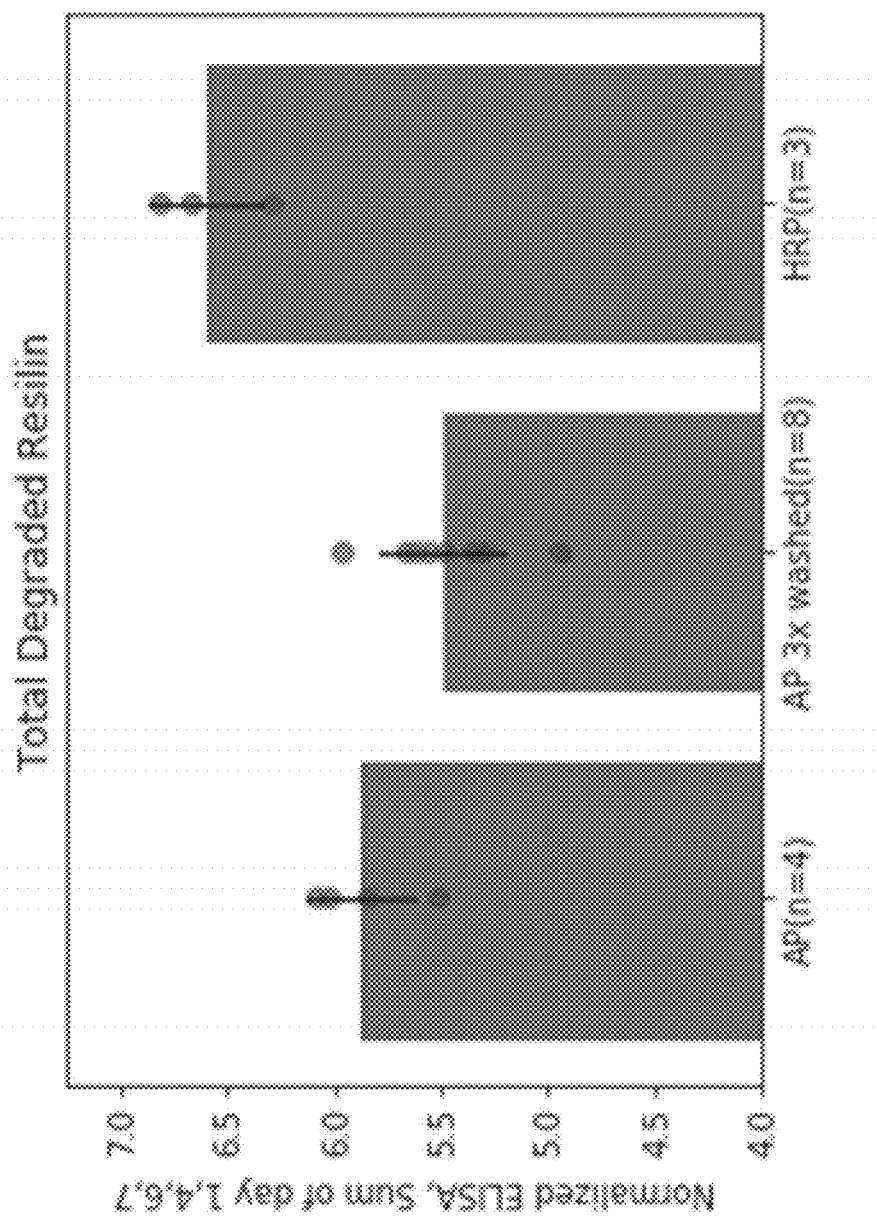
FIG. 6 shows the total degraded resilin as measured by ELISA using an antibody specific for the FLAG tag on resilin from resilin solid compositions cross-linked via ammonium persulfate plus heat (AP); ammonium persulfate plus heat and washed 3 times to remove excess cross-linking solution (AP 3× washed); and enzymatic cross-linking via horseradish peroxidase (HRP).

The total degraded resilin from ammonium persulfate cross-linked resilin compositions (AP) and enzymatically cross-linked resilin compositions (HRP) as measured by ELISA is shown in FIG. 6. Increased degradation and secretion of resilin fragments from cross-linked resilin compositions is observed in the HRP samples as compared to AP samples.

This data shows that ammonium persulfate cross-linking is preferred over enzymatic cross-linking for preparation of stable resilin compositions. For enzymatically cross-linked resilin compositions, the cross-linking enzyme remains in the composition and results in degradation of the composition.

Example 4: Stability of Cross-Linked Full-Length Resilin Vs. Resilin Mixture

Resilin samples generated with varying levels of degradation products and full-length resilin were subject to enzymatic cross-linking as described above. The stability of the cross-linked samples was assessed over time by determining the duration each cross-linked samples remained a solid through daily observation. Table 4 shows the time as a solid for each cross-linked sample. As shown in Table 4, samples comprising full-length resilin had a longer duration of stability than the samples that did not comprise full-length resilin.

TABLE 4

Stability of cross-linked resilin

| Sample | 110 kDa band? | Degradation | Time as solid |
|---|---|---|---|
| A | Yes | Substantial | 13 days |
| B | No | Substantial | 8 days |
| C | No | Substantial | 6 days |
| D | No | Substantial | 6 days |
| E | Yes | Minimal | N/A |
| F | Yes | Minimal | 27 days |
| G | No | Substantial | 8 days |
| H | Yes | Minimal | 15 days |
| I | Yes | Substantial | 15 days |
| J | No | Substantial | 6 days |
| K | Yes | Minimal | 13 days |
| L | Yes | Minimal | 13 days |

Example 5: Resilin Foam

Crosslinking resilin in the presence of a thickening additive, e.g., fumed silica, and sodium bicarbonate resulted in a foamed resilin with a relatively uniform distribution of bubbles. Altering the amount of fumed silica impacted average bubble size, giving us a lever to tune foamed resilin solids. The results are shown in Table 5.

TABLE 5

Data on resilin foam

| Property | |
| --- | --- |
| Diameter of bubbles of resilin foam with 5 wt % fumed silica (mm) | 0.2-2 mm |
| Diameter of bubbles of resilin foam with 10 wt % fumed silica (mm) | 0.05-0.2 mm |
| Amount of sodium bicarbonate (% wt) | 0.2-2% wt |
| Amount of thickener (% wt) | 0-10% wt |

A solution of resilin was prepared. 0.81 g of resilin was dissolved in 2.19 mL PBS at pH of 7.4. A foaming agent was added and the solution was vortexed to introduce bubbles and crosslinked via heat or light. Fifty mg of xantham gum was added to the solution followed by 0.65 mL of 225 mM ammonium persulfate. Xanthum gum was used as the foaming agent because it also increased viscosity which aided in trapping the bubbles in solution. The solution was then vortexed and heated at 80° C. for 3.5 h.

In some samples, ruthenium (II) and white light were used to crosslink the resilin. In such experiments, 0.405 g resilin lot 3 was dissolved in 1.10 mL PBS. Then, 0.3 mL of 100 mM ammonium persulfate and 0.3 mL of 10 mM Ru(II) catalyst. In other samples, 0.405 g resilin lot 3 was dissolved in 1.10 mL PBS. Then, 25 mg of xantham gum was added, followed by 0.3 mL of 100 mM ammonium persulfate and 0.3 mL of 10 mM Ru(II) catalyst.

Figure 7:
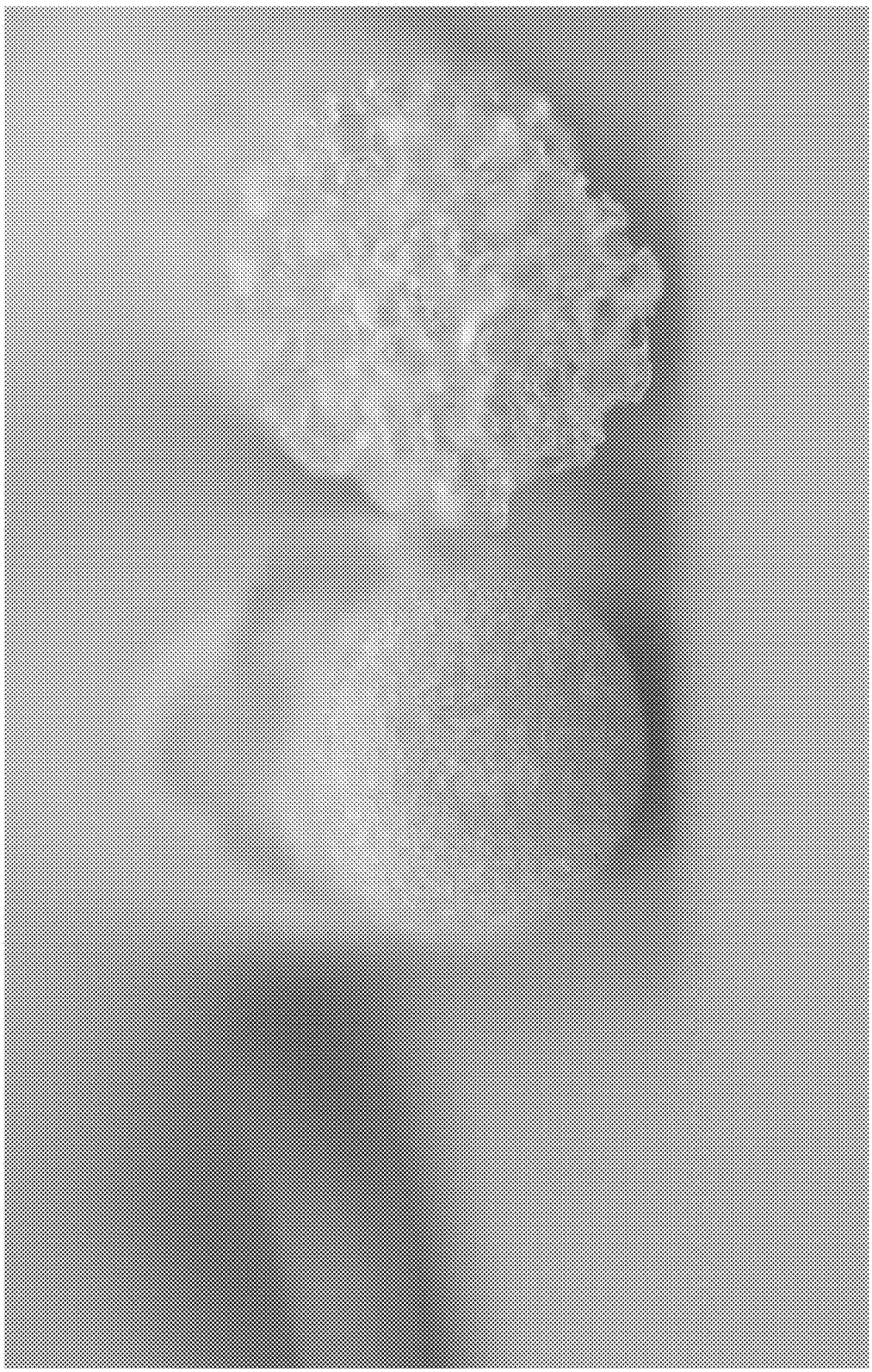
FIG. 7 shows a photograph of resilin foam with 10 wt % fumed silica (left) and 5 wt % fumed silica (right).
Figure 8:
FIG. 8 shows a photograph of resilin foam with 5 wt % fumed silica. A quarter dollar is included for comparison.

In some samples, sodium bicarbonate was used as a chemical blowing agent. Sodium bicarbonate was added to the resilin solution and crosslinked. A thickener, fumed silica, was added in some samples. Too much sodium bicarbonate (33 mg/mL or more) inhibited gelation. Using between 6-20 mg/mL of sodium bicarbonate to resilin solution resulted in resilin solids after 3.5 hours at 80° C. with large bubbles. Adding a thickener, fumed silica, to between 4-10 wt %, resulted in a resilin foam with an even distribution of bubbles (FIGS. 7 and 8). Too little fumed silica resulted in a half-foamed resilin solid and adding more than 5 wt % fumed silica resulted in a foamed resilin with smaller bubbles (FIG. 7). The diameter of bubbles of resilin foam with 5 wt % fumed silica was 0.2 to 2 mm. The diameter of bubbles of resilin foam with 10 wt % fumed silica was 0.05 to 0.2 mm.

Specifically, 0.27 g of resilin lot 3 was dissolved in 0.73 mL PBS at pH of 7.4. Then, 37, 18, 10 or 6 mg of sodium bicarbonate was added to the solution followed by 0.22 mL of 225 mM ammonium persulfate and between 0-10 wt % fumed silica. The solution was vortexed and heated at 80° C. for 3.5 h. Experiments were performed in a capped 2 mL tube.

In some samples, an ISCO pump was used to introduce dissolved nitrogen at either 1600 psi or 500 psi while crosslinking the resilin at 83° C. Crosslinking at these pressures proceeded at a slower rate than crosslinking at atmospheric pressure, likely due to the increased amounts of dissolved oxygen.

Specifically, 1.1 mL solution of 225 or 550 mM ammonium persulfate in water was added to a 5 mL solution of 27 wt % resilin in PBS. This solution was then centrifuged for 5 min at 7197 rcf and added to the ISCO pump. The pump was then hooked up to house nitrogen and the ISCO pump was set to its maximum volume of 266 mL, purged with nitrogen for a 3 minutes and then sealed. Then, the pump was either set to 500 psi or 1600 psi and heated for between 2-6 h at 83° C. After releasing the pressure, the resilin was heated for an additional 1-2 hours at 83° C.

Example 6: Solvent Exchange and Comparison of Cross-Linked Resilin in Aqueous Solvent Vs. Polar Nonaqueous Solvent As described in detail below, a cross-linked mixture of recombinant resilin in an aqueous solvent was treated with a solvent exchange to replace the solvent with a polar nonaqueous solvent to form a composition with material properties better suited for certain applications.

A resilin powder comprising 19 mass % full-length resilin as measured via SEC (size exclusion chromatography), with the rest of the powder comprising partially degraded resilin, was prepared.

The resilin powder was then dissolved in 1× phosphate buffered saline (PBS), the reported weight percent of resilin is weight by weight (w/w). A 1 g solution of 27 wt % resilin is prepared by adding 0.27 g of resilin to 0.73 g of PBS solution. The resilin solution was then cross-linked in a mold to form a water-based resilin solid composition. The resilin solid formed was a 15 mm diameter×5 mm height disc.

To generate a glycerol-based resilin solid, the water-based solid is exchanged in 20× its volume of 60% glycerol (60:40 glycerol:water (v:v)) at 60 deg C. in a closed container for 16 h. Then, the solid is exchanged in 20× its volume of glycerol at 60 deg C. in an unsealed container for 16 h.

Figure 9:
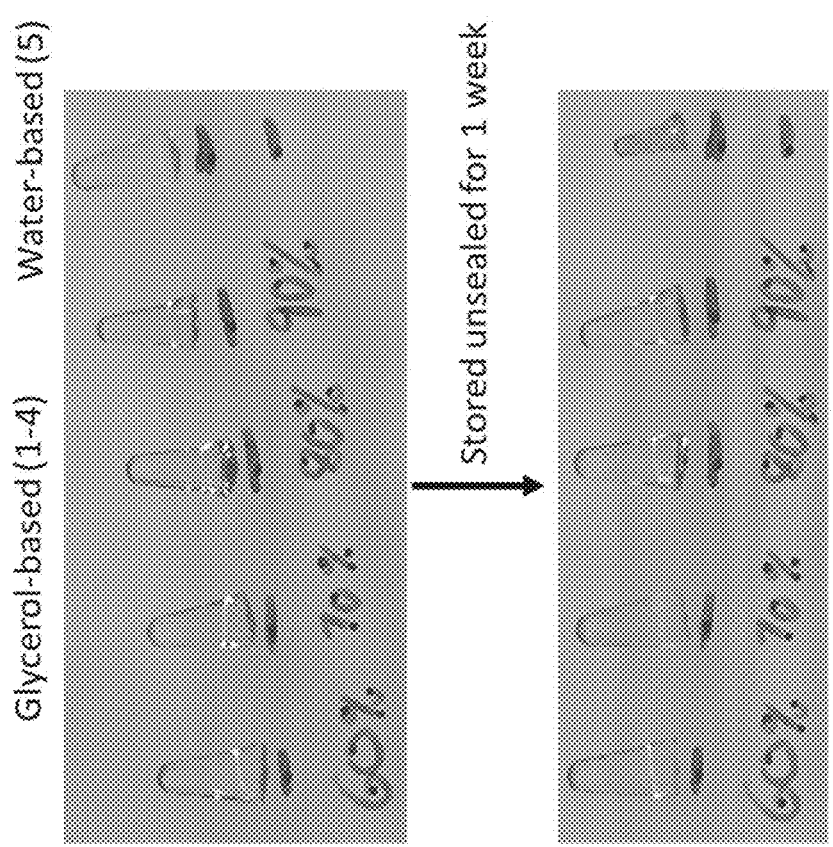
FIG. 9 shows an image of glycerol-based and water-based cross-linked resilin compositions after cross-linking (top) and after 7 days of unsealed storage for one week (bottom).

Samples of water-based and glycerol-based resilin solids were stored unsealed for 1 week at room temperature. As shown in FIG. 9, water-based resilin solids dehydrated after only 1 week, while glycerol-based resilin solids retained their original shape without any visible degradation or dehydration.

Example 7: Solvent Exchange and Comparison of Properties of Multiple Polar Nonaqueous Resilin Solvents Resilin solids in polar nonaqueous solvents were prepared from cross-linked resilin in 1× phosphate buffered saline (PBS) as follows:

Resilin solid in propylene glycol solvent was prepared by exchanging the resilin solid in 20× its volume of propylene glycol at 60 deg C. in an unsealed container for 16 h or for 2 days (i.e., 2 d. inc.).

Resilin solid in 60-100% glycerol solvent was prepared by exchanging the resilin solid in 20× its volume of 60% glycerol (60:40 glycerol:water (v:v)) at 60 deg C. in a closed container for 16 h. Then, the solid is exchanged in 20× its volume of glycerol at 60 deg C. in an unsealed container for 16 h.

Resilin solid in 100% glycerol solvent was prepared by exchanging the resilin solid in 20× its volume of glycerol at 60 deg C. in an unsealed container for 16 h or for 2 days (i.e., 2 d. inc.).

Resilin solid in ethylene glycol solvent was prepared by exchanging the resilin solid in 20× its volume of ethylene glycol at 60 deg C. in an unsealed container for 16 h.

Resilin solid in propylene glycol solvent was prepared by exchanging the resilin solid in 20× its volume of propylene glycol at 60 deg C. in an unsealed container for 16 h.

To form a resilin solid based on a purification via coacervation, a 27 wt % (w/w) resilin solution was incubated at −5 deg C. and a liquid-liquid phase separation occurred. The bottom coacervate layer was isolated and ammonium persulfate (APS) powder was mixed into the coacervate to a final concentration of 36 mM APS. This solution was then crosslinked at 80 deg C. for 2.5 h. The solid was then exchanged following the typical solvent exchange procedure.

Unless otherwise stated, the resilin powder used is 19 mass % full-length as measured via size-exclusion chromatography (SEC) and the rest of the powder is composed of partially degraded resilin. The 27 wt % "full-length resilin" sample was prepared from resilin powder that is 87 mass % full-length monomeric resilin as measured via SEC.

To characterize the relative amount of the predominant species of resilin in a resilin composition using SEC, resilin powder was dissolved in 5M Guanidine Thiocyanate and injected onto a Yarra SEC-3000 SEC-HPLC column to separate constituents on the basis of molecular weight. Refractive index was used as the detection modality. BSA was used as a general protein standard with the assumption that >90% of all proteins demonstrate do/dc values (the response factor of refractive index) within ~7% of each other. Poly(ethylene oxide) was used as a retention time standard, and a BSA calibrator was used as a check standard to ensure consistent performance of the method. A range corresponding to resilin was assessed from 60-40 kDa; higher peaks observed which may correspond to aggregate or polymerized resilin were not included in this quantification. The relative percentage of this resilin peak was reported as mass % and area % to determine the amount of full length resilin in a composition as a portion of total resilin.

A Malvern Kinexus Rheometer RNX2110 was then used to generate stress strain curves for each of the compositions produced as described above. The following protocol was applied at a temperature of 22 deg C.: Step 1: Initial Gap—6.5 mm; Step 2: Descent to final Gap. Steps 1 and 2 were repeated 5×. Values of elastic modulus as measured by the rheometer are relative only, and cannot be compared to materials tested under different conditions or with different instruments.

Stress-strain curves were generated plotting engineering stress vs. engineering strain. Engineering stress is calculated by the following formula: Engineering stress=(Normal Force (N)/A (mm$^2$) of resilin solid in contact with rheometer geometry)×10$^6$. Engineering strain is the absolute value of compressive strain=ABS((current compressed height of resilin solid (mm)−height of uncompressed solid (mm))/ht. of uncompressed solid (mm))*100.

Figure 10A:
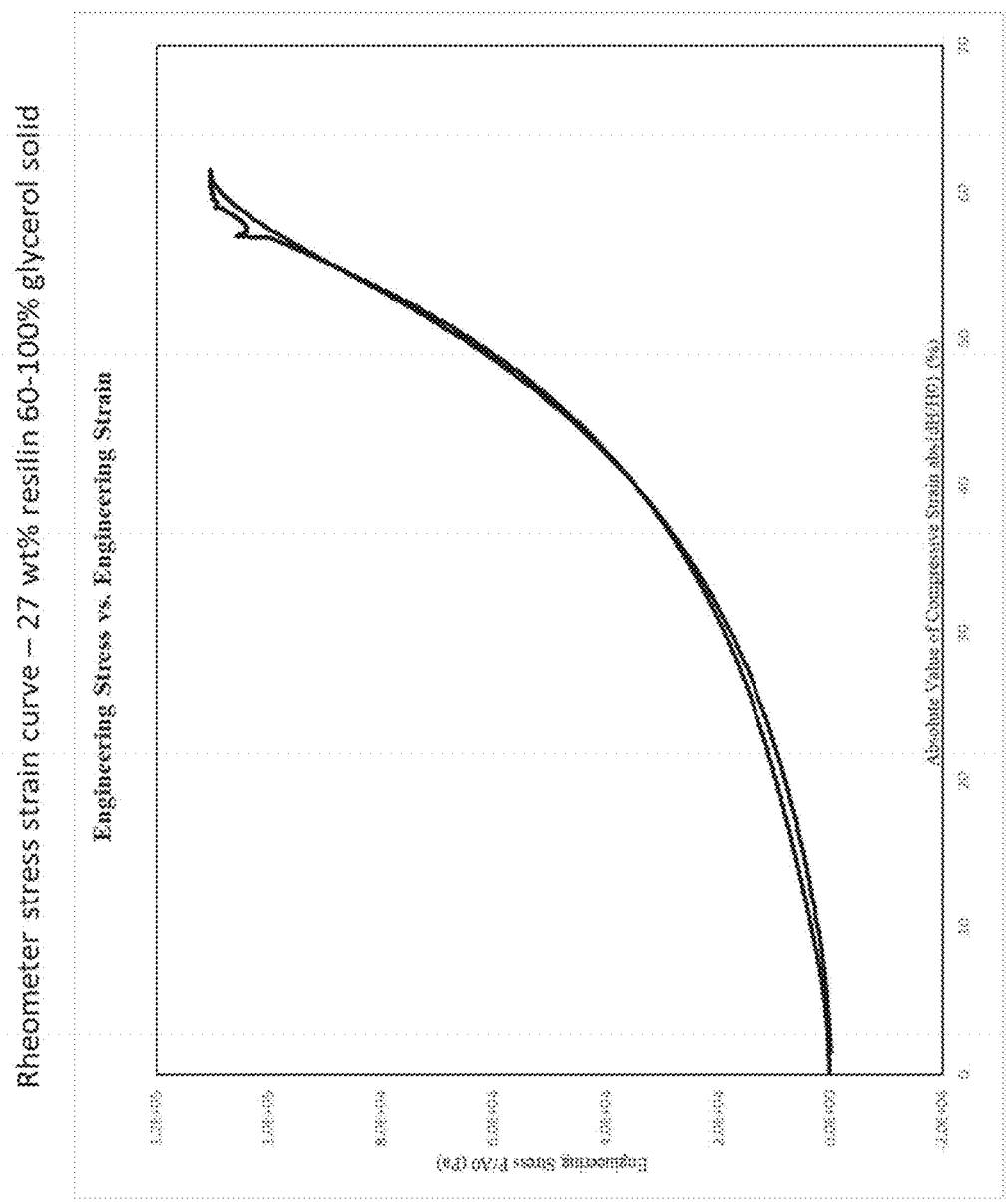
FIGS. 10A, 10B, and 10C depict stress strain curves as measured by a rheometer for the following cross-linked resilin compositions: 27% by weight resilin in a glycerol solvent prepared by a 60% glycerol solvent exchange followed by a 100% glycerol solvent exchange (FIG. 10A); 27% by weight resilin in a propylene glycol solvent (FIG. 10B); and 27% full length resilin (i.e., about 80% full length resilin as a proportion of all resilin) in a propylene glycol solvent (FIG. 10C).
Figure 10B:
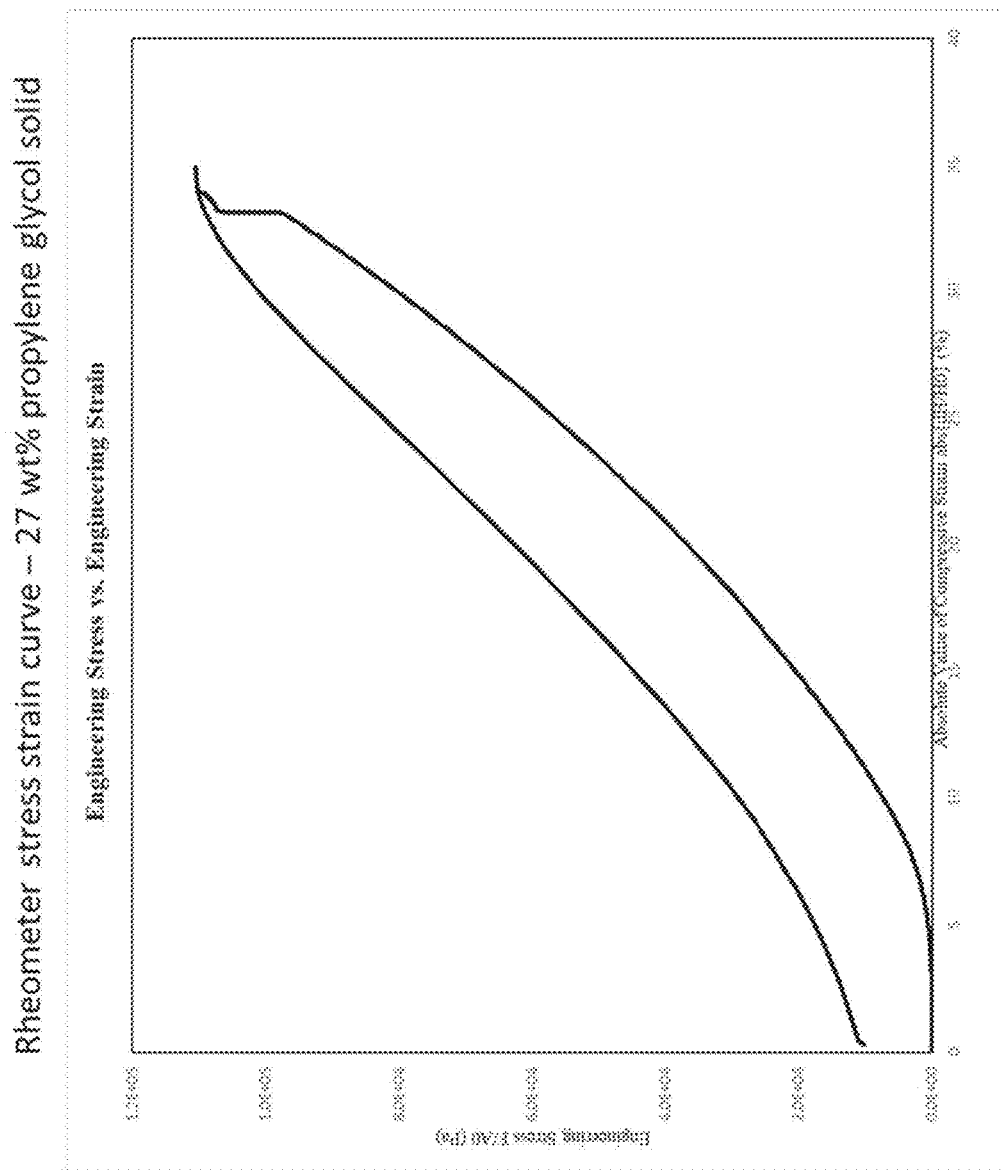
Figure 10C:
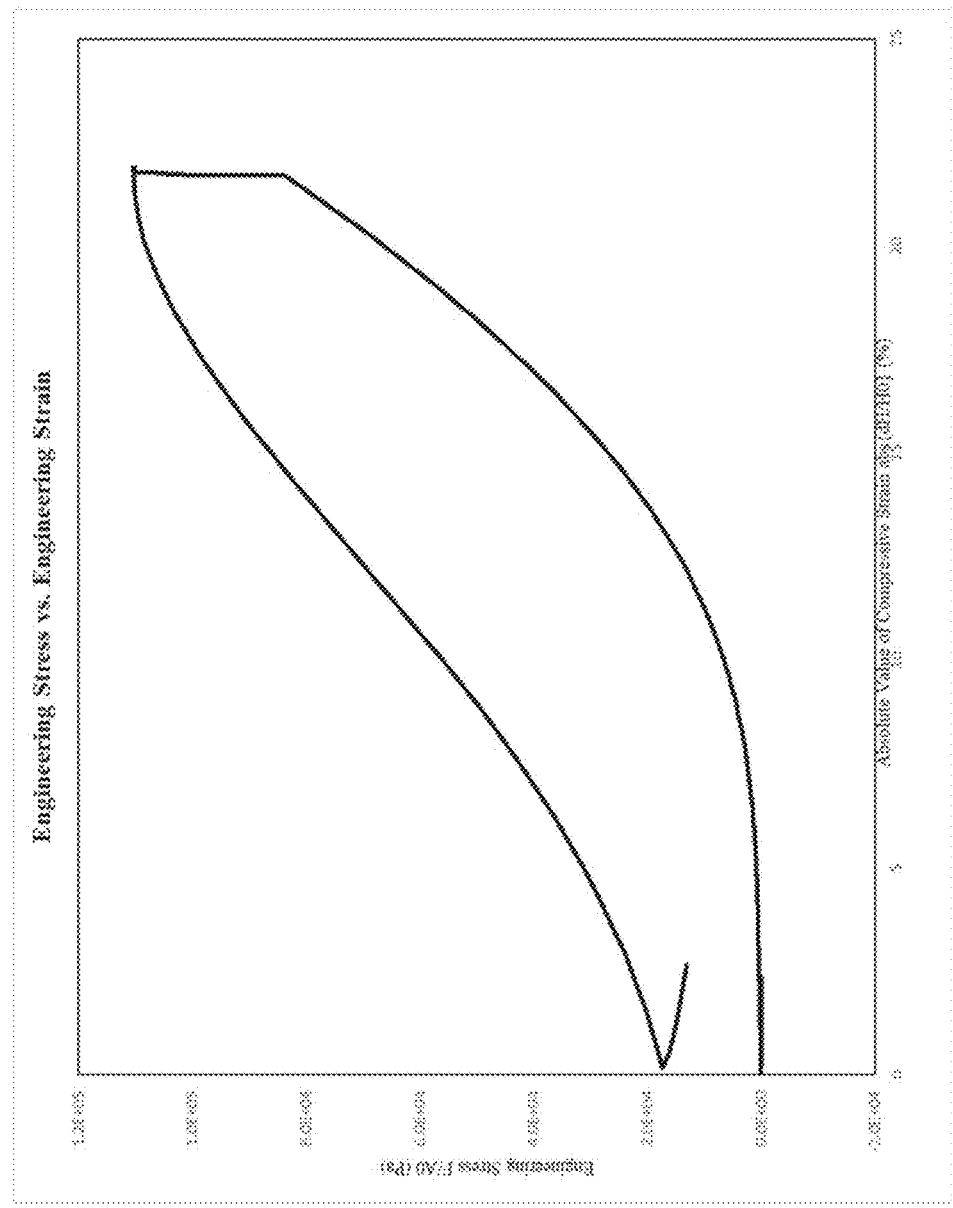

FIG. 10A shows a stress-strain curve for 27 wt % cross-linked resilin in 60-100% glycerol. FIG. 10B shows a stress-strain curve for 27 wt % cross-linked resilin in propylene glycol. FIG. 10C shows a stress-strain curve for 27 wt % full length cross-linked resilin in propylene glycol. For comparative purposes, rheometry data was also generated from Dr. Sholl's insert.

Figure 11:
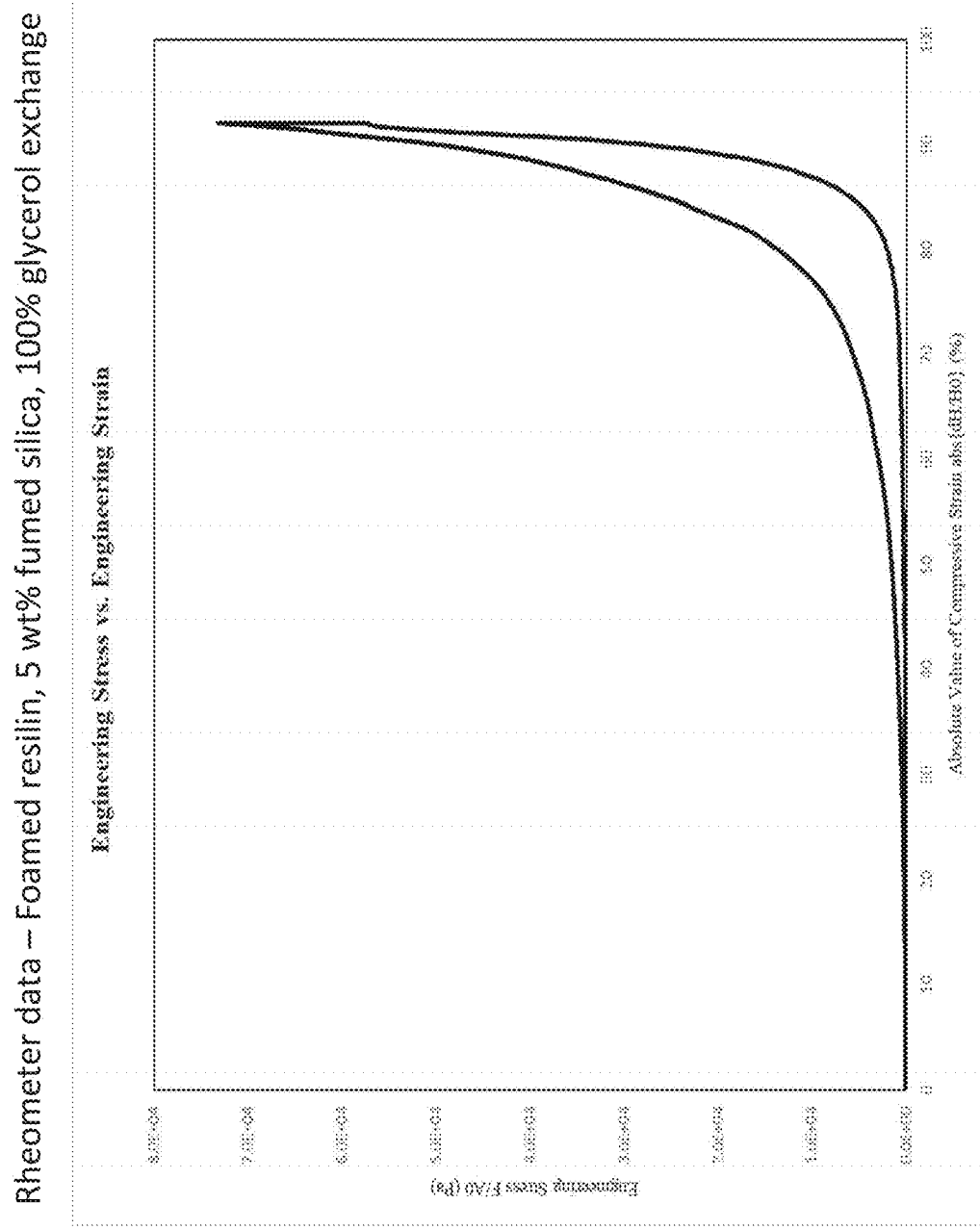
FIG. 11 shows a stress-strain curve of resilin foam with 5 wt % fumed silica.

As shown in FIG. 11, the stress-strain curve of foamed resilin was shaped more like a hockey stick. This is a result of the air pockets in the foamed resilin, which are compressed first, followed by compression of the resilin material.

From the rheometry data, relative values of elastic modulus and resilience were determined as shown in Table 5. Relative Resilience (%) was calculated by taking the area under the load curve and dividing it by the area under the unload curve on the engineering stress vs strain plot and multiplying this value by 100. Relative Elastic modulus was calculated by taking the slope of the load curve from between 10 and 20% absolute compressive strain.

As shown, the exchange of cross-linked resilin solvent from an aqueous water-based solvent to a polar nonaqueous solvent resulted in a stiffer material with a similar resilience and a similar elasticity. All cross-linked resilin compositions were elastic under the conditions tested (<20 N Force).

A rheometer was also used to measure resilience for a 5% by weight foamed resilin produced as described in Example 5 with a fumed silica as the blower in 100% glycerol solvent. The results are also shown in Table 6.

TABLE 6

Relative values of elastic modulus and resilience for cross-linked resilin in different solvents

| Solid Sample Description | Sample ID | Resilience (%) | Elastic Modulus (kPa) |
|---|---|---|---|
| Dr Scholl's insert, 20 mm diameter | | 92 | 1.3 |
| 20 wt % resilin, propylene glycol | A | 59 | 4.9 |
| 27 wt % resilin, propylene glycol | B | 64 | 3.9 |
| 40 wt % resilin, propylene glycol | C | 59 | 6.6 |
| Resilin Coacervate, propylene glycol | D | 48 | 6.8 |
| 27 wt % full-length resilin, propylene glycol | E | 34 | 8.5 |
| 27 wt % resilin, 60-100% glycerol | F | 94 | 0.9 |
| 27 wt % resilin, 100% glycerol | H | 70 | 3.8 |
| 27 wt % resilin, ethylene glycol | I | 90 | 2.2 |
| 27 wt % resilin, water-based solid | J | 86 | 1 |
| 5 wt % foamed resilin (fumed silica), 100% glycerol | | 35 | |

Figure 12:
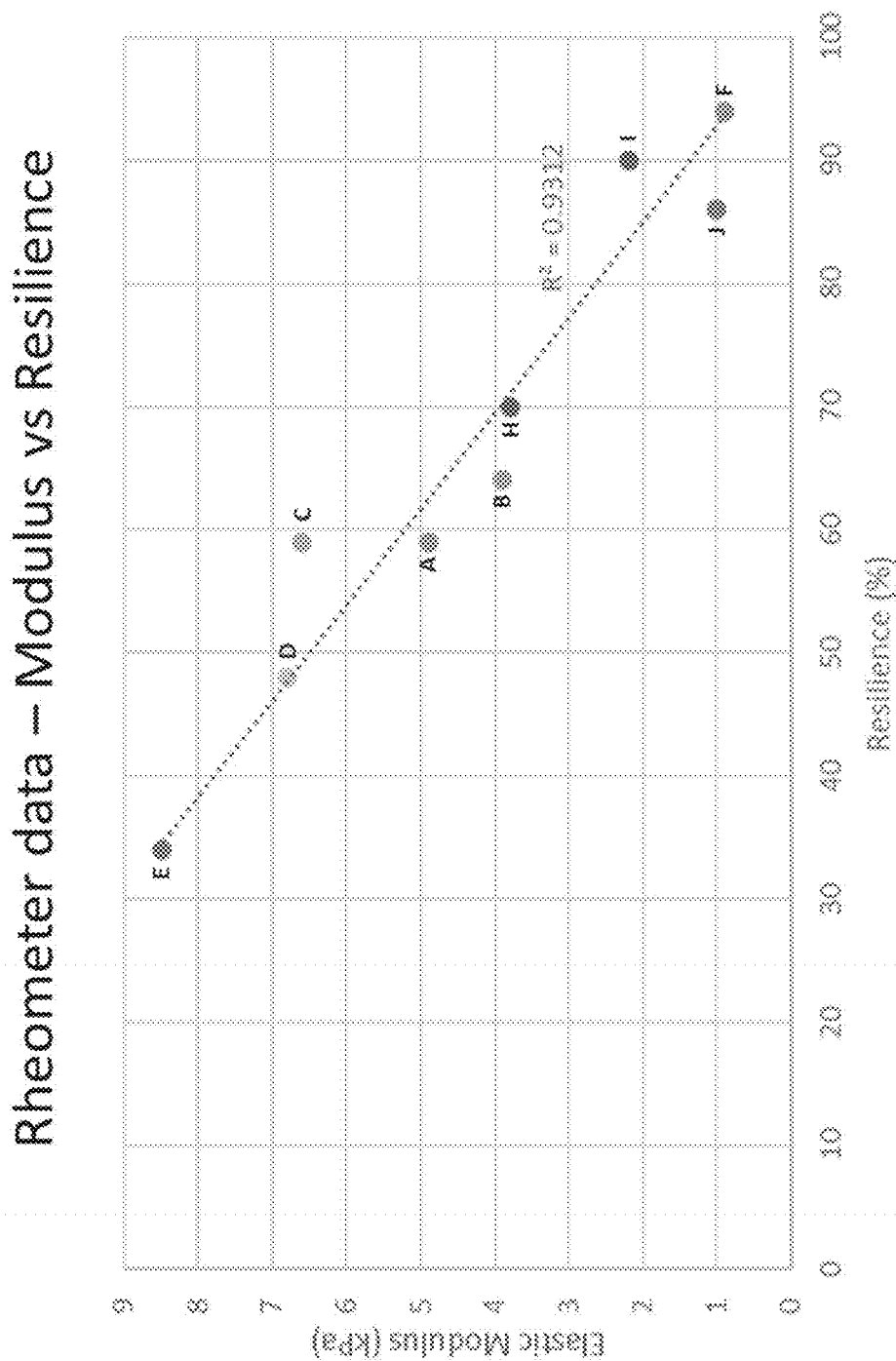
FIG. 12 shows a plot of the relative values of resilience and elastic modulus as measured by a rheometer for each of the following cross-linked resilin solid compositions: 20 wt % resilin, propylene glycol ("A"); 27 wt % resilin, propylene glycol ("B"); 40 wt % resilin, propylene glycol ("C"); resilin coacervate, propylene glycol ("D"); 27 wt % full-length resilin, propylene glycol ("E"); 27 wt % resilin, 60-100% glycerol ("F"); 27 wt % resilin, 100% glycerol ("H"); and 27 wt % resilin, ethylene glycol("I").

The relative values of resilience and elastic modulus from Table 6 were plotted as shown in FIG. 12. This plot shows the relationship between resilience and elastic modulus when tuning the cross-linked resilin properties via solvent exchange.

A rheometer was also used to measure relative resilience and elastic modulus for cross-linked resilin solids in propylene glycol prepared separately. The results are shown in Table 7.

TABLE 7

Rheometer data for identically prepared propylene glycol solids

| Solid Sample Description | Resilience (%) | Elastic Modulus (KPa) |
|---|---|---|
| 27 wt % resilin, propylene glycol, solid 1 | 64 | 3.9 |
| 27 wt % resilin, propylene glycol, solid 2 | 59 | 5.8 |
| 27 wt % resilin, propylene glycol, solid 3 | 63 | 4.3 |

A rheometer was also used to measure relative resilience and elastic modulus for cross-linked resilin solids in different solvents through repeated applications of force to determine the effects of the repeated applications of force on these parameters. The results are shown in Table 8.

TABLE 8

Rheometer data: Resilience and modulus data from multiple compressions

| Solid Sample Description | Resilience (%) | Elastic Modulus (KPa) |
|---|---|---|
| Dr. Scholl's insesrt, 20 mm diameter, 1$^{st}$ compression | 92 | 1.3 |

TABLE 8-continued

Rheometer data: Resilience and modulus data from multiple compressions

| Solid Sample Description | Resilience (%) | Elastic Modulus (KPa) |
|---|---|---|
| Dr. Scholl's insesrt, 20 mm diameter, $2^{nd}$ compression | 92 | 1.3 |
| Dr. Scholl's insesrt, 20 mm diameter, $3^{rd}$ compression | 95 | 1.3 |
| 27 wt % resilin, 60-100% glycerol, $1^{st}$ compression | 94 | 0.9 |
| 27 wt % resilin, 60-100% glycerol, $2^{nd}$ compression | 88 | 0.9 |
| 27 wt % resilin, 60-100% glycerol, $3^{rd}$ compression | 100 | 0.7 |
| 27 wt % resilin, propylene glycol, $1^{st}$ compression | 64 | 3.9 |
| 27 wt % resilin, propylene glycol, $2^{nd}$ compression | 64 | 3.8 |
| 27 wt % resilin, propylene glycol, $3^{rd}$ compression | 65 | 3.1 |
| 27 wt % resilin, propylene glycol, $4^{th}$ compression | 63 | 3.8 |
| 27 wt % resilin, propylene glycol, $5^{th}$ compression | 61 | 3.9 |
| 27 wt % full length resilin, propylene glycol, $1^{st}$ compression | 34 | 8.5 |
| 27 wt % full length resilin, propylene glycol, $2^{nd}$ compression | 39 | 7.7 |
| 27 wt % full length resilin, propylene glycol, $3^{rd}$ compression | 37 | 7.7 |

Example 8: Stiffness of Resilin Solids Vs. A Typical Midsole

Cross-linked silk solid compositions were prepared in water, 60-100% glycerol, 100% glycerol, propylene glycol (16 hour incubation), and propylene glycol (2 day incubation as described in Example 6. The stiffness of these materials was tested using a Shore 00 Durometer (AD-100-00) via ASTM: D-2240. A Dr. Scholl's Insole and a typical midsole were also tested for comparative purposes. The results are shown in Table 9.

TABLE 9

Stiffness of different resilin compositions vs. atypical midsole

| Solid Sample Description | Hardness | Scale |
|---|---|---|
| Dr. Scholl's Insole | 35-45 | OO |
| Typical midsole | 55-63 | OO |
| Resilin - water-based | 0-4 | OO |
| Resilin - 60% to 100% glycerol | 10-16 | OO |
| Resilin - 100% glycerol | 25-35 | OO |
| Resilin - 100% propylene glycol | 30-40 | OO |
| Resilin - 100% propylene glycol - 2 d inc. | 50 | OO |
| Resilin foam, 5% wt fumed silica - 60% to 100% glycerol | 10-30 | OO |

Example 9: Elastic to Plastic Transition Measured by Zwick Compression Curves Zwick compression data was obtained for 27 wt % resilin ethylene glycol solid ("A"), 27 wt % resilin propylene glycol solid ("C"), coacervate resilin propylene glycol solid ("D"), 27 wt % resilin 60-100% glycerol solid ("G"), and 27 wt % resilin 100% glycerol solid ("H"). Each of these samples were prepared as described in Example 5.

Specifically, compression data for the above samples were tested using Zwick tensile tester with 5 kN load cell and 5 kN compression platens (Zwick/Roell Z5.0). Solid dimensions for each solid was a disc of 15 mm×5 mm. The materials were tested using a D695 Compressive Properties of Rigid Plastics compression program at a temperature of 22 C (ambient) and a humidity of 65% (ambient).

Figure 13:
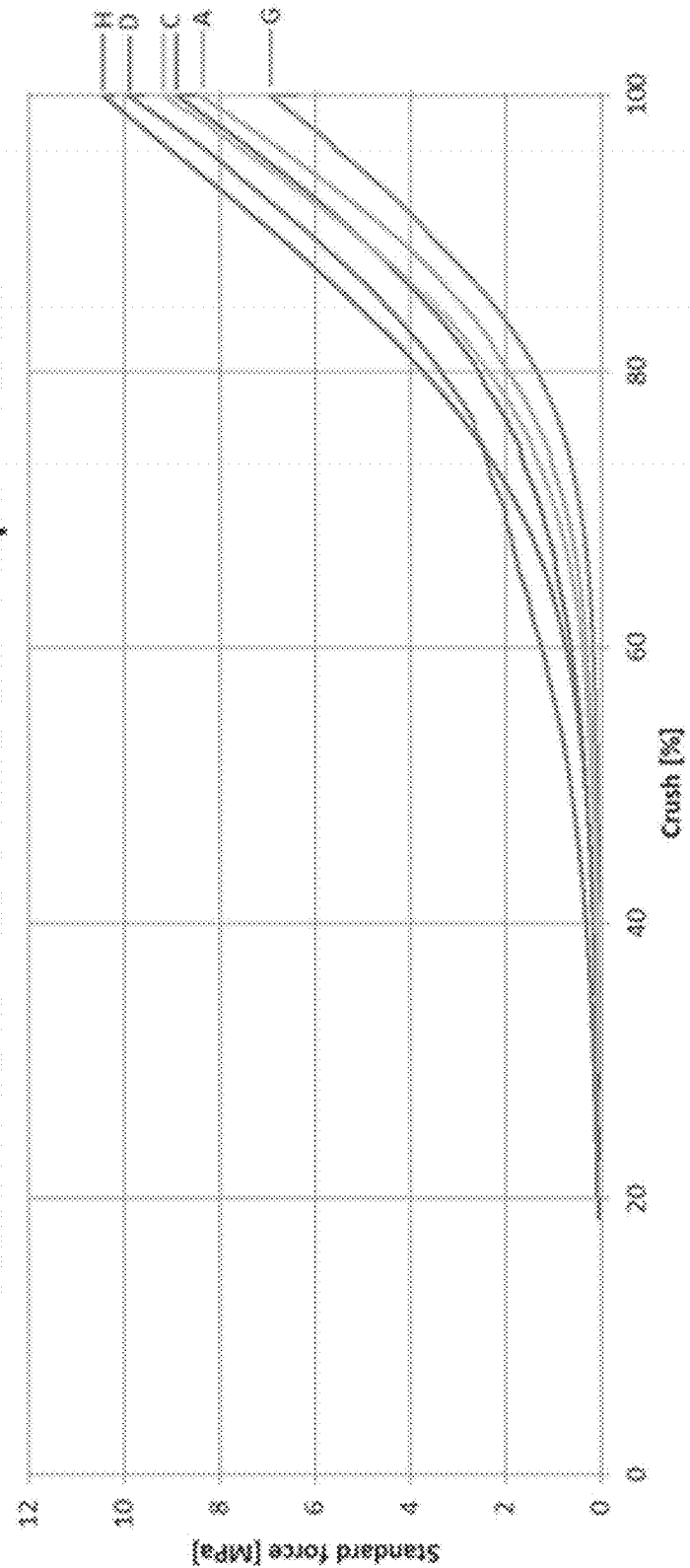
FIG. 13 shows a plot of applied force vs. strain curves as measured from the Zwick tensile tester for each of the following cross-linked resilin solids: 27 wt % resilin ethylene glycol solid ("A"), 27 wt % resilin propylene glycol solid ("C), coacervate resilin propylene glycol solid ("D"), 27 wt % resilin 60-100% glycerol solid ("G"), and 27 wt % resilin 100% glycerol solid ("$_H$").

Force vs. strain curves as measured from the Zwick tensile tester for each solid are shown in FIG. 13. No elastic to plastic transition is visible for any of the resilin solids at up to 2 kN of applied compressive force. Instead, when the resilin solids broke under compressive stress it was via tearing and not elastic deformation.

Example 10: Analysis of Resilience and Compression of Propylene Glycol Resilin Solids Rebound resilience and compressive stress at 25% strain was measured using a ASTM D7121 and ASTM D575 test for 27 wt % resilin solid exchanged into propylene glycol, prepared as in Example 5. The dimensions of the solid tested were a 1.125 inch diameter disc with a height of 0.8 inches. 3 different samples with these dimensions were submitted. The results are shown in Table 10.

TABLE 10

Data on resilience and compression of propylene glycol resilin solids

| Spec Ref | Test | Unit | A | B | C |
|---|---|---|---|---|---|
| ASTM D7121 | Rebound resilience | % | 46.2 | 39.2 | 52.3 |
| ASTM D575 | Compressive stress at 25% strain | psi | 6.7 | 8.1 | 6.2 |

The data shown in Table 10 can be compared to other rubbers or elastomers tested via the same ASTM test. The ASTM test number is sufficient to reproduce the results. This data and the durometer data are the only data that can be directly compared to other rubbers of elastomers.

ADDITIONAL CONSIDERATIONS

The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the invention, which is set forth in the claims.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

| SEQUENCE LISTING | | |
|---|---|---|
| SEQ ID NO: | Species | Sequence |
| 1 | Drosophila sechellia | RPEPPVNSYLPPSDSYGAPGQSGAGGRPSDTYGAPGGGNGGRPSDSYGAPG QGQGQGQGQGGYGGKPSDSYGAPGGGNGNGGRPSSSYGAPGGGNGGRPSDT YGAPGGGNGGRPSDTYGAPGGGNGNGGRPSSSYGAPGQGQGNGNGGRPSS SYGAPGGGNGGRPSDTYGAPGGGNGGRPSDTYGAPGGGNNGGRPSSSYGAP GGGNGGRPSDTYGAPGGGNGNGSGGRPSSSYGAPAQGQGQGGFGGRPSDSYGA PGQNQKPSDSYGAPGSGNGSAGRPSSSYGAPGSGPGGRPSDSYGPPASGSG AGGAGGSGPGGADYDNDEPAKYEFNYQVEDAPSGLSFGHSEMRDGDFTTGQ YNVLLPDGRKQIVEYEADQQGYRPQIRYEGDANDGSGPSGPSGPGGPGGQN LGADGYSSGRPGNGNGNGGYSSGRPGGQDLGPSGYSSGRPGGQDLGAGG YSNVKPGGQDLGPGGYSSGRPGGQDLGRDGYSSGRPGGQDLGAGAYSNGRP GGNGNGGSDGGRVIIGGRVIGGQDGGDQGYSSGRPGGQDLGRDGYSSGRPG GRPGGNGQDSQDGQGYSSGRPGQGGRNGFGPGGQNGDNDGSGYRY |
| 2 | Drosophila sechellia | RPEPPVNSYLPPSDSYGAPGQSGAGGRPSDTYGAPGGGNGGRPSDSYGAPG QGQGQGQGQGGYGGKPSDSYGAPGGGNGNGGRPSSSYGAPGGGNGGRPSDT YGAPGGGNGGRPSDTYGAPGGGNGNGGRPSSSYGAPGQGQGNGNGGRPSS SYGAPGGGNGGRPSDTYGAPGGGNGGRPSDTYGAPGGGNNGGRPSSSYGAP GGGNGGRPSDTYGAPGGGNGNGSGGRPSSSYGAPAQGQGQGGFGGRPSDSYGA PGQNQKPSDSYGAPGSGNGSAGRPSSSYGAPGSGPGGRPSDSYGPPASG |
| 3 | Drosophila sechellia | GKPSDSYGAPGGGNGNGGRPSSSYGAPGGGNGGRPSDTYGAPGGGNGGRPS DTYGAPGGGNGNGGRPSSSYGAPGQGQGNGNGGRPSSSYGAPGGGNGGRP SDTYGAPGGGNGGRPSDTYGAPGGGNNGGRPSSSYGAPGGGNGGRPSDTYG APGGGNGNGSGGRPSSSYGAPAQGQGGFGGRPSDSYGAPGQNQKPSDSYGA PGSGNGS |
| 4 | Acromyrmex echinatior | FGENRGNGGKPSTSYGVPDSNGNNRGGFGNGGSEGRPSTSYGLPDASRNNG NGFGNVGNEDKPSTNYGIPANGNKVSGFGNVGSEGRPSTSYGVPGANGNQG FGSGGIGGRPSTSYGVPGVNGNNGGGFENVGRPSTSYGTPDARGNNGGSFR NGDIGGRPSTNYGIPGANGNHG |
| 5 | Aeshna | APSRGGGHGGGSISSSYGAPSKGSGGFGGGSISSSYGAPSKGSVGGGVSSS YGAPAIGGGSFGGGSFGGGSFGGGSFGGGAPSSSYGAPSSSYSAPSSSYGA PSKGSGGFGSSGGFSSFSSAPSSSYGAPSASYSTPSSSYGAPSSGGFGAGG GFSSG |
| 6 | Aeshna | EPPVGGSQSYLPSSSYGAPSAGTGFGHGGGSPSQSYGAPSFGGGSVGGGS HFGGGSHSGGGGGGYPSQSYGAPSRPSGSSFQAFGGAPSSSYGAPSSQYGA PSGGGGSYAIQGGSFSSGGSRAPSQAYGAPSNNAGLSHQSQSFGGGLSSSY GAPSAGFGGQSHGGGYSQGGNGGGHGGSSGGGYSYQSFGGGNGGGHGGSRP SSSYGAPSSSYGAPSGGKGVSGGFVSQPSGSYGAPSQSYGAPSRGGGHGGG SISSSYGAPSKGSGGFGGGSISSSYGAPSKGSVGGGVSSSYGAPAIGGGSF GGGSFGGGSFGGGSFGGGAPSSSYGAPSSSYSAPSSSYGAPSKGSGGFGSS GGFSSFSSAPSSSYGAPSASYSTPSSSYGAPSSGGFGAGGGFSSGGYSGGG GGYSSGGSGGFGGHGGSGGAGGYSGGGGYSGGGSGGGQKYDSNGGYVYS |
| 7 | Haematobia irritans | AGGGNGGGGTGGTPSSSYGAPSNGGGSNGNGFGSPSSSYGAPGSGGSNGNG GGRPSLSYGAPGSGGSNGNGGGRPSSSYGAPGAGGSNGNGGGRPSSSYGAP GAGGSNGNGGGRPSSSYGAPGAGGSNGNGGGRPSSSYGAPGAGGSNGNGGS RPSSTYGAP |
| 8 | Haematobia irritans | RPEPPVNSYLPPPLNNYGAPGAGGGSSDGSPLAPSDAYGAPDLGGGSGGSG QGPSSSYGAPGLGGGNGGAPSSSYGAPGLGGGNGGSRRPSSSYGAPGAGGG NGGGGTGGTPSSSYGAPSNGGGSNGNGFGSPSSSYGAPGSGGSNGNGGGRP SLSYGAPGSGGSNGNGGGRPSSSYGAPGAGGSNGNGGGRPSSSYGAPGAGG SNGNGGGRPSSSYGAPGAGGSNGNGGGRPSSSYGAPGAGGSNGNGGSRPSS TYGAPGAGGSNGNGCGNKPSSSYGAPSAGSNGNGGSEQGSSGSPSDSYGPP ASGTGRGRNGGGGGAGGGRRGQPNQEYLPPNQGDNGNNGGSGGDDGYDYSQ SGDGGGQGGSGGSGNGGDDGSNIVEYEAGQEGYRPQTRYEGEANEGGQGSG GAGGSDGTDGYEYEQNGGDGGAGGSGGPGTGQDLGENGYSSGRPGGDNGGG GGYSNGNGQGDGGQDLGSNGYSSGAPNGQNGGRRNGGGQNNGQGYSSGRP NGNGSGGRNGNGGRGNGGGYRNGNGNGGGNGNGSGSGSGNNGYNYDQQGSN GFGAGGQNGENDGSGYRYS |
| 9 | Ctenocephali des felis | ANGNGFEGASNGLSATYGAPNGGGFGGNGNGGGAPSSSYGAPGAGNGGNGGG RPSSSYGAPGAGGSNGFGGRPSSSYGAPGNGNGANGGRGGRPSSRYGAPG NGNGNGNGGRPSSSYGAPGSNGNGGRPSSSYGAPGSGNGFGGNGGRPSSS SYGAPGANGNGNGGAIGQPSSSYGAPGQNGNGGGLSSTYGAPGAGNGGFGG NGGGLSSTYGAPGSGNGGFGGNGLSSTYGAPGSGNGGFGGNGGGLSSTYGA P |
| 10 | Ctenocephali des felis | PGGAGGAGGYPGGAGGAGGAGGYPGGSAGGAGGYPGGSGSGVGGYPGGSNG GAGGYPGGSNGGAGGYPGGSNGGAGGYPGGSNGGAGGYPGGSNGNGGYSNG GSNGGAGGYPGGSNGNGGYPGSGSNGGAGGYPGGSNGNGGYPG |

SEQUENCE LISTING

| SEQ ID NO: | Species | Sequence |
|---|---|---|
| 11 | Bombus terrestris | FDGQNGIGGGDSGRNGLSNSYGVPGSNGGRNGNGRGNGFGGGQPSSSYGAP SNGLGGNGGSGAGRPSSSYGAPGGGNGFGGGQPSSSYGAPSNGLGGNGAGR PSSSYGAPGGGNGFGGGSNGAGKNGFGGAPSNSYGPPENGNGFGGGNGGGS PSGLYGPPGRNGGNGGNGGNGGRPSSSYGTPERNGGRPSGLYGPP |
| 12 | Tribolium costaneum | NGFGGGQNGGRLSSTYGPPGQGGNGFGGGQNGGRPSSTYGPPGQGGNGFGG GQNGGRPSSTYGPPGQGGNGFGGGQNGGRPSSTYGPPGQGGNGFGGGQNGG RPSSTYGPPGQGGNGFGGGQNGGRPSSTYGPPGQGGNGFGGGQNGGKPSST YGPPGQGGNGFGGGQNGGRPSSTYGPPGQG |
| 13 | Tribolium costaneum | RAEPPVNSYLPPSQNGGPSSTYGPPGFQPGTPLGGGNGGHPPSQGGNGGF GGRHPDSDQRPGTSYLPPQNGGAGRPGVTYGPPGQGGGQNGGGPSSTYGP PGQGGNGFGGGQNGGRLSSTYGPPGQGGNGFGGGQNGGRPSSTYGPPGQGG NGFGGGQNGGRPSSTYGPPGQGGNGFGGGQNGGRPSSTYGPPGQGGNGFGG GQNGGRPSSTYGPPGQGGNGFGGGQNGGRPSSTYGPPGQGGNGFGGGQNGG KPSSTYGPPGQGGNGFGGGQNGGRPSSTYGPPGQGGNGNGGGHNGQRPGGS YLPPSQGGNGGYPSGGPGGYPSGGPGGNGGYGGEEESTEPAKYEFEYQVDD DEHNTHFGHQESRDGDKATGEYNVLLPDGRKQVVQYEADSEGYKPKISYEG GNGNGGGYPSGGPGGAGNGGYPSGGPQGGNGGYPSGGPQGGNGGYPSGGPQG GNGGYPSGGPQGGNGGYPSGGPQGGNGGYPSGGPQGGNGGYPSGGPQGGNG GYPSGGPQGGNGGYTSGGPQGGNGGYPSGGPQGGNGGSGPY |
| 14 | Tribolium costaneum | QLTKRDAPLSGGYPSGGPANSYLPPGGASQPSGNYGAPSGGFGGKSGGFGG SGGFGGAPSQSYGAPSGGFGGSSSFGKSGGFGGAPSQSYGAPSGGFGGSSS FGKSSGGFGGAPSQSYGAPSGGFGGSSSFGKSGGFGGAPSQSYGAPSGGFG GSSSFGKSGGFGGAPSQSYGAPSGGFGGKSSSFSSAPSQSYGAPSGGFGGK SGGFGGAPSQSYGAPSGGFGGKSGGFGGAPSQSYGAPSGGFGGSSSFGKSG GFGGAPSQSYGAPSGGFGGSSSFGKSSGFGHGSGAPSQSYGAPSRSQPQSN YLPPSTSYGTPVSSAKSSGSFGGAPSQSYGAPSQHAPSQSYGAPSRSFSQ APSQSYGAPSQGHAPAPQQSYSAPSQSYGAPSGGFGGGHGGFGGQGQGFGG GRSQPSQSYGAPAPSQSYGAPSAGGQQYASNGGYSY |
| 15 | Apis mellifera | RSEPPVNSYLPPSGNGNGGGGGGSSNVYGPPGFDGQNGIGEGDNGRNGISN SYGVPTGGNGYNGDSSGNGRPGTNGGRNGNGNGRGNGYGGGQPSNSYGPPS NGHGGNGAGRPSSSYGAPGGGNGFAGGSNGKNGFGGGPSSSYGPPENGNGF NGGNGGPSGLYGPPGRNGGNGGNGGNGGRPSGSYGTPERNGGRLGGLYGAP GRNGNNGGNGYPSGGLNGGNGGYPSGGPGNGGANGGYPSGGSNGDNGGYPS GGPNGNGNGGGYGQDENNEPAKYEFSYEVKDEQSGADYHGHTESRDGDRAQ GEFNVLLPDGRKQIVEYEADQDGFKPQIRYEGEANSQGYGSGGPGGNGGDN GYPSGGPGGNGYSSGRPNGGSDFSDGGYPSTRPGGENGGYRNGNNGGNGNG GYPSGNGGDAAANGGYQY |
| 16 | Apis mellifera | DAPISGSYLPPSTSYGTPNLGGGGPSSTYGAPSGGGGRPSSSYGAPSSTY GAPSSTYGAPSNGGGRPSSTYGAPSNGGGRPSSSYGAPSSSYGAPSSTYGA PSNGGGRPSSSYGAPSFGGGGFGGGNGLSTSYGAPSRGGGGGGSISSSY GAPTGGGGGPSTTYGAPNGGGNGYSRPSSTYGTPSTGGGSFGGSGGYSGG GGGYSGGGNGYSGGGGGYSGGNGGYSGGNGGGYSGGNGGYSGGGGGYSGGGGG YSGGGGGYSGGGNGYSGGGGGYSGGNGGYSGGNGGYSGGGGGYSGGGGG GQSYASNGGYQY |
| 17 | Nasonia vitripennis | RPEPPVNSYLPPGQGGFGGGRPSGASPSDQYGPPDFQGAGGRGGQAAGGN FGGGGNGFGGAPSSSYGPPGFGSNEPNKFSGAGGGGAGRPQDSYGPPAGGN GFAGSAGAGNSGRPGGAAAGGRPSDSYGPPQGGGSGFGGGNAGRPSDSYGP PSAGGGGFGGGSPGGGFGGGSPGGGFGGGNQGAPQSSYGPPASGFGGQGGA GQGRPSDSYGPPGGGSGGRPSQGGNGFGGGNAGRPSDSYGPPAAGGGGFGG NAGGNGGGNGFGGGRPSGSPGGFGGQGGGGRPSDSYLPPSGGSFGGGNGR QPGGFGQQGGNGAGQQNGGGGAGRPSSSYGPPSNGNGGGFSGQNGGRGSPS SGGGFGGAGGSPSSSYGPPAGGSGFGNNGGAGGRPSSSYGPPSSGGNGFGS GGQGGQGGQGGQGGRPSSSYGPPSNGNGGFGGGNGGRPSSNGYPQGQGNGN GGFGGQGGNGGRPSSSYGPPGGDSGYPSGGPSGNFGGSNAGGGGGGFGGQV QDSYGPPPSGAVNGNGNGYSSGGPGGNGLDEGNDEPAKYEFSYEVKDDQSD GRKQIVEYEADQDGFKPQIRYEGEANTGAGGAGGYPSGGGDSGYPSGPSG AGGNAGYPSGGGGAGGFGGNGGSNGYPSGGPSGGGQFGGQQGGNGGYP SGPQGGSFGGGSQGSGGYPSGGPGGNGGNNNFGGGNAGYPSGGPSGGN GFNQGGQNQGGSGGGYPSGSGGDAAANGGYQYS |
| 18 | Nasonia vitripennis | RAEAPISGNYLPPSTSYGTPNLGGGGGGGGFGGGAPSSSYGAPSSGGGFG GSFGGGAPSSSYGAPSTGGSFGGGAPSSSYGAPSSGGSFGGSFGGGAPSSS YGAPSFGGNAPSSSYGAPSAGGSFGGGAPSNSYGPPSSSYGAPSAGGSFGG SSGGSFGGSFGGGAPSSSYGAPAPSRPSSNYGAPSRPSSNYGAPSSGGSGF GGGSGFGGGRPSSSYGAPSGSFGGGFGGGAPSSSYGAPAPSRPSSNYGAP APSRPSSNYGAPAPSRPSSSYGAPSRPSSNYGAPSRPSSNYGAPSSGGSGF GGGSGFGGGRPSSSYGAPSGSFGGGFGGGAPSSSYGAPAPSRPSSNYGPP SSSYGAPSSGGSGFGGGAPSSSYGAPSFGGSSNAVSRPSSSYGAPSSGGG QSYASNGGYQY |

SEQUENCE LISTING

| SEQ ID NO: | Species | Sequence |
|---|---|---|
| 19 | Pediculus humanus corporis | EPPVKTSYLPPSASRSLNSQYGAPAFTDSNELVAPSPNSNFHDSYNQQQQS FDLSNGLSVPSAAGRLSNTYGVPSAQGANVPSFDSSDSIAVDAAGRSGNSF SSHVPSSTYGAPGNGFGGGSRSSQSGAPSSVYGPPQARNNNFGNGAAPSSV YGPPQARNNNFGNGGAPSQVYGPPKARNNNFGNGAAPSSVYGPPQARNNNF GNGAAPSSVYGPPQARNNNFANSAAPSQVYGPPQARNNNFGNGAAPSSVYG PPQSSSFSSPSGRSGQLPSATYGAPFERNGFGSQGSSGFQGYEPSKRSQTT EDPFAEPAKYEYDYKVQASDETGTEFGHKESRENESARGAYHVLLPDGRMQ IVQYEADETGYRPQIRYEDTGYPSAASSRSNNGFNGYQY |
| 20 | Anopheles gambiae str. PEST | KREAPLPPSGSYLPPSGGAGGYPAAQTPSSSYGAPTGGAGSWGGNGGNGGR GHSNGGGSSFGGSAPSAPSQSYGAPSFGGQSSGGFGGHSSGGFGGHSSGGH GGNGNGNGNGYSSGRPSSQYGPPQQQQQQQSFRPPSTSYGVPAAPSQSYGA PAQQHSNGGNGGYSSGRPSTQYGAPAQSNGNGFGNGRPSSSYGAPARPSTQ YGAPSAGNGNGYAGNGNGRSYSNGNGNGHGNGHSNGNGNNGYSRGPARQPS QQYGPPAQAPSSQYGAPAQTPSSQYGAPAQTPSSQYGAPAQTPSSQYGAPA QTPSSQYGAPAPSPPSQQYGAPAPSRPSQQYGAPAQTPSSQYGAPAQTPSS QYGAPAQTPSSQYGAPAQTPSSQYGAPAQQPSSQYGAPAPSRPSQQYGAPA QQPSAQYGAPAQTPSSQYGAPAPSPPSQQYGAPAQAPSSQYGAPAPSSQYG APAQQPSSQYGAPAQTPSSQYGAPSFGPTGGASFSSGNGNVGGSYQVSSTG NGFSQASFSASSFSPNGRTSLSAGGFSSGAPSAQSAGGYSSGGPSQVPATL PQSYSSNGGYNY |
| 21 | Glossina morsitans | RPEPPVNTYLPPSAGGGSGGGSPLAPSDTYGAPGVNGGGGGGGGPSSTYGA PGSGGGNGNGGGGFGKPSSTYGAPGLGGGGNGGGRPSETYGAPSGGGGNGF GKPSSTYGAPNGGGNGGPGRPSSTYGAPGSGGGNGGGSGRPSSTYGAPGLG GGNGGSGRPSSMYGAPGLGGGNGGSGRPSSTYGAPGSGGGNGGSGRPSSTY GAPGSGGGNGGSGRPSSTYGAPGNGNGGNGFGRPSSTYGAPGSGGSNGNGK PSSTYGAPGSGGGGRPSDSYGPPASGNGGRNGNGNGQSQEYLPPGQSGSG GGGGYGGGSGSGGSGGGGGGYGGDQDNNVVEYEADQEGYRPQTRYEGDGS QGGFGGDGDGYSYEQNGVGGDGGGAGGAGGYSNGQNLGANGYSSGRPNGGN GGGRRGGGGGGGSGGGQNLGSNGYSSGAPNGFGGGNGQGYSGGRSNGNGG GGGGRNGGRYRNGGGGGGRNGGGSNGYNYDQPGSNGFGRGGGNGENDGSG YHY |
| 22 | Atta cephalotes | RSEPPVNSYLHPGSDTSGTNGGRTDLSTQYGAPDFNNRGNGNSGATSFGGS GAGNGPSKLYDVPIRGNTGGNGLGQFRGNGFESGQPSSSYGAPKGGFGENR GNRGRPSTSYGVPDSNRNNRGGFGNGGSEARPSTSYGVPGANGNQGGFGSG SIGGRPSTSYGVPGANGNNGDSFRNGDIGGRPSTNYGAPGANGNHGGGNGG NGRPSNNYGVPGANGNTNGKGRLNGNSGGGPSNNYGSPNGFGKGLSTSYGS PNRGGNDNHYPSRGSFINGGINGYSSGSPNGNAGNFGHGDESFGRGGGEGE NTGEGYNANAQEESTEPAKYEFSYKVKDQQTGSDYSHTETRDGDHAQGEFN VLLPDGRKQIVEYEADQDGFKPQTRYEGEANADGYYGSGLNDNNDGYSSGR PDSESGGFANSGFNGGSSNGGYPNGGPGERKLGGFNNGGSSSGYQSGRSAGQ SFGRDNAGDLNNDIGGYFSNSPNNIGDSDNANVGSNRQNDGNSGYQY |
| 23 | Anopheles darlingi | KREAPLPPSGSYLPPSGGGGGGGYPAAQTPSSSYGAPAGGAGGWGGNGNG NGNGNGGRGGYSNGGGHSGSAPSQSYGAPSAPSQSYGAPSQSYGAPAAAPS QSYGAPSFGGNGGGASHGSGGFTGGHGGNGNGNGYSSGRPSSQYGPPQQQQ QPQQQSFRPPSTSYGVPAAPSSSYGAPSANGFSNGGRPSSQYGAPAPQSNG NEFGAPRPSSSYGAPSRPSTQYGAPSNGNGNGYAGHGNGNGHGNGNGHSNG NGNGYNRGPARQPSSQYGPPSQGPPSSQYGPPSQYGPPSSGTSFIAYGPPS QGPPSSQYGAPAPSRPSSQYGAPAQTPSSQYGAPAQTPSSQYGPPRQSSPQ FGAPAPRPPSSQYGAPAQAPSSQYGAPAQTPSSQYGAPAQAPSSQYGAPAP SRPSSQYGVPAQAPSSQYGAPAQAPSSQYGAPAQTPSSQYGAPSFGSTGGS SFGGNGGVGGSYQTASSGNGFSQASFSASSFSSNGRSSQSAGGYSSGGPSQ VPATIPQQYSSGGGSYSSGGHSQVPATLPQQYSSNGGYNY |
| 24 | Acromyrmex echinatior | RSEPPVNSYLPPGPGTSGANGGQTDLSIQYRASDFNNRGNVNGNSGATSFG GPGASNGPSKLYDVPIGGNAGGNGLGQFRGNGFEGGQPSSSYGAPNGGFGE NRGNGGKPSTSYGVPDSNGNNRGGFGNGGSEGRPSTSYGLPDASRNNGNGF GNVGNEDKPSTNYGIPANGNKVSGFGNVGSEGRPSTSYGVPGANGNQGFGS GGIGGRPSTSYGVPGVNGNNGGGFENVGRPSTSYGTPDARGNNGGSFRNGD IGGRPSTNYGIPGANGNHGGGNGGNGGNGRPSSNYGVPGGNGNTNGKGRFNGNS GGRPSNSYGSPNGFGKGLSTSYSPSNRDGNGNHYPSGDSNRGSFVNGGING YPSGSPNGNAGNFRHGDESFGRGGEGGGRSTGEGYNANAQEESTEPAKYEF SYKVKDQQTGSDYSHTETRDGDHAQGEFNVLLPDGRKQIVEYEADQDGFKP QIRYEGEANADGEYDSGGLNDNNDGYSSGRPSESGGFANNSGFNGGSSNG GYPSGGSGEGKLGFNSGGNSGYQSGRPAGQSFGRDNAGDLSNDIGGFSNSP NNIGGDNANVGSNRQNGGNSGYQY |
| 25 | Acyrthosiphon pisum | ESPYGGGSSNSNGNGRNGGYGGKGQYGGGNGGGVGSSSASPFFSGANQYGS QSGLSGAANNRYPSFGSKFGGNKGSYGGSSSRNNGRYSGSASGYGSGSSG GLGSTGRSTGGYGGGSSGSYGSGSSGSLGSSTGSNGIIYGAGSSGGFGSGSS GSYGGGSSGGFGSGSSGSYGGGSSGGFGSGSSGSYGGGSSGGFGSGSSGSY |

US 12,268,275 B2

53                                                          54
-continued

| SEQ ID NO: | Species | Sequence |
|---|---|---|
| | | GGGSSGGFGSGSSGNYGSGSSGSYGSGGGGLGGASSGNNDGYGAGGSGSYD QLGGANGNGLGGSGNDPLSEPANYEFSYEVNAPESGAIFGHKESRQGEEAT GVYHVLLPDGRTQIVEYEADEDGYKPKITYTDPVGGYAGDRQSGNSYGGNG GFGGSGSLGGSGGNLGGLYNGGGSSNNGAGYGGSSSSLGSRYGGSGGSSGS GVGGGYGGSGSSSGGIGSSYGGSGSLSGGLGGGYGGSGSSSGGLGGGYGGS GGSSGGGFGGLGGSGGSSGSGYGSGSSSGGLGNSYGGSGSSNGGLGGGYS GSGGSSGGLGGGYGASSGSSGSGLGGGYGGSGSSSGGLGSGYGGLGSSSGG LGGGYGSGSSSGGLGGGYGGSGSSNGGIGGGYGGSSGSSGGLGGGYGGSG SSSSGGLGGGYGGSGGSNSGLGSSYGGSGSTNGGLGGGYGGLGSSSGGLGGG YGGSGGSNGGIGGGYGGSGSGSGSQGSAYGGSGSSSGSQGGGYGGSGSSSG GLGGGYGSSSGSSSGLGGSYGSNRNGLGSGSSYS |
| 26 | Drosophila virilis | RPEPPVNSYLPPSPGDSYGAPGQGQGQGQGGFGGKPSDSYGAPGAGNGNGN GRPSSSYGAPGQGQGQGGFGGKPSDSYGAPGAGNGNGNGRPSSSYGAPGQG QGQGGFGGRPSSSYGAPGQGQGQGGFGGKPSDTYGAPGAGNGNGRPSSSYGAP GQGQGGIGGKPSDSYGAPGAGNGNGNGRPSSSYGAPGQGQGGFGGKPSDTY GAPGAGNGNGRPSSSYGAPGQGQGGFGGKPSDTYGAPGAGNGNGNGRPSSS YGAPGQGQGGFGGKPSDTYGAPGAGNGNGRPSSSYGAPGQGQGQGGFGGKP SDSYGPPASGAGAGGAGGPGAGGGGDYDNDEPAKYEFNYQVEDAPSGLSFG HSEMRDGDFTTGQYNVLLPDGRKQIVEYEADQQGYRPQVRYEGDANGNGGP GGAGGPGGQDLGQNGYSSGRPGGQDLGQGGYSNGRPGGQDLGQNGYSGGRP GGQDLGQNGYSGGRPGGQDLGQNGYSGGRPGGQDLGQNGYSGGRPGGQDLG QNGYSGGRPGGQDLGQNGYSGGRPGGNGGSDGGRVIIGGRVIGQDGGBDGQG YSSGRPNGQDGGFGQDNTDGRGYSSGKPGQGRNGNGNSFGPGGQNGDNDGS GYRY |
| 27 | Drosophila erecta | RPEPPVNSYLPPSDSYGAPGQSGPGGRPSDSYGAPGGGNGGRPSDSYGAPG LGQGQGQGQGGFGGKPSDSYGAPGAGNGNGGRPSSSYGAPGAGNGGRPS DTYGAPGGGSGGRPSDTYGAPGGGNGNGGRPSSSYGAPGQGQGNGNSGR PSSSYGAPGAGNGGRPSDTYGAPGGGNGGRPSSSYGAPGAGNGGNGGRPSD TYGAPGGGNGNGNGNGSGGRPSSSYGAPGQGQGGFGGRPSDSYGAPGQN QKPSDSYGAPGSGSGSGNGNGGRPSSSYGAPGSGPGGRPSDSYGPPASGSG AGGAGGSGPGGADYDNDIVEYEADQQGYRPQIRYEGDANDGSGPSGPGGQN LGADGYSSGRPGNGNGNGGYSGGRPGGQDLGPSGYSGGRPGGQDLGAGG YSNGRPGGQDLGPSGYSGGRPGGQDLGPSGYSGGRPGGQDLGAGGYSNGRP GGNGNGNGGADGGRVIIGGRVIGGQDGGDQGYSGGRPGGQDLGRDGYSSGR PGGRPGANGQDNQDGQGYSSGRSGKGGRNSFGPGGQNGDNDGSGYRY |
| 28 | Lutzomyia longipalpis | RPEPPANTYLPPSSSYAAPGQQGGSGFGGGGGSGGSGGFGQPGAFGRPSSS YGPPSQGGAGGGFGSDSQFGGGFGGGAGGFGSGGSGAPGASQRPSSSYGPP GQTGGGGFGAQGAPGSSFGPGGGFGGGSPGQAGSPGFQRPSSSYGPPGQSP GGGFSQQGGAPGASQRPSSTYGAPGQGAGGFGQGGSSGGFGGTGGSVAIGGR PSSSYGAPGQGSSGGFGGGSGGFGSQAPSTSYGAPGQGSPGGGFGSQGGPG GQPGSPGFGGSQRPSSSYGPPGQGGAPGQGGSPGFGASSRSGGAGGFGASQ QPSSSYGPPGQGAGSGFQGTGGGFGGPGQRPGFGGSQTPATSYGAPGQAGG ASGGFGGAGAQRPSSSYGPPGQASGFGGGSSGGGFGGGSSGGFGGNQGGFG GNQGGFGGSQTPSSSYGAPSFGSGGSPGAAGGAGGFGQGGVGGSGQPGGFG GGDQGYPPRGGPGGFGPGSGGSGAGGPIAGGSGSGYPGGSDSGSNEPAKYD FSYQVDDPASGTSFGHSEQRDGDYTSGQYNVLLPDGRKQIVEYEADLGGYR PQIKYEGGSSGGAGGYPSGGPGSQGGAGGYPSGGPGGPGSPGGAGGYQSGA AGGAGGYPSGGPGGPGAGGYPSGGPGGPGSQAGGFSGGFGGGSDGAFGGAG GFSQGGAGGGDAGYPRGGPGGFGGAGSPGFGGSGSPGFGGSGSPGAQGSSG FGGTGGGFGGGADYPRGGPGAGQSGFQDGRGATGGAGQPGGRGSFGRPGS ARGGSSSNGYANGGAEGYPRDNPQNRGSGYS |
| 29 | Rhodnius prolixus | KRDDPLRRFLAPLVGGGNGSGGGGGGYNYNKPANGLSLPGGGGALPPATSY GVPDRPAPVPSSPPSSSYGAPQPSPNYGAPSSSYGAPSQQPSRSYGAPSQG PSTSYSQRPSSSYGAPAPQTPSSSYGAPAQQPSGSYGAPSGGGGSSGYTGG AQRPSGSYGAPSQGGPSGNYGPPSQQPSSNYGAPSQTPSSNYGAPAQRPST SYGAPSQPPSSSYGSPPQRASGYPSSSSGPSNGYSPPAQRPSSSYGPPSQQ PASSYGAPSQTPSSNYGPPAPIPSSNYGAPSQPPSKPSAPSSSYGTPSQTP STSYGAPSQAPSSSYGAPSRPSPPSSSYGAPSQPSSSYGPPSRPSQPSSP SSGYGAPSQGPSSSYGAPSRPSSPSSSYGAPPSSSYGAPSRPSPPSSSYGA PSQGPSSSYGPPSRPSQPSSPSSGYGAPSQGPSSSYGAPSRPSSPSSSYGA PPSSSYGAPSRPSPPSSSYGAPSQGPSSSYGPPSRPSQPSSPSSSYGAPSQ GPSSSYGAPSRPSPPSSSYGAPSQGPSSSYGPPSRPSQPSSTYGVPSGGRP STPSSSYGAPPQALSSTYGAPSGRPGAPSQKPSSSYGAPSLGGNASRGPKS SPPSSSYGAPSVGTSVSSYAPSQGGAGGFQSSRPSSSYGAPSTGPSSTYGP PSQPPSSSYGVPSQPPSSNYGVPSQGVSGSVGSSSPSSSYGAPSQIPSSSY GAPSQSSIGGFGSSRPSSSYGAPPQAPSSSYSAPLRAPSTSYGAPSGGSGS NFGSKPSTNYGAPSQPPSTNYGPPSQPPSSSYGTPSRAPSPTYSTPQSSGT SFGSRPSSSYGVPSQPTTNYGAPSQTPSSNYGAPPASSAPSSTYGRPSQSP SSSYGAPSPSSSSSSYESPSQPPSSSYGAPSQGPSSSYGAPSRPSSTYGAP |

SEQUENCE LISTING

| SEQ ID NO: | Species | Sequence |
|---|---|---|
| | | SPSSPSTNYGAPAPSSNYGTPAQDLTGSYAAPSQPPSAGYGAPSGQPSSGG<br>KQNFQVKNPFAGQTHQVPAVSSISFGLPSQSFNTAIQGQEPSQSYGAPTA<br>SSPSSSYGAPTGTGSSQPGQSYASNGGYSYS |
| 30 | Rhodnius prolixus | QPPFNHYLPAARGSGSNSAQYTAPSSKFGTSTGQYGQPPSEVPRGLQQGSY<br>AEDVHSSRSVNPSSQNGIPSGHFSSLSSNYGAPSSDYSRSFLRYGTLSNKY<br>GVPNSALGSLSSRNNKTPATQLSYQPSSHYDSRSTSEDQFISSRVSDSQYG<br>ASSVRRFLPSSQYSTPSSQYGTPSSQYGTPSSQYGTPSSQYGTPSSQYGTP<br>SSQYGTPSSQYGTPSSQYGTPSSQYGTPSSQYGTPSSPPSQYGGPYSMRTS<br>APNSQYGTPSSFRTSPSSQFGSSSAHSSSLSKFRSVPSSPYGTLSAIRSTH<br>SSQYGTPSSFSDSTSSSHNGLPSHYPGSGFSGSSVNDQKSYTGNVFGQSHS<br>RVANGDQHARSYTLAGGNEISEPAKYDFNYDVSDGEQGVEFGQEESRDGEE<br>TNGSYHVLLPDGRRQRVQYTAGQYGYKPTISYENTGTLTTGRQQFSNGFYN<br>VQQSGSESQEHLGRSTGQNSYGGSNGYESGVGYQSGVGRRSRPAGSY |
| 31 | Solenopsis invicta | RSEPPINSYLPPRAGSSGANGGRTDLTTQYGAPDFNNGGGATSFSGNGAGD<br>GPSKLYDVPVRGNAGGNGLGRGNGFGGGQPSSSYGAPNGGSNENRGNGGRP<br>STSYGVPGANGNNGGGFGNGGDKGRPSTSYGVPDASGSSQGSFGNVGNGGR<br>PSTNYGVPGANGNGGGFGNAANEGKPSTSYGVPGANGNSQGGFGNGGRPST<br>GYGVPGANGNNGGGFGGRPSTSYGAPGANGNHRGGNNGNASPSTNYGVPGG<br>NNGNTNGKGRFNGGNSGGGPSNNYGVPNENAFGGGLSTSYGPPSRGGNGNS<br>GYPSGGSNGGSFVNNGANGYPSGGPNGNAGNFGDGRGGKGGGSSGEGYNDN<br>AQEGSTEPAKYEFSYKVKDQQTGSEYSHTETRDGDRAQGEFNVLLPDGRKQ<br>IVEYEADQDGFKPQIRYEGEANAGGGYSSGGSNDNNDGYSSGRPGSEAGGF<br>ANNSGFNGSGTNGGRSSGGPGDGNPGGFNSGGGGYQSGRPAGQSFGRDND<br>GGLSGDIGGYFANSPSNNIGGSDSANVGSNRQNGGNGGYQY |
| 32 | Culex quinque-fasciatus | KREAPLPGGSYLPPSNGGGAGGYPAAGPPSGSYGPPSNGNGNGNGAGGYPS<br>APSQQYGAPAGGAPSQQYGAPSNGNGGAGGYPSAPSQQYGAPNGNGNGGFG<br>GRPQAPSQQYGAPSNGNGGARPSQQYGAPNGGNGNGRPQTPSSQYGAPSGG<br>APSSQYGAPSGGAPSQQYGAPNGGNGNGRPQTPSSQYGAPSGGAPSQQYGA<br>PNGGNGNGRPQTPSSQYGAPSGGAPSQYGAPSGGAPSSQYGAPAGGAPSS<br>QYGAPAGGAPSSQYGAPAGGAPSSQYGAPAGGAPSSQYGAPAGGAPSSQYG<br>APSSQYGAPAGGAPSSQYGAPAGGAPSSQYGAPSGGAPSSQYGAPSGGAPS<br>SQYGAPAGGAPSSQYGAPSGGAPSS |
| 33 | Bactrocera cucurbitae | RPEPPVNSYLPPSANGNGNGGGRPSSQYGAPGLGSNSNGNGNGNGGGRPSS<br>QYGVPGLGGNGNGNGGGGRPSSSYGAPGLGGNGNGNGNGGGRPSSQYG<br>VPGLGGNGNGNGNGGRPSSTYGAPGLRGNGNGNGNGRPSSTYGAPGG<br>LGGNGNGNGNGNGRPSSTYGAPGLGGNGNGNGNGRPSSTYGAPGLNGNG<br>LGGGQKPSDSYGPPASGNGNGYSNGGNGNGNGGGRPGQEYLPPGRNGNGNG<br>NGGRGNGNGGGANGYDYSQGGSDSGESGIVDYEADQGGYRPQIRYEGEANN<br>GAGGLGGGAGGANGYDYEQNGNGLGGGNGYSNGQDLGSNGYSSGRPNGNGN<br>GNGNGNGNGYSGRNGKGRNGNGGGQGLGRNGYSDRPSGQDLGDNGYASGR<br>PGGNGNGNGGNGNGYSNGNGYSNGNGNGTGNGGGQYNGNGNGYSDGRPGGQ<br>DNLDGQGYSSGRPNGFGPGGQNGDNDGNGYRY |
| 34 | Trichogramma pretiosum | RPEPPVNSYLPPGQGGQGGFGGSSGGRPGGGSPSNQYGPPNFQNGGGQNGGS<br>GFGGNGNGNSFGPPSNSYGPPEFGSPGAGSFGGGRPQDTYGPPSNGNGNGN<br>GFGGNGNGGGRPSSRPSDSYGPPSSGNGFGGGNSGRPSESYGPPQNGGGSG<br>NGNQGGGNGFGNGGGRGGQGKPSDSYGPPNSGNRPGSSNGGGQQQNGFGGG<br>NGGRPSNTYGPPGGGNGGGRPGGSSGGFGGQNGGRPSDSYGPPSNGNGNGG<br>RPSNNYGPPNSGGGNGNGFGGSNGKPSNSYGPPSNGNGGGFGGSNGRPSNS<br>YGPPSGGNGGGFGGSSAVGRPGNSGSPSSSGSGFGGNGGASRPSSSYGPPS<br>NGGGFGNGGGSNGRPSSSYGPPNSGSNGGGFGGQNGNGRQNGNNGQGGFGG<br>QPSSSYGPPSNGNGFGGGGSNGYPQNSQGGNGNGFGQGSGGRPSSSYGPP<br>SNGGGGGDNGYSSGGPGGFGGQPQDSYGPPPSGAVDGNNGFSSGGSSGDNN<br>GYSSGGPGGNGFEDGNDEPAKYEFSYEVKDEQSGSSFGHTEMRDGDRAQGE<br>FNVLLPDGRKQIVEYEADQDGFKPQIRYEGEANTGGAGGYPSGGPGGQGGN<br>GNGGYPSGGPSNGGFGGQNGGNGGYPSGGPSGGGFGGQNGGSGGYPSGGP<br>SGGGFGGQGGFGGQNSGGNGGYSSGGPASGGFGGQNGGNGGYPSGGPSGGG<br>FGGQGGFGGQNSGGNGGYPSGGPSSGGFGGQNGGGGGNYPAGSGGDAEANG<br>GYQYS |
| 35 | Drosophila sechellia | QSGAGGRPSDTYGAPGGGNGGRPSDSYGAPGQGQGQGQGGGYGGKPSDSY<br>GAPGGGNGNGGGRPSSSYGAPGGGNGGRPSDTYGAPGGGNGGRPSDTYGAPG<br>GGNGNGGRPSSSYGAPGQGQGNGNGGGRPSSSYGAPGGGNGGRPSDTYGAP<br>GGGNGGRPSDTYGAPGGGNNGGRPSSSYGAPGGGNGGRPSDTYGAPGGGNG<br>NGSGGRPSSSYGAPAQGQGGFGGRPSDSYGAPGQNQKPSDSYGAPGSGNGS<br>AGRPSSSYGAPGSGPGGRPSDSYGP |
| 36 | Drosophila sechellia | QSGAGGRPSDTYGAPGGGNGGRPSDSYGAPGQGQGQGQGGGYGGKPSDSY<br>GAPGGGNGNGGGRPSSSYGAPGGGNGGRPSDTYGAPGGGNGGRPSDTYGAPG<br>GGNGNGGRPSSSYGAPGQGQGNGNGGGRPSSSYGAPGGGNGGRPSDTYGAP<br>GGGNGGRPSDTYGAPGGGNNGGRPSSSYGAPGGGNGGRPSDTYGAPGGGNG |

| SEQ ID NO: | Species | Sequence |
|---|---|---|
| | | NGSGGRPSSSYGAPAQGQGGFGGRPSDSYGAPGQNQKPSDSYGAPGSGNGS AGRPSSSYGAPGSGPGGRPSDSYGP |
| 37 | Drosophila sechellia | QSGAGGRPSDTYGAPGGGNGGRPSDSYGAPGQGQGQGQGGYGGKPSDSY GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 38 | Drosophila sechellia | QSGAGGRPSDTYGAPGGGNGGRPSDSYGAPGQGQGQGQGGYGGKPSDSY GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 39 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 40 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 41 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 42 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 43 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 44 | Drosophila sechellia | YSSGRPGNGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 45 | 3XFLAG | GDYKDDDDKDYKDDDDKDYKDDDDK |
| 46 | Alpha mating factor precursor protein sequence | MRFPSIFTAVLFAASSALAAPVNTTTEDETAQIPAEAVIGYSDLEGDFDVA VLPFSNSTNNGLLFINTTIASIAAKEEGVSLEKR |
| 47 | EA repeat | EAEA |
| 48 | Linker | SG |
| 49 | full-length Drosophila sechellia resilin sequence (Ds_ACB) | *MRFPSIFTAVLFAASSALAAPVNTTTEDETAQIPAEAVIGYSDLEGDFDVA VLPFSNSTNNGLLFINTTIASIAAKEEGVSLEKR*EAEAgrpeppynsylpp sdsygapgqsgaggrpsdtygapgggnggrpsdsygapgqgqgqgqggy ggkpsdsygapgggngnggrpsssygapgggnggrpsdtygapgggnggrp sdtygapgggngnggrpsssygapgqgqgngnggrpsssygapgggnggr psdtygapgggnggrpsdtygapgggnnggrpsssygapgggnggrpsdty gapgggngngsggrpsssygapaqgqggfggrpsdsygapgqnqkpsdsyg apgsgngsagrpsssygapgsgpggrpsdsygppasgsgaggaggsgpgga dydndepakyefnyqvedapsglsfghsemrdgdfttgqynvllpdgrkqi veyeadqqgyrpqiryegdandgsgpsgpsgpggpggqnlgadgyssgrpg ngngnggyssgrpggqdlgpsgysggrpggqdlgaggysnvkpggqdlg pggysggrpggqdlgrdgysggrpggqdlgagaysngrpggngnggsdggr viiggrviggqdggdqgysggrpggqdlgrdgyssgrpggrpggngdsqd gqgyssgrpgqggrngfgpggqngdndgsgyry*SG*DYKDDDDKDYKDDDDK DYKDDDDK |

The invention claimed is:

1. A method of cross-linking recombinant resilin, comprising:
providing a composition comprising purified recombinant resilin, wherein the composition comprises full-length recombinant resilin in an amount in a range from 10% and 90% by weight of the purified recombinant resilin;
placing said recombinant resilin in a cross-linking solution comprising ammonium persulfate and an aqueous solvent, wherein the cross-linking solution does not include a photocatalyst or a cross-linking enzyme;
incubating said recombinant resilin in said cross-linking solution at a temperature of at least 60° C., thereby generating a cross-linked recombinant resilin solid composition in the aqueous solvent; and
solvent exchanging the aqueous solvent in the cross-linked recombinant resilin solid composition with a polar, non-aqueous solvent to thereby provide a polar, non-aqueous based crosslinked resilin solid.

2. The method of claim 1, wherein said incubation is performed for at least 15 minutes, at least 30 minutes, at least 45 minutes, at least 60 minutes, at least 90 minutes, or at least 2 hours.

3. The method of claim 1, wherein said recombinant resilin in said cross-linking solution is incubated at a temperature of from 60° C. to 85° C., from 70° C. to 85° C. or from 75° C. to 85° C.

4. The method of claim 1, wherein said cross-linked recombinant resilin solid composition is stable at room temperature for more than 5 days, more than 10 days, more than 20 days, or more than 40 days.

5. The method of claim 1, wherein said purified recombinant resilin is prepared by recombinantly expressing a gene encoding said recombinant resilin in a modified organism in a culture, and purifying expressed recombinant resilin from said culture.

6. A solid recombinant resilin composition comprising a solid cross-linked recombinant resilin in a polar nonaqueous solvent selected from glycerol, propylene glycol, and ethylene glycol, wherein the composition comprises full-length recombinant resilin in an amount in a range from 10% and 90% by weight of the solid cross-linked recombinant resilin.

7. The method of claim 1, wherein said solvent exchange is performed for at least 8 hours, at least 16 hours, at least 24 hours, or at least 48 hours.

8. The method of claim 1, wherein said solvent exchange is performed at about 60° C.

9. The method of claim 1, wherein said cross-linked recombinant resilin solid composition comprises at least 20%, at least 50%, at least 70%, or at least 80% full length resilin as a portion of all resilin as measured by size exclusion chromatography.

10. The method of claim 1, wherein exchanging said solvent changes the elastic modulus, the resilience, the hardness, the maximum elastic compressive load, or the material lifetime of the cross-linked recombinant resilin solid composition.

11. A method of preparing a recombinant resilin foam, comprising:
admixing a recombinant resilin with a cross-linking solution comprising ammonium persulfate in an aqueous solvent, wherein the cross-linking solution does not include a photocatalyst or a cross-linking enzyme, wherein the recombinant resilin comprises full-length recombinant resilin in an amount in a range from 10% and 90% by weight of the recombinant resilin;
incubating said recombinant resilin in said cross-linking solution at a temperature of at least 60° C. in the presence of a foaming agent that introduces bubbles into the resilin while crosslinking, thereby generating a cross-linked recombinant resilin solid foam in the aqueous solvent; and
solvent exchanging the aqueous solvent in the cross-linked recombinant resilin solid foam with a polar, non-aqueous solvent to thereby provide a polar, non-aqueous based crosslinked resilin solid foam.

12. The method of claim 11, wherein the solvent exchanging is performed in a solution containing at least 20× the volume of the polar, non-aqueous solvent relative to the resilin solid.

13. The method of claim 1, wherein the solvent exchanging is performed in a solution containing at least 20× the volume of the polar, non-aqueous solvent relative to the resilin solid.

14. A solid composition comprising a solid cross-linked resilin composition in a polar nonaqueous solvent selected from glycerol, propylene glycol, and ethylene glycol, wherein said cross-linked resilin is foamed, wherein the composition comprises full-length recombinant resilin in an amount in a range from 10% and 90% by weight of the solid cross-linked resilin.

15. The method of claim 1, wherein said cross-linked recombinant resilin solid composition comprises a hardness of at least 10 as measured using a Shore 00 Durometer via ASTM D2240.

16. The method of claim 1, wherein said cross-linked recombinant resilin solid composition comprises a rebound resilience from about 40% to about 60% as measured by ASTM D7121.

17. The method of claim 1, wherein said cross-linked recombinant resilin solid composition comprises a compressive stress at 25% of about 6 to about 8 psi as measured by ASTM D575.

18. The method of claim 1, wherein said cross-linked recombinant resilin solid composition does not undergo an elastic to plastic transition below 2 kN of compressive force as measured by a Zwick compression test.

19. The method of claim 1, wherein said cross-linked recombinant resilin solid composition does not comprise a cross-linking enzyme or a photocatalyst.

20. The method of claim 1, wherein the polar, non-aqueous solvent is selected from glycerol, propylene glycol, and ethylene glycol.

21. The method of claim 11, wherein the foaming agent comprises a chemical blowing agent or a physical blowing agent.

22. The method of claim 21, wherein the chemical blowing agent comprises sodium bicarbonate, potassium bicarbonate, ammonium, azodicarbonamide, isocyanate, hydrazine, isopropanol, 5-phenyltetrazole, triazole, 4,4'oxybis(benzenesulfonyl hydrazide) (OBSH), trihydrazine triazine (THT), hydrogen phosphate, tartaric acid, citric acid, and toluenesulphonyl semicarbazide (TSS).

23. The method of claim 21, wherein the physical blowing agent comprises chlorofluorocarbon (CFC), dissolved nitrogen, $N_2$, $CH_4$, $H_2$, $CO_2$, Ar, pentane, isopentane, hexane, methylene dichloride, and dichlorotetra-fluoroethane.

* * * * *

SEQUENCE LISTING

<160> NUMBER OF SEQ ID NOS: 65

<210> SEQ ID NO 1
<211> LENGTH: 606
<212> TYPE: PRT
<213> ORGANISM: Drosophila sechellia

<400> SEQUENCE: 1

```
Arg Pro Glu Pro Pro Val Asn Ser Tyr Leu Pro Pro Ser Asp Ser Tyr
1               5                   10                  15

Gly Ala Pro Gly Gln Ser Gly Ala Gly Gly Arg Pro Ser Asp Thr Tyr
            20                  25                  30

Gly Ala Pro Gly Gly Asn Gly Gly Arg Pro Ser Asp Ser Tyr Gly
            35                  40                  45

Ala Pro Gly Gln Gly Gln Gly Gln Gly Gln Gly Gly Tyr Gly
        50                  55                  60

Gly Lys Pro Ser Asp Ser Tyr Gly Ala Pro Gly Gly Asn Gly Asn
65                  70                  75                  80

Gly Gly Arg Pro Ser Ser Ser Tyr Gly Ala Pro Gly Gly Asn Gly
                85                  90                  95

Gly Arg Pro Ser Asp Thr Tyr Gly Ala Pro Gly Gly Asn Gly Gly
            100                 105                 110

Arg Pro Ser Asp Thr Tyr Gly Ala Pro Gly Gly Gly Asn Gly Asn
            115                 120                 125

Gly Gly Arg Pro Ser Ser Tyr Gly Ala Pro Gly Gln Gly Gln Gly
        130                 135                 140

Asn Gly Asn Gly Gly Arg Pro Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
                165                 170                 175

Asn Gly Gly Arg Pro Ser Asp Thr Tyr Gly Ala Pro Gly Gly Gly Asn
            180                 185                 190

Asn Gly Gly Arg Pro Ser Ser Ser Tyr Gly Ala Pro Gly Gly Gly Asn
            195                 200                 205

Gly Gly Arg Pro Ser Asp Thr Tyr Gly Ala Pro Gly Gly Gly Asn Gly
        210                 215                 220

Asn Gly Ser Gly Gly Arg Pro Ser Ser Ser Tyr Gly Ala Pro Ala Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Ser Ala Gly Arg Pro Ser Ser Ser Tyr Gly Ala Pro Gly Ser
        275                 280                 285

Gly Pro Gly Gly Arg Pro Ser Asp Ser Tyr Gly Pro Pro Ala Ser Gly
        290                 295                 300

Ser Gly Ala Gly Gly Ala Gly Ser Gly Pro Gly Gly Ala Asp Tyr
305                 310                 315                 320

Asp Asn Asp Glu Pro Ala Lys Tyr Glu Phe Asn Tyr Gln Val Glu Asp
                325                 330                 335

Ala Pro Ser Gly Leu Ser Phe Gly His Ser Glu Met Arg Asp Gly Asp
            340                 345                 350

Phe Thr Thr Gly Gln Tyr Asn Val Leu Leu Pro Asp Gly Arg Lys Gln
        355                 360                 365
```

```
Ile Val Glu Tyr Glu Ala Asp Gln Gln Gly Tyr Arg Pro Gln Ile Arg
    370                 375                 380

Tyr Glu Gly Asp Ala Asn Asp Gly Ser Gly Pro Ser Gly Pro Ser Gly
385                 390                 395                 400

Pro Gly Gly Pro Gly Gly Gln Asn Leu Gly Ala Asp Gly Tyr Ser Ser
                405                 410                 415

Gly Arg Pro Gly Asn Gly Asn Gly Asn Gly Asn Gly Gly Tyr Ser Ser
                420                 425                 430

Gly Arg Pro Gly Gly Gln Asp Leu Gly Pro Ser Gly Tyr Ser Gly Gly
                435                 440                 445

Arg Pro Gly Gly Gln Asp Leu Gly Ala Gly Gly Tyr Ser Asn Val Lys
    450                 455                 460

Pro Gly Gly Gln Asp Leu Gly Pro Gly Gly Tyr Ser Gly Gly Arg Pro
465                 470                 475                 480

Gly Gly Gln Asp Leu Gly Arg Asp Gly Tyr Ser Gly Gly Arg Pro Gly
                485                 490                 495

Gly Gln Asp Leu Gly Ala Gly Ala Tyr Ser Asn Gly Arg Pro Gly Gly
            500                 505                 510

Asn Gly Asn Gly Gly Ser Asp Gly Gly Arg Val Ile Ile Gly Gly Arg
            515                 520                 525

Val Ile Gly Gly Gln Asp Gly Gly Asp Gln Gly Tyr Ser Gly Gly Arg
    530                 535                 540

Pro Gly Gly Gln Asp Leu Gly Arg Asp Gly Tyr Ser Ser Gly Arg Pro
545                 550                 555                 560

Gly Gly Arg Pro Gly Gly Asn Gly Gln Asp Ser Gln Asp Gly Gln Gly
                565                 570                 575

Tyr Ser Ser Gly Arg Pro Gly Gln Gly Gly Arg Asn Gly Phe Gly Pro
                580                 585                 590

Gly Gly Gln Asn Gly Asp Asn Asp Gly Ser Gly Tyr Arg Tyr
                595                 600                 605

<210> SEQ ID NO 2
<211> LENGTH: 304
<212> TYPE: PRT
<213> ORGANISM: Drosophila sechellia

<400> SEQUENCE: 2

Arg Pro Glu Pro Pro Val Asn Ser Tyr Leu Pro Ser Asp Ser Tyr
1               5                   10                  15

Gly Ala Pro Gly Gln Ser Gly Ala Gly Gly Arg Pro Ser Asp Thr Tyr
                20                  25                  30

Gly Ala Pro Gly Gly Gly Asn Gly Gly Arg Pro Ser Asp Ser Tyr Gly
            35                  40                  45

Ala Pro Gly Gln Gly Gln Gly Gln Gly Gln Gly Gly Tyr Gly
        50                  55                  60

Gly Lys Pro Ser Asp Ser Tyr Gly Ala Pro Gly Gly Asn Gly Asn
65                  70                  75                  80

Gly Gly Arg Pro Ser Ser Ser Tyr Gly Ala Pro Gly Gly Asn Gly
                85                  90                  95

Gly Arg Pro Ser Asp Thr Tyr Gly Ala Pro Gly Gly Asn Gly Gly
                100                 105                 110

Arg Pro Ser Asp Thr Tyr Gly Ala Pro Gly Gly Gly Asn Gly Asn
            115                 120                 125

Gly Gly Arg Pro Ser Ser Ser Tyr Gly Ala Pro Gly Gln Gly Gln Gly
    130                 135                 140
```

Asn Gly Asn Gly Gly Arg Pro Ser Ser Tyr Gly Ala Pro Gly Gly
145                 150                 155                 160

Gly Asn Gly Gly Arg Pro Ser Asp Thr Tyr Gly Ala Pro Gly Gly
            165                 170                 175

Asn Gly Gly Arg Pro Ser Asp Thr Tyr Gly Ala Pro Gly Gly Asn
            180                 185                 190

Asn Gly Gly Arg Pro Ser Ser Tyr Gly Ala Pro Gly Gly Asn
            195                 200                 205

Gly Gly Arg Pro Ser Asp Thr Tyr Gly Ala Pro Gly Gly Asn Gly
        210                 215                 220

Asn Gly Ser Gly Gly Arg Pro Ser Ser Ser Tyr Gly Ala Pro Ala Gln
225                 230                 235                 240

Gly Gln Gly Gly Phe Gly Gly Arg Pro Ser Asp Ser Tyr Gly Ala Pro
            245                 250                 255

Gly Gln Asn Gln Lys Pro Ser Asp Ser Tyr Gly Ala Pro Gly Ser Gly
            260                 265                 270

Asn Gly Ser Ala Gly Arg Pro Ser Ser Tyr Gly Ala Pro Gly Ser
            275                 280                 285

Gly Pro Gly Gly Arg Pro Ser Asp Ser Tyr Gly Pro Pro Ala Ser Gly
        290                 295                 300

<210> SEQ ID NO 3
<211> LENGTH: 211
<212> TYPE: PRT
<213> ORGANISM: Drosophila sechellia

<400> SEQUENCE: 3

Gly Lys Pro Ser Asp Ser Tyr Gly Ala Pro Gly Gly Asn Gly Asn
1               5                   10                  15

Gly Gly Arg Pro Ser Ser Tyr Gly Ala Pro Gly Gly Asn Gly
            20                  25                  30

Gly Arg Pro Ser Asp Thr Tyr Gly Ala Pro Gly Gly Asn Gly Gly
            35                  40                  45

Arg Pro Ser Asp Thr Tyr Gly Ala Pro Gly Gly Gly Asn Gly Asn
50                  55                  60

Gly Gly Arg Pro Ser Ser Ser Tyr Gly Ala Pro Gly Gln Gly Gln Gly
65                  70                  75                  80

Asn Gly Asn Gly Gly Arg Pro Ser Ser Tyr Gly Ala Pro Gly Gly
            85                  90                  95

Gly Asn Gly Gly Arg Pro Ser Asp Thr Tyr Gly Ala Pro Gly Gly Gly
            100                 105                 110

Asn Gly Gly Arg Pro Ser Asp Thr Tyr Gly Ala Pro Gly Gly Asn
            115                 120                 125

Asn Gly Gly Arg Pro Ser Ser Ser Tyr Gly Ala Pro Gly Gly Asn
            130                 135                 140

Gly Gly Arg Pro Ser Asp Thr Tyr Gly Ala Pro Gly Gly Gly Asn Gly
145                 150                 155                 160

Asn Gly Ser Gly Gly Arg Pro Ser Ser Ser Tyr Gly Ala Pro Ala Gln
            165                 170                 175

Gly Gln Gly Gly Phe Gly Gly Arg Pro Ser Asp Ser Tyr Gly Ala Pro
            180                 185                 190

Gly Gln Asn Gln Lys Pro Ser Asp Ser Tyr Gly Ala Pro Gly Ser Gly
            195                 200                 205

Asn Gly Ser

210

<210> SEQ ID NO 4
<211> LENGTH: 175
<212> TYPE: PRT
<213> ORGANISM: Acromyrmex echinatior

<400> SEQUENCE: 4

```
Phe Gly Glu Asn Arg Gly Asn Gly Gly Lys Pro Ser Thr Ser Tyr Gly
1               5                   10                  15

Val Pro Asp Ser Asn Gly Asn Asn Arg Gly Gly Phe Gly Asn Gly Gly
            20                  25                  30

Ser Glu Gly Arg Pro Ser Thr Ser Tyr Gly Leu Pro Asp Ala Ser Arg
        35                  40                  45

Asn Asn Gly Asn Gly Phe Gly Asn Val Gly Asn Glu Asp Lys Pro Ser
    50                  55                  60

Thr Asn Tyr Gly Ile Pro Ala Asn Gly Asn Lys Val Ser Gly Phe Gly
65                  70                  75                  80

Asn Val Gly Ser Glu Gly Arg Pro Ser Thr Ser Tyr Gly Val Pro Gly
                85                  90                  95

Ala Asn Gly Asn Gln Gly Phe Gly Ser Gly Ile Gly Arg Pro
            100                 105                 110

Ser Thr Ser Tyr Gly Val Pro Gly Val Asn Gly Asn Asn Gly Gly
            115                 120                 125

Phe Glu Asn Val Gly Arg Pro Ser Thr Ser Tyr Gly Thr Pro Asp Ala
    130                 135                 140

Arg Gly Asn Asn Gly Gly Ser Phe Arg Asn Gly Asp Ile Gly Gly Arg
145                 150                 155                 160

Pro Ser Thr Asn Tyr Gly Ile Pro Gly Ala Asn Gly Asn His Gly
                165                 170                 175
```

<210> SEQ ID NO 5
<211> LENGTH: 158
<212> TYPE: PRT
<213> ORGANISM: Aeshna sp.

<400> SEQUENCE: 5

```
Ala Pro Ser Arg Gly Gly Gly His Gly Gly Gly Ser Ile Ser Ser
1               5                   10                  15

Tyr Gly Ala Pro Ser Lys Gly Ser Gly Phe Gly Gly Ser Ile
            20                  25                  30

Ser Ser Ser Tyr Gly Ala Pro Ser Lys Gly Ser Val Gly Gly Val
        35                  40                  45

Ser Ser Ser Tyr Gly Ala Pro Ala Ile Gly Gly Ser Phe Gly Gly
    50                  55                  60

Gly Ser Phe Gly Gly Ser Phe Gly Gly Ser Phe Gly Gly
65                  70                  75                  80

Ala Pro Ser Ser Ser Tyr Gly Ala Pro Ser Ser Tyr Ser Ala Pro
            85                  90                  95

Ser Ser Ser Tyr Gly Ala Pro Ser Lys Gly Ser Gly Gly Phe Gly Ser
            100                 105                 110

Ser Gly Gly Phe Ser Ser Phe Ser Ala Pro Ser Ser Tyr Gly
    115                 120                 125

Ala Pro Ser Ala Ser Tyr Ser Thr Pro Ser Ser Tyr Gly Ala Pro
    130                 135                 140

Ser Ser Gly Gly Phe Gly Ala Gly Gly Gly Phe Ser Ser Gly
```

```
145             150             155

<210> SEQ ID NO 6
<211> LENGTH: 457
<212> TYPE: PRT
<213> ORGANISM: Aeshna sp.

<400> SEQUENCE: 6

Glu Pro Pro Val Gly Gly Ser Gln Ser Tyr Leu Pro Pro Ser Ser
1               5                   10                  15

Tyr Gly Ala Pro Ser Ala Gly Thr Gly Phe Gly His Gly Gly Ser
                20                  25                  30

Pro Ser Gln Ser Tyr Gly Ala Pro Ser Phe Gly Gly Ser Val Gly
            35                  40                  45

Gly Gly Ser His Phe Gly Gly Ser His Ser Gly Gly Gly Gly
        50                  55                  60

Gly Tyr Pro Ser Gln Ser Tyr Gly Ala Pro Ser Arg Pro Ser Gly Ser
65                  70                  75                  80

Ser Phe Gln Ala Phe Gly Gly Ala Pro Ser Ser Tyr Gly Ala Pro
                85                  90                  95

Ser Ser Gln Tyr Gly Ala Pro Ser Gly Gly Gly Ser Tyr Ala Ile
            100                 105                 110

Gln Gly Gly Ser Phe Ser Ser Gly Gly Ser Arg Ala Pro Ser Gln Ala
        115                 120                 125

Tyr Gly Ala Pro Ser Asn Asn Ala Gly Leu Ser His Gln Ser Gln Ser
130                 135                 140

Phe Gly Gly Gly Leu Ser Ser Ser Tyr Gly Ala Pro Ser Ala Gly Phe
145                 150                 155                 160

Gly Gly Gln Ser His Gly Gly Gly Tyr Ser Gln Gly Gly Asn Gly Gly
                165                 170                 175

Gly His Gly Gly Ser Ser Gly Gly Tyr Ser Tyr Gln Ser Phe Gly
            180                 185                 190

Gly Gly Asn Gly Gly Gly His Gly Gly Ser Arg Pro Ser Ser Ser Tyr
        195                 200                 205

Gly Ala Pro Ser Ser Tyr Gly Ala Pro Ser Gly Gly Lys Gly Val
    210                 215                 220

Ser Gly Gly Phe Val Ser Gln Pro Ser Gly Ser Tyr Gly Ala Pro Ser
225                 230                 235                 240

Gln Ser Tyr Gly Ala Pro Ser Arg Gly Gly His Gly Gly Gly Ser
                245                 250                 255

Ile Ser Ser Ser Tyr Gly Ala Pro Ser Lys Gly Ser Gly Gly Phe Gly
            260                 265                 270

Gly Gly Ser Ile Ser Ser Ser Tyr Gly Ala Pro Ser Lys Gly Ser Val
        275                 280                 285

Gly Gly Gly Val Ser Ser Tyr Gly Ala Pro Ala Ile Gly Gly
    290                 295                 300

Ser Phe Gly Gly Gly Ser Phe Gly Gly Gly Ser Phe Gly Gly Gly Ser
305                 310                 315                 320

Phe Gly Gly Gly Ala Pro Ser Ser Tyr Gly Ala Pro Ser Ser Ser
                325                 330                 335

Tyr Ser Ala Pro Ser Ser Tyr Gly Ala Pro Ser Lys Gly Ser Gly
            340                 345                 350

Gly Phe Gly Ser Ser Gly Gly Phe Ser Ser Phe Ser Ser Ala Pro Ser
        355                 360                 365
```

```
Ser Ser Tyr Gly Ala Pro Ser Ala Ser Tyr Ser Thr Pro Ser Ser Ser
        370                 375                 380

Tyr Gly Ala Pro Ser Ser Gly Gly Phe Gly Ala Gly Gly Gly Phe Ser
385                 390                 395                 400

Ser Gly Gly Tyr Ser Gly Gly Gly Gly Tyr Ser Ser Gly Ser
                405                 410                 415

Gly Gly Phe Gly Gly His Gly Gly Ser Gly Gly Ala Gly Gly Tyr Ser
            420                 425                 430

Gly Gly Gly Gly Tyr Ser Gly Gly Gly Ser Gly Gly Gln Lys Tyr
                435                 440                 445

Asp Ser Asn Gly Gly Tyr Val Tyr Ser
        450                 455

<210> SEQ ID NO 7
<211> LENGTH: 162
<212> TYPE: PRT
<213> ORGANISM: Haematobia irritans

<400> SEQUENCE: 7

Ala Gly Gly Gly Asn Gly Gly Gly Gly Thr Gly Gly Thr Pro Ser Ser
1               5                   10                  15

Ser Tyr Gly Ala Pro Ser Asn Gly Gly Gly Ser Asn Gly Asn Gly Phe
            20                  25                  30

Gly Ser Pro Ser Ser Ser Tyr Gly Ala Pro Gly Ser Gly Gly Ser Asn
        35                  40                  45

Gly Asn Gly Gly Gly Arg Pro Ser Leu Ser Tyr Gly Ala Pro Gly Ser
    50                  55                  60

Gly Gly Ser Asn Gly Asn Gly Gly Arg Pro Ser Ser Ser Tyr Gly
65                  70                  75                  80

Ala Pro Gly Ala Gly Gly Ser Asn Gly Asn Gly Gly Arg Pro Ser
                85                  90                  95

Ser Ser Tyr Gly Ala Pro Gly Ala Gly Gly Ser Asn Gly Asn Gly Gly
            100                 105                 110

Gly Arg Pro Ser Ser Ser Tyr Gly Ala Pro Gly Ala Gly Gly Ser Asn
        115                 120                 125

Gly Asn Gly Gly Arg Pro Ser Ser Ser Tyr Gly Ala Pro Gly Ala
    130                 135                 140

Gly Gly Ser Asn Gly Asn Gly Gly Ser Arg Pro Ser Ser Thr Tyr Gly
145                 150                 155                 160

Ala Pro

<210> SEQ ID NO 8
<211> LENGTH: 580
<212> TYPE: PRT
<213> ORGANISM: Haematobia irritans

<400> SEQUENCE: 8

Arg Pro Glu Pro Pro Val Asn Ser Tyr Leu Pro Pro Leu Asn Asn
1               5                   10                  15

Tyr Gly Ala Pro Gly Ala Gly Gly Ser Ser Asp Gly Ser Pro Leu
            20                  25                  30

Ala Pro Ser Asp Ala Tyr Gly Ala Pro Asp Leu Gly Gly Ser Gly
        35                  40                  45

Gly Ser Gly Gln Gly Pro Ser Ser Ser Tyr Gly Ala Pro Gly Leu Gly
    50                  55                  60

Gly Gly Asn Gly Gly Ala Pro Ser Ser Ser Tyr Gly Ala Pro Gly Leu
```

```
                65                  70                  75                  80
Gly Gly Gly Asn Gly Gly Ser Arg Arg Pro Ser Ser Tyr Gly Ala
                    85                  90                  95
Pro Gly Ala Gly Gly Asn Gly Gly Gly Thr Gly Gly Thr Pro
            100                 105                 110
Ser Ser Ser Tyr Gly Ala Pro Ser Asn Gly Gly Ser Asn Gly Asn
                115                 120                 125
Gly Phe Gly Ser Pro Ser Ser Tyr Gly Ala Pro Gly Ser Gly Gly
    130                 135                 140
Ser Asn Gly Asn Gly Gly Arg Pro Ser Leu Ser Tyr Gly Ala Pro
145                 150                 155                 160
Gly Ser Gly Gly Ser Asn Gly Asn Gly Gly Arg Pro Ser Ser Ser
                    165                 170                 175
Tyr Gly Ala Pro Gly Ala Gly Gly Ser Asn Gly Asn Gly Gly Arg
            180                 185                 190
Pro Ser Ser Ser Tyr Gly Ala Pro Ala Gly Gly Ser Asn Gly Asn
                195                 200                 205
Gly Gly Gly Arg Pro Ser Ser Tyr Gly Ala Pro Gly Ala Gly Gly
    210                 215                 220
Ser Asn Gly Asn Gly Gly Arg Pro Ser Ser Ser Tyr Gly Ala Pro
225                 230                 235                 240
Gly Ala Gly Gly Ser Asn Gly Asn Gly Gly Ser Arg Pro Ser Ser Thr
                    245                 250                 255
Tyr Gly Ala Pro Gly Ala Gly Gly Ser Asn Gly Asn Gly Cys Gly Asn
            260                 265                 270
Lys Pro Ser Ser Ser Tyr Gly Ala Pro Ser Ala Gly Ser Asn Gly Asn
                275                 280                 285
Gly Gly Ser Glu Gln Gly Ser Ser Gly Ser Pro Ser Asp Ser Tyr Gly
    290                 295                 300
Pro Pro Ala Ser Gly Thr Gly Arg Gly Arg Asn Gly Gly Gly Gly
305                 310                 315                 320
Ala Gly Gly Gly Arg Arg Gly Gln Pro Asn Gln Glu Tyr Leu Pro Pro
                    325                 330                 335
Asn Gln Gly Asp Asn Gly Asn Asn Gly Gly Ser Gly Gly Asp Asp Gly
                340                 345                 350
Tyr Asp Tyr Ser Gln Ser Gly Asp Gly Gly Gln Gly Gly Ser Gly
            355                 360                 365
Gly Ser Gly Asn Gly Gly Asp Asp Gly Ser Asn Ile Val Glu Tyr Glu
    370                 375                 380
Ala Gly Gln Glu Gly Tyr Arg Pro Gln Ile Arg Tyr Glu Gly Glu Ala
385                 390                 395                 400
Asn Glu Gly Gly Gln Gly Ser Gly Gly Ala Gly Ser Asp Gly Thr
                    405                 410                 415
Asp Gly Tyr Glu Tyr Glu Gln Asn Gly Gly Asp Gly Gly Ala Gly Gly
            420                 425                 430
Ser Gly Gly Pro Gly Thr Gly Gln Asp Leu Gly Glu Asn Gly Tyr Ser
    435                 440                 445
Ser Gly Arg Pro Gly Gly Asp Asn Gly Gly Gly Gly Tyr Ser Asn
                450                 455                 460
Gly Asn Gly Gln Gly Asp Gly Gln Asp Leu Gly Ser Asn Gly Tyr
465                 470                 475                 480
Ser Ser Gly Ala Pro Asn Gly Gln Asn Gly Gly Arg Arg Asn Gly Gly
                    485                 490                 495
```

Gly Gln Asn Asn Asn Gly Gln Gly Tyr Ser Ser Gly Arg Pro Asn Gly
                500                 505                 510

Asn Gly Ser Gly Gly Arg Asn Gly Asn Gly Gly Arg Gly Asn Gly Gly
            515                 520                 525

Gly Tyr Arg Asn Gly Asn Gly Asn Gly Gly Asn Gly Asn Gly Ser
        530                 535                 540

Gly Ser Gly Ser Gly Asn Asn Gly Tyr Asn Tyr Asp Gln Gln Gly Ser
545                 550                 555                 560

Asn Gly Phe Gly Ala Gly Gly Gln Asn Gly Glu Asn Asp Gly Ser Gly
                565                 570                 575

Tyr Arg Tyr Ser
        580

<210> SEQ ID NO 9
<211> LENGTH: 256
<212> TYPE: PRT
<213> ORGANISM: Ctenocephalides felis

<400> SEQUENCE: 9

Ala Asn Gly Asn Gly Phe Glu Gly Ala Ser Asn Gly Leu Ser Ala Thr
1               5                   10                  15

Tyr Gly Ala Pro Asn Gly Gly Phe Gly Gly Asn Gly Asn Gly Gly
            20                  25                  30

Ala Pro Ser Ser Ser Tyr Gly Ala Pro Gly Ala Gly Asn Gly Gly Asn
                35                  40                  45

Gly Gly Gly Arg Pro Ser Ser Ser Tyr Gly Ala Pro Gly Ala Gly Gly
        50                  55                  60

Ser Gly Asn Gly Phe Gly Gly Arg Pro Ser Ser Ser Tyr Gly Ala Pro
65                  70                  75                  80

Gly Asn Gly Asn Gly Ala Asn Gly Gly Arg Gly Gly Arg Pro Ser Ser
                85                  90                  95

Arg Tyr Gly Ala Pro Gly Asn Gly Asn Gly Asn Gly Asn Gly Asn Gly
            100                 105                 110

Gly Arg Pro Ser Ser Ser Tyr Gly Ala Pro Gly Ser Asn Gly Asn Gly
        115                 120                 125

Gly Arg Pro Ser Ser Ser Tyr Gly Ala Pro Gly Ser Gly Asn Gly Phe
    130                 135                 140

Gly Gly Asn Gly Gly Arg Pro Ser Ser Ser Tyr Gly Ala Pro Gly Ala
145                 150                 155                 160

Asn Gly Asn Gly Asn Gly Gly Ala Ile Gly Gln Pro Ser Ser Ser Tyr
                165                 170                 175

Gly Ala Pro Gly Gln Asn Gly Asn Gly Gly Leu Ser Ser Thr Tyr
            180                 185                 190

Gly Ala Pro Gly Ala Gly Asn Gly Gly Phe Gly Gly Asn Gly Gly Gly
        195                 200                 205

Leu Ser Ser Thr Tyr Gly Ala Pro Gly Ser Gly Asn Gly Gly Phe Gly
    210                 215                 220

Gly Asn Gly Leu Ser Ser Thr Tyr Gly Ala Pro Gly Ser Gly Asn Gly
225                 230                 235                 240

Gly Phe Gly Gly Asn Gly Gly Leu Ser Ser Thr Tyr Gly Ala Pro
                245                 250                 255

<210> SEQ ID NO 10
<211> LENGTH: 146
<212> TYPE: PRT

<213> ORGANISM: Ctenocephalides felis

<400> SEQUENCE: 10

Pro Gly Gly Ala Gly Ala Gly Gly Tyr Pro Gly Gly Ala Gly Gly
1               5                   10                  15

Ala Gly Gly Ala Gly Gly Tyr Pro Gly Gly Ser Ala Gly Gly Ala Gly
            20                  25                  30

Gly Tyr Pro Gly Gly Ser Gly Ser Gly Val Gly Gly Tyr Pro Gly Gly
        35                  40                  45

Ser Asn Gly Gly Ala Gly Gly Tyr Pro Gly Gly Ser Asn Gly Gly Ala
    50                  55                  60

Gly Gly Tyr Pro Gly Gly Ser Asn Gly Gly Ala Gly Gly Tyr Pro Gly
65                  70                  75                  80

Gly Ser Asn Gly Gly Ala Gly Gly Tyr Pro Gly Gly Ser Asn Gly Asn
                85                  90                  95

Gly Gly Tyr Ser Asn Gly Gly Ser Asn Gly Gly Ala Gly Gly Tyr
            100                 105                 110

Pro Gly Gly Ser Asn Gly Asn Gly Tyr Pro Gly Ser Gly Ser Asn
        115                 120                 125

Gly Gly Ala Gly Tyr Pro Gly Gly Ser Asn Gly Asn Gly Gly Tyr
    130                 135                 140

Pro Gly
145

<210> SEQ ID NO 11
<211> LENGTH: 201
<212> TYPE: PRT
<213> ORGANISM: Bombus terrestris

<400> SEQUENCE: 11

Phe Asp Gly Gln Asn Gly Ile Gly Gly Asp Ser Gly Arg Asn Gly
1               5                   10                  15

Leu Ser Asn Ser Tyr Gly Val Pro Gly Ser Asn Gly Gly Arg Asn Gly
            20                  25                  30

Asn Gly Arg Gly Asn Gly Phe Gly Gly Gln Pro Ser Ser Ser Tyr
        35                  40                  45

Gly Ala Pro Ser Asn Gly Leu Gly Asn Gly Gly Ser Gly Ala Gly
    50                  55                  60

Arg Pro Ser Ser Ser Tyr Gly Ala Pro Gly Gly Asn Gly Phe Gly
65                  70                  75                  80

Gly Gly Gln Pro Ser Ser Ser Tyr Gly Ala Pro Ser Asn Gly Leu Gly
                85                  90                  95

Gly Asn Gly Ala Gly Arg Pro Ser Ser Ser Tyr Gly Ala Pro Gly Gly
            100                 105                 110

Gly Asn Gly Phe Gly Gly Gly Ser Asn Gly Ala Gly Lys Asn Gly Phe
        115                 120                 125

Gly Gly Ala Pro Ser Asn Ser Tyr Gly Pro Pro Glu Asn Gly Asn Gly
    130                 135                 140

Phe Gly Gly Asn Gly Gly Ser Pro Ser Gly Leu Tyr Gly Pro
145                 150                 155                 160

Pro Gly Arg Asn Gly Gly Asn Gly Gly Asn Gly Gly Asn Gly Gly Asn
                165                 170                 175

Gly Gly Arg Pro Ser Ser Ser Tyr Gly Thr Pro Glu Arg Asn Gly Gly
            180                 185                 190

Arg Pro Ser Gly Leu Tyr Gly Pro Pro

<210> SEQ ID NO 12
<211> LENGTH: 183
<212> TYPE: PRT
<213> ORGANISM: Tribolium castaneum

<400> SEQUENCE: 12

Asn Gly Phe Gly Gly Gln Asn Gly Arg Leu Ser Ser Thr Tyr
1               5                   10                  15

Gly Pro Pro Gly Gln Gly Gly Asn Gly Phe Gly Gly Gln Asn Gly
            20                  25                  30

Gly Arg Pro Ser Ser Thr Tyr Gly Pro Pro Gly Gln Gly Gly Asn Gly
        35                  40                  45

Phe Gly Gly Gln Asn Gly Gly Arg Pro Ser Ser Thr Tyr Gly Pro
    50                  55                  60

Pro Gly Gln Gly Gly Asn Gly Phe Gly Gly Gln Asn Gly Gly Arg
65                  70                  75                  80

Pro Ser Ser Thr Tyr Gly Pro Pro Gly Gln Gly Gly Asn Gly Phe Gly
                85                  90                  95

Gly Gly Gln Asn Gly Gly Arg Pro Ser Ser Thr Tyr Gly Pro Pro Gly
            100                 105                 110

Gln Gly Gly Asn Gly Phe Gly Gly Gln Asn Gly Gly Arg Pro Ser
        115                 120                 125

Ser Thr Tyr Gly Pro Pro Gly Gln Gly Gly Asn Gly Phe Gly Gly Gly
    130                 135                 140

Gln Asn Gly Gly Lys Pro Ser Ser Thr Tyr Gly Pro Pro Gly Gln Gly
145                 150                 155                 160

Gly Asn Gly Phe Gly Gly Gln Asn Gly Gly Arg Pro Ser Ser Thr
                165                 170                 175

Tyr Gly Pro Pro Gly Gln Gly
            180

<210> SEQ ID NO 13
<211> LENGTH: 551
<212> TYPE: PRT
<213> ORGANISM: Tribolium castaneum

<400> SEQUENCE: 13

Arg Ala Glu Pro Pro Val Asn Ser Tyr Leu Pro Pro Ser Gln Asn Gly
1               5                   10                  15

Gly Pro Ser Ser Thr Tyr Gly Pro Pro Gly Phe Gln Pro Gly Thr Pro
            20                  25                  30

Leu Gly Gly Gly Asn Gly Gly His Pro Ser Gln Gly Gly Asn
        35                  40                  45

Gly Gly Phe Gly Gly Arg His Pro Asp Ser Asp Gln Arg Pro Gly Thr
    50                  55                  60

Ser Tyr Leu Pro Pro Gly Gln Asn Gly Gly Ala Gly Arg Pro Gly Val
65                  70                  75                  80

Thr Tyr Gly Pro Pro Gly Gln Gly Gly Gln Asn Gly Gly Pro
                85                  90                  95

Ser Ser Thr Tyr Gly Pro Pro Gly Gln Gly Gly Asn Gly Phe Gly Gly
            100                 105                 110

Gly Gln Asn Gly Gly Arg Leu Ser Ser Thr Tyr Gly Pro Pro Gly Gln
        115                 120                 125

Gly Gly Asn Gly Phe Gly Gly Gly Gln Asn Gly Gly Arg Pro Ser Ser

```
            130                 135                 140
Thr Tyr Gly Pro Pro Gly Gln Gly Gly Asn Gly Phe Gly Gly Gln
145                 150                 155                 160

Asn Gly Gly Arg Pro Ser Ser Thr Tyr Gly Pro Pro Gly Gln Gly Gly
                165                 170                 175

Asn Gly Phe Gly Gly Gln Asn Gly Gly Arg Pro Ser Ser Thr Tyr
            180                 185                 190

Gly Pro Pro Gly Gln Gly Gly Asn Gly Phe Gly Gly Gln Asn Gly
                195                 200                 205

Gly Arg Pro Ser Ser Thr Tyr Gly Pro Pro Gly Gln Gly Gly Asn Gly
            210                 215                 220

Phe Gly Gly Gln Asn Gly Gly Arg Pro Ser Ser Thr Tyr Gly Pro
225                 230                 235                 240

Pro Gly Gln Gly Gly Asn Gly Phe Gly Gly Gln Asn Gly Gly Lys
                245                 250                 255

Pro Ser Ser Thr Tyr Gly Pro Pro Gly Gln Gly Gly Asn Gly Phe Gly
                260                 265                 270

Gly Gly Gln Asn Gly Gly Arg Pro Ser Ser Thr Tyr Gly Pro Pro Gly
            275                 280                 285

Gln Gly Gly Asn Gly Asn Gly Gly His Asn Gly Gln Arg Pro Gly
        290                 295                 300

Gly Ser Tyr Leu Pro Pro Ser Gln Gly Gly Asn Gly Gly Tyr Pro Ser
305                 310                 315                 320

Gly Gly Pro Gly Gly Tyr Pro Ser Gly Gly Pro Gly Gly Asn Gly Gly
                325                 330                 335

Tyr Gly Gly Glu Glu Glu Ser Thr Glu Pro Ala Lys Tyr Glu Phe Glu
            340                 345                 350

Tyr Gln Val Asp Asp Glu His Asn Thr His Phe Gly His Gln Glu
        355                 360                 365

Ser Arg Asp Gly Asp Lys Ala Thr Gly Glu Tyr Asn Val Leu Leu Pro
370                 375                 380

Asp Gly Arg Lys Gln Val Val Gln Tyr Glu Ala Asp Ser Glu Gly Tyr
385                 390                 395                 400

Lys Pro Lys Ile Ser Tyr Glu Gly Gly Asn Gly Asn Gly Gly Tyr Pro
                405                 410                 415

Ser Gly Gly Pro Gly Gly Ala Gly Asn Gly Gly Tyr Pro Ser Gly Gly
                420                 425                 430

Pro Gln Gly Gly Asn Gly Gly Tyr Pro Ser Gly Gly Pro Gln Gly Gly
            435                 440                 445

Asn Gly Gly Tyr Pro Ser Gly Gly Pro Gln Gly Gly Asn Gly Gly Tyr
        450                 455                 460

Pro Ser Gly Gly Pro Gln Gly Gly Asn Gly Gly Tyr Pro Ser Gly Gly
465                 470                 475                 480

Pro Gln Gly Gly Asn Gly Gly Tyr Pro Ser Gly Gly Pro Gln Gly Gly
                485                 490                 495

Asn Gly Gly Tyr Pro Ser Gly Gly Pro Gln Gly Gly Asn Gly Gly Tyr
            500                 505                 510

Pro Ser Gly Gly Pro Gln Gly Gly Asn Gly Gly Tyr Thr Ser Gly Gly
        515                 520                 525

Pro Gln Gly Gly Asn Gly Gly Tyr Pro Ser Gly Gly Pro Gln Gly Gly
        530                 535                 540

Asn Gly Gly Ser Gly Pro Tyr
545                 550
```

<210> SEQ ID NO 14
<211> LENGTH: 444
<212> TYPE: PRT
<213> ORGANISM: Tribolium castaneum

<400> SEQUENCE: 14

```
Gln Leu Thr Lys Arg Asp Ala Pro Leu Ser Gly Gly Tyr Pro Ser Gly
1               5                   10                  15

Gly Pro Ala Asn Ser Tyr Leu Pro Pro Gly Gly Ala Ser Gln Pro Ser
            20                  25                  30

Gly Asn Tyr Gly Ala Pro Ser Gly Gly Phe Gly Lys Ser Gly Gly
        35                  40                  45

Phe Gly Gly Ser Gly Gly Phe Gly Gly Ala Pro Ser Gln Ser Tyr Gly
    50                  55                  60

Ala Pro Ser Gly Gly Phe Gly Gly Ser Ser Ser Phe Gly Lys Ser Gly
65                  70                  75                  80

Gly Phe Gly Gly Ala Pro Ser Gln Ser Tyr Gly Ala Pro Ser Gly Gly
                85                  90                  95

Phe Gly Gly Ser Ser Ser Phe Gly Lys Ser Gly Gly Phe Gly Gly
            100                 105                 110

Ala Pro Ser Gln Ser Tyr Gly Ala Pro Ser Gly Gly Phe Gly Gly Ser
            115                 120                 125

Ser Ser Phe Gly Lys Ser Gly Gly Phe Gly Gly Ala Pro Ser Gln Ser
    130                 135                 140

Tyr Gly Ala Pro Ser Gly Gly Phe Gly Gly Ser Ser Ser Phe Gly Lys
145                 150                 155                 160

Ser Gly Gly Phe Gly Gly Ala Pro Ser Gln Ser Tyr Gly Ala Pro Ser
                165                 170                 175

Gly Gly Phe Gly Gly Lys Ser Ser Phe Ser Ser Ala Pro Ser Gln
            180                 185                 190

Ser Tyr Gly Ala Pro Ser Gly Gly Phe Gly Gly Lys Ser Gly Gly Phe
    195                 200                 205

Gly Gly Ala Pro Ser Gln Ser Tyr Gly Ala Pro Ser Gly Gly Phe Gly
210                 215                 220

Gly Lys Ser Gly Gly Phe Gly Gly Ala Pro Ser Gln Ser Tyr Gly Ala
225                 230                 235                 240

Pro Ser Gly Gly Phe Gly Gly Ser Ser Ser Phe Gly Lys Ser Gly Gly
                245                 250                 255

Phe Gly Gly Ala Pro Ser Gln Ser Tyr Gly Ala Pro Ser Gly Gly Phe
            260                 265                 270

Gly Gly Ser Ser Ser Phe Gly Lys Ser Gly Phe Gly His Gly Ser
    275                 280                 285

Gly Ala Pro Ser Gln Ser Tyr Gly Ala Pro Arg Ser Gln Pro Gln
        290                 295                 300

Ser Asn Tyr Leu Pro Pro Ser Thr Ser Tyr Gly Thr Pro Val Ser Ser
305                 310                 315                 320

Ala Lys Ser Ser Gly Ser Phe Gly Gly Ala Pro Ser Gln Ser Tyr Gly
                325                 330                 335

Ala Pro Ser Gln Ser His Ala Pro Gln Ser Tyr Gly Ala Pro Ser
            340                 345                 350

Arg Ser Phe Ser Gln Ala Pro Ser Gln Ser Tyr Gly Ala Pro Ser Gln
    355                 360                 365

Gly His Ala Pro Ala Pro Gln Gln Ser Tyr Ser Ala Pro Ser Gln Ser
```

```
                    370                 375                 380
Tyr Gly Ala Pro Ser Gly Gly Phe Gly Gly His Gly Gly Phe Gly
385                 390                 395                 400

Gly Gln Gly Gln Gly Phe Gly Gly Arg Ser Gln Pro Ser Gln Ser
                    405                 410                 415

Tyr Gly Ala Pro Ala Pro Ser Gln Ser Tyr Gly Ala Pro Ser Ala Gly
                420                 425                 430

Gly Gln Gln Tyr Ala Ser Asn Gly Gly Tyr Ser Tyr
                435                 440

<210> SEQ ID NO 15
<211> LENGTH: 426
<212> TYPE: PRT
<213> ORGANISM: Apis mellifera

<400> SEQUENCE: 15

Arg Ser Glu Pro Pro Val Asn Ser Tyr Leu Pro Pro Ser Gly Asn Gly
1               5                   10                  15

Asn Gly Gly Gly Gly Gly Ser Ser Asn Val Tyr Gly Pro Pro Gly
                20                  25                  30

Phe Asp Gly Gln Asn Gly Ile Gly Glu Gly Asp Asn Gly Arg Asn Gly
            35                  40                  45

Ile Ser Asn Ser Tyr Gly Val Pro Thr Gly Gly Asn Gly Tyr Asn Gly
        50                  55                  60

Asp Ser Ser Gly Asn Gly Arg Pro Gly Thr Asn Gly Gly Arg Asn Gly
65                  70                  75                  80

Asn Gly Asn Gly Arg Gly Asn Gly Tyr Gly Gly Gln Pro Ser Asn
                85                  90                  95

Ser Tyr Gly Pro Pro Ser Asn Gly His Gly Asn Gly Ala Gly Arg
            100                 105                 110

Pro Ser Ser Ser Tyr Gly Ala Pro Gly Gly Gly Asn Gly Phe Ala Gly
        115                 120                 125

Gly Ser Asn Gly Lys Asn Gly Phe Gly Gly Gly Pro Ser Ser Ser Tyr
    130                 135                 140

Gly Pro Pro Glu Asn Gly Asn Gly Phe Asn Gly Gly Asn Gly Gly Pro
145                 150                 155                 160

Ser Gly Leu Tyr Gly Pro Pro Gly Arg Asn Gly Gly Asn Gly Gly Asn
                165                 170                 175

Gly Gly Asn Gly Gly Arg Pro Ser Gly Ser Tyr Gly Thr Pro Glu Arg
            180                 185                 190

Asn Gly Gly Arg Leu Gly Gly Leu Tyr Gly Ala Pro Gly Arg Asn Gly
        195                 200                 205

Asn Asn Gly Gly Asn Gly Tyr Pro Ser Gly Gly Leu Asn Gly Gly Asn
    210                 215                 220

Gly Gly Tyr Pro Ser Gly Gly Pro Gly Asn Gly Gly Ala Asn Gly Gly
225                 230                 235                 240

Tyr Pro Ser Gly Gly Ser Asn Gly Asp Asn Gly Gly Tyr Pro Ser Gly
                245                 250                 255

Gly Pro Asn Gly Asn Gly Asn Gly Asn Gly Gly Tyr Gly Gln Asp Glu
            260                 265                 270

Asn Asn Glu Pro Ala Lys Tyr Glu Phe Ser Tyr Glu Val Lys Asp Glu
        275                 280                 285

Gln Ser Gly Ala Asp Tyr Gly His Thr Glu Ser Arg Asp Gly Asp Arg
    290                 295                 300
```

Ala Gln Gly Glu Phe Asn Val Leu Leu Pro Asp Gly Arg Lys Gln Ile
305                 310                 315                 320

Val Glu Tyr Glu Ala Asp Gln Asp Gly Phe Lys Pro Gln Ile Arg Tyr
            325                 330                 335

Glu Gly Glu Ala Asn Ser Gln Gly Tyr Gly Ser Gly Gly Pro Gly Gly
            340                 345                 350

Asn Gly Gly Asp Asn Gly Tyr Pro Ser Gly Pro Gly Asn Gly
            355                 360                 365

Tyr Ser Ser Gly Arg Pro Asn Gly Gly Ser Asp Phe Ser Asp Gly Gly
    370                 375                 380

Tyr Pro Ser Thr Arg Pro Gly Gly Glu Asn Gly Gly Tyr Arg Asn Gly
385                 390                 395                 400

Asn Asn Gly Gly Asn Gly Asn Gly Gly Tyr Pro Ser Gly Asn Gly Gly
            405                 410                 415

Asp Ala Ala Ala Asn Gly Gly Tyr Gln Tyr
            420                 425

<210> SEQ ID NO 16
<211> LENGTH: 318
<212> TYPE: PRT
<213> ORGANISM: Apis mellifera

<400> SEQUENCE: 16

Asp Ala Pro Ile Ser Gly Ser Tyr Leu Pro Ser Thr Ser Tyr Gly
1               5                   10                  15

Thr Pro Asn Leu Gly Gly Gly Pro Ser Ser Thr Tyr Gly Ala Pro
            20                  25                  30

Ser Gly Gly Gly Gly Arg Pro Ser Ser Tyr Gly Ala Pro Ser
    35                  40                  45

Ser Thr Tyr Gly Ala Pro Ser Thr Tyr Gly Ala Pro Ser Asn Gly
    50                  55                  60

Gly Gly Arg Pro Ser Ser Thr Tyr Gly Ala Pro Ser Asn Gly Gly
65                  70                  75                  80

Arg Pro Ser Ser Ser Tyr Gly Ala Pro Ser Ser Tyr Gly Ala Pro
            85                  90                  95

Ser Ser Thr Tyr Gly Ala Pro Ser Asn Gly Gly Arg Pro Ser Ser
            100                 105                 110

Ser Tyr Gly Ala Pro Ser Phe Gly Gly Gly Gly Phe Gly Gly Gly
            115                 120                 125

Asn Gly Leu Ser Thr Ser Tyr Gly Ala Pro Ser Arg Gly Gly Gly Gly
    130                 135                 140

Gly Gly Gly Ser Ile Ser Ser Ser Tyr Gly Ala Pro Thr Gly Gly
145                 150                 155                 160

Gly Gly Gly Pro Ser Thr Thr Tyr Gly Ala Pro Asn Gly Gly Asn
            165                 170                 175

Gly Tyr Ser Arg Pro Ser Ser Tyr Gly Thr Pro Ser Thr Gly Gly
    180                 185                 190

Gly Ser Phe Gly Gly Ser Gly Gly Tyr Ser Gly Gly Gly Gly Tyr
    195                 200                 205

Ser Gly Gly Gly Asn Gly Tyr Ser Gly Gly Gly Gly Tyr Ser
    210                 215                 220

Gly Gly Asn Gly Gly Gly Tyr Ser Gly Gly Asn Gly Gly Tyr
225                 230                 235                 240

Ser Gly Gly Asn Gly Gly Gly Tyr Ser Gly Gly Gly Gly Gly Tyr
            245                 250                 255

```
Ser Gly Gly Gly Gly Gly Tyr Ser Gly Gly Asn Gly Tyr Ser
            260                 265                 270

Gly Gly Gly Gly Gly Tyr Ser Gly Gly Asn Gly Tyr Ser Gly
        275                 280                 285

Gly Asn Gly Gly Tyr Ser Gly Gly Gly Gly Tyr Ser Gly Gly
    290                 295                 300

Gly Gly Gly Gln Ser Tyr Ala Ser Asn Gly Gly Tyr Gln Tyr
305                 310                 315

<210> SEQ ID NO 17
<211> LENGTH: 747
<212> TYPE: PRT
<213> ORGANISM: Nasonia vitripennis

<400> SEQUENCE: 17

Arg Pro Glu Pro Pro Val Asn Ser Tyr Leu Pro Pro Gly Gln Gly Gly
1               5                   10                  15

Gly Phe Gly Gly Gly Arg Pro Ser Gly Ala Ser Pro Ser Asp Gln Tyr
            20                  25                  30

Gly Pro Pro Asp Phe Gln Gly Ala Gly Gly Arg Gly Gly Gln Ala Ala
        35                  40                  45

Gly Gly Asn Phe Gly Gly Gly Asn Gly Phe Gly Gly Ala Pro Ser
    50                  55                  60

Ser Ser Tyr Gly Pro Pro Gly Phe Gly Ser Asn Glu Pro Asn Lys Phe
65                  70                  75                  80

Ser Gly Ala Gly Gly Gly Ala Gly Arg Pro Gln Asp Ser Tyr Gly
            85                  90                  95

Pro Pro Ala Gly Gly Asn Gly Phe Ala Gly Ser Ala Gly Ala Gly Asn
        100                 105                 110

Ser Gly Arg Pro Gly Gly Ala Ala Gly Gly Arg Pro Ser Asp Ser
    115                 120                 125

Tyr Gly Pro Pro Gln Gly Gly Ser Gly Phe Gly Gly Gly Asn Ala
    130                 135                 140

Gly Arg Pro Ser Asp Ser Tyr Gly Pro Pro Ser Ala Gly Gly Gly Gly
145                 150                 155                 160

Phe Gly Gly Gly Ser Pro Gly Gly Gly Phe Gly Gly Ser Pro Gly
            165                 170                 175

Gly Gly Phe Gly Gly Gly Asn Gln Gly Ala Pro Gln Ser Ser Tyr Gly
        180                 185                 190

Pro Pro Ala Ser Gly Phe Gly Gly Gln Gly Gly Ala Gly Gln Gly Arg
    195                 200                 205

Pro Ser Asp Ser Tyr Gly Pro Pro Gly Gly Gly Ser Gly Gly Arg Pro
    210                 215                 220

Ser Gln Gly Gly Asn Gly Phe Gly Gly Asn Ala Gly Arg Pro Ser
225                 230                 235                 240

Asp Ser Tyr Gly Pro Pro Ala Ala Gly Gly Gly Phe Gly Gly Asn
            245                 250                 255

Ala Gly Gly Asn Gly Gly Gly Asn Gly Phe Gly Gly Arg Pro Ser
        260                 265                 270

Gly Ser Pro Gly Gly Phe Gly Gln Gly Gly Gly Arg Pro Ser
    275                 280                 285

Asp Ser Tyr Leu Pro Pro Ser Gly Gly Ser Gly Phe Gly Gly Asn
    290                 295                 300

Gly Arg Gln Pro Gly Gly Phe Gly Gln Gln Gly Gly Asn Gly Ala Gly
```

```
                    305                 310                 315                 320
             Gln Gln Asn Gly Gly Gly Ala Gly Arg Pro Ser Ser Ser Tyr Gly
                             325                 330                 335

Pro Pro Ser Asn Gly Asn Gly Gly Phe Ser Gly Gln Asn Gly Gly
                             340                 345                 350

Arg Gly Ser Pro Ser Gly Gly Gly Phe Gly Gly Ala Gly Gly Ser
                             355                 360                 365

Pro Ser Ser Ser Tyr Gly Pro Pro Ala Gly Ser Gly Phe Gly Asn
                             370                 375                 380

Asn Gly Gly Ala Gly Gly Arg Pro Ser Ser Tyr Gly Pro Pro Ser
             385                 390                 395                 400

Ser Gly Gly Asn Gly Phe Gly Ser Gly Gly Gln Gly Gln Gly Gly
                                 405                 410                 415

Gln Gly Gly Gln Gly Gly Arg Pro Ser Ser Ser Tyr Gly Pro Ser
                             420                 425                 430

Asn Gly Asn Gly Gly Phe Gly Gly Gly Asn Gly Gly Arg Pro Ser Ser
             435                 440                 445

Asn Gly Tyr Pro Gln Gly Gln Gly Asn Gly Asn Gly Gly Phe Gly Gly
                 450                 455                 460

Gln Gly Gly Asn Gly Gly Arg Pro Ser Ser Ser Tyr Gly Pro Pro Gly
             465                 470                 475                 480

Gly Asp Ser Gly Tyr Pro Ser Gly Gly Pro Ser Gly Asn Phe Gly Gly
                             485                 490                 495

Ser Asn Ala Gly Gly Gly Gly Gly Phe Gly Gly Gln Val Gln Asp
                             500                 505                 510

Ser Tyr Gly Pro Pro Ser Gly Ala Val Asn Gly Asn Gly Asn Gly
                             515                 520                 525

Tyr Ser Ser Gly Gly Pro Gly Asn Gly Leu Asp Glu Gly Asn Asp
                             530                 535                 540

Glu Pro Ala Lys Tyr Glu Phe Ser Tyr Glu Val Lys Asp Asp Gln Ser
             545                 550                 555                 560

Asp Gly Arg Lys Gln Ile Val Glu Tyr Glu Ala Asp Gln Asp Gly Phe
                             565                 570                 575

Lys Pro Gln Ile Arg Tyr Glu Gly Glu Ala Asn Thr Gly Ala Gly Gly
                             580                 585                 590

Ala Gly Gly Tyr Pro Ser Gly Gly Gly Gly Asp Ser Gly Tyr Pro Ser
                             595                 600                 605

Gly Pro Ser Gly Ala Gly Gly Asn Ala Gly Tyr Pro Ser Gly Gly Gly
                             610                 615                 620

Gly Gly Ala Gly Gly Phe Gly Gly Asn Gly Gly Ser Asn Gly Tyr
             625                 630                 635                 640

Pro Ser Gly Gly Pro Ser Gly Gln Gly Gln Phe Gly Gly Gln Gln
                             645                 650                 655

Gly Gly Asn Gly Gly Tyr Pro Ser Gly Pro Gln Gly Gly Ser Gly Phe
                             660                 665                 670

Gly Gly Gly Ser Gln Gly Ser Gly Ser Gly Gly Tyr Pro Ser Gly Gly
                             675                 680                 685

Pro Gly Gly Asn Gly Gly Asn Asn Asn Phe Gly Gly Gly Asn Ala Gly
                             690                 695                 700

Tyr Pro Ser Gly Gly Pro Ser Gly Gly Asn Gly Phe Asn Gln Gly Gly
             705                 710                 715                 720

Gln Asn Gln Gly Gly Ser Gly Gly Gly Tyr Pro Ser Gly Ser Gly Gly
                             725                 730                 735
```

Asp Ala Ala Ala Asn Gly Gly Tyr Gln Tyr Ser
            740                 745

<210> SEQ ID NO 18
<211> LENGTH: 419
<212> TYPE: PRT
<213> ORGANISM: Nasonia vitripennis

<400> SEQUENCE: 18

Arg Ala Glu Ala Pro Ile Ser Gly Asn Tyr Leu Pro Pro Ser Thr Ser
1               5                   10                  15

Tyr Gly Thr Pro Asn Leu Gly Gly Gly Gly Gly Gly Gly Gly Gly Phe
            20                  25                  30

Gly Gly Gly Ala Pro Ser Ser Ser Tyr Gly Ala Pro Ser Ser Gly Gly
        35                  40                  45

Gly Phe Gly Gly Ser Phe Gly Gly Ala Pro Ser Ser Ser Tyr Gly
    50                  55                  60

Ala Pro Ser Thr Gly Gly Ser Phe Gly Gly Ala Pro Ser Ser Ser
65                  70                  75                  80

Tyr Gly Ala Pro Ser Ser Gly Gly Ser Phe Gly Gly Ser Phe Gly Gly
            85                  90                  95

Gly Ala Pro Ser Ser Ser Tyr Gly Ala Pro Ser Phe Gly Gly Asn Ala
        100                 105                 110

Pro Ser Ser Ser Tyr Gly Ala Pro Ala Gly Gly Ser Phe Gly Gly
    115                 120                 125

Gly Ala Pro Ser Asn Ser Tyr Gly Pro Pro Ser Ser Ser Tyr Gly Ala
130                 135                 140

Pro Ser Ala Gly Gly Ser Phe Gly Gly Ser Ser Gly Gly Ser Phe Gly
145                 150                 155                 160

Gly Ser Phe Gly Gly Gly Ala Pro Ser Ser Ser Tyr Gly Ala Pro Ala
            165                 170                 175

Pro Ser Arg Pro Ser Ser Asn Tyr Gly Ala Pro Ser Arg Pro Ser Ser
        180                 185                 190

Asn Tyr Gly Ala Pro Ser Ser Gly Gly Ser Phe Gly Gly Gly Ser
    195                 200                 205

Gly Phe Gly Gly Gly Arg Pro Ser Ser Tyr Gly Ala Pro Ser Ser
210                 215                 220

Gly Ser Phe Gly Gly Gly Phe Gly Gly Gly Ala Pro Ser Ser Ser Tyr
225                 230                 235                 240

Gly Ala Pro Ala Pro Ser Arg Pro Ser Ser Asn Tyr Gly Ala Pro Ala
            245                 250                 255

Pro Ser Arg Pro Ser Ser Asn Tyr Gly Ala Pro Ala Pro Ser Arg Pro
        260                 265                 270

Ser Ser Ser Tyr Gly Ala Pro Ser Arg Pro Ser Ser Asn Tyr Gly Ala
    275                 280                 285

Pro Ser Arg Pro Ser Ser Asn Tyr Gly Ala Pro Ser Ser Gly Gly Ser
    290                 295                 300

Gly Phe Gly Gly Gly Ser Gly Phe Gly Gly Arg Pro Ser Ser Ser
305                 310                 315                 320

Tyr Gly Ala Pro Ser Ser Gly Ser Phe Gly Gly Gly Phe Gly Gly Gly
            325                 330                 335

Ala Pro Ser Ser Ser Tyr Gly Ala Pro Ala Pro Ser Arg Pro Ser Ser
        340                 345                 350

Asn Tyr Gly Pro Pro Ser Ser Ser Tyr Gly Ala Pro Ser Ser Gly Gly

```
                355                 360                 365
Ser Gly Gly Phe Gly Gly Ala Pro Ser Ser Tyr Gly Ala Pro
    370                 375                 380

Ser Phe Gly Gly Ser Ser Asn Ala Val Ser Arg Pro Ser Ser Tyr
385                 390                 395                 400

Gly Ala Pro Ser Ser Gly Gly Gln Ser Tyr Ala Ser Asn Gly Gly
                405                 410                 415

Tyr Gln Tyr

<210> SEQ ID NO 19
<211> LENGTH: 396
<212> TYPE: PRT
<213> ORGANISM: Pediculus humanus

<400> SEQUENCE: 19

Glu Pro Pro Val Lys Thr Ser Tyr Leu Pro Ser Ala Ser Arg Ser
1               5                   10                  15

Leu Asn Ser Gln Tyr Gly Ala Pro Ala Phe Thr Asp Ser Asn Glu Leu
                20                  25                  30

Val Ala Pro Ser Pro Asn Ser Asn Phe His Asp Ser Tyr Asn Gln Gln
                35                  40                  45

Gln Gln Ser Phe Asp Leu Ser Asn Gly Leu Ser Val Pro Ser Ala Ala
            50                  55                  60

Gly Arg Leu Ser Asn Thr Tyr Gly Val Pro Ser Ala Gln Gly Ala Asn
65                  70                  75                  80

Val Pro Ser Phe Asp Ser Ser Asp Ser Ile Ala Val Asp Ala Ala Gly
                85                  90                  95

Arg Ser Gly Asn Ser Phe Ser Ser His Val Pro Ser Ser Thr Tyr Gly
                100                 105                 110

Ala Pro Gly Asn Gly Phe Gly Gly Ser Arg Ser Ser Gln Ser Gly
            115                 120                 125

Ala Pro Ser Ser Val Tyr Gly Pro Pro Gln Ala Arg Asn Asn Asn Phe
            130                 135                 140

Gly Asn Gly Ala Ala Pro Ser Ser Val Tyr Gly Pro Pro Gln Ala Arg
145                 150                 155                 160

Asn Asn Asn Phe Gly Asn Gly Ala Pro Ser Gln Val Tyr Gly Pro
                165                 170                 175

Pro Lys Ala Arg Asn Asn Asn Phe Gly Asn Gly Ala Ala Pro Ser Ser
                180                 185                 190

Val Tyr Gly Pro Pro Gln Ala Arg Asn Asn Asn Phe Gly Asn Gly Ala
            195                 200                 205

Ala Pro Ser Ser Val Tyr Gly Pro Pro Gln Ala Arg Asn Asn Asn Phe
            210                 215                 220

Ala Asn Ser Ala Ala Pro Ser Gln Val Tyr Gly Pro Pro Gln Ala Arg
225                 230                 235                 240

Asn Asn Asn Phe Gly Asn Gly Ala Ala Pro Ser Ser Val Tyr Gly Pro
                245                 250                 255

Pro Gln Ser Ser Ser Phe Ser Ser Pro Ser Gly Arg Ser Gly Gln Leu
            260                 265                 270

Pro Ser Ala Thr Tyr Gly Ala Pro Phe Glu Arg Asn Gly Phe Gly Ser
            275                 280                 285

Gln Gly Ser Ser Gly Phe Gln Gly Tyr Glu Pro Ser Lys Arg Ser Gln
            290                 295                 300

Thr Thr Glu Asp Pro Phe Ala Glu Pro Ala Lys Tyr Glu Tyr Asp Tyr
```

```
            305                 310                 315                 320

Lys Val Gln Ala Ser Asp Glu Thr Gly Thr Glu Phe Gly His Lys Glu
                325                 330                 335

Ser Arg Glu Asn Glu Ser Ala Arg Gly Ala Tyr His Val Leu Leu Pro
                340                 345                 350

Asp Gly Arg Met Gln Ile Val Gln Tyr Glu Ala Asp Glu Thr Gly Tyr
                355                 360                 365

Arg Pro Gln Ile Arg Tyr Glu Asp Thr Gly Tyr Pro Ser Ala Ala Ser
                370                 375                 380

Ser Arg Ser Asn Asn Gly Phe Asn Gly Tyr Gln Tyr
385                 390                 395

<210> SEQ ID NO 20
<211> LENGTH: 573
<212> TYPE: PRT
<213> ORGANISM: Anopheles gambiae

<400> SEQUENCE: 20

Lys Arg Glu Ala Pro Leu Pro Pro Ser Gly Ser Tyr Leu Pro Pro Ser
1               5                   10                  15

Gly Gly Ala Gly Gly Tyr Pro Ala Ala Gln Thr Pro Ser Ser Ser Tyr
                20                  25                  30

Gly Ala Pro Thr Gly Gly Ala Gly Ser Trp Gly Gly Asn Gly Gly Asn
                35                  40                  45

Gly Gly Arg Gly His Ser Asn Gly Gly Ser Ser Phe Gly Gly Ser
    50                  55                  60

Ala Pro Ser Ala Pro Ser Gln Ser Tyr Gly Ala Pro Ser Phe Gly Gly
65                  70                  75                  80

Gln Ser Ser Gly Gly Phe Gly Gly His Ser Ser Gly Gly Phe Gly Gly
                85                  90                  95

His Ser Ser Gly Gly His Gly Gly Asn Gly Asn Gly Asn Gly Asn Gly
                100                 105                 110

Tyr Ser Ser Gly Arg Pro Ser Ser Gln Tyr Gly Pro Pro Gln Gln Gln
                115                 120                 125

Gln Gln Gln Gln Ser Phe Arg Pro Pro Ser Thr Ser Tyr Gly Val Pro
                130                 135                 140

Ala Ala Pro Ser Gln Ser Tyr Gly Ala Pro Ala Gln His Ser Asn
145                 150                 155                 160

Gly Gly Asn Gly Gly Tyr Ser Ser Gly Arg Pro Ser Thr Gln Tyr Gly
                165                 170                 175

Ala Pro Ala Gln Ser Asn Gly Asn Gly Phe Gly Asn Gly Arg Pro Ser
                180                 185                 190

Ser Ser Tyr Gly Ala Pro Ala Arg Pro Ser Thr Gln Tyr Gly Ala Pro
                195                 200                 205

Ser Ala Gly Asn Gly Asn Gly Tyr Ala Gly Asn Gly Asn Gly Arg Ser
                210                 215                 220

Tyr Ser Asn Gly Asn Gly Asn Gly His Gly Asn Gly His Ser Asn Gly
225                 230                 235                 240

Asn Gly Asn Asn Gly Tyr Ser Arg Gly Pro Ala Arg Gln Pro Ser Gln
                245                 250                 255

Gln Tyr Gly Pro Pro Ala Gln Ala Pro Ser Ser Gln Tyr Gly Ala Pro
                260                 265                 270

Ala Gln Thr Pro Ser Ser Gln Tyr Gly Ala Pro Ala Gln Thr Pro Ser
                275                 280                 285
```

```
Ser Gln Tyr Gly Ala Pro Ala Gln Thr Pro Ser Ser Gln Tyr Gly Ala
    290                 295                 300

Pro Ala Gln Thr Pro Ser Ser Gln Tyr Gly Ala Pro Ala Pro Ser Arg
305                 310                 315                 320

Pro Ser Gln Gln Tyr Gly Ala Pro Ala Pro Ser Arg Pro Ser Gln Gln
                325                 330                 335

Tyr Gly Ala Pro Ala Gln Thr Pro Ser Ser Gln Tyr Gly Ala Pro Ala
            340                 345                 350

Gln Thr Pro Ser Ser Gln Tyr Gly Ala Pro Ala Gln Thr Pro Ser Ser
        355                 360                 365

Gln Tyr Gly Ala Pro Ala Gln Thr Pro Ser Ser Gln Tyr Gly Ala Pro
    370                 375                 380

Ala Gln Gln Pro Ser Ser Gln Tyr Gly Ala Pro Ala Pro Ser Arg Pro
385                 390                 395                 400

Ser Gln Gln Tyr Gly Ala Pro Ala Gln Gln Pro Ser Ala Gln Tyr Gly
                405                 410                 415

Ala Pro Ala Gln Thr Pro Ser Ser Gln Tyr Gly Ala Pro Ala Pro Ser
            420                 425                 430

Arg Pro Ser Gln Gln Tyr Gly Ala Pro Ala Gln Ala Pro Ser Ser Gln
        435                 440                 445

Tyr Gly Ala Pro Ala Pro Ser Ser Gln Tyr Gly Ala Pro Ala Gln Gln
    450                 455                 460

Pro Ser Ser Gln Tyr Gly Ala Pro Ala Gln Thr Pro Ser Ser Gln Tyr
465                 470                 475                 480

Gly Ala Pro Ser Phe Gly Pro Thr Gly Gly Ala Ser Phe Ser Ser Gly
                485                 490                 495

Asn Gly Asn Val Gly Gly Ser Tyr Gln Val Ser Ser Thr Gly Asn Gly
                500                 505                 510

Phe Ser Gln Ala Ser Phe Ser Ala Ser Ser Phe Ser Pro Asn Gly Arg
            515                 520                 525

Thr Ser Leu Ser Ala Gly Gly Phe Ser Ser Gly Ala Pro Ser Ala Gln
        530                 535                 540

Ser Ala Gly Gly Tyr Ser Ser Gly Gly Pro Ser Gln Val Pro Ala Thr
545                 550                 555                 560

Leu Pro Gln Ser Tyr Ser Ser Asn Gly Tyr Asn Tyr
                565                 570

<210> SEQ ID NO 21
<211> LENGTH: 513
<212> TYPE: PRT
<213> ORGANISM: Glossina morsitans

<400> SEQUENCE: 21

Arg Pro Glu Pro Pro Val Asn Thr Tyr Leu Pro Pro Ser Ala Gly Gly
1               5                   10                  15

Gly Ser Gly Gly Gly Ser Pro Leu Ala Pro Ser Asp Thr Tyr Gly Ala
            20                  25                  30

Pro Gly Val Asn Gly Gly Gly Gly Gly Gly Pro Ser Ser Thr
        35                  40                  45

Tyr Gly Ala Pro Gly Ser Gly Gly Asn Gly Asn Gly Gly Gly
    50                  55                  60

Phe Gly Lys Pro Ser Ser Thr Tyr Gly Ala Pro Gly Leu Gly Gly
65                  70                  75                  80

Gly Asn Gly Gly Gly Arg Pro Ser Glu Thr Tyr Gly Ala Pro Ser Gly
                85                  90                  95
```

```
Gly Gly Gly Asn Gly Phe Gly Lys Pro Ser Ser Thr Tyr Gly Ala Pro
            100                 105                 110

Asn Gly Gly Gly Asn Gly Pro Gly Arg Pro Ser Ser Thr Tyr
            115                 120                 125

Gly Ala Pro Gly Ser Gly Gly Asn Gly Gly Ser Gly Arg Pro Ser
130                 135                 140

Ser Thr Tyr Gly Ala Pro Gly Leu Gly Gly Gly Asn Gly Gly Ser Gly
145                 150                 155                 160

Arg Pro Ser Ser Met Tyr Gly Ala Pro Gly Leu Gly Gly Gly Asn Gly
                165                 170                 175

Gly Ser Gly Arg Pro Ser Ser Thr Tyr Gly Ala Pro Ser Gly Gly
            180                 185                 190

Gly Asn Gly Gly Ser Gly Arg Pro Ser Ser Thr Tyr Gly Ala Pro Gly
        195                 200                 205

Ser Gly Gly Gly Asn Gly Gly Ser Gly Arg Pro Ser Ser Thr Tyr Gly
210                 215                 220

Ala Pro Gly Asn Gly Asn Gly Gly Asn Gly Phe Gly Arg Pro Ser Ser
225                 230                 235                 240

Thr Tyr Gly Ala Pro Gly Ser Gly Gly Ser Asn Gly Asn Gly Lys Pro
                245                 250                 255

Ser Ser Thr Tyr Gly Ala Pro Gly Ser Gly Gly Gly Gly Arg Pro
            260                 265                 270

Ser Asp Ser Tyr Gly Pro Pro Ala Ser Gly Asn Gly Arg Asn Gly
        275                 280                 285

Asn Gly Asn Gly Gln Ser Gln Glu Tyr Leu Pro Pro Gly Gln Ser Gly
290                 295                 300

Ser Gly Gly Gly Gly Tyr Gly Gly Gly Ser Gly Ser Gly Gly Ser
305                 310                 315                 320

Gly Gly Gly Gly Gly Gly Gly Tyr Gly Gly Asp Gln Asp Asn Asn Val
            325                 330                 335

Val Glu Tyr Glu Ala Asp Gln Glu Gly Tyr Arg Pro Gln Ile Arg Tyr
            340                 345                 350

Glu Gly Asp Gly Ser Gln Gly Gly Phe Gly Gly Asp Gly Asp Gly Tyr
            355                 360                 365

Ser Tyr Glu Gln Asn Gly Val Gly Gly Asp Gly Gly Ala Gly Gly
370                 375                 380

Ala Gly Gly Tyr Ser Asn Gly Gln Asn Leu Gly Ala Asn Gly Tyr Ser
385                 390                 395                 400

Ser Gly Arg Pro Asn Gly Gly Asn Gly Gly Arg Arg Gly Gly Gly
            405                 410                 415

Gly Gly Gly Gly Gly Ser Gly Gly Gln Asn Leu Gly Ser Asn Gly
            420                 425                 430

Tyr Ser Ser Gly Ala Pro Asn Gly Phe Gly Gly Asn Gly Gln Gly
            435                 440                 445

Tyr Ser Gly Gly Arg Ser Asn Gly Asn Gly Gly Gly Gly Gly Arg
            450                 455                 460

Asn Gly Gly Arg Tyr Arg Asn Gly Gly Gly Gly Gly Gly Arg Asn
465                 470                 475                 480

Gly Gly Gly Ser Asn Gly Tyr Asn Tyr Asp Gln Pro Gly Ser Asn Gly
            485                 490                 495

Phe Gly Arg Gly Gly Asn Gly Glu Asn Asp Gly Ser Gly Tyr His
            500                 505                 510
```

Tyr

<210> SEQ ID NO 22
<211> LENGTH: 506
<212> TYPE: PRT
<213> ORGANISM: Atta cephalotes

<400> SEQUENCE: 22

```
Arg Ser Glu Pro Pro Val Asn Ser Tyr Leu His Pro Gly Ser Asp Thr
1               5                   10                  15

Ser Gly Thr Asn Gly Gly Arg Thr Asp Leu Ser Thr Gln Tyr Gly Ala
            20                  25                  30

Pro Asp Phe Asn Asn Arg Gly Asn Gly Asn Ser Gly Ala Thr Ser Phe
        35                  40                  45

Gly Gly Ser Gly Ala Gly Asn Gly Pro Ser Lys Leu Tyr Asp Val Pro
    50                  55                  60

Ile Arg Gly Asn Thr Gly Gly Asn Gly Leu Gly Gln Phe Arg Gly Asn
65                  70                  75                  80

Gly Phe Glu Ser Gly Gln Pro Ser Ser Tyr Gly Ala Pro Lys Gly
                85                  90                  95

Gly Phe Gly Glu Asn Arg Gly Asn Arg Gly Arg Pro Ser Thr Ser Tyr
            100                 105                 110

Gly Val Pro Asp Ser Asn Arg Asn Asn Arg Gly Gly Phe Gly Asn Gly
            115                 120                 125

Gly Ser Glu Ala Arg Pro Ser Thr Ser Tyr Gly Val Pro Gly Ala Asn
130                 135                 140

Gly Asn Gln Gly Gly Phe Gly Ser Gly Ser Ile Gly Gly Arg Pro Ser
145                 150                 155                 160

Thr Ser Tyr Gly Val Pro Gly Ala Asn Gly Asn Asn Gly Asp Ser Phe
            165                 170                 175

Arg Asn Gly Asp Ile Gly Gly Arg Pro Ser Thr Asn Tyr Gly Ala Pro
            180                 185                 190

Gly Ala Asn Gly Asn His Gly Gly Asn Gly Asn Gly Arg Pro
            195                 200                 205

Ser Asn Asn Tyr Gly Val Pro Gly Ala Asn Gly Asn Thr Asn Gly Lys
210                 215                 220

Gly Arg Leu Asn Gly Asn Ser Gly Gly Pro Ser Asn Asn Tyr Gly
225                 230                 235                 240

Ser Pro Asn Gly Phe Gly Lys Gly Leu Ser Thr Ser Tyr Gly Ser Pro
            245                 250                 255

Asn Arg Gly Gly Asn Asp Asn His Tyr Pro Ser Arg Gly Ser Phe Ile
            260                 265                 270

Asn Gly Gly Ile Asn Gly Tyr Ser Ser Gly Ser Pro Asn Gly Asn Ala
            275                 280                 285

Gly Asn Phe Gly His Gly Asp Glu Ser Phe Gly Arg Gly Gly Gly Glu
            290                 295                 300

Gly Glu Asn Thr Gly Glu Gly Tyr Asn Ala Asn Ala Gln Glu Glu Ser
305                 310                 315                 320

Thr Glu Pro Ala Lys Tyr Glu Phe Ser Tyr Lys Val Lys Asp Gln Gln
                325                 330                 335

Thr Gly Ser Asp Tyr Ser His Thr Glu Thr Arg Asp Gly Asp His Ala
            340                 345                 350

Gln Gly Glu Phe Asn Val Leu Leu Pro Asp Gly Arg Lys Gln Ile Val
            355                 360                 365
```

-continued

```
Glu Tyr Glu Ala Asp Gln Asp Gly Phe Lys Pro Gln Ile Arg Tyr Glu
    370                 375                 380

Gly Glu Ala Asn Ala Asp Gly Gly Tyr Gly Ser Gly Leu Asn Asp Asn
385                 390                 395                 400

Asn Asp Gly Tyr Ser Ser Gly Arg Pro Asp Ser Glu Ser Gly Gly Phe
                405                 410                 415

Ala Asn Ser Gly Phe Asn Gly Gly Ser Ser Asn Gly Gly Tyr Pro Asn
            420                 425                 430

Gly Gly Pro Gly Glu Arg Lys Leu Gly Gly Phe Asn Asn Gly Gly Ser
        435                 440                 445

Ser Gly Tyr Gln Ser Gly Arg Ser Ala Gly Gln Ser Phe Gly Arg Asp
    450                 455                 460

Asn Ala Gly Asp Leu Asn Asn Asp Ile Gly Gly Tyr Phe Ser Asn Ser
465                 470                 475                 480

Pro Asn Asn Ile Gly Asp Ser Asp Asn Ala Asn Val Gly Ser Asn Arg
                485                 490                 495

Gln Asn Asp Gly Asn Ser Gly Tyr Gln Tyr
            500                 505

<210> SEQ ID NO 23
<211> LENGTH: 550
<212> TYPE: PRT
<213> ORGANISM: Anopheles darlingi

<400> SEQUENCE: 23

Lys Arg Glu Ala Pro Leu Pro Pro Ser Gly Ser Tyr Leu Pro Pro Ser
1               5                   10                  15

Gly Gly Gly Gly Gly Gly Gly Tyr Pro Ala Ala Gln Thr Pro Ser
            20                  25                  30

Ser Ser Tyr Gly Ala Pro Ala Gly Gly Ala Gly Gly Trp Gly Gly Asn
            35                  40                  45

Gly Asn Gly Asn Gly Asn Gly Asn Gly Gly Arg Gly Gly Tyr Ser Asn
    50                  55                  60

Gly Gly Gly His Ser Gly Ser Ala Pro Ser Gln Ser Tyr Gly Ala Pro
65                  70                  75                  80

Ser Ala Pro Ser Gln Ser Tyr Gly Ala Pro Ser Gln Ser Tyr Gly Ala
                85                  90                  95

Pro Ala Ala Ala Pro Ser Gln Ser Tyr Gly Ala Pro Ser Phe Gly Gly
            100                 105                 110

Asn Gly Gly Gly Ala Ser His Gly Ser Gly Gly Phe Thr Gly Gly His
            115                 120                 125

Gly Gly Asn Gly Asn Gly Asn Gly Tyr Ser Ser Gly Arg Pro Ser Ser
    130                 135                 140

Gln Tyr Gly Pro Pro Gln Gln Gln Gln Gln Gln Gln Gln Ser Phe
145                 150                 155                 160

Arg Pro Pro Ser Thr Ser Tyr Gly Val Pro Ala Ala Pro Ser Ser Ser
                165                 170                 175

Tyr Gly Ala Pro Ser Ala Asn Gly Phe Ser Asn Gly Arg Pro Ser
            180                 185                 190

Ser Gln Tyr Gly Ala Pro Ala Pro Gln Ser Asn Gly Asn Glu Phe Gly
            195                 200                 205

Ala Pro Arg Pro Ser Ser Tyr Gly Ala Pro Ser Arg Pro Ser Thr
    210                 215                 220

Gln Tyr Gly Ala Pro Ser Asn Gly Asn Gly Asn Gly Tyr Ala Gly His
225                 230                 235                 240
```

```
Gly Asn Gly Asn Gly His Gly Asn Gly Asn Gly His Ser Asn Gly Asn
                245                 250                 255

Gly Asn Gly Tyr Asn Arg Gly Pro Ala Arg Gln Pro Ser Ser Gln Tyr
                260                 265                 270

Gly Pro Pro Ser Gln Gly Pro Pro Ser Ser Gln Tyr Gly Pro Pro Ser
                275                 280                 285

Gln Tyr Gly Pro Pro Ser Ser Gly Thr Ser Phe Ile Ala Tyr Gly Pro
                290                 295                 300

Pro Ser Gln Gly Pro Pro Ser Ser Gln Tyr Gly Ala Pro Ala Pro Ser
305                 310                 315                 320

Arg Pro Ser Ser Gln Tyr Gly Ala Pro Ala Gln Thr Pro Ser Ser Gln
                325                 330                 335

Tyr Gly Ala Pro Ala Gln Thr Pro Ser Ser Gln Tyr Gly Pro Pro Arg
                340                 345                 350

Gln Ser Ser Pro Gln Phe Gly Ala Pro Ala Pro Arg Pro Pro Ser Ser
                355                 360                 365

Gln Tyr Gly Ala Pro Ala Gln Ala Pro Ser Ser Gln Tyr Gly Ala Pro
                370                 375                 380

Ala Gln Thr Pro Ser Ser Gln Tyr Gly Ala Pro Ala Gln Ala Pro Ser
385                 390                 395                 400

Ser Gln Tyr Gly Ala Pro Ala Pro Ser Arg Pro Ser Ser Gln Tyr Gly
                405                 410                 415

Val Pro Ala Gln Ala Pro Ser Ser Gln Tyr Gly Ala Pro Ala Gln Ala
                420                 425                 430

Pro Ser Ser Gln Tyr Gly Ala Pro Ala Gln Thr Pro Ser Ser Gln Tyr
                435                 440                 445

Gly Ala Pro Ser Phe Gly Ser Thr Gly Gly Ser Ser Phe Gly Gly Asn
                450                 455                 460

Gly Gly Val Gly Gly Ser Tyr Gln Thr Ala Ser Ser Gly Asn Gly Phe
465                 470                 475                 480

Ser Gln Ala Ser Phe Ser Ala Ser Ser Phe Ser Ser Asn Gly Arg Ser
                485                 490                 495

Ser Gln Ser Ala Gly Tyr Ser Ser Gly Pro Ser Gln Val Pro
                500                 505                 510

Ala Thr Ile Pro Gln Gln Tyr Ser Ser Gly Gly Ser Tyr Ser Ser
                515                 520                 525

Gly Gly His Ser Gln Val Pro Ala Thr Leu Pro Gln Gln Tyr Ser Ser
                530                 535                 540

Asn Gly Gly Tyr Asn Tyr
545                 550

<210> SEQ ID NO 24
<211> LENGTH: 585
<212> TYPE: PRT
<213> ORGANISM: Acromyrmex echinatior

<400> SEQUENCE: 24

Arg Ser Glu Pro Pro Val Asn Ser Tyr Leu Pro Pro Gly Pro Gly Thr
1               5                   10                  15

Ser Gly Ala Asn Gly Gly Gln Thr Asp Leu Ser Ile Gln Tyr Arg Ala
                20                  25                  30

Ser Asp Phe Asn Asn Arg Gly Asn Val Asn Gly Asn Ser Gly Ala Thr
                35                  40                  45

Ser Phe Gly Gly Pro Gly Ala Ser Asn Gly Pro Ser Lys Leu Tyr Asp
```

```
              50                  55                  60
Val Pro Ile Gly Gly Asn Ala Gly Gly Asn Gly Leu Gly Gln Phe Arg
 65                  70                  75                  80

Gly Asn Gly Phe Glu Gly Gly Gln Pro Ser Ser Tyr Gly Ala Pro
                 85                  90                  95

Asn Gly Gly Phe Gly Glu Asn Arg Gly Asn Gly Lys Pro Ser Thr
                100                 105                 110

Ser Tyr Gly Val Pro Asp Ser Asn Gly Asn Asn Arg Gly Gly Phe Gly
                115                 120                 125

Asn Gly Gly Ser Glu Gly Arg Pro Ser Thr Ser Tyr Gly Leu Pro Asp
                130                 135                 140

Ala Ser Arg Asn Asn Gly Asn Gly Phe Gly Asn Val Gly Asn Glu Asp
145                 150                 155                 160

Lys Pro Ser Thr Asn Tyr Gly Ile Pro Ala Asn Gly Asn Lys Val Ser
                165                 170                 175

Gly Phe Gly Asn Val Gly Ser Glu Gly Arg Pro Ser Thr Ser Tyr Gly
                180                 185                 190

Val Pro Gly Ala Asn Gly Asn Gln Gly Phe Gly Ser Gly Gly Ile Gly
                195                 200                 205

Gly Arg Pro Ser Thr Ser Tyr Gly Val Pro Gly Val Asn Gly Asn Asn
                210                 215                 220

Gly Gly Gly Phe Glu Asn Val Gly Arg Pro Ser Thr Ser Tyr Gly Thr
225                 230                 235                 240

Pro Asp Ala Arg Gly Asn Asn Gly Gly Ser Phe Arg Asn Gly Asp Ile
                245                 250                 255

Gly Gly Arg Pro Ser Thr Asn Tyr Gly Ile Pro Gly Ala Asn Gly Asn
                260                 265                 270

His Gly Gly Asn Gly Gly Asn Gly Arg Pro Ser Ser Asn Tyr Gly
                275                 280                 285

Val Pro Gly Gly Asn Gly Asn Thr Asn Gly Lys Gly Arg Phe Asn Gly
                290                 295                 300

Asn Ser Gly Gly Arg Pro Ser Asn Ser Tyr Gly Ser Pro Asn Gly Phe
305                 310                 315                 320

Gly Lys Gly Leu Ser Thr Ser Tyr Ser Pro Ser Asn Arg Asp Gly Asn
                325                 330                 335

Gly Asn His Tyr Pro Ser Gly Asp Ser Asn Arg Gly Ser Phe Val Asn
                340                 345                 350

Gly Gly Ile Asn Gly Tyr Pro Ser Gly Ser Pro Asn Gly Asn Ala Gly
                355                 360                 365

Asn Phe Arg His Gly Asp Glu Ser Phe Gly Arg Gly Gly Glu Gly Gly
370                 375                 380

Gly Arg Ser Thr Gly Glu Gly Tyr Asn Ala Asn Ala Gln Glu Glu Ser
385                 390                 395                 400

Thr Glu Pro Ala Lys Tyr Glu Phe Ser Tyr Lys Val Lys Asp Gln Gln
                405                 410                 415

Thr Gly Ser Asp Tyr Ser His Thr Glu Thr Arg Asp Gly Asp His Ala
                420                 425                 430

Gln Gly Glu Phe Asn Val Leu Leu Pro Asp Gly Arg Lys Gln Ile Val
                435                 440                 445

Glu Tyr Glu Ala Asp Gln Asp Gly Phe Lys Pro Gln Ile Arg Tyr Glu
                450                 455                 460

Gly Glu Ala Asn Ala Asp Gly Glu Tyr Asp Ser Gly Gly Leu Asn Asp
465                 470                 475                 480
```

```
Asn Asn Asp Gly Tyr Ser Ser Gly Arg Pro Gly Ser Glu Ser Gly Gly
                485                 490                 495

Phe Ala Asn Asn Ser Gly Phe Asn Gly Gly Ser Ser Asn Gly Gly Tyr
            500                 505                 510

Pro Ser Gly Gly Ser Gly Glu Gly Lys Leu Gly Phe Asn Ser Gly Gly
            515                 520                 525

Asn Ser Gly Tyr Gln Ser Gly Arg Pro Ala Gly Gln Ser Phe Gly Arg
            530                 535                 540

Asp Asn Ala Gly Asp Leu Ser Asn Asp Ile Gly Gly Phe Ser Asn Ser
545                 550                 555                 560

Pro Asn Asn Ile Gly Gly Asp Asn Ala Asn Val Gly Ser Asn Arg Gln
                565                 570                 575

Asn Gly Gly Asn Ser Gly Tyr Gln Tyr
                580                 585

<210> SEQ ID NO 25
<211> LENGTH: 748
<212> TYPE: PRT
<213> ORGANISM: Acyrthosiphon pisum

<400> SEQUENCE: 25

Glu Ser Pro Tyr Gly Gly Gly Ser Ser Asn Ser Asn Gly Asn Gly Arg
1               5                   10                  15

Asn Gly Gly Tyr Gly Gly Lys Gly Gln Tyr Gly Gly Asn Gly Gly
            20                  25                  30

Gly Val Gly Ser Ser Ser Ala Ser Pro Phe Phe Ser Gly Ala Asn Gln
            35                  40                  45

Tyr Gly Ser Gln Ser Gly Leu Ser Gly Ala Ala Asn Asn Arg Tyr Pro
    50                  55                  60

Ser Phe Gly Ser Lys Phe Gly Gly Asn Lys Gly Ser Tyr Gly Gly Ser
65              70                  75                  80

Ser Ser Arg Asn Asn Gly Arg Tyr Gly Ser Gly Ser Ala Ser Gly Tyr
                85                  90                  95

Gly Ser Gly Ser Ser Gly Leu Gly Ser Thr Gly Arg Ser Thr Gly
            100                 105                 110

Gly Tyr Gly Gly Gly Ser Ser Gly Ser Tyr Gly Ser Gly Ser Ser Gly
            115                 120                 125

Ser Leu Gly Ser Ser Thr Gly Ser Asn Gly Ile Tyr Gly Ala Gly Ser
    130                 135                 140

Ser Gly Gly Phe Gly Ser Gly Ser Ser Gly Ser Tyr Gly Gly Gly Ser
145                 150                 155                 160

Ser Gly Gly Phe Gly Ser Gly Ser Ser Gly Ser Tyr Gly Gly Gly Ser
                165                 170                 175

Ser Gly Gly Phe Gly Ser Gly Ser Ser Gly Ser Tyr Gly Gly Gly Ser
                180                 185                 190

Ser Gly Gly Phe Gly Ser Gly Ser Ser Gly Ser Tyr Gly Gly Gly Ser
                195                 200                 205

Ser Gly Gly Phe Gly Ser Gly Ser Ser Gly Asn Tyr Gly Ser Gly Ser
                210                 215                 220

Ser Gly Ser Tyr Gly Ser Gly Gly Gly Leu Gly Gly Ala Ser Ser
225                 230                 235                 240

Gly Asn Asn Asp Gly Tyr Gly Ala Gly Ser Gly Ser Tyr Asp Gln
                245                 250                 255

Leu Gly Gly Ala Asn Gly Asn Gly Leu Gly Gly Ser Gly Asn Asp Pro
```

-continued

```
                260                 265                 270
Leu Ser Glu Pro Ala Asn Tyr Glu Phe Ser Tyr Glu Val Asn Ala Pro
            275                 280                 285

Glu Ser Gly Ala Ile Phe Gly His Lys Glu Ser Arg Gln Gly Glu Glu
            290                 295                 300

Ala Thr Gly Val Tyr His Val Leu Leu Pro Asp Gly Arg Thr Gln Ile
305                 310                 315                 320

Val Glu Tyr Glu Ala Asp Glu Asp Gly Tyr Lys Pro Lys Ile Thr Tyr
            325                 330                 335

Thr Asp Pro Val Gly Gly Tyr Ala Gly Asp Arg Gln Ser Gly Asn Ser
            340                 345                 350

Tyr Gly Gly Asn Gly Gly Phe Gly Gly Ser Gly Ser Leu Gly Gly Ser
            355                 360                 365

Gly Gly Asn Leu Gly Gly Leu Tyr Asn Gly Gly Ser Ser Asn Asn
            370                 375                 380

Gly Ala Gly Tyr Gly Gly Ser Ser Ser Leu Gly Ser Arg Tyr Gly
385                 390                 395                 400

Gly Ser Gly Gly Ser Ser Gly Ser Gly Val Gly Gly Tyr Gly Gly
                405                 410                 415

Ser Gly Ser Ser Ser Gly Gly Ile Gly Ser Ser Tyr Gly Gly Ser Gly
                420                 425                 430

Ser Leu Ser Gly Gly Leu Gly Gly Tyr Gly Ser Gly Ser Ser
            435                 440                 445

Ser Gly Gly Leu Gly Gly Tyr Gly Ser Gly Gly Ser Ser Gly
            450                 455                 460

Gly Gly Phe Gly Gly Leu Gly Gly Ser Gly Ser Ser Gly Ser Gly
465                 470                 475                 480

Tyr Gly Gly Ser Gly Ser Ser Gly Gly Leu Gly Asn Ser Tyr Gly
                485                 490                 495

Gly Ser Gly Ser Ser Asn Gly Gly Leu Gly Gly Tyr Ser Gly Ser
                500                 505                 510

Gly Gly Ser Ser Gly Gly Leu Gly Gly Tyr Gly Ala Ser Ser Gly
                515                 520                 525

Ser Ser Gly Ser Gly Leu Gly Gly Tyr Gly Gly Ser Gly Ser Ser
            530                 535                 540

Ser Gly Gly Leu Gly Ser Gly Tyr Gly Gly Leu Gly Ser Ser Gly
545                 550                 555                 560

Gly Leu Gly Gly Gly Tyr Gly Ser Gly Ser Ser Ser Gly Gly Leu
                565                 570                 575

Gly Gly Gly Tyr Gly Gly Ser Gly Ser Ser Asn Gly Gly Ile Gly
            580                 585                 590

Gly Tyr Gly Gly Ser Ser Gly Ser Ser Gly Gly Leu Gly Gly Tyr
            595                 600                 605

Gly Gly Ser Gly Ser Ser Ser Gly Gly Leu Gly Gly Tyr Gly Gly
            610                 615                 620

Ser Gly Gly Ser Asn Ser Gly Leu Gly Ser Ser Tyr Gly Gly Ser Gly
625                 630                 635                 640

Ser Thr Asn Gly Gly Leu Gly Gly Gly Tyr Gly Gly Leu Gly Ser Ser
                645                 650                 655

Ser Gly Gly Leu Gly Gly Gly Tyr Gly Gly Ser Gly Gly Ser Asn Gly
            660                 665                 670

Gly Ile Gly Gly Gly Tyr Gly Gly Ser Ser Gly Ser Gly Gly Ser Gln
            675                 680                 685
```

-continued

Gly Ser Ala Tyr Gly Gly Ser Gly Ser Ser Gly Ser Gln Gly Gly
        690                 695                 700

Gly Tyr Gly Gly Ser Gly Ser Ser Gly Gly Leu Gly Gly Gly Tyr
705                 710                 715                 720

Gly Ser Ser Ser Gly Ser Ser Gly Leu Gly Gly Ser Tyr Gly Ser
                725                 730                 735

Asn Arg Asn Gly Leu Gly Ser Gly Ser Ser Tyr Ser
            740                 745

<210> SEQ ID NO 26
<211> LENGTH: 616
<212> TYPE: PRT
<213> ORGANISM: Drosophila virilis

<400> SEQUENCE: 26

Arg Pro Glu Pro Pro Val Asn Ser Tyr Leu Pro Pro Ser Pro Gly Asp
1               5                   10                  15

Ser Tyr Gly Ala Pro Gly Gln Gly Gln Gly Gln Gly Gly Phe
            20                  25                  30

Gly Gly Lys Pro Ser Asp Ser Tyr Gly Ala Pro Gly Ala Gly Asn Gly
        35                  40                  45

Asn Gly Asn Gly Arg Pro Ser Ser Tyr Gly Ala Pro Gly Gln Gly
    50                  55                  60

Gln Gly Gln Gly Gly Phe Gly Gly Lys Pro Ser Asp Ser Tyr Gly Ala
65                  70                  75                  80

Pro Gly Ala Gly Asn Gly Asn Gly Asn Gly Arg Pro Ser Ser Ser Tyr
                85                  90                  95

Gly Ala Pro Gly Gln Gly Gln Gly Gln Gly Gly Phe Gly Gly Arg Pro
            100                 105                 110

Ser Ser Ser Tyr Gly Ala Pro Gly Gln Gly Gln Gly Gly Phe Gly Gly
        115                 120                 125

Lys Pro Ser Asp Thr Tyr Gly Ala Pro Gly Ala Gly Asn Gly Asn Gly
    130                 135                 140

Arg Pro Ser Ser Tyr Gly Ala Pro Gly Gln Gly Gln Gly Gly Ile
145                 150                 155                 160

Gly Gly Lys Pro Ser Asp Ser Tyr Gly Ala Pro Gly Ala Gly Asn Gly
                165                 170                 175

Asn Gly Asn Gly Arg Pro Ser Ser Tyr Gly Ala Pro Gly Gln Gly
            180                 185                 190

Gln Gly Gly Phe Gly Gly Lys Pro Ser Asp Thr Tyr Gly Ala Pro Gly
        195                 200                 205

Ala Gly Asn Gly Asn Gly Arg Pro Ser Ser Tyr Gly Ala Pro Gly
    210                 215                 220

Gln Gly Gln Gly Gly Phe Gly Gly Lys Pro Ser Asp Thr Tyr Gly Ala
225                 230                 235                 240

Pro Gly Ala Gly Asn Gly Asn Gly Asn Gly Arg Pro Ser Ser Ser Tyr
                245                 250                 255

Gly Ala Pro Gly Gln Gly Gln Gly Gly Phe Gly Gly Lys Pro Ser Asp
            260                 265                 270

Thr Tyr Gly Ala Pro Gly Ala Gly Asn Gly Asn Gly Arg Pro Ser Ser
        275                 280                 285

Ser Tyr Gly Ala Pro Gly Gln Gly Gln Gly Gln Gly Gly Phe Gly Gly
    290                 295                 300

Lys Pro Ser Asp Ser Tyr Gly Pro Pro Ala Ser Gly Ala Gly Ala Gly

```
                305                 310                 315                 320
Gly Ala Gly Gly Pro Gly Ala Gly Gly Gly Asp Tyr Asp Asn Asp
                325                 330                 335
Glu Pro Ala Lys Tyr Glu Phe Asn Tyr Gln Val Glu Asp Ala Pro Ser
                340                 345                 350
Gly Leu Ser Phe Gly His Ser Glu Met Arg Asp Gly Asp Phe Thr Thr
                355                 360                 365
Gly Gln Tyr Asn Val Leu Leu Pro Asp Gly Arg Lys Gln Ile Val Glu
            370                 375                 380
Tyr Glu Ala Asp Gln Gln Gly Tyr Arg Pro Gln Val Arg Tyr Glu Gly
385                 390                 395                 400
Asp Ala Asn Gly Asn Gly Gly Pro Gly Gly Ala Gly Gly Pro Gly Gly
                405                 410                 415
Gln Asp Leu Gly Gln Asn Gly Tyr Ser Ser Gly Arg Pro Gly Gly Gln
                420                 425                 430
Asp Leu Gly Gln Gly Gly Tyr Ser Asn Gly Arg Pro Gly Gly Gln Asp
                435                 440                 445
Leu Gly Gln Asn Gly Tyr Ser Gly Gly Arg Pro Gly Gly Gln Asp Leu
            450                 455                 460
Gly Gln Asn Gly Tyr Ser Gly Gly Arg Pro Gly Gly Gln Asp Leu Gly
465                 470                 475                 480
Gln Asn Gly Tyr Ser Gly Gly Arg Pro Gly Gly Gln Asp Leu Gly Gln
                485                 490                 495
Asn Gly Tyr Ser Gly Gly Arg Pro Gly Gly Gln Asp Leu Gly Gln Asn
                500                 505                 510
Gly Tyr Ser Gly Gly Arg Pro Gly Gly Gln Asp Leu Gly Gln Asn Gly
                515                 520                 525
Tyr Ser Gly Gly Arg Pro Gly Gly Asn Gly Gly Ser Asp Gly Gly Arg
            530                 535                 540
Val Ile Ile Gly Gly Arg Val Ile Gly Gln Asp Gly Gly Asp Gly Gln
545                 550                 555                 560
Gly Tyr Ser Ser Gly Arg Pro Asn Gly Gln Asp Gly Gly Phe Gly Gln
                565                 570                 575
Asp Asn Thr Asp Gly Arg Gly Tyr Ser Ser Gly Lys Pro Gly Gln Gly
                580                 585                 590
Arg Asn Gly Asn Gly Asn Ser Phe Gly Pro Gly Gln Asn Gly Asp
            595                 600                 605
Asn Asp Gly Ser Gly Tyr Arg Tyr
    610                 615

<210> SEQ ID NO 27
<211> LENGTH: 557
<212> TYPE: PRT
<213> ORGANISM: Drosophila erecta

<400> SEQUENCE: 27

Arg Pro Glu Pro Pro Val Asn Ser Tyr Leu Pro Ser Asp Ser Tyr
1               5                   10                  15
Gly Ala Pro Gly Gln Ser Gly Pro Gly Gly Arg Pro Ser Asp Ser Tyr
                20                  25                  30
Gly Ala Pro Gly Gly Gly Asn Gly Gly Arg Pro Ser Asp Ser Tyr Gly
            35                  40                  45
Ala Pro Gly Leu Gly Gln Gly Gln Gly Gln Gly Gln Gly Gln Gly Gly
50                  55                  60
```

```
Phe Gly Gly Lys Pro Ser Asp Ser Tyr Gly Ala Pro Gly Ala Gly Asn
 65                  70                  75                  80
Gly Asn Gly Gly Arg Pro Ser Ser Tyr Gly Ala Pro Gly Ala Gly
                 85                  90                  95
Asn Gly Gly Arg Pro Ser Asp Thr Tyr Gly Ala Pro Gly Gly Ser
             100                 105                 110
Gly Gly Arg Pro Ser Asp Thr Tyr Gly Ala Pro Gly Gly Asn Gly
         115                 120                 125
Asn Gly Asn Gly Gly Arg Pro Ser Ser Tyr Gly Ala Pro Gly Gln
    130                 135                 140
Gly Gln Gly Asn Gly Asn Ser Gly Arg Pro Ser Ser Tyr Gly Ala
145                 150                 155                 160
Pro Gly Ala Gly Asn Gly Gly Arg Pro Ser Asp Thr Tyr Gly Ala Pro
                165                 170                 175
Gly Gly Gly Asn Gly Gly Arg Pro Ser Ser Tyr Gly Ala Pro Gly
             180                 185                 190
Ala Gly Asn Gly Gly Asn Gly Gly Arg Pro Ser Asp Thr Tyr Gly Ala
             195                 200                 205
Pro Gly Gly Gly Asn Gly Asn Gly Asn Gly Asn Gly Asn Gly Ser Gly
         210                 215                 220
Gly Arg Pro Ser Ser Ser Tyr Gly Ala Pro Gly Gln Gly Gln Gly Gly
225                 230                 235                 240
Phe Gly Gly Arg Pro Ser Asp Ser Tyr Gly Ala Pro Gly Gln Asn Gln
                245                 250                 255
Lys Pro Ser Asp Ser Tyr Gly Ala Pro Gly Ser Gly Ser Gly Ser Gly
            260                 265                 270
Asn Gly Asn Gly Gly Arg Pro Ser Ser Tyr Gly Ala Pro Gly Ser
    275                 280                 285
Gly Pro Gly Gly Arg Pro Ser Asp Ser Tyr Gly Pro Pro Ala Ser Gly
        290                 295                 300
Ser Gly Ala Gly Gly Ala Gly Ser Gly Pro Gly Gly Ala Asp Tyr
305                 310                 315                 320
Asp Asn Asp Ile Val Glu Tyr Glu Ala Asp Gln Gln Gly Tyr Arg Pro
                325                 330                 335
Gln Ile Arg Tyr Glu Gly Asp Ala Asn Asp Gly Ser Gly Pro Ser Gly
            340                 345                 350
Pro Gly Gly Gln Asn Leu Gly Ala Asp Gly Tyr Ser Ser Gly Arg Pro
        355                 360                 365
Gly Asn Gly Asn Gly Asn Gly Asn Gly Tyr Ser Gly Gly Arg Pro
    370                 375                 380
Gly Gly Gln Asp Leu Gly Pro Ser Gly Tyr Ser Gly Gly Arg Pro Gly
385                 390                 395                 400
Gly Gln Asp Leu Gly Ala Gly Gly Tyr Ser Asn Gly Arg Pro Gly Gly
                405                 410                 415
Gln Asp Leu Gly Pro Ser Gly Tyr Ser Gly Gly Arg Pro Gly Gly Gln
            420                 425                 430
Asp Leu Gly Pro Ser Gly Tyr Ser Gly Gly Arg Pro Gly Gly Gln Asp
        435                 440                 445
Leu Gly Ala Gly Gly Tyr Ser Asn Gly Arg Pro Gly Gly Asn Gly Asn
    450                 455                 460
Gly Asn Gly Gly Ala Asp Gly Gly Arg Val Ile Ile Gly Gly Arg Val
465                 470                 475                 480
Ile Gly Gly Gln Asp Gly Gly Asp Gln Gly Tyr Ser Gly Gly Arg Pro
```

-continued

```
                485                 490                 495

Gly Gly Gln Asp Leu Gly Arg Asp Gly Tyr Ser Ser Gly Arg Pro Gly
            500                 505                 510

Gly Arg Pro Gly Ala Asn Gly Gln Asp Asn Gln Asp Gly Gln Gly Tyr
        515                 520                 525

Ser Ser Gly Arg Ser Gly Lys Gly Gly Arg Asn Ser Phe Gly Pro Gly
    530                 535                 540

Gly Gln Asn Gly Asp Asn Asp Gly Ser Gly Tyr Arg Tyr
545                 550                 555

<210> SEQ ID NO 28
<211> LENGTH: 796
<212> TYPE: PRT
<213> ORGANISM: Lutzomyia longipalpis

<400> SEQUENCE: 28

Arg Pro Glu Pro Pro Ala Asn Thr Tyr Leu Pro Pro Ser Ser Ser Tyr
1               5                   10                  15

Ala Ala Pro Gly Gln Gln Gly Gly Ser Gly Phe Gly Gly Gly Gly Gly
            20                  25                  30

Ser Gly Gly Ser Gly Gly Phe Gly Gln Pro Gly Ala Phe Gly Arg Pro
        35                  40                  45

Ser Ser Ser Tyr Gly Pro Pro Ser Gln Gly Gly Ala Gly Gly Gly Phe
    50                  55                  60

Gly Ser Asp Ser Gln Phe Gly Gly Gly Phe Gly Gly Gly Ala Gly Gly
65                  70                  75                  80

Phe Gly Ser Gly Gly Ser Gly Ala Pro Gly Ala Ser Gln Arg Pro Ser
                85                  90                  95

Ser Ser Tyr Gly Pro Pro Gly Gln Thr Gly Gly Gly Gly Phe Gly Ala
            100                 105                 110

Gln Gly Ala Pro Gly Ser Ser Phe Gly Pro Gly Gly Gly Phe Gly Gly
        115                 120                 125

Gly Ser Pro Gly Gln Ala Gly Ser Pro Gly Phe Gln Arg Pro Ser Ser
    130                 135                 140

Ser Tyr Gly Pro Pro Gly Gln Ser Pro Gly Gly Gly Phe Ser Gln Gln
145                 150                 155                 160

Gly Gly Ala Pro Gly Ala Ser Gln Arg Pro Ser Ser Thr Tyr Gly Ala
                165                 170                 175

Pro Gly Gln Gly Ala Gly Gly Phe Gly Gln Gly Gly Ser Gly Gly Phe
            180                 185                 190

Gly Gly Thr Gly Gly Ser Val Ala Ile Gly Gly Arg Pro Ser Ser Ser
        195                 200                 205

Tyr Gly Ala Pro Gly Gln Gly Ser Ser Gly Gly Phe Gly Gly Gly Ser
    210                 215                 220

Gly Gly Phe Gly Ser Gln Ala Pro Ser Thr Ser Tyr Gly Ala Pro Gly
225                 230                 235                 240

Gln Gly Ser Pro Gly Gly Gly Phe Gly Ser Gln Gly Gly Pro Gly Gly
                245                 250                 255

Gln Pro Gly Ser Pro Gly Phe Gly Gly Ser Gln Arg Pro Ser Ser Ser
            260                 265                 270

Tyr Gly Pro Pro Gly Gln Gly Gly Ala Pro Gly Gln Gly Gly Ser Pro
        275                 280                 285

Gly Phe Gly Ala Ser Ser Arg Ser Gly Gly Ala Gly Gly Phe Gly Ala
    290                 295                 300

-continued

```
Ser Gln Gln Pro Ser Ser Ser Tyr Gly Pro Gly Gly Ala Gly
305                 310                 315                 320

Ser Gly Phe Gln Gly Thr Gly Gly Gly Phe Gly Gly Pro Gly Gln Arg
            325                 330                 335

Pro Gly Phe Gly Gly Ser Gln Thr Pro Ala Thr Ser Tyr Gly Ala Pro
            340                 345                 350

Gly Gln Ala Gly Gly Ala Ser Gly Phe Gly Gly Ala Gly Ala Gln
            355                 360                 365

Arg Pro Ser Ser Ser Tyr Gly Pro Pro Gly Gln Ala Ser Gly Phe Gly
    370                 375                 380

Gly Gly Ser Ser Gly Gly Gly Phe Gly Gly Ser Ser Gly Gly Phe
385                 390                 395                 400

Gly Gly Asn Gln Gly Gly Phe Gly Gly Asn Gln Gly Gly Phe Gly Gly
            405                 410                 415

Ser Gln Thr Pro Ser Ser Tyr Gly Ala Pro Ser Phe Gly Ser Gly
            420                 425                 430

Gly Ser Pro Gly Ala Ala Gly Ala Gly Gly Phe Gly Gln Gly Gly
            435                 440                 445

Val Gly Gly Ser Gly Gln Pro Gly Gly Phe Gly Gly Asp Gln Gly
450                 455                 460

Tyr Pro Pro Arg Gly Gly Pro Gly Gly Phe Gly Pro Gly Ser Gly Gly
465                 470                 475                 480

Ser Gly Ala Gly Gly Pro Ile Ala Gly Ser Gly Ser Gly Tyr Pro
            485                 490                 495

Gly Gly Ser Asp Ser Gly Ser Asn Glu Pro Ala Lys Tyr Asp Phe Ser
            500                 505                 510

Tyr Gln Val Asp Asp Pro Ala Ser Gly Thr Ser Phe Gly His Ser Glu
    515                 520                 525

Gln Arg Asp Gly Asp Tyr Thr Ser Gly Gln Tyr Asn Val Leu Leu Pro
    530                 535                 540

Asp Gly Arg Lys Gln Ile Val Glu Tyr Glu Ala Asp Leu Gly Gly Tyr
545                 550                 555                 560

Arg Pro Gln Ile Lys Tyr Glu Gly Gly Ser Gly Gly Ala Gly Gly
            565                 570                 575

Tyr Pro Ser Gly Gly Pro Gly Ser Gln Gly Gly Ala Gly Gly Tyr Pro
            580                 585                 590

Ser Gly Gly Pro Gly Gly Pro Gly Ser Pro Gly Gly Ala Gly Gly Tyr
    595                 600                 605

Gln Ser Gly Ala Ala Gly Gly Ala Gly Tyr Pro Ser Gly Gly Pro
610                 615                 620

Gly Gly Pro Gly Ala Gly Gly Tyr Pro Ser Gly Gly Pro Gly Gly Pro
625                 630                 635                 640

Gly Ser Gln Ala Gly Gly Phe Ser Gly Phe Gly Gly Ser Asp
            645                 650                 655

Gly Ala Phe Gly Gly Ala Gly Gly Phe Ser Gln Gly Gly Ala Gly Gly
            660                 665                 670

Gly Asp Ala Gly Tyr Pro Arg Gly Gly Pro Gly Gly Phe Gly Ala
    675                 680                 685

Gly Ser Pro Gly Phe Gly Ser Gly Ser Pro Gly Phe Gly Gly Ser
            690                 695                 700

Gly Ser Pro Gly Ala Gln Gly Ser Ser Gly Phe Gly Thr Gly Gly
705                 710                 715                 720

Gly Phe Gly Gly Gly Ala Asp Gly Tyr Pro Arg Gly Gly Pro Gly Ala
```

-continued

```
                725                 730                 735
Gly Gln Ser Gly Phe Gln Asp Gly Arg Gly Ala Thr Gly Gly Ala Gly
            740                 745                 750
Gln Pro Gly Gly Arg Gly Ser Phe Gly Arg Pro Gly Ser Ala Arg Gly
            755                 760                 765
Gly Ser Ser Asn Gly Tyr Ala Asn Gly Gly Ala Glu Gly Tyr Pro
            770                 775                 780
Arg Asp Asn Pro Gln Asn Arg Gly Ser Gly Tyr Ser
785                 790                 795

<210> SEQ ID NO 29
<211> LENGTH: 1051
<212> TYPE: PRT
<213> ORGANISM: Rhodnius prolixus

<400> SEQUENCE: 29

Lys Arg Asp Asp Pro Leu Arg Arg Phe Leu Ala Pro Leu Val Gly Gly
1               5                   10                  15
Gly Asn Gly Ser Gly Gly Gly Gly Tyr Asn Tyr Asn Lys Pro
            20                  25                  30
Ala Asn Gly Leu Ser Leu Pro Gly Gly Gly Ala Leu Pro Pro Ala
            35                  40                  45
Thr Ser Tyr Gly Val Pro Asp Arg Pro Ala Pro Val Pro Ser Ser Pro
50                  55                  60
Pro Ser Ser Ser Tyr Gly Ala Pro Gln Pro Ser Pro Asn Tyr Gly Ala
65                  70                  75                  80
Pro Ser Ser Ser Tyr Gly Ala Pro Ser Gln Gln Pro Ser Arg Ser Tyr
            85                  90                  95
Gly Ala Pro Ser Gln Gly Pro Ser Thr Ser Tyr Ser Gln Arg Pro Ser
            100                 105                 110
Ser Ser Tyr Gly Ala Pro Ala Pro Gln Thr Pro Ser Ser Ser Tyr Gly
            115                 120                 125
Ala Pro Ala Gln Gln Pro Ser Gly Ser Tyr Gly Ala Pro Ser Gly Gly
            130                 135                 140
Gly Gly Ser Ser Gly Tyr Thr Gly Gly Ala Gln Arg Pro Ser Gly Ser
145                 150                 155                 160
Tyr Gly Ala Pro Ser Gln Gly Gly Pro Ser Gly Asn Tyr Gly Pro Pro
            165                 170                 175
Ser Gln Gln Pro Ser Ser Asn Tyr Gly Ala Pro Ser Gln Thr Pro Ser
            180                 185                 190
Ser Asn Tyr Gly Ala Pro Ala Gln Arg Pro Ser Thr Ser Tyr Gly Ala
            195                 200                 205
Pro Ser Gln Pro Pro Ser Ser Tyr Gly Ser Pro Pro Gln Arg Ala
            210                 215                 220
Ser Gly Tyr Pro Ser Ser Ser Gly Pro Ser Asn Gly Tyr Ser Pro
225                 230                 235                 240
Pro Ala Gln Arg Pro Ser Ser Tyr Gly Pro Ser Gln Gln Pro
            245                 250                 255
Ala Ser Ser Tyr Gly Ala Pro Ser Gln Thr Pro Ser Ser Asn Tyr Gly
            260                 265                 270
Pro Pro Ala Pro Ile Pro Ser Ser Asn Tyr Gly Ala Pro Ser Gln Pro
            275                 280                 285
Pro Ser Lys Pro Ser Ala Pro Ser Ser Tyr Gly Thr Pro Ser Gln
            290                 295                 300
```

```
Thr Pro Ser Thr Ser Tyr Gly Ala Pro Ser Gln Ala Pro Ser Ser Ser
305                 310                 315                 320

Tyr Gly Ala Pro Ser Arg Pro Ser Pro Ser Ser Ser Tyr Gly Ala
            325                 330                 335

Pro Ser Gln Gly Pro Ser Ser Ser Tyr Gly Pro Pro Ser Arg Pro Ser
                340                 345                 350

Gln Pro Ser Ser Pro Ser Ser Gly Tyr Gly Ala Pro Ser Gln Gly Pro
            355                 360                 365

Ser Ser Ser Tyr Gly Ala Pro Ser Arg Pro Ser Pro Ser Ser Ser
    370                 375                 380

Tyr Gly Ala Pro Pro Ser Ser Tyr Gly Ala Pro Ser Arg Pro Ser
385                 390                 395                 400

Pro Pro Ser Ser Ser Tyr Gly Ala Pro Ser Gln Gly Pro Ser Ser Ser
                405                 410                 415

Tyr Gly Pro Pro Ser Arg Pro Ser Gln Pro Ser Ser Pro Ser Ser Gly
            420                 425                 430

Tyr Gly Ala Pro Ser Gln Gly Pro Ser Ser Tyr Gly Ala Pro Ser
            435                 440                 445

Arg Pro Ser Ser Pro Ser Ser Ser Tyr Gly Ala Pro Pro Ser Ser Ser
450                 455                 460

Tyr Gly Ala Pro Ser Arg Pro Ser Pro Pro Ser Ser Ser Tyr Gly Ala
465                 470                 475                 480

Pro Ser Gln Gly Pro Ser Ser Ser Tyr Gly Pro Pro Ser Arg Pro Ser
            485                 490                 495

Gln Pro Ser Ser Pro Ser Ser Ser Tyr Gly Ala Pro Ser Gln Gly Pro
            500                 505                 510

Ser Ser Ser Tyr Gly Ala Pro Ser Arg Pro Ser Pro Pro Ser Ser Ser
            515                 520                 525

Tyr Gly Ala Pro Ser Gln Gly Pro Ser Ser Ser Tyr Gly Pro Pro Ser
            530                 535                 540

Arg Pro Ser Gln Pro Ser Ser Thr Tyr Gly Val Pro Ser Gly Gly Arg
545                 550                 555                 560

Pro Ser Thr Pro Ser Ser Ser Tyr Gly Ala Pro Pro Gln Ala Leu Ser
            565                 570                 575

Ser Thr Tyr Gly Ala Pro Ser Gly Arg Pro Gly Ala Pro Ser Gln Lys
            580                 585                 590

Pro Ser Ser Ser Tyr Gly Ala Pro Ser Leu Gly Gly Asn Ala Ser Arg
            595                 600                 605

Gly Pro Lys Ser Ser Pro Pro Ser Ser Ser Tyr Gly Ala Pro Ser Val
            610                 615                 620

Gly Thr Ser Val Ser Ser Tyr Ala Pro Ser Gln Gly Gly Ala Gly Gly
625                 630                 635                 640

Phe Gln Ser Ser Arg Pro Ser Ser Tyr Gly Ala Pro Ser Thr Gly
            645                 650                 655

Pro Ser Ser Thr Tyr Gly Pro Pro Ser Gln Pro Pro Ser Ser Ser Tyr
            660                 665                 670

Gly Val Pro Ser Gln Pro Pro Ser Ser Asn Tyr Gly Val Pro Ser Gln
            675                 680                 685

Gly Val Ser Gly Ser Val Gly Ser Ser Pro Ser Ser Tyr Gly
            690                 695                 700

Ala Pro Ser Gln Ile Pro Ser Ser Tyr Gly Ala Pro Ser Gln Ser
705                 710                 715                 720

Ser Ile Gly Gly Phe Gly Ser Ser Arg Pro Ser Ser Ser Tyr Gly Ala
```

```
                    725                 730                 735

Pro Pro Gln Ala Pro Ser Ser Tyr Ser Ala Pro Leu Arg Ala Pro
            740                 745                 750

Ser Thr Ser Tyr Gly Ala Pro Ser Gly Gly Ser Gly Ser Asn Phe Gly
            755                 760                 765

Ser Lys Pro Ser Thr Asn Tyr Gly Ala Pro Ser Gln Pro Pro Ser Thr
            770                 775                 780

Asn Tyr Gly Pro Pro Ser Gln Pro Pro Ser Ser Tyr Gly Thr Pro
785                 790                 795                 800

Ser Arg Ala Pro Ser Pro Thr Tyr Ser Thr Pro Gln Ser Ser Gly Thr
                    805                 810                 815

Ser Phe Gly Ser Arg Pro Ser Ser Tyr Gly Val Pro Ser Gln Pro
                    820                 825                 830

Thr Thr Asn Tyr Gly Ala Pro Ser Gln Thr Pro Ser Ser Asn Tyr Gly
                    835                 840                 845

Ala Pro Pro Ala Ser Ser Ala Pro Ser Ser Thr Tyr Gly Arg Pro Ser
850                 855                 860

Gln Ser Pro Ser Ser Ser Tyr Gly Ala Pro Ser Pro Ser Ser Ser Ser
865                 870                 875                 880

Ser Ser Tyr Glu Ser Pro Ser Gln Pro Pro Ser Ser Tyr Gly Ala
                    885                 890                 895

Pro Ser Gln Gly Pro Ser Ser Tyr Gly Ala Pro Ser Arg Pro Ser
            900                 905                 910

Ser Thr Tyr Gly Ala Pro Ser Pro Ser Ser Pro Ser Thr Asn Tyr Gly
            915                 920                 925

Ala Pro Ala Pro Ser Ser Asn Tyr Gly Thr Pro Ala Gln Asp Leu Thr
930                 935                 940

Gly Ser Tyr Ala Ala Pro Ser Gln Pro Pro Ser Ala Gly Tyr Gly Ala
945                 950                 955                 960

Pro Ser Gly Gln Pro Ser Ser Gly Gly Lys Gln Asn Phe Gln Val Lys
            965                 970                 975

Asn Pro Phe Ala Gly Gln Thr His Gln Val Tyr Pro Ala Val Ser Ser
            980                 985                 990

Ile Ser Phe Gly Leu Pro Ser Gln  Ser Phe Asn Thr Ala  Ile Gln Gly
            995                 1000                1005

Gln Glu  Pro Ser Gln Ser Tyr  Gly Ala Pro Thr Ala  Ser Ser Pro
    1010                1015                1020

Ser Ser  Ser Tyr Gly Ala Pro  Thr Gly Thr Gly Ser  Ser Gln Pro
    1025                1030                1035

Gly Gln  Ser Tyr Ala Ser Asn  Gly Gly Tyr Ser Tyr  Ser
    1040                1045                1050

<210> SEQ ID NO 30
<211> LENGTH: 506
<212> TYPE: PRT
<213> ORGANISM: Rhodnius prolixus

<400> SEQUENCE: 30

Gln Pro Pro Phe Asn His Tyr Leu Pro Ala Ala Arg Gly Ser Gly Ser
1               5                   10                  15

Asn Ser Ala Gln Tyr Thr Ala Pro Ser Ser Lys Phe Gly Thr Ser Thr
            20                  25                  30

Gly Gln Tyr Gly Gln Pro Pro Ser Glu Val Pro Arg Gly Leu Gln Gln
        35                  40                  45
```

```
Gly Ser Tyr Ala Glu Asp Val His Ser Ser Arg Ser Val Asn Pro Ser
    50                  55                  60

Ser Gln Asn Gly Ile Pro Ser Gly His Phe Ser Ser Leu Ser Ser Asn
65                  70                  75                  80

Tyr Gly Ala Pro Ser Ser Asp Tyr Ser Arg Ser Phe Leu Arg Tyr Gly
                85                  90                  95

Thr Leu Ser Asn Lys Tyr Gly Val Pro Asn Ser Ala Leu Gly Ser Leu
                100                 105                 110

Ser Ser Arg Asn Asn Lys Thr Pro Ala Thr Gln Leu Ser Tyr Gln Pro
            115                 120                 125

Ser Ser His Tyr Asp Ser Arg Ser Thr Ser Glu Asp Gln Phe Ile Ser
        130                 135                 140

Ser Arg Val Ser Asp Ser Gln Tyr Gly Ala Ser Ser Val Arg Arg Phe
145                 150                 155                 160

Leu Pro Ser Ser Gln Tyr Ser Thr Pro Ser Ser Gln Tyr Gly Thr Pro
                165                 170                 175

Ser Ser Gln Tyr Gly Thr Pro Ser Ser Gln Tyr Gly Thr Pro Ser Ser
                180                 185                 190

Gln Tyr Gly Thr Pro Ser Ser Gln Tyr Gly Thr Pro Ser Ser Gln Tyr
            195                 200                 205

Gly Thr Pro Ser Ser Gln Tyr Gly Thr Pro Ser Ser Gln Tyr Gly Thr
        210                 215                 220

Pro Ser Ser Gln Tyr Gly Thr Pro Ser Ser Gln Tyr Gly Thr Pro Ser
225                 230                 235                 240

Ser Pro Pro Ser Gln Tyr Gly Gly Pro Tyr Ser Met Arg Thr Ser Ala
                245                 250                 255

Pro Asn Ser Gln Tyr Gly Thr Pro Ser Ser Phe Arg Thr Ser Pro Ser
                260                 265                 270

Ser Gln Phe Gly Ser Ser Ala His Ser Ser Leu Ser Lys Phe
            275                 280                 285

Arg Ser Val Pro Ser Ser Pro Tyr Gly Thr Leu Ser Ala Ile Arg Ser
    290                 295                 300

Thr His Ser Ser Gln Tyr Gly Thr Pro Ser Ser Phe Ser Asp Ser Thr
305                 310                 315                 320

Ser Ser Ser His Asn Gly Leu Pro Ser His Tyr Pro Gly Ser Gly Phe
                325                 330                 335

Ser Gly Ser Ser Val Asn Asp Gln Lys Ser Tyr Thr Gly Asn Val Phe
            340                 345                 350

Gly Gln Ser His Ser Arg Val Ala Asn Gly Asp Gln His Ala Arg Ser
        355                 360                 365

Tyr Thr Leu Ala Gly Gly Asn Glu Ile Ser Glu Pro Ala Lys Tyr Asp
    370                 375                 380

Phe Asn Tyr Asp Val Ser Asp Gly Glu Gln Gly Val Glu Phe Gly Gln
385                 390                 395                 400

Glu Glu Ser Arg Asp Gly Glu Glu Thr Asn Gly Ser Tyr His Val Leu
                405                 410                 415

Leu Pro Asp Gly Arg Arg Gln Arg Val Gln Tyr Thr Ala Gly Gln Tyr
                420                 425                 430

Gly Tyr Lys Pro Thr Ile Ser Tyr Glu Asn Thr Gly Thr Leu Thr Thr
            435                 440                 445

Gly Arg Gln Gln Phe Ser Asn Gly Phe Tyr Asn Val Gln Gln Ser Gly
        450                 455                 460

Ser Glu Ser Gln Glu His Leu Gly Arg Ser Thr Gly Gln Asn Ser Tyr
```

```
                    465                 470                 475                 480
Gly Gly Ser Asn Gly Tyr Glu Ser Gly Val Gly Tyr Gln Ser Gly Val
                485                 490                 495
Gly Arg Arg Ser Arg Pro Ala Gly Ser Tyr
                500                 505

<210> SEQ ID NO 31
<211> LENGTH: 551
<212> TYPE: PRT
<213> ORGANISM: Solenopsis invicta

<400> SEQUENCE: 31

Arg Ser Glu Pro Pro Ile Asn Ser Tyr Leu Pro Pro Arg Ala Gly Ser
1               5                   10                  15
Ser Gly Ala Asn Gly Gly Arg Thr Asp Leu Thr Thr Gln Tyr Gly Ala
                20                  25                  30
Pro Asp Phe Asn Asn Gly Gly Ala Thr Ser Phe Ser Gly Asn Gly
            35                  40                  45
Ala Gly Asp Gly Pro Ser Lys Leu Tyr Asp Val Pro Val Arg Gly Asn
50                  55                  60
Ala Gly Gly Asn Gly Leu Gly Arg Gly Asn Gly Phe Gly Gly Gln
65                  70                  75                  80
Pro Ser Ser Ser Tyr Gly Ala Pro Asn Gly Gly Ser Asn Glu Asn Arg
                85                  90                  95
Gly Asn Gly Gly Arg Pro Ser Thr Ser Tyr Gly Val Pro Gly Ala Asn
                100                 105                 110
Gly Asn Asn Gly Gly Phe Gly Asn Gly Gly Asp Lys Gly Arg Pro
            115                 120                 125
Ser Thr Ser Tyr Gly Val Pro Asp Ala Ser Gly Ser Ser Gln Gly Ser
130                 135                 140
Phe Gly Asn Val Gly Asn Gly Gly Arg Pro Ser Thr Asn Tyr Gly Val
145                 150                 155                 160
Pro Gly Ala Asn Gly Asn Gly Gly Phe Gly Asn Ala Ala Asn Glu
                165                 170                 175
Gly Lys Pro Ser Thr Ser Tyr Gly Val Pro Gly Ala Asn Gly Asn Ser
                180                 185                 190
Gln Gly Gly Phe Gly Asn Gly Gly Arg Pro Ser Thr Gly Tyr Gly Val
            195                 200                 205
Pro Gly Ala Asn Gly Asn Asn Gly Gly Phe Gly Gly Arg Pro Ser
210                 215                 220
Thr Ser Tyr Gly Ala Pro Gly Ala Asn Gly Asn His Arg Gly Gly Asn
225                 230                 235                 240
Gly Gly Asn Ala Ser Pro Ser Thr Asn Tyr Gly Val Pro Gly Gly Asn
                245                 250                 255
Asn Gly Asn Thr Asn Gly Lys Gly Arg Phe Asn Gly Gly Asn Ser Gly
                260                 265                 270
Gly Gly Pro Ser Asn Asn Tyr Gly Val Pro Asn Glu Asn Ala Phe Gly
            275                 280                 285
Gly Gly Leu Ser Thr Ser Tyr Gly Pro Pro Ser Arg Gly Gly Asn Gly
290                 295                 300
Asn Ser Gly Tyr Pro Ser Gly Gly Ser Asn Gly Ser Phe Val Asn
305                 310                 315                 320
Asn Gly Ala Asn Gly Tyr Pro Ser Gly Gly Pro Asn Gly Asn Ala Gly
                325                 330                 335
```

-continued

```
Asn Phe Gly Asp Gly Arg Gly Gly Lys Gly Gly Ser Gly Glu
            340                 345                 350

Gly Tyr Asn Asp Asn Ala Gln Glu Gly Ser Thr Glu Pro Ala Lys Tyr
        355                 360                 365

Glu Phe Ser Tyr Lys Val Lys Asp Gln Gln Thr Gly Ser Glu Tyr Ser
    370                 375                 380

His Thr Glu Thr Arg Asp Gly Asp Arg Ala Gln Gly Glu Phe Asn Val
385                 390                 395                 400

Leu Leu Pro Asp Gly Arg Lys Gln Ile Val Glu Tyr Glu Ala Asp Gln
                405                 410                 415

Asp Gly Phe Lys Pro Gln Ile Arg Tyr Glu Gly Glu Ala Asn Ala Gly
            420                 425                 430

Gly Gly Tyr Ser Ser Gly Gly Ser Asn Asp Asn Asp Gly Tyr Ser
        435                 440                 445

Ser Gly Arg Pro Gly Ser Glu Ala Gly Gly Phe Ala Asn Asn Ser Gly
    450                 455                 460

Phe Asn Gly Ser Gly Thr Asn Gly Gly Arg Ser Ser Gly Gly Pro Gly
465                 470                 475                 480

Asp Gly Asn Pro Gly Gly Phe Asn Ser Gly Gly Gly Gly Tyr Gln
                485                 490                 495

Ser Gly Arg Pro Ala Gly Gln Ser Phe Gly Arg Asp Asn Asp Gly Gly
    500                 505                 510

Leu Ser Gly Asp Ile Gly Gly Tyr Phe Ala Asn Ser Pro Ser Asn Asn
            515                 520                 525

Ile Gly Gly Ser Asp Ser Ala Asn Val Gly Ser Asn Arg Gln Asn Gly
        530                 535                 540

Gly Asn Gly Gly Tyr Gln Tyr
545                 550

<210> SEQ ID NO 32
<211> LENGTH: 382
<212> TYPE: PRT
<213> ORGANISM: Culex quinquefasciatus

<400> SEQUENCE: 32

Lys Arg Glu Ala Pro Leu Pro Gly Gly Ser Tyr Leu Pro Pro Ser Asn
1               5                   10                  15

Gly Gly Gly Ala Gly Gly Tyr Pro Ala Ala Gly Pro Pro Ser Gly Ser
            20                  25                  30

Tyr Gly Pro Pro Ser Asn Gly Asn Gly Asn Gly Ala Gly Gly
        35                  40                  45

Tyr Pro Ser Ala Pro Ser Gln Gln Tyr Gly Ala Pro Gly Gly Ala
    50                  55                  60

Pro Ser Gln Gln Tyr Gly Ala Pro Ser Asn Gly Asn Gly Gly Ala Gly
65                  70                  75                  80

Gly Tyr Pro Ser Ala Pro Ser Gln Gln Tyr Gly Ala Pro Asn Gly Asn
                85                  90                  95

Gly Asn Gly Gly Phe Gly Gly Arg Pro Gln Ala Pro Ser Gln Gln Tyr
                100                 105                 110

Gly Ala Pro Ser Asn Gly Asn Gly Gly Ala Arg Pro Ser Gln Gln Tyr
            115                 120                 125

Gly Ala Pro Asn Gly Asn Gly Asn Gly Arg Pro Gln Thr Pro Ser
        130                 135                 140

Ser Gln Tyr Gly Ala Pro Ser Gly Gly Ala Pro Ser Ser Gln Tyr Gly
145                 150                 155                 160
```

```
Ala Pro Ser Gly Gly Ala Pro Ser Gln Gln Tyr Ala Pro Asn Gly
            165                 170                 175

Gly Asn Gly Asn Gly Arg Pro Gln Thr Pro Ser Ser Gln Tyr Gly Ala
        180                 185                 190

Pro Ser Gly Gly Ala Pro Ser Gln Gln Tyr Gly Ala Pro Asn Gly Gly
            195                 200                 205

Asn Gly Asn Gly Arg Pro Gln Thr Pro Ser Ser Gln Tyr Gly Ala Pro
        210                 215                 220

Ser Gly Gly Ala Pro Ser Gln Tyr Gly Ala Pro Ser Gly Gly Ala
225                 230                 235                 240

Pro Ser Ser Gln Tyr Gly Ala Pro Ala Gly Gly Ala Pro Ser Ser Gln
            245                 250                 255

Tyr Gly Ala Pro Ala Gly Gly Ala Pro Ser Ser Gln Tyr Gly Ala Pro
            260                 265                 270

Ala Gly Gly Ala Pro Ser Ser Gln Tyr Gly Ala Pro Ala Gly Gly Ala
            275                 280                 285

Pro Ser Ser Gln Tyr Gly Ala Pro Ala Gly Gly Ala Pro Ser Ser Gln
            290                 295                 300

Tyr Gly Ala Pro Ser Ser Gln Tyr Gly Ala Pro Ala Gly Gly Ala Pro
305                 310                 315                 320

Ser Ser Gln Tyr Gly Ala Pro Ala Gly Gly Ala Pro Ser Ser Gln Tyr
            325                 330                 335

Gly Ala Pro Ser Gly Gly Ala Pro Ser Ser Gln Tyr Gly Ala Pro Ser
            340                 345                 350

Gly Gly Ala Pro Ser Ser Gln Tyr Gly Ala Pro Ala Gly Gly Ala Pro
            355                 360                 365

Ser Ser Gln Tyr Gly Ala Pro Ser Gly Gly Ala Pro Ser Ser
            370                 375                 380

<210> SEQ ID NO 33
<211> LENGTH: 491
<212> TYPE: PRT
<213> ORGANISM: Bactrocera cucurbitae

<400> S

```
                145                 150                 155                 160
Asn Gly Asn Gly Asn Gly Arg Pro Ser Ser Thr Tyr Gly Ala Pro Gly
                165                 170                 175
Leu Gly Gly Asn Gly Asn Gly Asn Gly Asn Gly Arg Pro Ser
            180                 185                 190
Ser Thr Tyr Gly Ala Pro Gly Leu Asn Gly Asn Gly Leu Gly Gly Gly
            195                 200                 205
Gln Lys Pro Ser Asp Ser Tyr Gly Pro Ala Ser Gly Asn Gly Asn
    210                 215                 220
Gly Tyr Ser Asn Gly Gly Asn Gly Asn Gly Asn Gly Gly Arg Pro
225                 230                 235                 240
Gly Gln Glu Tyr Leu Pro Pro Gly Arg Asn Gly Asn Gly Asn Gly Asn
                245                 250                 255
Gly Gly Arg Gly Asn Gly Asn Gly Gly Ala Asn Gly Tyr Asp Tyr
            260                 265                 270
Ser Gln Gly Gly Ser Asp Ser Gly Glu Ser Ile Val Asp Tyr Glu
    275                 280                 285
Ala Asp Gln Gly Gly Tyr Arg Pro Gln Ile Arg Tyr Glu Gly Glu Ala
    290                 295                 300
Asn Asn Gly Ala Gly Gly Leu Gly Gly Ala Gly Ala Asn Gly
305                 310                 315                 320
Tyr Asp Tyr Glu Gln Asn Gly Asn Gly Leu Gly Gly Asn Gly Tyr
                325                 330                 335
Ser Asn Gly Gln Asp Leu Gly Ser Asn Gly Tyr Ser Ser Gly Arg Pro
            340                 345                 350
Asn Gly Asn Gly Asn Gly Asn Gly Asn Gly Asn Gly Tyr Ser
            355                 360                 365
Gly Arg Asn Gly Lys Gly Arg Asn Gly Asn Gly Gly Gln Gly Leu
    370                 375                 380
Gly Arg Asn Gly Tyr Ser Asp Gly Arg Pro Ser Gly Gln Asp Leu Gly
385                 390                 395                 400
Asp Asn Gly Tyr Ala Ser Gly Arg Pro Gly Gly Asn Gly Asn Gly Asn
                405                 410                 415
Gly Gly Asn Gly Asn Gly Tyr Ser Asn Gly Asn Gly Tyr Ser Asn Gly
            420                 425                 430
Asn Gly Asn Gly Thr Gly Asn Gly Gly Gln Tyr Asn Gly Asn Gly
            435                 440                 445
Asn Gly Tyr Ser Asp Gly Arg Pro Gly Gly Gln Asp Asn Leu Asp Gly
    450                 455                 460
Gln Gly Tyr Ser Ser Gly Arg Pro Asn Gly Phe Gly Pro Gly Gly Gln
465                 470                 475                 480
Asn Gly Asp Asn Asp Gly Asn Gly Tyr Arg Tyr
                485                 490

<210> SEQ ID NO 34
<211> LENGTH: 770
<212> TYPE: PRT
<213> ORGANISM: Trichogramma pretiosum

<400> SEQUENCE: 34

Arg Pro Glu Pro Pro Val Asn Ser Tyr Leu Pro Gly Gln Gly Gly
1               5                   10                  15

Gln Gly Gly Phe Gly Gly Ser Gly Gly Arg Pro Gly Gly Gly Ser Pro
            20                  25                  30
```

```
Ser Asn Gln Tyr Gly Pro Pro Asn Phe Gln Asn Gly Gly Gln Asn
         35                  40                  45
Gly Gly Ser Gly Phe Gly Asn Gly Asn Gly Asn Ser Phe Gly Pro
 50                  55                  60
Pro Ser Asn Ser Tyr Gly Pro Pro Glu Phe Gly Ser Pro Gly Ala Gly
 65                  70                  75                  80
Ser Phe Gly Gly Arg Pro Gln Asp Thr Tyr Gly Pro Pro Ser Asn
                 85                  90                  95
Gly Asn Gly Asn Gly Asn Gly Phe Gly Asn Gly Asn Gly Gly
             100                 105                 110
Arg Pro Ser Ser Arg Pro Ser Asp Ser Tyr Gly Pro Pro Ser Ser Gly
             115                 120                 125
Asn Gly Phe Gly Gly Gly Asn Ser Gly Arg Pro Ser Glu Ser Tyr Gly
             130                 135                 140
Pro Pro Gln Asn Gly Gly Ser Gly Asn Gly Asn Gln Gly Gly
 145                 150                 155                 160
Asn Gly Phe Gly Asn Gly Gly Arg Gly Gln Gly Lys Pro Ser
                 165                 170                 175
Asp Ser Tyr Gly Pro Pro Asn Ser Gly Asn Arg Pro Gly Ser Ser Asn
                 180                 185                 190
Gly Gly Gly Gln Gln Gln Asn Gly Phe Gly Gly Asn Gly Gly Arg
             195                 200                 205
Pro Ser Asn Thr Tyr Gly Pro Pro Gly Gly Gly Asn Gly Gly Gly Arg
             210                 215                 220
Pro Gly Gly Ser Ser Gly Gly Phe Gly Gly Gln Asn Gly Gly Arg Pro
 225                 230                 235                 240
Ser Asp Ser Tyr Gly Pro Pro Ser Asn Gly Asn Gly Asn Gly Arg
                 245                 250                 255
Pro Ser Asn Asn Tyr Gly Pro Pro Asn Ser Gly Gly Asn Gly Asn
                 260                 265                 270
Gly Phe Gly Gly Ser Asn Gly Lys Pro Ser Asn Ser Tyr Gly Pro Pro
             275                 280                 285
Ser Asn Gly Asn Gly Gly Phe Gly Gly Ser Asn Gly Arg Pro Ser
             290                 295                 300
Asn Ser Tyr Gly Pro Pro Ser Gly Asn Gly Gly Phe Gly Gly
 305                 310                 315                 320
Ser Ser Ala Val Gly Arg Pro Gly Asn Ser Gly Pro Ser Ser Ser
                 325                 330                 335
Gly Ser Gly Phe Gly Gly Asn Gly Gly Ala Ser Arg Pro Ser Ser Ser
                 340                 345                 350
Tyr Gly Pro Pro Ser Asn Gly Gly Phe Gly Asn Gly Gly Ser
                 355                 360                 365
Asn Gly Arg Pro Ser Ser Tyr Gly Pro Pro Asn Ser Gly Ser Asn
             370                 375                 380
Gly Gly Gly Phe Gly Gly Gln Asn Gly Asn Gly Arg Gln Asn Gly Asn
 385                 390                 395                 400
Asn Gly Gln Gly Gly Phe Gly Gly Gln Pro Ser Ser Tyr Gly Pro
             405                 410                 415
Pro Ser Asn Gly Asn Gly Phe Gly Gly Gly Ser Asn Gly Tyr
                 420                 425                 430
Pro Gln Asn Ser Gln Gly Gly Asn Gly Asn Gly Phe Gly Gln Gly Ser
             435                 440                 445
Gly Gly Arg Pro Ser Ser Ser Tyr Gly Pro Pro Ser Asn Gly Gly Gly
```

```
                450               455               460
Gly Gly Asp Asn Gly Tyr Ser Ser Gly Gly Pro Gly Gly Phe Gly Gly
465                 470               475               480

Gln Pro Gln Asp Ser Tyr Gly Pro Pro Ser Gly Ala Val Asp Gly
                485               490               495

Asn Asn Gly Phe Ser Ser Gly Ser Ser Gly Asp Asn Asn Gly Tyr
                500               505               510

Ser Ser Gly Gly Pro Gly Gly Asn Gly Phe Glu Asp Gly Asn Asp Glu
                515               520               525

Pro Ala Lys Tyr Glu Phe Ser Tyr Glu Val Lys Asp Glu Gln Ser Gly
                530               535               540

Ser Ser Phe Gly His Thr Glu Met Arg Asp Gly Asp Arg Ala Gln Gly
545               550               555               560

Glu Phe Asn Val Leu Leu Pro Asp Gly Arg Lys Gln Ile Val Glu Tyr
                565               570               575

Glu Ala Asp Gln Asp Gly Phe Lys Pro Gln Ile Arg Tyr Glu Gly Glu
                580               585               590

Ala Asn Thr Gly Gly Ala Gly Gly Tyr Pro Ser Gly Gly Pro Gly Gly
                595               600               605

Gln Gly Gly Asn Gly Asn Gly Gly Tyr Pro Ser Gly Gly Pro Ser Asn
610               615               620

Gly Gly Phe Gly Gly Gln Asn Gly Gly Gly Asn Gly Gly Tyr Pro Ser
625               630               635               640

Gly Gly Pro Ser Gly Gly Gly Phe Gly Gly Gln Asn Gly Gly Ser Gly
                645               650               655

Gly Tyr Pro Ser Gly Gly Pro Ser Gly Gly Gly Phe Gly Gly Gln Gly
                660               665               670

Gly Phe Gly Gly Gln Asn Ser Gly Gly Asn Gly Gly Tyr Ser Ser Gly
                675               680               685

Gly Pro Ala Ser Gly Gly Phe Gly Gly Gln Asn Gly Gly Asn Gly Gly
                690               695               700

Tyr Pro Ser Gly Gly Pro Ser Gly Gly Gly Phe Gly Gly Gln Gly Gly
705               710               715               720

Phe Gly Gly Gln Asn Ser Gly Gly Asn Gly Gly Tyr Pro Ser Gly Gly
                725               730               735

Pro Ser Gly Gly Phe Gly Gly Gln Asn Gly Gly Gly Gly Gly Asn
                740               745               750

Tyr Pro Ala Gly Ser Gly Gly Asp Ala Glu Ala Asn Gly Gly Tyr Gln
                755               760               765

Tyr Ser
770

<210> SEQ ID NO 35
<211> LENGTH: 280
<212> TYPE: PRT
<213> ORGANISM: Drosophila sechellia

<400> SEQUENCE: 35

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
                20                  25                  30

Gly Gln Gly Gln Gly Gln Gly Gln Gly Gly Tyr Gly Gly Lys Pro Ser
                35                  40                  45
```

```
Asp Ser Tyr Gly Ala Pro Gly Gly Asn Gly Asn Gly Gly Arg Pro
    50                  55                  60

Ser Ser Ser Tyr Gly Ala Pro Gly Gly Asn Gly Gly Arg Pro Ser
65              70                  75                  80

Asp Thr Tyr Gly Ala Pro Gly Gly Asn Gly Gly Arg Pro Ser Asp
                85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn
            115                 120                 125

Gly Arg Pro Ser Ser Ser Tyr Gly Ala Pro Gly Gly Asn Gly Gly
    130                 135                 140

Arg Pro Ser Asp Thr Tyr Gly Ala Pro Gly Gly Asn Gly Gly Arg
145             150                 155                 160

Pro Ser Asp Thr Tyr Gly Ala Pro Gly Gly Asn Asn Gly Gly Arg
            165                 170                 175

Pro Ser Ser Tyr Gly Ala Pro Gly Gly Gly Asn Gly Gly Arg Pro
        180                 185                 190

Ser Asp Thr Tyr Gly Ala Pro Gly Gly Asn Gly Asn Gly Ser Gly
            195                 200                 205

Gly Arg Pro Ser Ser Ser Tyr Gly Ala Pro Ala Gln Gly Gln Gly
    210                 215                 220

Phe Gly Gly Arg Pro Ser Asp Ser Tyr Gly Ala Pro Gln Asn Gln
225             230                 235                 240

Lys Pro Ser Asp Ser Tyr Gly Ala Pro Gly Ser Gly Asn Gly Ser Ala
                245                 250                 255

Gly Arg Pro Ser Ser Ser Tyr Gly Ala Pro Gly Ser Gly Pro Gly Gly
    260                 265                 270

Arg Pro Ser Asp Ser Tyr Gly Pro
    275                 280

<210> SEQ ID NO 36
<211> LENGTH: 280
<212> TYPE: PRT
<213> ORGANISM: Drosophila sechellia

<400> SEQUENCE: 36

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gly Tyr Gly Gly Lys Pro Ser
        35                  40                  45

Asp Ser Tyr Gly Ala Pro Gly Gly Asn Gly Asn Gly Gly Arg Pro
    50                  55                  60

Ser Ser Ser Tyr Gly Ala Pro Gly Gly Asn Gly Gly Arg Pro Ser
65              70                  75                  80

Asp Thr Tyr Gly Ala Pro Gly Gly Asn Gly Gly Arg Pro Ser Asp
                85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn
            115                 120                 125

Gly Arg Pro Ser Ser Ser Tyr Gly Ala Pro Gly Gly Asn Gly Gly
    130                 135                 140
```

-continued

```
Arg Pro Ser Asp Thr Tyr Gly Ala Pro Gly Gly Gly Asn Gly Gly Arg
145                 150                 155                 160

Pro Ser Asp Thr Tyr Gly Ala Pro Gly Gly Asn Asn Gly Gly Arg
                165                 170                 175

Pro Ser Ser Tyr Gly Ala Pro Gly Gly Asn Gly Gly Arg Pro
            180                 185                 190

Ser Asp Thr Tyr Gly Ala Pro Gly Gly Asn Gly Asn Gly Ser Gly
                195                 200                 205

Gly Arg Pro Ser Ser Tyr Gly Ala Pro Ala Gln Gly Gln Gly Gly
        210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255

Gly Arg Pro Ser Ser Ser Tyr Gly Ala Pro Gly Ser Gly Pro Gly Gly
            260                 265                 270

Arg Pro Ser Asp Ser Tyr Gly Pro
            275                 280

<210> SEQ ID NO 37
<211> LENGTH: 280
<212> TYPE: PRT
<213> ORGANISM: Drosophila sechellia

<400> SEQUENCE: 37

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gly Tyr Gly Gly Lys Pro Ser
        35                  40                  45

Asp Ser Tyr Gly Ala Pro Gly Gly Gly Asn Gly Asn Gly Gly Arg Pro
50                  55                  60

Ser Ser Tyr Gly Ala Pro Gly Gly Gly Asn Gly Gly Arg Pro Ser
65                  70                  75                  80

Asp Thr Tyr Gly Ala Pro Gly Gly Gly Asn Gly Gly Arg Pro Ser Asp
                85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn Gly
        115                 120                 125

Gly Arg Pro Ser Ser Ser Tyr Gly Ala Pro Gly Gly Gly Asn Gly Gly
    130                 135                 140

Arg Pro Ser Asp Thr Tyr Gly Ala Pro Gly Gly Gly Asn Gly Gly Arg
145                 150                 155                 160

Pro Ser Asp Thr Tyr Gly Ala Pro Gly Gly Asn Asn Gly Gly Arg
                165                 170                 175

Pro Ser Ser Ser Tyr Gly Ala Pro Gly Gly Gly Asn Gly Gly Arg Pro
            180                 185                 190

Ser Asp Thr Tyr Gly Ala Pro Gly Gly Asn Gly Asn Gly Ser Gly
                195                 200                 205

Gly Arg Pro Ser Ser Ser Tyr Gly Ala Pro Ala Gln Gly Gln Gly Gly
        210                 215                 220

Phe Gly Gly Arg Pro Ser Asp Ser Tyr Gly Ala Pro Gly Gln Asn Gln
```

```
225                 230                 235                 240

Lys Pro Ser Asp Ser Tyr Gly Ala Pro Gly Ser Gly Asn Gly Ser Ala
                245                 250                 255

Gly Arg Pro Ser Ser Tyr Gly Ala Pro Gly Ser Gly Pro Gly Gly
            260                 265                 270

Arg Pro Ser Asp Ser Tyr Gly Pro
            275                 280

<210> SEQ ID NO 38
<211> LENGTH: 280
<212> TYPE: PRT
<213> ORGANISM: Drosophila sechellia

<400> SEQUENCE: 38

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gln Gly Gly Tyr Gly Lys Pro Ser
        35                  40                  45

Asp Ser Tyr Gly Ala Pro Gly Gly Gly Asn Gly Asn Gly Gly Arg Pro
50                  55                  60

Ser Ser Tyr Gly Ala Pro Gly Gly Gly Asn Gly Arg Pro Ser
65                  70                  75                  80

Asp Thr Tyr Gly Ala Pro Gly Gly Gly Asn Gly Gly Arg Pro Ser Asp
                85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn Gly
        115                 120                 125

Gly Arg Pro Ser Ser Ser Tyr Gly Ala Pro Gly Gly Gly Asn Gly Gly
    130                 135                 140

Arg Pro Ser Asp Thr Tyr Gly Ala Pro Gly Gly Gly Asn Gly Gly Arg
145                 150                 155                 160

Pro Ser Asp Thr Tyr Gly Ala Pro Gly Gly Gly Asn Asn Gly Gly Arg
                165                 170                 175

Pro Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Asn Gly Ser Gly
        195                 200                 205

Gly Arg Pro Ser Ser Ser Tyr Gly Ala Pro Ala Gln Gly Gln Gly Gly
    210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255

Gly Arg Pro Ser Ser Tyr Gly Ala Pro Gly Ser Gly Pro Gly Gly
            260                 265                 270

Arg Pro Ser Asp Ser Tyr Gly Pro
            275                 280

<210> SEQ ID NO 39
<211> LENGTH: 162
<212> TYPE: PRT
<213> ORGANISM: Drosophila sechellia
```

-continued

```
<400> SEQUENCE: 39

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
                100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln

<210> SEQ ID NO 40
<211> LENGTH: 162
<212> TYPE: PRT
<213> ORGANISM: Drosophila sechellia

<400> SEQUENCE: 40

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
                100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln

<210> SEQ ID NO 41
<211> LENGTH: 162
<212> TYPE: PRT
<213> ORGANISM: Drosophila sechellia
```

<400> SEQUENCE: 41

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Gly Ser Asp Gly Gly Arg Val Ile Ile
                100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln

<210> SEQ ID NO 42
<211> LENGTH: 162
<212> TYPE: PRT
<213> ORGANISM: Drosophila sechellia

<400> SEQUENCE: 42

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Gly Ser Asp Gly Gly Arg Val Ile Ile
                100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln

<210> SEQ ID NO 43
<211> LENGTH: 162
<212> TYPE: PRT

<213> ORGANISM: Drosophila sechellia

<400> SEQUENCE: 43

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Gly Ser Asp Gly Gly Arg Val Ile Ile
            100                 105                 110

Gly Gly Arg Val Ile Gly Gly Gln Asp Gly Gly Asp Gln Gly Tyr Ser
        115                 120                 125

Gly Gly Arg Pro Gly Gly Gln Asp Leu Gly Arg Asp Gly Tyr Ser Ser
    130                 135                 140

Gly Arg Pro Gly Gly Arg Pro Gly Gly Asn Gly Gln Asp Ser Gln Asp
145                 150                 155                 160

Gly Gln

<210> SEQ ID NO 44
<211> LENGTH: 162
<212> TYPE: PRT
<213> ORGANISM: Drosophila sechellia

<400> SEQUENCE: 44

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Gly Ser Asp Gly Gly Arg Val Ile Ile
            100                 105                 110

Gly Gly Arg Val Ile Gly Gly Gln Asp Gly Gly Asp Gln Gly Tyr Ser
        115                 120                 125

Gly Gly Arg Pro Gly Gly Gln Asp Leu Gly Arg Asp Gly Tyr Ser Ser
    130                 135                 140

Gly Arg Pro Gly Gly Arg Pro Gly Gly Asn Gly Gln Asp Ser Gln Asp
145                 150                 155                 160

Gly Gln

<210> SEQ ID NO 45
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Asp Tyr Lys Asp Asp Asp Lys Asp Tyr Lys Asp Asp Asp
1               5                   10                  15

Lys Asp Tyr Lys Asp Asp Asp Asp Lys
                20                  25

<210> SEQ ID NO 46
<211> LENGTH: 85
<212> TYPE: PRT
<213> ORGANISM: Unknown
<220> FEATURE:
<223> OTHER INFORMATION: Description of Unknown:
      Alpha mating factor precursor protein sequence

<400> SEQUENCE: 46

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ala Glu Ala
1

<210> SEQ ID NO 48
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly
1

<210> SEQ ID NO 49
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 49

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
                35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Arg Pro Glu Pro Pro Val
                85                  90                  95

Asn Ser Tyr Leu Pro Pro Ser Asp Ser Tyr Gly Ala Pro Gly Gln Ser
                100                 105                 110

Gly Ala Gly Gly Arg Pro Ser Asp Thr Tyr Gly Ala Pro Gly Gly Gly
                115                 120                 125

Asn Gly Gly Arg Pro Ser Asp Ser Tyr Gly Ala Pro Gly Gln Gly Gln
130                 135                 140

Gly Gln Gly Gln Gly Gln Gly Tyr Gly Gly Lys Pro Ser Asp Ser
145                 150                 155                 160

Tyr Gly Ala Pro Gly Gly Asn Gly Asn Gly Gly Arg Pro Ser Ser
                165                 170                 175

Ser Tyr Gly Ala Pro Gly Gly Gly Asn Gly Gly Arg Pro Ser Asp Thr
                180                 185                 190

Tyr Gly Ala Pro Gly Gly Gly Asn Gly Gly Arg Pro Ser Asp Thr Tyr
                195                 200                 205

Gly Ala Pro Gly Gly Gly Asn Gly Asn Gly Gly Arg Pro Ser Ser
        210                 215                 220

Ser Tyr Gly Ala Pro Gly Gln Gly Gln Gly Asn Gly Asn Gly Gly Arg
225                 230                 235                 240

Pro Ser Ser Ser Tyr Gly Ala Pro Gly Gly Asn Gly Gly Arg Pro
                245                 250                 255

Ser Asp Thr Tyr Gly Ala Pro Gly Gly Asn Gly Gly Arg Pro Ser
                260                 265                 270

Asp Thr Tyr Gly Ala Pro Gly Gly Asn Asn Gly Gly Arg Pro Ser
            275                 280                 285

Ser Ser Tyr Gly Ala Pro Gly Gly Gly Asn Gly Gly Arg Pro Ser Asp
        290                 295                 300

Thr Tyr Gly Ala Pro Gly Gly Gly Asn Gly Asn Gly Ser Gly Gly Arg
305                 310                 315                 320

Pro Ser Ser Tyr Gly Ala Pro Ala Gln Gly Gln Gly Gly Phe Gly
                325                 330                 335

Gly Arg Pro Ser Asp Ser Tyr Gly Ala Pro Gly Gln Asn Gln Lys Pro
                340                 345                 350

Ser Asp Ser Tyr Gly Ala Pro Gly Ser Gly Asn Gly Ser Ala Gly Arg
                355                 360                 365

Pro Ser Ser Tyr Gly Ala Pro Gly Ser Gly Pro Gly Gly Arg Pro
                370                 375                 380

Ser Asp Ser Tyr Gly Pro Pro Ala Ser Gly Ser Gly Ala Gly Gly Ala
385                 390                 395                 400

Gly Gly Ser Gly Pro Gly Gly Ala Asp Tyr Asp Asn Asp Glu Pro Ala
```

```
                    405                 410                 415
Lys Tyr Glu Phe Asn Tyr Gln Val Glu Asp Ala Pro Ser Gly Leu Ser
            420                 425                 430

Phe Gly His Ser Glu Met Arg Asp Gly Asp Phe Thr Thr Gly Gln Tyr
        435                 440                 445

Asn Val Leu Leu Pro Asp Gly Arg Lys Gln Ile Val Glu Tyr Glu Ala
    450                 455                 460

Asp Gln Gln Gly Tyr Arg Pro Gln Ile Arg Tyr Glu Gly Asp Ala Asn
465                 470                 475                 480

Asp Gly Ser Gly Pro Ser Gly Pro Ser Gly Pro Gly Gly Pro Gly Gly
                485                 490                 495

Gln Asn Leu Gly Ala Asp Gly Tyr Ser Ser Gly Arg Pro Gly Asn Gly
                500                 505                 510

Asn Gly Asn Gly Asn Gly Gly Tyr Ser Ser Gly Arg Pro Gly Gly Gln
            515                 520                 525

Asp Leu Gly Pro Ser Gly Tyr Ser Gly Gly Arg Pro Gly Gly Gln Asp
        530                 535                 540

Leu Gly Ala Gly Gly Tyr Ser Asn Val Lys Pro Gly Gly Gln Asp Leu
545                 550                 555                 560

Gly Pro Gly Gly Tyr Ser Gly Gly Arg Pro Gly Gly Gln Asp Leu Gly
                565                 570                 575

Arg Asp Gly Tyr Ser Gly Gly Arg Pro Gly Gly Gln Asp Leu Gly Ala
            580                 585                 590

Gly Ala Tyr Ser Asn Gly Arg Pro Gly Gly Asn Gly Asn Gly Gly Ser
        595                 600                 605

Asp Gly Gly Arg Val Ile Ile Gly Gly Arg Val Ile Gly Gly Gln Asp
    610                 615                 620

Gly Gly Asp Gln Gly Tyr Ser Gly Gly Arg Pro Gly Gly Gln Asp Leu
625                 630                 635                 640

Gly Arg Asp Gly Tyr Ser Ser Gly Arg Pro Gly Gly Arg Pro Gly Gly
                645                 650                 655

Asn Gly Gln Asp Ser Gln Asp Gly Gln Gly Tyr Ser Ser Gly Arg Pro
            660                 665                 670

Gly Gln Gly Gly Arg Asn Gly Phe Gly Pro Gly Gly Gln Asn Gly Asp
        675                 680                 685

Asn Asp Gly Ser Gly Tyr Arg Tyr Ser Gly Asp Tyr Lys Asp Asp Asp
    690                 695                 700

Asp Lys Asp Tyr Lys Asp Asp Asp Lys Asp Tyr Lys Asp Asp Asp
705                 710                 715                 720

Asp Lys

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 50
```

```
Ser Xaa Xaa Tyr Gly Xaa Pro
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Gly Asn Gly
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gln Gly Gly
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gln Gly Asn
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gln Gly Gln
1

<210> SEQ ID NO 56
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 56

Gly Gln Gly Gln Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Pro Gly Gly Gln
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Pro Gly Gly Asn
1               5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Ser Phe
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Asn Gly Gly
1

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Ala Gly Gly
1               5
```

```
<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid

<400> SEQUENCE: 62

Xaa Xaa Glu Pro Pro Val Ser Tyr Leu Pro Pro Ser
1               5                   10

<210> SEQ ID NO 63
<211> LENGTH: 4
<212> TYPE: PRT
<213> ORGANISM: Unknown
<220> FEATURE:
<223> OTHER INFORMATION: Description of Unknown:
      "GRPE" sequence

<400> SEQUENCE: 63

Gly Arg Pro Glu
1

<210> SEQ ID NO 64
<211> LENGTH: 3000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(3000)
<223> OTHER INFORMATION: This sequence may encompass 1-100 "Tyr Gly Xaa
      Pro Xaa Xaa Xaa Xaa Xaa Xaa Xaa Xaa Xaa Xaa Xaa Xaa Xaa Xaa
      Xaa Xaa Xaa Xaa Xaa Xaa Xaa Xaa Xaa Xaa Xaa" repeating units
<220> FEATURE:
<221> NAME/KEY: MOD_RES
<222> LOCATION: (3)..(3)
<223> OTHER INFORMATION: A, L, P, T or V
<220> FEATURE:
<221> NAME/KEY: MOD_RES
<222> LOCATION: (5)..(24)
<223> OTHER INFORMATION: Any amino acid
<220> FEATURE:
<221> NAME/KEY: MISC_FEATURE
<222> LOCATION: (5)..(24)
<223> OTHER INFORMATION: This region may encompass 3-20 residues
<220> FEATURE:
<221> NAME/KEY: MOD_RES
<222> LOCATION: (25)..(28)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (29)..(30)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (33)..(33)
<223> OTHER INFORMATION: A, L, P, T or V
<220> FEATURE:
<221> NAME/KEY: MOD_RES
<222> LOCATION: (35)..(54)
<223> OTHER INFORMATION: Any amino acid
<220> FEATURE:
<221> NAME/KEY: MISC_FEATURE
<222> LOCATION: (35)..(54)
```

```
<223> OTHER INFORMATION: This region may encompass 3-20 residues
<220> FEATURE:
<221> NAME/KEY: MOD_RES
<222> LOCATION: (55)..(58)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (59)..(60)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (63)..(63)
<223> OTHER INFORMATION: A, L, P, T or V
<220> FEATURE:
<221> NAME/KEY: MOD_RES
<222> LOCATION: (65)..(84)
<223> OTHER INFORMATION: Any amino acid
<220> FEATURE:
<221> NAME/KEY: MISC_FEATURE
<222> LOCATION: (65)..(84)
<223> OTHER INFORMATION: This region may encompass 3-20 residues
<220> FEATURE:
<221> NAME/KEY: MOD_RES
<222> LOCATION: (85)..(88)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (89)..(90)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (93)..(93)
<223> OTHER INFORMATION: A, L, P, T or V
<220> FEATURE:
<221> NAME/KEY: MOD_RES
<222> LOCATION: (95)..(114)
<223> OTHER INFORMATION: Any amino acid
<220> FEATURE:
<221> NAME/KEY: MISC_FEATURE
<222> LOCATION: (95)..(114)
<223> OTHER INFORMATION: This region may encompass 3-20 residues
<220> FEATURE:
<221> NAME/KEY: MOD_RES
<222> LOCATION: (115)..(118)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (119)..(120)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (123)..(123)
<223> OTHER INFORMATION: A, L, P, T or V
<220> FEATURE:
<221> NAME/KEY: MOD_RES
<222> LOCATION: (125)..(144)
<223> OTHER INFORMATION: Any amino acid
<220> FEATURE:
<221> NAME/KEY: MISC_FEATURE
<222> LOCATION: (125)..(144)
<223> OTHER INFORMATION: This region may encompass 3-20 residues
<220> FEATURE:
<221> NAME/KEY: MOD_RES
<222> LOCATION: (145)..(148)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (149)..(150)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
```

```
<222> LOCATION: (153)..(153)
<223> OTHER INFORMATION: A, L, P, T or V
<220> FEATURE:
<221> NAME/KEY: MOD_RES
<222> LOCATION: (155)..(174)
<223> OTHER INFORMATION: Any amino acid
<220> FEATURE:
<221> NAME/KEY: MISC_FEATURE
<222> LOCATION: (155)..(174)
<223> OTHER INFORMATION: This region may encompass 3-20 residues
<220> FEATURE:
<221> NAME/KEY: MOD_RES
<222> LOCATION: (175)..(178)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (179)..(180)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (183)..(183)
<223> OTHER INFORMATION: A, L, P, T or V
<220> FEATURE:
<221> NAME/KEY: MOD_RES
<222> LOCATION: (185)..(204)
<223> OTHER INFORMATION: Any amino acid
<220> FEATURE:
<221> NAME/KEY: MISC_FEATURE
<222> LOCATION: (185)..(204)
<223> OTHER INFORMATION: This region may encompass 3-20 residues
<220> FEATURE:
<221> NAME/KEY: MOD_RES
<222> LOCATION: (205)..(208)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (209)..(210)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (213)..(213)
<223> OTHER INFORMATION: A, L, P, T or V
<220> FEATURE:
<221> NAME/KEY: MOD_RES
<222> LOCATION: (215)..(234)
<223> OTHER INFORMATION: Any amino acid
<220> FEATURE:
<221> NAME/KEY: MISC_FEATURE
<222> LOCATION: (215)..(234)
<223> OTHER INFORMATION: This region may encompass 3-20 residues
<220> FEATURE:
<221> NAME/KEY: MOD_RES
<222> LOCATION: (235)..(238)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (239)..(240)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (243)..(243)
<223> OTHER INFORMATION: A, L, P, T or V
<220> FEATURE:
<221> NAME/KEY: MOD_RES
<222> LOCATION: (245)..(264)
<223> OTHER INFORMATION: Any amino acid
<220> FEATURE:
<221> NAME/KEY: MISC_FEATURE
<222> LOCATION: (245)..(264)
<223> OTHER INFORMATION: This region may encompass 3-20 residues
<220> FEATURE:
<221> NAME/KEY: MOD_RES
<222> LOCATION: (265)..(268)
```

```
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (269)..(270)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (273)..(273)
<223> OTHER INFORMATION: A, L, P, T or V
<220> FEATURE:
<221> NAME/KEY: MOD_RES
<222> LOCATION: (275)..(294)
<223> OTHER INFORMATION: Any amino acid
<220> FEATURE:
<221> NAME/KEY: MISC_FEATURE
<222> LOCATION: (275)..(294)
<223> OTHER INFORMATION: This region may encompass 3-20 residues
<220> FEATURE:
<221> NAME/KEY: MOD_RES
<222> LOCATION: (295)..(298)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (299)..(300)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (303)..(303)
<223> OTHER INFORMATION: A, L, P, T or V
<220> FEATURE:
<221> NAME/KEY: MOD_RES
<222> LOCATION: (305)..(324)
<223> OTHER INFORMATION: Any amino acid
<220> FEATURE:
<221> NAME/KEY: MISC_FEATURE
<222> LOCATION: (305)..(324)
<223> OTHER INFORMATION: This region may encompass 3-20 residues
<220> FEATURE:
<221> NAME/KEY: MOD_RES
<222> LOCATION: (325)..(328)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (329)..(330)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (333)..(333)
<223> OTHER INFORMATION: A, L, P, T or V
<220> FEATURE:
<221> NAME/KEY: MOD_RES
<222> LOCATION: (335)..(354)
<223> OTHER INFORMATION: Any amino acid
<220> FEATURE:
<221> NAME/KEY: MISC_FEATURE
<222> LOCATION: (335)..(354)
<223> OTHER INFORMATION: This region may encompass 3-20 residues
<220> FEATURE:
<221> NAME/KEY: MOD_RES
<222> LOCATION: (355)..(358)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (359)..(360)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (363)..(363)
<223> OTHER INFORMATION: A, L, P, T or V
<220> FEATURE:
<221> NAME/KEY: MOD_RES
```

-continued

```
<222> LOCATION: (365)..(384)
<223> OTHER INFORMATION: Any amino acid
<220> FEATURE:
<221> NAME/KEY: MISC_FEATURE
<222> LOCATION: (365)..(384)
<223> OTHER INFORMATION: This region may encompass 3-20 residues
<220> FEATURE:
<221> NAME/KEY: MOD_RES
<222> LOCATION: (385)..(388)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (389)..(390)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (393)..(393)
<223> OTHER INFORMATION: A, L, P, T or V
<220> FEATURE:
<221> NAME/KEY: MOD_RES
<222> LOCATION: (395)..(414)
<223> OTHER INFORMATION: Any amino acid
<220> FEATURE:
<221> NAME/KEY: MISC_FEATURE
<222> LOCATION: (395)..(414)
<223> OTHER INFORMATION: This region may encompass 3-20 residues
<220> FEATURE:
<221> NAME/KEY: MOD_RES
<222> LOCATION: (415)..(418)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (419)..(420)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (423)..(423)
<223> OTHER INFORMATION: A, L, P, T or V
<220> FEATURE:
<221> NAME/KEY: MOD_RES
<222> LOCATION: (425)..(444)
<223> OTHER INFORMATION: Any amino acid
<220> FEATURE:
<221> NAME/KEY: MISC_FEATURE
<222> LOCATION: (425)..(444)
<223> OTHER INFORMATION: This region may encompass 3-20 residues
<220> FEATURE:
<221> NAME/KEY: MOD_RES
<222> LOCATION: (445)..(448)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (449)..(450)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (453)..(453)
<223> OTHER INFORMATION: A, L, P, T or V
<220> FEATURE:
<221> NAME/KEY: MOD_RES
<222> LOCATION: (455)..(474)
<223> OTHER INFORMATION: Any amino acid
<220> FEATURE:
<221> NAME/KEY: MISC_FEATURE
<222> LOCATION: (455)..(474)
<223> OTHER INFORMATION: This region may encompass 3-20 residues
<220> FEATURE:
<221> NAME/KEY: MOD_RES
<222> LOCATION: (475)..(478)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
```

```
<222> LOCATION: (479)..(480)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (483)..(483)
<223> OTHER INFORMATION: A, L, P, T or V
<220> FEATURE:
<221> NAME/KEY: MOD_RES
<222> LOCATION: (485)..(504)
<223> OTHER INFORMATION: Any amino acid
<220> FEATURE:
<221> NAME/KEY: MISC_FEATURE
<222> LOCATION: (485)..(504)
<223> OTHER INFORMATION: This region may encompass 3-20 residues
<220> FEATURE:
<221> NAME/KEY: MOD_RES
<222> LOCATION: (505)..(508)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (509)..(510)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (513)..(513)
<223> OTHER INFORMATION: A, L, P, T or V
<220> FEATURE:
<221> NAME/KEY: MOD_RES
<222> LOCATION: (515)..(534)
<223> OTHER INFORMATION: Any amino acid
<220> FEATURE:
<221> NAME/KEY: MISC_FEATURE
<222> LOCATION: (515)..(534)
<223> OTHER INFORMATION: This region may encompass 3-20 residues
<220> FEATURE:
<221> NAME/KEY: MOD_RES
<222> LOCATION: (535)..(538)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (539)..(540)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (543)..(543)
<223> OTHER INFORMATION: A, L, P, T or V
<220> FEATURE:
<221> NAME/KEY: MOD_RES
<222> LOCATION: (545)..(564)
<223> OTHER INFORMATION: Any amino acid
<220> FEATURE:
<221> NAME/KEY: MISC_FEATURE
<222> LOCATION: (545)..(564)
<223> OTHER INFORMATION: This region may encompass 3-20 residues
<220> FEATURE:
<221> NAME/KEY: MOD_RES
<222> LOCATION: (565)..(568)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (569)..(570)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (573)..(573)
<223> OTHER INFORMATION: A, L, P, T or V
<220> FEATURE:
<221> NAME/KEY: MOD_RES
<222> LOCATION: (575)..(594)
<223> OTHER INFORMATION: Any amino acid
<220> FEATURE:
<221> NAME/KEY: MISC_FEATURE
```

```
<222> LOCATION: (575)..(594)
<223> OTHER INFORMATION: This region may encompass 3-20 residues
<220> FEATURE:
<221> NAME/KEY: MOD_RES
<222> LOCATION: (595)..(598)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (599)..(600)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (603)..(603)
<223> OTHER INFORMATION: A, L, P, T or V
<220> FEATURE:
<221> NAME/KEY: MOD_RES
<222> LOCATION: (605)..(624)
<223> OTHER INFORMATION: Any amino acid
<220> FEATURE:
<221> NAME/KEY: MISC_FEATURE
<222> LOCATION: (605)..(624)
<223> OTHER INFORMATION: This region may encompass 3-20 residues
<220> FEATURE:
<221> NAME/KEY: MOD_RES
<222> LOCATION: (625)..(628)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (629)..(630)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (633)..(633)
<223> OTHER INFORMATION: A, L, P, T or V
<220> FEATURE:
<221> NAME/KEY: MOD_RES
<222> LOCATION: (635)..(654)
<223> OTHER INFORMATION: Any amino acid
<220> FEATURE:
<221> NAME/KEY: MISC_FEATURE
<222> LOCATION: (635)..(654)
<223> OTHER INFORMATION: This region may encompass 3-20 residues
<220> FEATURE:
<221> NAME/KEY: MOD_RES
<222> LOCATION: (655)..(658)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (659)..(660)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (663)..(663)
<223> OTHER INFORMATION: A, L, P, T or V
<220> FEATURE:
<221> NAME/KEY: MOD_RES
<222> LOCATION: (665)..(684)
<223> OTHER INFORMATION: Any amino acid
<220> FEATURE:
<221> NAME/KEY: MISC_FEATURE
<222> LOCATION: (665)..(684)
<223> OTHER INFORMATION: This region may encompass 3-20 residues
<220> FEATURE:
<221> NAME/KEY: MOD_RES
<222> LOCATION: (685)..(688)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (689)..(690)
<223> OTHER INFORMATION: This region may encompass one of the following
      sequences: S, D, T, N, L, DS, DT, LS, SS, ST, TN, or TS
<220> FEATURE:
```

```
<221> NAME/KEY: MOD_RES
<222> LOCATION: (693)..(693)
<223> OTHER INFORMATION: A, L, P, T or V
<220> FEATURE:
<221> NAME/KEY: MOD_RES
<222> LOCATION: (695)..(714)
<223> OTHER INFORMATION: Any amino acid
<220> FEATURE:
<221> NAME/KEY: MISC_FEATURE
<222> LOCATION: (695)..(714)
<223> OTHER INFORMATION: This region may encompass 3-20 residues
<220> FEATURE:
<221> NAME/KEY: MOD_RES
<222> LOCATION: (715)..(718)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (719)..(720)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (723)..(723)
<223> OTHER INFORMATION: A, L, P, T or V
<220> FEATURE:
<221> NAME/KEY: MOD_RES
<222> LOCATION: (725)..(744)
<223> OTHER INFORMATION: Any amino acid
<220> FEATURE:
<221> NAME/KEY: MISC_FEATURE
<222> LOCATION: (725)..(744)
<223> OTHER INFORMATION: This region may encompass 3-20 residues
<220> FEATURE:
<221> NAME/KEY: MOD_RES
<222> LOCATION: (745)..(748)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (749)..(750)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (753)..(753)
<223> OTHER INFORMATION: A, L, P, T or V
<220> FEATURE:
<221> NAME/KEY: MOD_RES
<222> LOCATION: (755)..(774)
<223> OTHER INFORMATION: Any amino acid
<220> FEATURE:
<221> NAME/KEY: MISC_FEATURE
<222> LOCATION: (755)..(774)
<223> OTHER INFORMATION: This region may encompass 3-20 residues
<220> FEATURE:
<221> NAME/KEY: MOD_RES
<222> LOCATION: (775)..(778)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (779)..(780)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (783)..(783)
<223> OTHER INFORMATION: A, L, P, T or V
<220> FEATURE:
<221> NAME/KEY: MOD_RES
<222> LOCATION: (785)..(804)
<223> OTHER INFORMATION: Any amino acid
<220> FEATURE:
<221> NAME/KEY: MISC_FEATURE
<222> LOCATION: (785)..(804)
<223> OTHER INFORMATION: This region may encompass 3-20 residues
<220> FEATURE:
<221> NAME/KEY: MOD_RES
```

```
<222> LOCATION: (805)..(808)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (809)..(810)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (813)..(813)
<223> OTHER INFORMATION: A, L, P, T or V
<220> FEATURE:
<221> NAME/KEY: MOD_RES
<222> LOCATION: (815)..(834)
<223> OTHER INFORMATION: Any amino acid
<220> FEATURE:
<221> NAME/KEY: MISC_FEATURE
<222> LOCATION: (815)..(834)
<223> OTHER INFORMATION: This region may encompass 3-20 residues
<220> FEATURE:
<221> NAME/KEY: MOD_RES
<222> LOCATION: (835)..(838)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (839)..(840)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (843)..(843)
<223> OTHER INFORMATION: A, L, P, T or V
<220> FEATURE:
<221> NAME/KEY: MOD_RES
<222> LOCATION: (845)..(864)
<223> OTHER INFORMATION: Any amino acid
<220> FEATURE:
<221> NAME/KEY: MISC_FEATURE
<222> LOCATION: (845)..(864)
<223> OTHER INFORMATION: This region may encompass 3-20 residues
<220> FEATURE:
<221> NAME/KEY: MOD_RES
<222> LOCATION: (865)..(868)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (869)..(870)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (873)..(873)
<223> OTHER INFORMATION: A, L, P, T or V
<220> FEATURE:
<221> NAME/KEY: MOD_RES
<222> LOCATION: (875)..(894)
<223> OTHER INFORMATION: Any amino acid
<220> FEATURE:
<221> NAME/KEY: MISC_FEATURE
<222> LOCATION: (875)..(894)
<223> OTHER INFORMATION: This region may encompass 3-20 residues
<220> FEATURE:
<221> NAME/KEY: MOD_RES
<222> LOCATION: (895)..(898)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (899)..(900)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (903)..(903)
<223> OTHER INFORMATION: A, L, P, T or V
<220> FEATURE:
```

```
<221> NAME/KEY: MOD_RES
<222> LOCATION: (905)..(924)
<223> OTHER INFORMATION: Any amino acid
<220> FEATURE:
<221> NAME/KEY: MISC_FEATURE
<222> LOCATION: (905)..(924)
<223> OTHER INFORMATION: This region may encompass 3-20 residues
<220> FEATURE:
<221> NAME/KEY: MOD_RES
<222> LOCATION: (925)..(928)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (929)..(930)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (933)..(933)
<223> OTHER INFORMATION: A, L, P, T or V
<220> FEATURE:
<221> NAME/KEY: MOD_RES
<222> LOCATION: (935)..(954)
<223> OTHER INFORMATION: Any amino acid
<220> FEATURE:
<221> NAME/KEY: MISC_FEATURE
<222> LOCATION: (935)..(954)
<223> OTHER INFORMATION: This region may encompass 3-20 residues
<220> FEATURE:
<221> NAME/KEY: MOD_RES
<222> LOCATION: (955)..(958)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (959)..(960)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (963)..(963)
<223> OTHER INFORMATION: A, L, P, T or V
<220> FEATURE:
<221> NAME/KEY: MOD_RES
<222> LOCATION: (965)..(984)
<223> OTHER INFORMATION: Any amino acid
<220> FEATURE:
<221> NAME/KEY: MISC_FEATURE
<222> LOCATION: (965)..(984)
<223> OTHER INFORMATION: This region may encompass 3-20 residues
<220> FEATURE:
<221> NAME/KEY: MOD_RES
<222> LOCATION: (985)..(988)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (989)..(990)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (993)..(993)
<223> OTHER INFORMATION: A, L, P, T or V
<220> FEATURE:
<221> NAME/KEY: MOD_RES
<222> LOCATION: (995)..(1014)
<223> OTHER INFORMATION: Any amino acid
<220> FEATURE:
<221> NAME/KEY: MISC_FEATURE
<222> LOCATION: (995)..(1014)
<223> OTHER INFORMATION: This region may encompass 3-20 residues
<220> FEATURE:
<221> NAME/KEY: MOD_RES
<222> LOCATION: (1015)..(1018)
<223> OTHER INFORMATION: This region may encompass one of the following
      sequences: GG, LS, APS, GAG, GGG, KPS, RPS, or GGGG
<220> FEATURE:
```

```
<221> NAME/KEY: MOD_RES
<222> LOCATION: (1019)..(1020)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1023)..(1023)
<223> OTHER INFORMATION: A, L, P, T or V
<220> FEATURE:
<221> NAME/KEY: MOD_RES
<222> LOCATION: (1025)..(1044)
<223> OTHER INFORMATION: Any amino acid
<220> FEATURE:
<221> NAME/KEY: MISC_FEATURE
<222> LOCATION: (1025)..(1044)
<223> OTHER INFORMATION: This region may encompass 3-20 residues
<220> FEATURE:
<221> NAME/KEY: MOD_RES
<222> LOCATION: (1045)..(1048)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1049)..(1050)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1053)..(1053)
<223> OTHER INFORMATION: A, L, P, T or V
<220> FEATURE:
<221> NAME/KEY: MOD_RES
<222> LOCATION: (1055)..(1074)
<223> OTHER INFORMATION: Any amino acid
<220> FEATURE:
<221> NAME/KEY: MISC_FEATURE
<222> LOCATION: (1055)..(1074)
<223> OTHER INFORMATION: This region may encompass 3-20 residues
<220> FEATURE:
<221> NAME/KEY: MOD_RES
<222> LOCATION: (1075)..(1078)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1079)..(1080)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1083)..(1083)
<223> OTHER INFORMATION: A, L, P, T or V
<220> FEATURE:
<221> NAME/KEY: MOD_RES
<222> LOCATION: (1085)..(1104)
<223> OTHER INFORMATION: Any amino acid
<220> FEATURE:
<221> NAME/KEY: MISC_FEATURE
<222> LOCATION: (1085)..(1104)
<223> OTHER INFORMATION: This region may encompass 3-20 residues
<220> FEATURE:
<221> NAME/KEY: MOD_RES
<222> LOCATION: (1105)..(1108)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1109)..(1110)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1113)..(1113)
<223> OTHER INFORMATION: A, L, P, T or V
<220> FEATURE:
<221> NAME/KEY: MOD_RES
<222> LOCATION: (1115)..(1134)
<223> OTHER INFORMATION: Any amino acid
<220> FEATURE:
```

```
-continued

<221> NAME/KEY: MISC_FEATURE
<222> LOCATION: (1115)..(1134)
<223> OTHER INFORMATION: This region may encompass 3-20 residues
<220> FEATURE:
<221> NAME/KEY: MOD_RES
<222> LOCATION: (1135)..(1138)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1139)..(1140)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1143)..(1143)
<223> OTHER INFORMATION: A, L, P, T or V
<220> FEATURE:
<221> NAME/KEY: MOD_RES
<222> LOCATION: (1145)..(1164)
<223> OTHER INFORMATION: Any amino acid
<220> FEATURE:
<221> NAME/KEY: MISC_FEATURE
<222> LOCATION: (1145)..(1164)
<223> OTHER INFORMATION: This region may encompass 3-20 residues
<220> FEATURE:
<221> NAME/KEY: MOD_RES
<222> LOCATION: (1165)..(1168)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1169)..(1170)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1173)..(1173)
<223> OTHER INFORMATION: A, L, P, T or V
<220> FEATURE:
<221> NAME/KEY: MOD_RES
<222> LOCATION: (1175)..(1194)
<223> OTHER INFORMATION: Any amino acid
<220> FEATURE:
<221> NAME/KEY: MISC_FEATURE
<222> LOCATION: (1175)..(1194)
<223> OTHER INFORMATION: This region may encompass 3-20 residues
<220> FEATURE:
<221> NAME/KEY: MOD_RES
<222> LOCATION: (1195)..(1198)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1199)..(1200)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1203)..(1203)
<223> OTHER INFORMATION: A, L, P, T or V
<220> FEATURE:
<221> NAME/KEY: MOD_RES
<222> LOCATION: (1205)..(1224)
<223> OTHER INFORMATION: Any amino acid
<220> FEATURE:
<221> NAME/KEY: MISC_FEATURE
<222> LOCATION: (1205)..(1224)
<223> OTHER INFORMATION: This region may encompass 3-20 residues
<220> FEATURE:
<221> NAME/KEY: MOD_RES
<222> LOCATION: (1225)..(1228)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1229)..(1230)
<223> OTHER INFORMATION: This region may encompass one of the following
      sequences: S, D, T, N, L, DS, DT, LS, SS, ST, TN, or TS
```

```
<220> FEATURE:
<221> NAME/KEY: MOD_RES
<222> LOCATION: (1233)..(1233)
<223> OTHER INFORMATION: A, L, P, T or V
<220> FEATURE:
<221> NAME/KEY: MOD_RES
<222> LOCATION: (1235)..(1254)
<223> OTHER INFORMATION: Any amino acid
<220> FEATURE:
<221> NAME/KEY: MISC_FEATURE
<222> LOCATION: (1235)..(1254)
<223> OTHER INFORMATION: This region may encompass 3-20 residues
<220> FEATURE:
<221> NAME/KEY: MOD_RES
<222> LOCATION: (1255)..(1258)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1259)..(1260)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1263)..(1263)
<223> OTHER INFORMATION: A, L, P, T or V
<220> FEATURE:
<221> NAME/KEY: MOD_RES
<222> LOCATION: (1265)..(1284)
<223> OTHER INFORMATION: Any amino acid
<220> FEATURE:
<221> NAME/KEY: MISC_FEATURE
<222> LOCATION: (1265)..(1284)
<223> OTHER INFORMATION: This region may encompass 3-20 residues
<220> FEATURE:
<221> NAME/KEY: MOD_RES
<222> LOCATION: (1285)..(1288)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1289)..(1290)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1293)..(1293)
<223> OTHER INFORMATION: A, L, P, T or V
<220> FEATURE:
<221> NAME/KEY: MOD_RES
<222> LOCATION: (1295)..(1314)
<223> OTHER INFORMATION: Any amino acid
<220> FEATURE:
<221> NAME/KEY: MISC_FEATURE
<222> LOCATION: (1295)..(1314)
<223> OTHER INFORMATION: This region may encompass 3-20 residues
<220> FEATURE:
<221> NAME/KEY: MOD_RES
<222> LOCATION: (1315)..(1318)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1319)..(1320)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1323)..(1323)
<223> OTHER INFORMATION: A, L, P, T or V
<220> FEATURE:
<221> NAME/KEY: MOD_RES
<222> LOCATION: (1325)..(1344)
<223> OTHER INFORMATION: Any amino acid
<220> FEATURE:
<221> NAME/KEY: MISC_FEATURE
<222> LOCATION: (1325)..(1344)
<223> OTHER INFORMATION: This region may encompass 3-20 residues
<220> FEATURE:
```

-continued

```
<221> NAME/KEY: MOD_RES
<222> LOCATION: (1345)..(1348)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1349)..(1350)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1353)..(1353)
<223> OTHER INFORMATION: A, L, P, T or V
<220> FEATURE:
<221> NAME/KEY: MOD_RES
<222> LOCATION: (1355)..(1374)
<223> OTHER INFORMATION: Any amino acid
<220> FEATURE:
<221> NAME/KEY: MISC_FEATURE
<222> LOCATION: (1355)..(1374)
<223> OTHER INFORMATION: This region may encompass 3-20 residues
<220> FEATURE:
<221> NAME/KEY: MOD_RES
<222> LOCATION: (1375)..(1378)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1379)..(1380)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1383)..(1383)
<223> OTHER INFORMATION: A, L, P, T or V
<220> FEATURE:
<221> NAME/KEY: MOD_RES
<222> LOCATION: (1385)..(1404)
<223> OTHER INFORMATION: Any amino acid
<220> FEATURE:
<221> NAME/KEY: MISC_FEATURE
<222> LOCATION: (1385)..(1404)
<223> OTHER INFORMATION: This region may encompass 3-20 residues
<220> FEATURE:
<221> NAME/KEY: MOD_RES
<222> LOCATION: (1405)..(1408)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1409)..(1410)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1413)..(1413)
<223> OTHER INFORMATION: A, L, P, T or V
<220> FEATURE:
<221> NAME/KEY: MOD_RES
<222> LOCATION: (1415)..(1434)
<223> OTHER INFORMATION: Any amino acid
<220> FEATURE:
<221> NAME/KEY: MISC_FEATURE
<222> LOCATION: (1415)..(1434)
<223> OTHER INFORMATION: This region may encompass 3-20 residues
<220> FEATURE:
<221> NAME/KEY: MOD_RES
<222> LOCATION: (1435)..(1438)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1439)..(1440)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1443)..(1443)
<223> OTHER INFORMATION: A, L, P, T or V
```

```
<220> FEATURE:
<221> NAME/KEY: MOD_RES
<222> LOCATION: (1445)..(1464)
<223> OTHER INFORMATION: Any amino acid
<220> FEATURE:
<221> NAME/KEY: MISC_FEATURE
<222> LOCATION: (1445)..(1464)
<223> OTHER INFORMATION: This region may encompass 3-20 residues
<220> FEATURE:
<221> NAME/KEY: MOD_RES
<222> LOCATION: (1465)..(1468)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1469)..(1470)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1473)..(1473)
<223> OTHER INFORMATION: A, L, P, T or V
<220> FEATURE:
<221> NAME/KEY: MOD_RES
<222> LOCATION: (1475)..(1494)
<223> OTHER INFORMATION: Any amino acid
<220> FEATURE:
<221> NAME/KEY: MISC_FEATURE
<222> LOCATION: (1475)..(1494)
<223> OTHER INFORMATION: This region may encompass 3-20 residues
<220> FEATURE:
<221> NAME/KEY: MOD_RES
<222> LOCATION: (1495)..(1498)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1499)..(1500)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1503)..(1503)
<223> OTHER INFORMATION: A, L, P, T or V
<220> FEATURE:
<221> NAME/KEY: MOD_RES
<222> LOCATION: (1505)..(1524)
<223> OTHER INFORMATION: Any amino acid
<220> FEATURE:
<221> NAME/KEY: MISC_FEATURE
<222> LOCATION: (1505)..(1524)
<223> OTHER INFORMATION: This region may encompass 3-20 residues
<220> FEATURE:
<221> NAME/KEY: MOD_RES
<222> LOCATION: (1525)..(1528)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1529)..(1530)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1533)..(1533)
<223> OTHER INFORMATION: A, L, P, T or V
<220> FEATURE:
<221> NAME/KEY: MOD_RES
<222> LOCATION: (1535)..(1554)
<223> OTHER INFORMATION: Any amino acid
<220> FEATURE:
<221> NAME/KEY: MISC_FEATURE
<222> LOCATION: (1535)..(1554)
<223> OTHER INFORMATION: This region may encompass 3-20 residues
<220> FEATURE:
<221> NAME/KEY: MOD_RES
<222> LOCATION: (1555)..(1558)
<223> OTHER INFORMATION: This region may encompass one of the following
      sequences: GG, LS, APS, GAG, GGG, KPS, RPS, or GGGG
```

-continued

```
<220> FEATURE:
<221> NAME/KEY: MOD_RES
<222> LOCATION: (1559)..(1560)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1563)..(1563)
<223> OTHER INFORMATION: A, L, P, T or V
<220> FEATURE:
<221> NAME/KEY: MOD_RES
<222> LOCATION: (1565)..(1584)
<223> OTHER INFORMATION: Any amino acid
<220> FEATURE:
<221> NAME/KEY: MISC_FEATURE
<222> LOCATION: (1565)..(1584)
<223> OTHER INFORMATION: This region may encompass 3-20 residues
<220> FEATURE:
<221> NAME/KEY: MOD_RES
<222> LOCATION: (1585)..(1588)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1589)..(1590)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1593)..(1593)
<223> OTHER INFORMATION: A, L, P, T or V
<220> FEATURE:
<221> NAME/KEY: MOD_RES
<222> LOCATION: (1595)..(1614)
<223> OTHER INFORMATION: Any amino acid
<220> FEATURE:
<221> NAME/KEY: MISC_FEATURE
<222> LOCATION: (1595)..(1614)
<223> OTHER INFORMATION: This region may encompass 3-20 residues
<220> FEATURE:
<221> NAME/KEY: MOD_RES
<222> LOCATION: (1615)..(1618)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1619)..(1620)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1623)..(1623)
<223> OTHER INFORMATION: A, L, P, T or V
<220> FEATURE:
<221> NAME/KEY: MOD_RES
<222> LOCATION: (1625)..(1644)
<223> OTHER INFORMATION: Any amino acid
<220> FEATURE:
<221> NAME/KEY: MISC_FEATURE
<222> LOCATION: (1625)..(1644)
<223> OTHER INFORMATION: This region may encompass 3-20 residues
<220> FEATURE:
<221> NAME/KEY: MOD_RES
<222> LOCATION: (1645)..(1648)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1649)..(1650)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1653)..(1653)
<223> OTHER INFORMATION: A, L, P, T or V
<220> FEATURE:
<221> NAME/KEY: MOD_RES
<222> LOCATION: (1655)..(1674)
<223> OTHER INFORMATION: Any amino acid
```

```
<220> FEATURE:
<221> NAME/KEY: MISC_FEATURE
<222> LOCATION: (1655)..(1674)
<223> OTHER INFORMATION: This region may encompass 3-20 residues
<220> FEATURE:
<221> NAME/KEY: MOD_RES
<222> LOCATION: (1675)..(1678)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1679)..(1680)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1683)..(1683)
<223> OTHER INFORMATION: A, L, P, T or V
<220> FEATURE:
<221> NAME/KEY: MOD_RES
<222> LOCATION: (1685)..(1704)
<223> OTHER INFORMATION: Any amino acid
<220> FEATURE:
<221> NAME/KEY: MISC_FEATURE
<222> LOCATION: (1685)..(1704)
<223> OTHER INFORMATION: This region may encompass 3-20 residues
<220> FEATURE:
<221> NAME/KEY: MOD_RES
<222> LOCATION: (1705)..(1708)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1709)..(1710)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1713)..(1713)
<223> OTHER INFORMATION: A, L, P, T or V
<220> FEATURE:
<221> NAME/KEY: MOD_RES
<222> LOCATION: (1715)..(1734)
<223> OTHER INFORMATION: Any amino acid
<220> FEATURE:
<221> NAME/KEY: MISC_FEATURE
<222> LOCATION: (1715)..(1734)
<223> OTHER INFORMATION: This region may encompass 3-20 residues
<220> FEATURE:
<221> NAME/KEY: MOD_RES
<222> LOCATION: (1735)..(1738)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1739)..(1740)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1743)..(1743)
<223> OTHER INFORMATION: A, L, P, T or V
<220> FEATURE:
<221> NAME/KEY: MOD_RES
<222> LOCATION: (1745)..(1764)
<223> OTHER INFORMATION: Any amino acid
<220> FEATURE:
<221> NAME/KEY: MISC_FEATURE
<222> LOCATION: (1745)..(1764)
<223> OTHER INFORMATION: This region may encompass 3-20 residues
<220> FEATURE:
<221> NAME/KEY: MOD_RES
<222> LOCATION: (1765)..(1768)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1769)..(1770)
<223> OTHER INFORMATION: This region may encompass one of the following
```

```
      sequences: S, D, T, N, L, DS, DT, LS, SS, ST, TN, or TS
<220> FEATURE:
<221> NAME/KEY: MOD_RES
<222> LOCATION: (1773)..(1773)
<223> OTHER INFORMATION: A, L, P, T or V
<220> FEATURE:
<221> NAME/KEY: MOD_RES
<222> LOCATION: (1775)..(1794)
<223> OTHER INFORMATION: Any amino acid
<220> FEATURE:
<221> NAME/KEY: MISC_FEATURE
<222> LOCATION: (1775)..(1794)
<223> OTHER INFORMATION: This region may encompass 3-20 residues
<220> FEATURE:
<221> NAME/KEY: MOD_RES
<222> LOCATION: (1795)..(1798)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1799)..(1800)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1803)..(1803)
<223> OTHER INFORMATION: A, L, P, T or V
<220> FEATURE:
<221> NAME/KEY: MOD_RES
<222> LOCATION: (1805)..(1824)
<223> OTHER INFORMATION: Any amino acid
<220> FEATURE:
<221> NAME/KEY: MISC_FEATURE
<222> LOCATION: (1805)..(1824)
<223> OTHER INFORMATION: This region may encompass 3-20 residues
<220> FEATURE:
<221> NAME/KEY: MOD_RES
<222> LOCATION: (1825)..(1828)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1829)..(1830)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1833)..(1833)
<223> OTHER INFORMATION: A, L, P, T or V
<220> FEATURE:
<221> NAME/KEY: MOD_RES
<222> LOCATION: (1835)..(1854)
<223> OTHER INFORMATION: Any amino acid
<220> FEATURE:
<221> NAME/KEY: MISC_FEATURE
<222> LOCATION: (1835)..(1854)
<223> OTHER INFORMATION: This region may encompass 3-20 residues
<220> FEATURE:
<221> NAME/KEY: MOD_RES
<222> LOCATION: (1855)..(1858)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1859)..(1860)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1863)..(1863)
<223> OTHER INFORMATION: A, L, P, T or V
<220> FEATURE:
<221> NAME/KEY: MOD_RES
<222> LOCATION: (1865)..(1884)
<223> OTHER INFORMATION: Any amino acid
<220> FEATURE:
<221> NAME/KEY: MISC_FEATURE
<222> LOCATION: (1865)..(1884)
<223> OTHER INFORMATION: This region may encompass 3-20 residues
```

-continued

```
<220> FEATURE:
<221> NAME/KEY: MOD_RES
<222> LOCATION: (1885)..(1888)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1889)..(1890)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1893)..(1893)
<223> OTHER INFORMATION: A, L, P, T or V
<220> FEATURE:
<221> NAME/KEY: MOD_RES
<222> LOCATION: (1895)..(1914)
<223> OTHER INFORMATION: Any amino acid
<220> FEATURE:
<221> NAME/KEY: MISC_FEATURE
<222> LOCATION: (1895)..(1914)
<223> OTHER INFORMATION: This region may encompass 3-20 residues
<220> FEATURE:
<221> NAME/KEY: MOD_RES
<222> LOCATION: (1915)..(1918)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1919)..(1920)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1923)..(1923)
<223> OTHER INFORMATION: A, L, P, T or V
<220> FEATURE:
<221> NAME/KEY: MOD_RES
<222> LOCATION: (1925)..(1944)
<223> OTHER INFORMATION: Any amino acid
<220> FEATURE:
<221> NAME/KEY: MISC_FEATURE
<222> LOCATION: (1925)..(1944)
<223> OTHER INFORMATION: This region may encompass 3-20 residues
<220> FEATURE:
<221> NAME/KEY: MOD_RES
<222> LOCATION: (1945)..(1948)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1949)..(1950)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1953)..(1953)
<223> OTHER INFORMATION: A, L, P, T or V
<220> FEATURE:
<221> NAME/KEY: MOD_RES
<222> LOCATION: (1955)..(1974)
<223> OTHER INFORMATION: Any amino acid
<220> FEATURE:
<221> NAME/KEY: MISC_FEATURE
<222> LOCATION: (1955)..(1974)
<223> OTHER INFORMATION: This region may encompass 3-20 residues
<220> FEATURE:
<221> NAME/KEY: MOD_RES
<222> LOCATION: (1975)..(1978)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (1979)..(1980)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (1983)..(1983)
```

```
<223> OTHER INFORMATION: A, L, P, T or V
<220> FEATURE:
<221> NAME/KEY: MOD_RES
<222> LOCATION: (1985)..(2004)
<223> OTHER INFORMATION: Any amino acid
<220> FEATURE:
<221> NAME/KEY: MISC_FEATURE
<222> LOCATION: (1985)..(2004)
<223> OTHER INFORMATION: This region may encompass 3-20 residues
<220> FEATURE:
<221> NAME/KEY: MOD_RES
<222> LOCATION: (2005)..(2008)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2009)..(2010)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2013)..(2013)
<223> OTHER INFORMATION: A, L, P, T or V
<220> FEATURE:
<221> NAME/KEY: MOD_RES
<222> LOCATION: (2015)..(2034)
<223> OTHER INFORMATION: Any amino acid
<220> FEATURE:
<221> NAME/KEY: MISC_FEATURE
<222> LOCATION: (2015)..(2034)
<223> OTHER INFORMATION: This region may encompass 3-20 residues
<220> FEATURE:
<221> NAME/KEY: MOD_RES
<222> LOCATION: (2035)..(2038)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2039)..(2040)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2043)..(2043)
<223> OTHER INFORMATION: A, L, P, T or V
<220> FEATURE:
<221> NAME/KEY: MOD_RES
<222> LOCATION: (2045)..(2064)
<223> OTHER INFORMATION: Any amino acid
<220> FEATURE:
<221> NAME/KEY: MISC_FEATURE
<222> LOCATION: (2045)..(2064)
<223> OTHER INFORMATION: This region may encompass 3-20 residues
<220> FEATURE:
<221> NAME/KEY: MOD_RES
<222> LOCATION: (2065)..(2068)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2069)..(2070)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2073)..(2073)
<223> OTHER INFORMATION: A, L, P, T or V
<220> FEATURE:
<221> NAME/KEY: MOD_RES
<222> LOCATION: (2075)..(2094)
<223> OTHER INFORMATION: Any amino acid
<220> FEATURE:
<221> NAME/KEY: MISC_FEATURE
<222> LOCATION: (2075)..(2094)
<223> OTHER INFORMATION: This region may encompass 3-20 residues
<220> FEATURE:
<221> NAME/KEY: MOD_RES
<222> LOCATION: (2095)..(2098)
<223> OTHER INFORMATION: This region may encompass one of the following
```

```
      sequences: GG, LS, APS, GAG, GGG, KPS, RPS, or GGGG
<220> FEATURE:
<221> NAME/KEY: MOD_RES
<222> LOCATION: (2099)..(2100)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2103)..(2103)
<223> OTHER INFORMATION: A, L, P, T or V
<220> FEATURE:
<221> NAME/KEY: MOD_RES
<222> LOCATION: (2105)..(2124)
<223> OTHER INFORMATION: Any amino acid
<220> FEATURE:
<221> NAME/KEY: MISC_FEATURE
<222> LOCATION: (2105)..(2124)
<223> OTHER INFORMATION: This region may encompass 3-20 residues
<220> FEATURE:
<221> NAME/KEY: MOD_RES
<222> LOCATION: (2125)..(2128)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2129)..(2130)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2133)..(2133)
<223> OTHER INFORMATION: A, L, P, T or V
<220> FEATURE:
<221> NAME/KEY: MOD_RES
<222> LOCATION: (2135)..(2154)
<223> OTHER INFORMATION: Any amino acid
<220> FEATURE:
<221> NAME/KEY: MISC_FEATURE
<222> LOCATION: (2135)..(2154)
<223> OTHER INFORMATION: This region may encompass 3-20 residues
<220> FEATURE:
<221> NAME/KEY: MOD_RES
<222> LOCATION: (2155)..(2158)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2159)..(2160)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2163)..(2163)
<223> OTHER INFORMATION: A, L, P, T or V
<220> FEATURE:
<221> NAME/KEY: MOD_RES
<222> LOCATION: (2165)..(2184)
<223> OTHER INFORMATION: Any amino acid
<220> FEATURE:
<221> NAME/KEY: MISC_FEATURE
<222> LOCATION: (2165)..(2184)
<223> OTHER INFORMATION: This region may encompass 3-20 residues
<220> FEATURE:
<221> NAME/KEY: MOD_RES
<222> LOCATION: (2185)..(2188)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2189)..(2190)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2193)..(2193)
<223> OTHER INFORMATION: A, L, P, T or V
<220> FEATURE:
<221> NAME/KEY: MOD_RES
<222> LOCATION: (2195)..(2214)
```

```
<223> OTHER INFORMATION: Any amino acid
<220> FEATURE:
<221> NAME/KEY: MISC_FEATURE
<222> LOCATION: (2195)..(2214)
<223> OTHER INFORMATION: This region may encompass 3-20 residues
<220> FEATURE:
<221> NAME/KEY: MOD_RES
<222> LOCATION: (2215)..(2218)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2219)..(2220)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2223)..(2223)
<223> OTHER INFORMATION: A, L, P, T or V
<220> FEATURE:
<221> NAME/KEY: MOD_RES
<222> LOCATION: (2225)..(2244)
<223> OTHER INFORMATION: Any amino acid
<220> FEATURE:
<221> NAME/KEY: MISC_FEATURE
<222> LOCATION: (2225)..(2244)
<223> OTHER INFORMATION: This region may encompass 3-20 residues
<220> FEATURE:
<221> NAME/KEY: MOD_RES
<222> LOCATION: (2245)..(2248)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2249)..(2250)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2253)..(2253)
<223> OTHER INFORMATION: A, L, P, T or V
<220> FEATURE:
<221> NAME/KEY: MOD_RES
<222> LOCATION: (2255)..(2274)
<223> OTHER INFORMATION: Any amino acid
<220> FEATURE:
<221> NAME/KEY: MISC_FEATURE
<222> LOCATION: (2255)..(2274)
<223> OTHER INFORMATION: This region may encompass 3-20 residues
<220> FEATURE:
<221> NAME/KEY: MOD_RES
<222> LOCATION: (2275)..(2278)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2279)..(2280)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2283)..(2283)
<223> OTHER INFORMATION: A, L, P, T or V
<220> FEATURE:
<221> NAME/KEY: MOD_RES
<222> LOCATION: (2285)..(2304)
<223> OTHER INFORMATION: Any amino acid
<220> FEATURE:
<221> NAME/KEY: MISC_FEATURE
<222> LOCATION: (2285)..(2304)
<223> OTHER INFORMATION: This region may encompass 3-20 residues
<220> FEATURE:
<221> NAME/KEY: MOD_RES
<222> LOCATION: (2305)..(2308)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2309)..(2310)
```

```
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2313)..(2313)
<223> OTHER INFORMATION: A, L, P, T or V
<220> FEATURE:
<221> NAME/KEY: MOD_RES
<222> LOCATION: (2315)..(2334)
<223> OTHER INFORMATION: Any amino acid
<220> FEATURE:
<221> NAME/KEY: MISC_FEATURE
<222> LOCATION: (2315)..(2334)
<223> OTHER INFORMATION: This region may encompass 3-20 residues
<220> FEATURE:
<221> NAME/KEY: MOD_RES
<222> LOCATION: (2335)..(2338)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2339)..(2340)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2343)..(2343)
<223> OTHER INFORMATION: A, L, P, T or V
<220> FEATURE:
<221> NAME/KEY: MOD_RES
<222> LOCATION: (2345)..(2364)
<223> OTHER INFORMATION: Any amino acid
<220> FEATURE:
<221> NAME/KEY: MISC_FEATURE
<222> LOCATION: (2345)..(2364)
<223> OTHER INFORMATION: This region may encompass 3-20 residues
<220> FEATURE:
<221> NAME/KEY: MOD_RES
<222> LOCATION: (2365)..(2368)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2369)..(2370)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2373)..(2373)
<223> OTHER INFORMATION: A, L, P, T or V
<220> FEATURE:
<221> NAME/KEY: MOD_RES
<222> LOCATION: (2375)..(2394)
<223> OTHER INFORMATION: Any amino acid
<220> FEATURE:
<221> NAME/KEY: MISC_FEATURE
<222> LOCATION: (2375)..(2394)
<223> OTHER INFORMATION: This region may encompass 3-20 residues
<220> FEATURE:
<221> NAME/KEY: MOD_RES
<222> LOCATION: (2395)..(2398)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2399)..(2400)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2403)..(2403)
<223> OTHER INFORMATION: A, L, P, T or V
<220> FEATURE:
<221> NAME/KEY: MOD_RES
<222> LOCATION: (2405)..(2424)
<223> OTHER INFORMATION: Any amino acid
<220> FEATURE:
<221> NAME/KEY: MISC_FEATURE
<222> LOCATION: (2405)..(2424)
```

```
<223> OTHER INFORMATION: This region may encompass 3-20 residues
<220> FEATURE:
<221> NAME/KEY: MOD_RES
<222> LOCATION: (2425)..(2428)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2429)..(2430)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2433)..(2433)
<223> OTHER INFORMATION: A, L, P, T or V
<220> FEATURE:
<221> NAME/KEY: MOD_RES
<222> LOCATION: (2435)..(2454)
<223> OTHER INFORMATION: Any amino acid
<220> FEATURE:
<221> NAME/KEY: MISC_FEATURE
<222> LOCATION: (2435)..(2454)
<223> OTHER INFORMATION: This region may encompass 3-20 residues
<220> FEATURE:
<221> NAME/KEY: MOD_RES
<222> LOCATION: (2455)..(2458)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2459)..(2460)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2463)..(2463)
<223> OTHER INFORMATION: A, L, P, T or V
<220> FEATURE:
<221> NAME/KEY: MOD_RES
<222> LOCATION: (2465)..(2484)
<223> OTHER INFORMATION: Any amino acid
<220> FEATURE:
<221> NAME/KEY: MISC_FEATURE
<222> LOCATION: (2465)..(2484)
<223> OTHER INFORMATION: This region may encompass 3-20 residues
<220> FEATURE:
<221> NAME/KEY: MOD_RES
<222> LOCATION: (2485)..(2488)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2489)..(2490)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2493)..(2493)
<223> OTHER INFORMATION: A, L, P, T or V
<220> FEATURE:
<221> NAME/KEY: MOD_RES
<222> LOCATION: (2495)..(2514)
<223> OTHER INFORMATION: Any amino acid
<220> FEATURE:
<221> NAME/KEY: MISC_FEATURE
<222> LOCATION: (2495)..(2514)
<223> OTHER INFORMATION: This region may encompass 3-20 residues
<220> FEATURE:
<221> NAME/KEY: MOD_RES
<222> LOCATION: (2515)..(2518)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2519)..(2520)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
```

```
<222> LOCATION: (2523)..(2523)
<223> OTHER INFORMATION: A, L, P, T or V
<220> FEATURE:
<221> NAME/KEY: MOD_RES
<222> LOCATION: (2525)..(2544)
<223> OTHER INFORMATION: Any amino acid
<220> FEATURE:
<221> NAME/KEY: MISC_FEATURE
<222> LOCATION: (2525)..(2544)
<223> OTHER INFORMATION: This region may encompass 3-20 residues
<220> FEATURE:
<221> NAME/KEY: MOD_RES
<222> LOCATION: (2545)..(2548)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2549)..(2550)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2553)..(2553)
<223> OTHER INFORMATION: A, L, P, T or V
<220> FEATURE:
<221> NAME/KEY: MOD_RES
<222> LOCATION: (2555)..(2574)
<223> OTHER INFORMATION: Any amino acid
<220> FEATURE:
<221> NAME/KEY: MISC_FEATURE
<222> LOCATION: (2555)..(2574)
<223> OTHER INFORMATION: This region may encompass 3-20 residues
<220> FEATURE:
<221> NAME/KEY: MOD_RES
<222> LOCATION: (2575)..(2578)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2579)..(2580)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2583)..(2583)
<223> OTHER INFORMATION: A, L, P, T or V
<220> FEATURE:
<221> NAME/KEY: MOD_RES
<222> LOCATION: (2585)..(2604)
<223> OTHER INFORMATION: Any amino acid
<220> FEATURE:
<221> NAME/KEY: MISC_FEATURE
<222> LOCATION: (2585)..(2604)
<223> OTHER INFORMATION: This region may encompass 3-20 residues
<220> FEATURE:
<221> NAME/KEY: MOD_RES
<222> LOCATION: (2605)..(2608)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2609)..(2610)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2613)..(2613)
<223> OTHER INFORMATION: A, L, P, T or V
<220> FEATURE:
<221> NAME/KEY: MOD_RES
<222> LOCATION: (2615)..(2634)
<223> OTHER INFORMATION: Any amino acid
<220> FEATURE:
<221> NAME/KEY: MISC_FEATURE
<222> LOCATION: (2615)..(2634)
<223> OTHER INFORMATION: This region may encompass 3-20 residues
<220> FEATURE:
<221> NAME/KEY: MOD_RES
<222> LOCATION: (2635)..(2638)
```

```
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2639)..(2640)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2643)..(2643)
<223> OTHER INFORMATION: A, L, P, T or V
<220> FEATURE:
<221> NAME/KEY: MOD_RES
<222> LOCATION: (2645)..(2664)
<223> OTHER INFORMATION: Any amino acid
<220> FEATURE:
<221> NAME/KEY: MISC_FEATURE
<222> LOCATION: (2645)..(2664)
<223> OTHER INFORMATION: This region may encompass 3-20 residues
<220> FEATURE:
<221> NAME/KEY: MOD_RES
<222> LOCATION: (2665)..(2668)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2669)..(2670)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2673)..(2673)
<223> OTHER INFORMATION: A, L, P, T or V
<220> FEATURE:
<221> NAME/KEY: MOD_RES
<222> LOCATION: (2675)..(2694)
<223> OTHER INFORMATION: Any amino acid
<220> FEATURE:
<221> NAME/KEY: MISC_FEATURE
<222> LOCATION: (2675)..(2694)
<223> OTHER INFORMATION: This region may encompass 3-20 residues
<220> FEATURE:
<221> NAME/KEY: MOD_RES
<222> LOCATION: (2695)..(2698)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2699)..(2700)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2703)..(2703)
<223> OTHER INFORMATION: A, L, P, T or V
<220> FEATURE:
<221> NAME/KEY: MOD_RES
<222> LOCATION: (2705)..(2724)
<223> OTHER INFORMATION: Any amino acid
<220> FEATURE:
<221> NAME/KEY: MISC_FEATURE
<222> LOCATION: (2705)..(2724)
<223> OTHER INFORMATION: This region may encompass 3-20 residues
<220> FEATURE:
<221> NAME/KEY: MOD_RES
<222> LOCATION: (2725)..(2728)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2729)..(2730)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2733)..(2733)
<223> OTHER INFORMATION: A, L, P, T or V
<220> FEATURE:
<221> NAME/KEY: MOD_RES
```

-continued

```
<222> LOCATION: (2735)..(2754)
<223> OTHER INFORMATION: Any amino acid
<220> FEATURE:
<221> NAME/KEY: MISC_FEATURE
<222> LOCATION: (2735)..(2754)
<223> OTHER INFORMATION: This region may encompass 3-20 residues
<220> FEATURE:
<221> NAME/KEY: MOD_RES
<222> LOCATION: (2755)..(2758)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2759)..(2760)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2763)..(2763)
<223> OTHER INFORMATION: A, L, P, T or V
<220> FEATURE:
<221> NAME/KEY: MOD_RES
<222> LOCATION: (2765)..(2784)
<223> OTHER INFORMATION: Any amino acid
<220> FEATURE:
<221> NAME/KEY: MISC_FEATURE
<222> LOCATION: (2765)..(2784)
<223> OTHER INFORMATION: This region may encompass 3-20 residues
<220> FEATURE:
<221> NAME/KEY: MOD_RES
<222> LOCATION: (2785)..(2788)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2789)..(2790)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2793)..(2793)
<223> OTHER INFORMATION: A, L, P, T or V
<220> FEATURE:
<221> NAME/KEY: MOD_RES
<222> LOCATION: (2795)..(2814)
<223> OTHER INFORMATION: Any amino acid
<220> FEATURE:
<221> NAME/KEY: MISC_FEATURE
<222> LOCATION: (2795)..(2814)
<223> OTHER INFORMATION: This region may encompass 3-20 residues
<220> FEATURE:
<221> NAME/KEY: MOD_RES
<222> LOCATION: (2815)..(2818)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2819)..(2820)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2823)..(2823)
<223> OTHER INFORMATION: A, L, P, T or V
<220> FEATURE:
<221> NAME/KEY: MOD_RES
<222> LOCATION: (2825)..(2844)
<223> OTHER INFORMATION: Any amino acid
<220> FEATURE:
<221> NAME/KEY: MISC_FEATURE
<222> LOCATION: (2825)..(2844)
<223> OTHER INFORMATION: This region may encompass 3-20 residues
<220> FEATURE:
<221> NAME/KEY: MOD_RES
<222> LOCATION: (2845)..(2848)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
```

-continued

```
<222> LOCATION: (2849)..(2850)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2853)..(2853)
<223> OTHER INFORMATION: A, L, P, T or V
<220> FEATURE:
<221> NAME/KEY: MOD_RES
<222> LOCATION: (2855)..(2874)
<223> OTHER INFORMATION: Any amino acid
<220> FEATURE:
<221> NAME/KEY: MISC_FEATURE
<222> LOCATION: (2855)..(2874)
<223> OTHER INFORMATION: This region may encompass 3-20 residues
<220> FEATURE:
<221> NAME/KEY: MOD_RES
<222> LOCATION: (2875)..(2878)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2879)..(2880)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2883)..(2883)
<223> OTHER INFORMATION: A, L, P, T or V
<220> FEATURE:
<221> NAME/KEY: MOD_RES
<222> LOCATION: (2885)..(2904)
<223> OTHER INFORMATION: Any amino acid
<220> FEATURE:
<221> NAME/KEY: MISC_FEATURE
<222> LOCATION: (2885)..(2904)
<223> OTHER INFORMATION: This region may encompass 3-20 residues
<220> FEATURE:
<221> NAME/KEY: MOD_RES
<222> LOCATION: (2905)..(2908)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2909)..(2910)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2913)..(2913)
<223> OTHER INFORMATION: A, L, P, T or V
<220> FEATURE:
<221> NAME/KEY: MOD_RES
<222> LOCATION: (2915)..(2934)
<223> OTHER INFORMATION: Any amino acid
<220> FEATURE:
<221> NAME/KEY: MISC_FEATURE
<222> LOCATION: (2915)..(2934)
<223> OTHER INFORMATION: This region may encompass 3-20 residues
<220> FEATURE:
<221> NAME/KEY: MOD_RES
<222> LOCATION: (2935)..(2938)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2939)..(2940)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2943)..(2943)
<223> OTHER INFORMATION: A, L, P, T or V
<220> FEATURE:
<221> NAME/KEY: MOD_RES
<222> LOCATION: (2945)..(2964)
<223> OTHER INFORMATION: Any amino acid
<220> FEATURE:
<221> NAME/KEY: MISC_FEATURE
```

```
<222> LOCATION: (2945)..(2964)
<223> OTHER INFORMATION: This region may encompass 3-20 residues
<220> FEATURE:
<221> NAME/KEY: MOD_RES
<222> LOCATION: (2965)..(2968)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2969)..(2970)
<223> OTHER INFORMATION: This region may encompass one of the following
      sequences: S, D, T, N, L, DS, DT, LS, SS, ST, TN, or TS
<220> FEATURE:
<221> NAME/KEY: MOD_RES
<222> LOCATION: (2973)..(2973)
<223> OTHER INFORMATION: A, L, P, T or V
<220> FEATURE:
<221> NAME/KEY: MOD_RES
<222> LOCATION: (2975)..(2994)
<223> OTHER INFORMATION: Any amino acid
<220> FEATURE:
<221> NAME/KEY: MISC_FEATURE
<222> LOCATION: (2975)..(2994)
<223> OTHER INFORMATION: This region may encompass 3-20 residues
<220> FEATURE:
<221> NAME/KEY: MOD_RES
<222> LOCATION: (2995)..(2998)
<223> OTHER INFORMATION: This region may encompass one of the following
      sequences: GG, LS, APS, GAG, GGG, KPS, RPS, or GGGG
<220> FEATURE:
<221> NAME/KEY: MOD_RES
<222> LOCATION: (2999)..(3000)
<223> OTHER INFORMATION: This region may encompass one of the following
      sequences: S, D, T, N, L, DS, DT, LS, SS, ST, TN, or TS
<220> FEATURE:
<223> OTHER INFORMATION: See specification as filed for detailed
      description of substitutions and preferred embodiments

<400> SEQUENCE: 64

Tyr Gly Xaa Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Tyr Gly
            20                  25                  30

Xaa Pro Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Tyr Gly Xaa Pro
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Tyr Gly Xaa Pro Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Tyr Gly Xaa Pro Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Tyr Gly Xaa Pro Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Tyr Gly Xaa Pro Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205
```

```
Xaa Xaa Tyr Gly Xaa Pro Xaa Xaa Xaa Xaa Xaa Xaa Xaa Xaa Xaa
    210             215                 220

Xaa Xaa Xaa Xaa Xaa Xaa Xaa Xaa Xaa Xaa Xaa Xaa Xaa Xaa Xaa
225                 230                 235                 240

Tyr Gly Xaa Pro Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Tyr Gly
            260                 265                 270

Xaa Pro Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Tyr Gly Xaa Pro
290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Tyr Gly Xaa Pro Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Tyr Gly Xaa Pro Xaa Xaa Xaa
355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Tyr Gly Xaa Pro Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Tyr Gly Xaa Pro Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Tyr Gly Xaa Pro Xaa Xaa Xaa Xaa Xaa Xaa Xaa Xaa Xaa
    450             455                 460

Xaa Xaa Xaa Xaa Xaa Xaa Xaa Xaa Xaa Xaa Xaa Xaa Xaa Xaa Xaa
465                 470                 475                 480

Tyr Gly Xaa Pro Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Tyr Gly
            500                 505                 510

Xaa Pro Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Tyr Gly Xaa Pro
530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Tyr Gly Xaa Pro Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Tyr Gly Xaa Pro Xaa Xaa Xaa
595                 600                 605

Xaa Xaa Xaa Xaa Xaa Xaa Xaa Xaa Xaa Xaa Xaa Xaa Xaa Xaa Xaa
610                 615                 620

Xaa Xaa Xaa Xaa Xaa Xaa Tyr Gly Xaa Pro Xaa Xaa Xaa Xaa Xaa
```

-continued

```
                625                 630                 635                 640
Xaa Xaa Xaa Xaa Xaa Xaa Xaa Xaa Xaa Xaa Xaa Xaa Xaa Xaa
                645                 650                 655

Xaa Xaa Xaa Xaa Tyr Gly Xaa Pro Xaa Xaa Xaa Xaa Xaa Xaa
                660                 665                 670

Xaa Xaa Xaa Xaa Xaa Xaa Xaa Xaa Xaa Xaa Xaa Xaa Xaa Xaa
            675                 680                 685

Xaa Xaa Tyr Gly Xaa Pro Xaa Xaa Xaa Xaa Xaa Xaa Xaa Xaa
        690                 695                 700

Xaa Xaa Xaa Xaa Xaa Xaa Xaa Xaa Xaa Xaa Xaa Xaa Xaa Xaa
705                 710                 715                 720

Tyr Gly Xaa Pro Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Tyr Gly
            740                 745                 750

Xaa Pro Xaa Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Tyr Gly Xaa Pro
    770                 775                 780

Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Tyr Gly Xaa Pro Xaa Xaa
            805                 810                 815

Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Tyr Gly Xaa Pro Xaa Xaa Xaa Xaa
        835                 840                 845

Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Tyr Gly Xaa Pro Xaa Xaa Xaa Xaa
865                 870                 875                 880

Xaa Xaa Xaa Xaa Xaa Xaa Xaa Xaa Xaa Xaa Xaa Xaa Xaa Xaa
            885                 890                 895

Xaa Xaa Xaa Xaa Tyr Gly Xaa Pro Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa
        915                 920                 925

Xaa Xaa Tyr Gly Xaa Pro Xaa Xaa Xaa Xaa Xaa Xaa Xaa Xaa
    930                 935                 940

Xaa Xaa Xaa Xaa Xaa Xaa Xaa Xaa Xaa Xaa Xaa Xaa Xaa Xaa
945                 950                 955                 960

Tyr Gly Xaa Pro Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Tyr Gly
            980                 985                 990

Xaa Pro Xaa Xaa Xaa Xaa Xaa Xaa  Xaa Xaa Xaa Xaa Xaa  Xaa Xaa Xaa
        995                 1000                1005

Xaa Xaa  Xaa Xaa Xaa Xaa Xaa  Xaa Xaa Xaa Xaa Xaa  Tyr Gly Xaa
    1010                1015                1020

Pro Xaa  Xaa Xaa Xaa Xaa Xaa  Xaa Xaa Xaa Xaa Xaa  Xaa Xaa Xaa
    1025                1030                1035

Xaa Xaa  Xaa Xaa Xaa Xaa Xaa  Xaa Xaa Xaa Xaa Xaa  Tyr Gly Xaa
    1040                1045                1050
```

Pro Xaa Xaa Xaa Xaa Xaa Xaa  Xaa Xaa Xaa Xaa Xaa  Xaa Xaa Xaa
    1055                1060                1065

Xaa Xaa Xaa Xaa Xaa Xaa Xaa  Xaa Xaa Xaa Xaa Xaa  Tyr Gly Xaa
    1070                1075                1080

Pro Xaa Xaa Xaa Xaa Xaa Xaa  Xaa Xaa Xaa Xaa Xaa  Xaa Xaa Xaa
    1085                1090                1095

Xaa Xaa Xaa Xaa Xaa Xaa Xaa  Xaa Xaa Xaa Xaa Xaa  Tyr Gly Xaa
    1100                1105                1110

Pro Xaa Xaa Xaa Xaa Xaa Xaa  Xaa Xaa Xaa Xaa Xaa  Xaa Xaa Xaa
    1115                1120                1125

Xaa Xaa Xaa Xaa Xaa Xaa Xaa  Xaa Xaa Xaa Xaa Xaa  Tyr Gly Xaa
    1130                1135                1140

Pro Xaa Xaa Xaa Xaa Xaa Xaa  Xaa Xaa Xaa Xaa Xaa  Xaa Xaa Xaa
    1145                1150                1155

Xaa Xaa Xaa Xaa Xaa Xaa Xaa  Xaa Xaa Xaa Xaa Xaa  Tyr Gly Xaa
    1160                1165                1170

Pro Xaa Xaa Xaa Xaa Xaa Xaa  Xaa Xaa Xaa Xaa Xaa  Xaa Xaa Xaa
    1175                1180                1185

Xaa Xaa Xaa Xaa Xaa Xaa Xaa  Xaa Xaa Xaa Xaa Xaa  Tyr Gly Xaa
    1190                1195                1200

Pro Xaa Xaa Xaa Xaa Xaa Xaa  Xaa Xaa Xaa Xaa Xaa  Xaa Xaa Xaa
    1205                1210                1215

Xaa Xaa Xaa Xaa Xaa Xaa Xaa  Xaa Xaa Xaa Xaa Xaa  Tyr Gly Xaa
    1220                1225                1230

Pro Xaa Xaa Xaa Xaa Xaa Xaa  Xaa Xaa Xaa Xaa Xaa  Xaa Xaa Xaa
    1235                1240                1245

Xaa Xaa Xaa Xaa Xaa Xaa Xaa  Xaa Xaa Xaa Xaa Xaa  Tyr Gly Xaa
    1250                1255                1260

Pro Xaa Xaa Xaa Xaa Xaa Xaa  Xaa Xaa Xaa Xaa Xaa  Xaa Xaa Xaa
    1265                1270                1275

Xaa Xaa Xaa Xaa Xaa Xaa Xaa  Xaa Xaa Xaa Xaa Xaa  Tyr Gly Xaa
    1280                1285                1290

Pro Xaa Xaa Xaa Xaa Xaa Xaa  Xaa Xaa Xaa Xaa Xaa  Xaa Xaa Xaa
    1295                1300                1305

Xaa Xaa Xaa Xaa Xaa Xaa Xaa  Xaa Xaa Xaa Xaa Xaa  Tyr Gly Xaa
    1310                1315                1320

Pro Xaa Xaa Xaa Xaa Xaa Xaa  Xaa Xaa Xaa Xaa Xaa  Xaa Xaa Xaa
    1325                1330                1335

Xaa Xaa Xaa Xaa Xaa Xaa Xaa  Xaa Xaa Xaa Xaa Xaa  Tyr Gly Xaa
    1340                1345                1350

Pro Xaa Xaa Xaa Xaa Xaa Xaa  Xaa Xaa Xaa Xaa Xaa  Xaa Xaa Xaa
    1355                1360                1365

Xaa Xaa Xaa Xaa Xaa Xaa Xaa  Xaa Xaa Xaa Xaa Xaa  Tyr Gly Xaa
    1370                1375                1380

Pro Xaa Xaa Xaa Xaa Xaa Xaa  Xaa Xaa Xaa Xaa Xaa  Xaa Xaa Xaa
    1385                1390                1395

Xaa Xaa Xaa Xaa Xaa Xaa Xaa  Xaa Xaa Xaa Xaa Xaa  Tyr Gly Xaa
    1400                1405                1410

Pro Xaa Xaa Xaa Xaa Xaa Xaa  Xaa Xaa Xaa Xaa Xaa  Xaa Xaa Xaa
    1415                1420                1425

Xaa Xaa Xaa Xaa Xaa Xaa Xaa  Xaa Xaa Xaa Xaa Xaa  Tyr Gly Xaa
    1430                1435                1440

```
Pro Xaa Xaa Xaa Xaa Xaa Xaa  Xaa Xaa Xaa Xaa Xaa  Xaa Xaa Xaa
    1445                1450                1455

Xaa Xaa Xaa Xaa Xaa Xaa Xaa  Xaa Xaa Xaa Xaa Xaa  Tyr Gly Xaa
1460                1465                1470

Pro Xaa Xaa Xaa Xaa Xaa Xaa  Xaa Xaa Xaa Xaa Xaa  Xaa Xaa Xaa
    1475                1480                1485

Xaa Xaa Xaa Xaa Xaa Xaa Xaa  Xaa Xaa Xaa Xaa Xaa  Tyr Gly Xaa
1490                1495                1500

Pro Xaa Xaa Xaa Xaa Xaa Xaa  Xaa Xaa Xaa Xaa Xaa  Xaa Xaa Xaa
    1505                1510                1515

Xaa Xaa Xaa Xaa Xaa Xaa Xaa  Xaa Xaa Xaa Xaa Xaa  Tyr Gly Xaa
1520                1525                1530

Pro Xaa Xaa Xaa Xaa Xaa Xaa  Xaa Xaa Xaa Xaa Xaa  Xaa Xaa Xaa
    1535                1540                1545

Xaa Xaa Xaa Xaa Xaa Xaa Xaa  Xaa Xaa Xaa Xaa Xaa  Tyr Gly Xaa
1550                1555                1560

Pro Xaa Xaa Xaa Xaa Xaa Xaa  Xaa Xaa Xaa Xaa Xaa  Xaa Xaa Xaa
    1565                1570                1575

Xaa Xaa Xaa Xaa Xaa Xaa Xaa  Xaa Xaa Xaa Xaa Xaa  Tyr Gly Xaa
1580                1585                1590

Pro Xaa Xaa Xaa Xaa Xaa Xaa  Xaa Xaa Xaa Xaa Xaa  Xaa Xaa Xaa
    1595                1600                1605

Xaa Xaa Xaa Xaa Xaa Xaa Xaa  Xaa Xaa Xaa Xaa Xaa  Tyr Gly Xaa
1610                1615                1620

Pro Xaa Xaa Xaa Xaa Xaa Xaa  Xaa Xaa Xaa Xaa Xaa  Xaa Xaa Xaa
    1625                1630                1635

Xaa Xaa Xaa Xaa Xaa Xaa Xaa  Xaa Xaa Xaa Xaa Xaa  Tyr Gly Xaa
1640                1645                1650

Pro Xaa Xaa Xaa Xaa Xaa Xaa  Xaa Xaa Xaa Xaa Xaa  Xaa Xaa Xaa
    1655                1660                1665

Xaa Xaa Xaa Xaa Xaa Xaa Xaa  Xaa Xaa Xaa Xaa Xaa  Tyr Gly Xaa
1670                1675                1680

Pro Xaa Xaa Xaa Xaa Xaa Xaa  Xaa Xaa Xaa Xaa Xaa  Xaa Xaa Xaa
    1685                1690                1695

Xaa Xaa Xaa Xaa Xaa Xaa Xaa  Xaa Xaa Xaa Xaa Xaa  Tyr Gly Xaa
1700                1705                1710

Pro Xaa Xaa Xaa Xaa Xaa Xaa  Xaa Xaa Xaa Xaa Xaa  Xaa Xaa Xaa
    1715                1720                1725

Xaa Xaa Xaa Xaa Xaa Xaa Xaa  Xaa Xaa Xaa Xaa Xaa  Tyr Gly Xaa
1730                1735                1740

Pro Xaa Xaa Xaa Xaa Xaa Xaa  Xaa Xaa Xaa Xaa Xaa  Xaa Xaa Xaa
    1745                1750                1755

Xaa Xaa Xaa Xaa Xaa Xaa Xaa  Xaa Xaa Xaa Xaa Xaa  Tyr Gly Xaa
1760                1765                1770

Pro Xaa Xaa Xaa Xaa Xaa Xaa  Xaa Xaa Xaa Xaa Xaa  Xaa Xaa Xaa
    1775                1780                1785

Xaa Xaa Xaa Xaa Xaa Xaa Xaa  Xaa Xaa Xaa Xaa Xaa  Tyr Gly Xaa
1790                1795                1800

Pro Xaa Xaa Xaa Xaa Xaa Xaa  Xaa Xaa Xaa Xaa Xaa  Xaa Xaa Xaa
    1805                1810                1815

Xaa Xaa Xaa Xaa Xaa Xaa Xaa  Xaa Xaa Xaa Xaa Xaa  Tyr Gly Xaa
1820                1825                1830

Pro Xaa Xaa Xaa Xaa Xaa Xaa  Xaa Xaa Xaa Xaa Xaa  Xaa Xaa Xaa
```

Xaa Xaa Xaa Xaa Xaa Xaa Xaa Xaa Xaa Xaa Xaa Tyr Gly Xaa
        1850                1855                1860

Pro Xaa Xaa Xaa Xaa Xaa Xaa Xaa Xaa Xaa Xaa Xaa Xaa Xaa
    1865                1870                1875

Xaa Xaa Xaa Xaa Xaa Xaa Xaa Xaa Xaa Xaa Xaa Tyr Gly Xaa
        1880                1885                1890

Pro Xaa Xaa Xaa Xaa Xaa Xaa Xaa Xaa Xaa Xaa Xaa Xaa Xaa
    1895                1900                1905

Xaa Xaa Xaa Xaa Xaa Xaa Xaa Xaa Xaa Xaa Xaa Tyr Gly Xaa
        1910                1915                1920

Pro Xaa Xaa Xaa Xaa Xaa Xaa Xaa Xaa Xaa Xaa Xaa Xaa Xaa
    1925                1930                1935

Xaa Xaa Xaa Xaa Xaa Xaa Xaa Xaa Xaa Xaa Xaa Tyr Gly Xaa
        1940                1945                1950

Pro Xaa Xaa Xaa Xaa Xaa Xaa Xaa Xaa Xaa Xaa Xaa Xaa Xaa
    1955                1960                1965

Xaa Xaa Xaa Xaa Xaa Xaa Xaa Xaa Xaa Xaa Xaa Tyr Gly Xaa
        1970                1975                1980

Pro Xaa Xaa Xaa Xaa Xaa Xaa Xaa Xaa Xaa Xaa Xaa Xaa Xaa
    1985                1990                1995

Xaa Xaa Xaa Xaa Xaa Xaa Xaa Xaa Xaa Xaa Xaa Tyr Gly Xaa
        2000                2005                2010

Pro Xaa Xaa Xaa Xaa Xaa Xaa Xaa Xaa Xaa Xaa Xaa Xaa Xaa
    2015                2020                2025

Xaa Xaa Xaa Xaa Xaa Xaa Xaa Xaa Xaa Xaa Xaa Tyr Gly Xaa
        2030                2035                2040

Pro Xaa Xaa Xaa Xaa Xaa Xaa Xaa Xaa Xaa Xaa Xaa Xaa Xaa
    2045                2050                2055

Xaa Xaa Xaa Xaa Xaa Xaa Xaa Xaa Xaa Xaa Xaa Tyr Gly Xaa
        2060                2065                2070

Pro Xaa Xaa Xaa Xaa Xaa Xaa Xaa Xaa Xaa Xaa Xaa Xaa Xaa
    2075                2080                2085

Xaa Xaa Xaa Xaa Xaa Xaa Xaa Xaa Xaa Xaa Xaa Tyr Gly Xaa
        2090                2095                2100

Pro Xaa Xaa Xaa Xaa Xaa Xaa Xaa Xaa Xaa Xaa Xaa Xaa Xaa
    2105                2110                2115

Xaa Xaa Xaa Xaa Xaa Xaa Xaa Xaa Xaa Xaa Xaa Tyr Gly Xaa
        2120                2125                2130

Pro Xaa Xaa Xaa Xaa Xaa Xaa Xaa Xaa Xaa Xaa Xaa Xaa Xaa
    2135                2140                2145

Xaa Xaa Xaa Xaa Xaa Xaa Xaa Xaa Xaa Xaa Xaa Tyr Gly Xaa
        2150                2155                2160

Pro Xaa Xaa Xaa Xaa Xaa Xaa Xaa Xaa Xaa Xaa Xaa Xaa Xaa
    2165                2170                2175

Xaa Xaa Xaa Xaa Xaa Xaa Xaa Xaa Xaa Xaa Xaa Tyr Gly Xaa
        2180                2185                2190

Pro Xaa Xaa Xaa Xaa Xaa Xaa Xaa Xaa Xaa Xaa Xaa Xaa Xaa
    2195                2200                2205

Xaa Xaa Xaa Xaa Xaa Xaa Xaa Xaa Xaa Xaa Xaa Tyr Gly Xaa
        2210                2215                2220

Pro Xaa Xaa Xaa Xaa Xaa Xaa Xaa Xaa Xaa Xaa Xaa Xaa Xaa
    2225                2230                2235

Xaa Xaa Xaa Xaa Xaa Xaa Xaa  Xaa Xaa Xaa Xaa Xaa  Tyr Gly Xaa
    2240            2245                2250

Pro Xaa Xaa Xaa Xaa Xaa Xaa  Xaa Xaa Xaa Xaa Xaa  Xaa Xaa Xaa
    2255            2260                2265

Xaa Xaa Xaa Xaa Xaa Xaa Xaa  Xaa Xaa Xaa Xaa Xaa  Tyr Gly Xaa
    2270            2275                2280

Pro Xaa Xaa Xaa Xaa Xaa Xaa  Xaa Xaa Xaa Xaa Xaa  Xaa Xaa Xaa
    2285            2290                2295

Xaa Xaa Xaa Xaa Xaa Xaa Xaa  Xaa Xaa Xaa Xaa Xaa  Tyr Gly Xaa
    2300            2305                2310

Pro Xaa Xaa Xaa Xaa Xaa Xaa  Xaa Xaa Xaa Xaa Xaa  Xaa Xaa Xaa
    2315            2320                2325

Xaa Xaa Xaa Xaa Xaa Xaa Xaa  Xaa Xaa Xaa Xaa Xaa  Tyr Gly Xaa
    2330            2335                2340

Pro Xaa Xaa Xaa Xaa Xaa Xaa  Xaa Xaa Xaa Xaa Xaa  Xaa Xaa Xaa
    2345            2350                2355

Xaa Xaa Xaa Xaa Xaa Xaa Xaa  Xaa Xaa Xaa Xaa Xaa  Tyr Gly Xaa
    2360            2365                2370

Pro Xaa Xaa Xaa Xaa Xaa Xaa  Xaa Xaa Xaa Xaa Xaa  Xaa Xaa Xaa
    2375            2380                2385

Xaa Xaa Xaa Xaa Xaa Xaa Xaa  Xaa Xaa Xaa Xaa Xaa  Tyr Gly Xaa
    2390            2395                2400

Pro Xaa Xaa Xaa Xaa Xaa Xaa  Xaa Xaa Xaa Xaa Xaa  Xaa Xaa Xaa
    2405            2410                2415

Xaa Xaa Xaa Xaa Xaa Xaa Xaa  Xaa Xaa Xaa Xaa Xaa  Tyr Gly Xaa
    2420            2425                2430

Pro Xaa Xaa Xaa Xaa Xaa Xaa  Xaa Xaa Xaa Xaa Xaa  Xaa Xaa Xaa
    2435            2440                2445

Xaa Xaa Xaa Xaa Xaa Xaa Xaa  Xaa Xaa Xaa Xaa Xaa  Tyr Gly Xaa
    2450            2455                2460

Pro Xaa Xaa Xaa Xaa Xaa Xaa  Xaa Xaa Xaa Xaa Xaa  Xaa Xaa Xaa
    2465            2470                2475

Xaa Xaa Xaa Xaa Xaa Xaa Xaa  Xaa Xaa Xaa Xaa Xaa  Tyr Gly Xaa
    2480            2485                2490

Pro Xaa Xaa Xaa Xaa Xaa Xaa  Xaa Xaa Xaa Xaa Xaa  Xaa Xaa Xaa
    2495            2500                2505

Xaa Xaa Xaa Xaa Xaa Xaa Xaa  Xaa Xaa Xaa Xaa Xaa  Tyr Gly Xaa
    2510            2515                2520

Pro Xaa Xaa Xaa Xaa Xaa Xaa  Xaa Xaa Xaa Xaa Xaa  Xaa Xaa Xaa
    2525            2530                2535

Xaa Xaa Xaa Xaa Xaa Xaa Xaa  Xaa Xaa Xaa Xaa Xaa  Tyr Gly Xaa
    2540            2545                2550

Pro Xaa Xaa Xaa Xaa Xaa Xaa  Xaa Xaa Xaa Xaa Xaa  Xaa Xaa Xaa
    2555            2560                2565

Xaa Xaa Xaa Xaa Xaa Xaa Xaa  Xaa Xaa Xaa Xaa Xaa  Tyr Gly Xaa
    2570            2575                2580

Pro Xaa Xaa Xaa Xaa Xaa Xaa  Xaa Xaa Xaa Xaa Xaa  Xaa Xaa Xaa
    2585            2590                2595

Xaa Xaa Xaa Xaa Xaa Xaa Xaa  Xaa Xaa Xaa Xaa Xaa  Tyr Gly Xaa
    2600            2605                2610

Pro Xaa Xaa Xaa Xaa Xaa Xaa  Xaa Xaa Xaa Xaa Xaa  Xaa Xaa Xaa
    2615            2620                2625

```
Xaa Xaa Xaa Xaa Xaa Xaa Xaa  Xaa Xaa Xaa Xaa Xaa  Tyr Gly Xaa
    2630                2635                2640

Pro Xaa Xaa Xaa Xaa Xaa Xaa  Xaa Xaa Xaa Xaa Xaa  Xaa Xaa Xaa
2645                2650                 2655

Xaa Xaa Xaa Xaa Xaa Xaa Xaa  Xaa Xaa Xaa Xaa Xaa  Tyr Gly Xaa
    2660                2665                2670

Pro Xaa Xaa Xaa Xaa Xaa Xaa  Xaa Xaa Xaa Xaa Xaa  Xaa Xaa Xaa
2675                2680                 2685

Xaa Xaa Xaa Xaa Xaa Xaa Xaa  Xaa Xaa Xaa Xaa Xaa  Tyr Gly Xaa
    2690                2695                2700

Pro Xaa Xaa Xaa Xaa Xaa Xaa  Xaa Xaa Xaa Xaa Xaa  Xaa Xaa Xaa
2705                2710                 2715

Xaa Xaa Xaa Xaa Xaa Xaa Xaa  Xaa Xaa Xaa Xaa Xaa  Tyr Gly Xaa
    2720                2725                2730

Pro Xaa Xaa Xaa Xaa Xaa Xaa  Xaa Xaa Xaa Xaa Xaa  Xaa Xaa Xaa
2735                2740                 2745

Xaa Xaa Xaa Xaa Xaa Xaa Xaa  Xaa Xaa Xaa Xaa Xaa  Tyr Gly Xaa
    2750                2755                2760

Pro Xaa Xaa Xaa Xaa Xaa Xaa  Xaa Xaa Xaa Xaa Xaa  Xaa Xaa Xaa
2765                2770                 2775

Xaa Xaa Xaa Xaa Xaa Xaa Xaa  Xaa Xaa Xaa Xaa Xaa  Tyr Gly Xaa
    2780                2785                2790

Pro Xaa Xaa Xaa Xaa Xaa Xaa  Xaa Xaa Xaa Xaa Xaa  Xaa Xaa Xaa
2795                2800                 2805

Xaa Xaa Xaa Xaa Xaa Xaa Xaa  Xaa Xaa Xaa Xaa Xaa  Tyr Gly Xaa
    2810                2815                2820

Pro Xaa Xaa Xaa Xaa Xaa Xaa  Xaa Xaa Xaa Xaa Xaa  Xaa Xaa Xaa
2825                2830                 2835

Xaa Xaa Xaa Xaa Xaa Xaa Xaa  Xaa Xaa Xaa Xaa Xaa  Tyr Gly Xaa
    2840                2845                2850

Pro Xaa Xaa Xaa Xaa Xaa Xaa  Xaa Xaa Xaa Xaa Xaa  Xaa Xaa Xaa
2855                2860                 2865

Xaa Xaa Xaa Xaa Xaa Xaa Xaa  Xaa Xaa Xaa Xaa Xaa  Tyr Gly Xaa
    2870                2875                2880

Pro Xaa Xaa Xaa Xaa Xaa Xaa  Xaa Xaa Xaa Xaa Xaa  Xaa Xaa Xaa
2885                2890                 2895

Xaa Xaa Xaa Xaa Xaa Xaa Xaa  Xaa Xaa Xaa Xaa Xaa  Tyr Gly Xaa
    2900                2905                2910

Pro Xaa Xaa Xaa Xaa Xaa Xaa  Xaa Xaa Xaa Xaa Xaa  Xaa Xaa Xaa
2915                2920                 2925

Xaa Xaa Xaa Xaa Xaa Xaa Xaa  Xaa Xaa Xaa Xaa Xaa  Tyr Gly Xaa
    2930                2935                2940

Pro Xaa Xaa Xaa Xaa Xaa Xaa  Xaa Xaa Xaa Xaa Xaa  Xaa Xaa Xaa
2945                2950                 2955

Xaa Xaa Xaa Xaa Xaa Xaa Xaa  Xaa Xaa Xaa Xaa Xaa  Tyr Gly Xaa
    2960                2965                2970

Pro Xaa Xaa Xaa Xaa Xaa Xaa  Xaa Xaa Xaa Xaa Xaa  Xaa Xaa Xaa
2975                2980                 2985

Xaa Xaa Xaa Xaa Xaa Xaa Xaa  Xaa Xaa Xaa Xaa Xaa
    2990                2995                3000

<210> SEQ ID NO 65
<211> LENGTH: 4000
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(4000)
<223> OTHER INFORMATION: This sequence may encompass 1-100 "Tyr Xaa Xaa
      Xaa Xaa Xaa Xaa Xaa Xaa Xaa Xaa Xaa Xaa Xaa Xaa Xaa Xaa Xaa Xaa
      Xaa Xaa Xaa Xaa Xaa Xaa Xaa Xaa Xaa Xaa Xaa Xaa Xaa Xaa Xaa Xaa
      Xaa Xaa Xaa Xaa Xaa" repeating units
<220> FEATURE:
<221> NAME/KEY: MOD_RES
<222> LOCATION: (2)..(5)
<223> OTHER INFORMATION: Any amino acid
<220> FEATURE:
<221> NAME/KEY: MISC_FEATURE
<222> LOCATION: (2)..(5)
<223> OTHER INFORMATION: This region may encompass 1-4 residues or this
      region may be absent in its entirety
<220> FEATURE:
<221> NAME/KEY: MOD_RES
<222> LOCATION: (6)..(10)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (11)..(40)
<223> OTHER INFORMATION: Any amino acid
<220> FEATURE:
<221> NAME/KEY: MISC_FEATURE
<222> LOCATION: (11)..(40)
<223> OTHER INFORMATION: This region may encompass 4-30 residues
<220> FEATURE:
<221> NAME/KEY: MOD_RES
<222> LOCATION: (42)..(45)
<223> OTHER INFORMATION: Any amino acid
<220> FEATURE:
<221> NAME/KEY: MISC_FEATURE
<222> LOCATION: (42)..(45)
<223> OTHER INFORMATION: This region may encompass 1-4 residues or this
      region may be absent in its entirety
<220> FEATURE:
<221> NAME/KEY: MOD_RES
<222> LOCATION: (46)..(50)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (51)..(80)
<223> OTHER INFORMATION: Any amino acid
<220> FEATURE:
<221> NAME/KEY: MISC_FEATURE
<222> LOCATION: (51)..(80)
<223> OTHER INFORMATION: This region may encompass 4-30 residues
<220> FEATURE:
<221> NAME/KEY: MOD_RES
<222> LOCATION: (82)..(85)
<223> OTHER INFORMATION: Any amino acid
<220> FEATURE:
<221> NAME/KEY: MISC_FEATURE
<222> LOCATION: (82)..(85)
<223> OTHER INFORMATION: This region may encompass 1-4 residues or this
      region may be absent in its entirety
<220> FEATURE:
<221> NAME/KEY: MOD_RES
<222> LOCATION: (86)..(90)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (91)..(120)
<223> OTHER INFORMATION: Any amino acid
<220> FEATURE:
<221> NAME/KEY: MISC_FEATURE
<222> LOCATION: (91)..(120)
<223> OTHER INFORMATION: This region may encompass 4-30 residues
<220> FEATURE:
<221> NAME/KEY: MOD_RES
```

```
<222> LOCATION: (122)..(125)
<223> OTHER INFORMATION: Any amino acid
<220> FEATURE:
<221> NAME/KEY: MISC_FEATURE
<222> LOCATION: (122)..(125)
<223> OTHER INFORMATION: This region may encompass 1-4 residues or this
      region may be absent in its entirety
<220> FEATURE:
<221> NAME/KEY: MOD_RES
<222> LOCATION: (126)..(130)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (131)..(160)
<223> OTHER INFORMATION: Any amino acid
<220> FEATURE:
<221> NAME/KEY: MISC_FEATURE
<222> LOCATION: (131)..(160)
<223> OTHER INFORMATION: This region may encompass 4-30 residues
<220> FEATURE:
<221> NAME/KEY: MOD_RES
<222> LOCATION: (162)..(165)
<223> OTHER INFORMATION: Any amino acid
<220> FEATURE:
<221> NAME/KEY: MISC_FEATURE
<222> LOCATION: (162)..(165)
<223> OTHER INFORMATION: This region may encompass 1-4 residues or this
      region may be absent in its entirety
<220> FEATURE:
<221> NAME/KEY: MOD_RES
<222> LOCATION: (166)..(170)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (171)..(200)
<223> OTHER INFORMATION: Any amino acid
<220> FEATURE:
<221> NAME/KEY: MISC_FEATURE
<222> LOCATION: (171)..(200)
<223> OTHER INFORMATION: This region may encompass 4-30 residues
<220> FEATURE:
<221> NAME/KEY: MOD_RES
<222> LOCATION: (202)..(205)
<223> OTHER INFORMATION: Any amino acid
<220> FEATURE:
<221> NAME/KEY: MISC_FEATURE
<222> LOCATION: (202)..(205)
<223> OTHER INFORMATION: This region may encompass 1-4 residues or this
      region may be absent in its entirety
<220> FEATURE:
<221> NAME/KEY: MOD_RES
<222> LOCATION: (206)..(210)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (211)..(240)
<223> OTHER INFORMATION: Any amino acid
<220> FEATURE:
<221> NAME/KEY: MISC_FEATURE
<222> LOCATION: (211)..(240)
<223> OTHER INFORMATION: This region may encompass 4-30 residues
<220> FEATURE:
<221> NAME/KEY: MOD_RES
<222> LOCATION: (242)..(245)
<223> OTHER INFORMATION: Any amino acid
<220> FEATURE:
<221> NAME/KEY: MISC_FEATURE
<222> LOCATION: (242)..(245)
<223> OTHER INFORMATION: This region may encompass 1-4 residues or this
      region may be absent in its entirety
<220> FEATURE:
<221> NAME/KEY: MOD_RES
<222> LOCATION: (246)..(250)
<223> OTHER INFORMATION: This region may encompass one of the following
      sequences: GQ, GN, RPG, RPGGQ, RPGGN, SSS, SKG, or SN
<220> FEATURE:
```

```
<221> NAME/KEY: MOD_RES
<222> LOCATION: (251)..(280)
<223> OTHER INFORMATION: Any amino acid
<220> FEATURE:
<221> NAME/KEY: MISC_FEATURE
<222> LOCATION: (251)..(280)
<223> OTHER INFORMATION: This region may encompass 4-30 residues
<220> FEATURE:
<221> NAME/KEY: MOD_RES
<222> LOCATION: (282)..(285)
<223> OTHER INFORMATION: Any amino acid
<220> FEATURE:
<221> NAME/KEY: MISC_FEATURE
<222> LOCATION: (282)..(285)
<223> OTHER INFORMATION: This region may encompass 1-4 residues or this
      region may be absent in its entirety
<220> FEATURE:
<221> NAME/KEY: MOD_RES
<222> LOCATION: (286)..(290)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (291)..(320)
<223> OTHER INFORMATION: Any amino acid
<220> FEATURE:
<221> NAME/KEY: MISC_FEATURE
<222> LOCATION: (291)..(320)
<223> OTHER INFORMATION: This region may encompass 4-30 residues
<220> FEATURE:
<221> NAME/KEY: MOD_RES
<222> LOCATION: (322)..(325)
<223> OTHER INFORMATION: Any amino acid
<220> FEATURE:
<221> NAME/KEY: MISC_FEATURE
<222> LOCATION: (322)..(325)
<223> OTHER INFORMATION: This region may encompass 1-4 residues or this
      region may be absent in its entirety
<220> FEATURE:
<221> NAME/KEY: MOD_RES
<222> LOCATION: (326)..(330)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (331)..(360)
<223> OTHER INFORMATION: Any amino acid
<220> FEATURE:
<221> NAME/KEY: MISC_FEATURE
<222> LOCATION: (331)..(360)
<223> OTHER INFORMATION: This region may encompass 4-30 residues
<220> FEATURE:
<221> NAME/KEY: MOD_RES
<222> LOCATION: (362)..(365)
<223> OTHER INFORMATION: Any amino acid
<220> FEATURE:
<221> NAME/KEY: MISC_FEATURE
<222> LOCATION: (362)..(365)
<223> OTHER INFORMATION: This region may encompass 1-4 residues or this
      region may be absent in its entirety
<220> FEATURE:
<221> NAME/KEY: MOD_RES
<222> LOCATION: (366)..(370)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (371)..(400)
<223> OTHER INFORMATION: Any amino acid
<220> FEATURE:
<221> NAME/KEY: MISC_FEATURE
<222> LOCATION: (371)..(400)
<223> OTHER INFORMATION: This region may encompass 4-30 residues
<220> FEATURE:
<221> NAME/KEY: MOD_RES
<222> LOCATION: (402)..(405)
<223> OTHER INFORMATION: Any amino acid
<220> FEATURE:
<221> NAME/KEY: MISC_FEATURE
```

```
<222> LOCATION: (402)..(405)
<223> OTHER INFORMATION: This region may encompass 1-4 residues or this
      region may be absent in its entirety
<220> FEATURE:
<221> NAME/KEY: MOD_RES
<222> LOCATION: (406)..(410)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (411)..(440)
<223> OTHER INFORMATION: Any amino acid
<220> FEATURE:
<221> NAME/KEY: MISC_FEATURE
<222> LOCATION: (411)..(440)
<223> OTHER INFORMATION: This region may encompass 4-30 residues
<220> FEATURE:
<221> NAME/KEY: MOD_RES
<222> LOCATION: (442)..(445)
<223> OTHER INFORMATION: Any amino acid
<220> FEATURE:
<221> NAME/KEY: MISC_FEATURE
<222> LOCATION: (442)..(445)
<223> OTHER INFORMATION: This region may encompass 1-4 residues or this
      region may be absent in its entirety
<220> FEATURE:
<221> NAME/KEY: MOD_RES
<222> LOCATION: (446)..(450)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (451)..(480)
<223> OTHER INFORMATION: Any amino acid
<220> FEATURE:
<221> NAME/KEY: MISC_FEATURE
<222> LOCATION: (451)..(480)
<223> OTHER INFORMATION: This region may encompass 4-30 residues
<220> FEATURE:
<221> NAME/KEY: MOD_RES
<222> LOCATION: (482)..(485)
<223> OTHER INFORMATION: Any amino acid
<220> FEATURE:
<221> NAME/KEY: MISC_FEATURE
<222> LOCATION: (482)..(485)
<223> OTHER INFORMATION: This region may encompass 1-4 residues or this
      region may be absent in its entirety
<220> FEATURE:
<221> NAME/KEY: MOD_RES
<222> LOCATION: (486)..(490)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (491)..(520)
<223> OTHER INFORMATION: Any amino acid
<220> FEATURE:
<221> NAME/KEY: MISC_FEATURE
<222> LOCATION: (491)..(520)
<223> OTHER INFORMATION: This region may encompass 4-30 residues
<220> FEATURE:
<221> NAME/KEY: MOD_RES
<222> LOCATION: (522)..(525)
<223> OTHER INFORMATION: Any amino acid
<220> FEATURE:
<221> NAME/KEY: MISC_FEATURE
<222> LOCATION: (522)..(525)
<223> OTHER INFORMATION: This region may encompass 1-4 residues or this
      region may be absent in its entirety
<220> FEATURE:
<221> NAME/KEY: MOD_RES
<222> LOCATION: (526)..(530)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (531)..(560)
<223> OTHER INFORMATION: Any amino acid
<220> FEATURE:
```

```
<221> NAME/KEY: MISC_FEATURE
<222> LOCATION: (531)..(560)
<223> OTHER INFORMATION: This region may encompass 4-30 residues
<220> FEATURE:
<221> NAME/KEY: MOD_RES
<222> LOCATION: (562)..(565)
<223> OTHER INFORMATION: Any amino acid
<220> FEATURE:
<221> NAME/KEY: MISC_FEATURE
<222> LOCATION: (562)..(565)
<223> OTHER INFORMATION: This region may encompass 1-4 residues or this
      region may be absent in its entirety
<220> FEATURE:
<221> NAME/KEY: MOD_RES
<222> LOCATION: (566)..(570)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (571)..(600)
<223> OTHER INFORMATION: Any amino acid
<220> FEATURE:
<221> NAME/KEY: MISC_FEATURE
<222> LOCATION: (571)..(600)
<223> OTHER INFORMATION: This region may encompass 4-30 residues
<220> FEATURE:
<221> NAME/KEY: MOD_RES
<222> LOCATION: (602)..(605)
<223> OTHER INFORMATION: Any amino acid
<220> FEATURE:
<221> NAME/KEY: MISC_FEATURE
<222> LOCATION: (602)..(605)
<223> OTHER INFORMATION: This region may encompass 1-4 residues or this
      region may be absent in its entirety
<220> FEATURE:
<221> NAME/KEY: MOD_RES
<222> LOCATION: (606)..(610)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (611)..(640)
<223> OTHER INFORMATION: Any amino acid
<220> FEATURE:
<221> NAME/KEY: MISC_FEATURE
<222> LOCATION: (611)..(640)
<223> OTHER INFORMATION: This region may encompass 4-30 residues
<220> FEATURE:
<221> NAME/KEY: MOD_RES
<222> LOCATION: (642)..(645)
<223> OTHER INFORMATION: Any amino acid
<220> FEATURE:
<221> NAME/KEY: MISC_FEATURE
<222> LOCATION: (642)..(645)
<223> OTHER INFORMATION: This region may encompass 1-4 residues or this
      region may be absent in its entirety
<220> FEATURE:
<221> NAME/KEY: MOD_RES
<222> LOCATION: (646)..(650)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (651)..(680)
<223> OTHER INFORMATION: Any amino acid
<220> FEATURE:
<221> NAME/KEY: MISC_FEATURE
<222> LOCATION: (651)..(680)
<223> OTHER INFORMATION: This region may encompass 4-30 residues
<220> FEATURE:
<221> NAME/KEY: MOD_RES
<222> LOCATION: (682)..(685)
<223> OTHER INFORMATION: Any amino acid
<220> FEATURE:
<221> NAME/KEY: MISC_FEATURE
<222> LOCATION: (682)..(685)
<223> OTHER INFORMATION: This region may encompass 1-4 residues or this
      region may be absent in its entirety
<220> FEATURE:
```

```
<221> NAME/KEY: MOD_RES
<222> LOCATION: (686)..(690)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (691)..(720)
<223> OTHER INFORMATION: Any amino acid
<220> FEATURE:
<221> NAME/KEY: MISC_FEATURE
<222> LOCATION: (691)..(720)
<223> OTHER INFORMATION: This region may encompass 4-30 residues
<220> FEATURE:
<221> NAME/KEY: MOD_RES
<222> LOCATION: (722)..(725)
<223> OTHER INFORMATION: Any amino acid
<220> FEATURE:
<221> NAME/KEY: MISC_FEATURE
<222> LOCATION: (722)..(725)
<223> OTHER INFORMATION: This region may encompass 1-4 residues or this
      region may be absent in its entirety
<220> FEATURE:
<221> NAME/KEY: MOD_RES
<222> LOCATION: (726)..(730)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (731)..(760)
<223> OTHER INFORMATION: Any amino acid
<220> FEATURE:
<221> NAME/KEY: MISC_FEATURE
<222> LOCATION: (731)..(760)
<223> OTHER INFORMATION: This region may encompass 4-30 residues
<220> FEATURE:
<221> NAME/KEY: MOD_RES
<222> LOCATION: (762)..(765)
<223> OTHER INFORMATION: Any amino acid
<220> FEATURE:
<221> NAME/KEY: MISC_FEATURE
<222> LOCATION: (762)..(765)
<223> OTHER INFORMATION: This region may encompass 1-4 residues or this
      region may be absent in its entirety
<220> FEATURE:
<221> NAME/KEY: MOD_RES
<222> LOCATION: (766)..(770)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (771)..(800)
<223> OTHER INFORMATION: Any amino acid
<220> FEATURE:
<221> NAME/KEY: MISC_FEATURE
<222> LOCATION: (771)..(800)
<223> OTHER INFORMATION: This region may encompass 4-30 residues
<220> FEATURE:
<221> NAME/KEY: MOD_RES
<222> LOCATION: (802)..(805)
<223> OTHER INFORMATION: Any amino acid
<220> FEATURE:
<221> NAME/KEY: MISC_FEATURE
<222> LOCATION: (802)..(805)
<223> OTHER INFORMATION: This region may encompass 1-4 residues or this
      region may be absent in its entirety
<220> FEATURE:
<221> NAME/KEY: MOD_RES
<222> LOCATION: (806)..(810)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (811)..(840)
<223> OTHER INFORMATION: Any amino acid
<220> FEATURE:
<221> NAME/KEY: MISC_FEATURE
<222> LOCATION: (811)..(840)
<223> OTHER INFORMATION: This region may encompass 4-30 residues
<220> FEATURE:
```

```
<221> NAME/KEY: MOD_RES
<222> LOCATION: (842)..(845)
<223> OTHER INFORMATION: Any amino acid
<220> FEATURE:
<221> NAME/KEY: MISC_FEATURE
<222> LOCATION: (842)..(845)
<223> OTHER INFORMATION: This region may encompass 1-4 residues or this
      region may be absent in its entirety
<220> FEATURE:
<221> NAME/KEY: MOD_RES
<222> LOCATION: (846)..(850)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (851)..(880)
<223> OTHER INFORMATION: Any amino acid
<220> FEATURE:
<221> NAME/KEY: MISC_FEATURE
<222> LOCATION: (851)..(880)
<223> OTHER INFORMATION: This region may encompass 4-30 residues
<220> FEATURE:
<221> NAME/KEY: MOD_RES
<222> LOCATION: (882)..(885)
<223> OTHER INFORMATION: Any amino acid
<220> FEATURE:
<221> NAME/KEY: MISC_FEATURE
<222> LOCATION: (882)..(885)
<223> OTHER INFORMATION: This region may encompass 1-4 residues or this
      region may be absent in its entirety
<220> FEATURE:
<221> NAME/KEY: MOD_RES
<222> LOCATION: (886)..(890)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (891)..(920)
<223> OTHER INFORMATION: Any amino acid
<220> FEATURE:
<221> NAME/KEY: MISC_FEATURE
<222> LOCATION: (891)..(920)
<223> OTHER INFORMATION: This region may encompass 4-30 residues
<220> FEATURE:
<221> NAME/KEY: MOD_RES
<222> LOCATION: (922)..(925)
<223> OTHER INFORMATION: Any amino acid
<220> FEATURE:
<221> NAME/KEY: MISC_FEATURE
<222> LOCATION: (922)..(925)
<223> OTHER INFORMATION: This region may encompass 1-4 residues or this
      region may be absent in its entirety
<220> FEATURE:
<221> NAME/KEY: MOD_RES
<222> LOCATION: (926)..(930)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (931)..(960)
<223> OTHER INFORMATION: Any amino acid
<220> FEATURE:
<221> NAME/KEY: MISC_FEATURE
<222> LOCATION: (931)..(960)
<223> OTHER INFORMATION: This region may encompass 4-30 residues
<220> FEATURE:
<221> NAME/KEY: MOD_RES
<222> LOCATION: (962)..(965)
<223> OTHER INFORMATION: Any amino acid
<220> FEATURE:
<221> NAME/KEY: MISC_FEATURE
<222> LOCATION: (962)..(965)
<223> OTHER INFORMATION: This region may encompass 1-4 residues or this
      region may be absent in its entirety
<220> FEATURE:
<221> NAME/KEY: MOD_RES
<222> LOCATION: (966)..(970)
<223> OTHER INFORMATION: This region may encompass one of the following
      sequences: GQ, GN, RPG, RPGGQ, RPGGN, SSS, SKG, or SN
```

-continued

```
<220> FEATURE:
<221> NAME/KEY: MOD_RES
<222> LOCATION: (971)..(1000)
<223> OTHER INFORMATION: Any amino acid
<220> FEATURE:
<221> NAME/KEY: MISC_FEATURE
<222> LOCATION: (971)..(1000)
<223> OTHER INFORMATION: This region may encompass 4-30 residues
<220> FEATURE:
<221> NAME/KEY: MOD_RES
<222> LOCATION: (1002)..(1005)
<223> OTHER INFORMATION: Any amino acid
<220> FEATURE:
<221> NAME/KEY: MISC_FEATURE
<222> LOCATION: (1002)..(1005)
<223> OTHER INFORMATION: This region may encompass 1-4 residues or this
      region may be absent in its entirety
<220> FEATURE:
<221> NAME/KEY: MOD_RES
<222> LOCATION: (1006)..(1010)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1011)..(1040)
<223> OTHER INFORMATION: Any amino acid
<220> FEATURE:
<221> NAME/KEY: MISC_FEATURE
<222> LOCATION: (1011)..(1040)
<223> OTHER INFORMATION: This region may encompass 4-30 residues
<220> FEATURE:
<221> NAME/KEY: MOD_RES
<222> LOCATION: (1042)..(1045)
<223> OTHER INFORMATION: Any amino acid
<220> FEATURE:
<221> NAME/KEY: MISC_FEATURE
<222> LOCATION: (1042)..(1045)
<223> OTHER INFORMATION: This region may encompass 1-4 residues or this
      region may be absent in its entirety
<220> FEATURE:
<221> NAME/KEY: MOD_RES
<222> LOCATION: (1046)..(1050)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1051)..(1080)
<223> OTHER INFORMATION: Any amino acid
<220> FEATURE:
<221> NAME/KEY: MISC_FEATURE
<222> LOCATION: (1051)..(1080)
<223> OTHER INFORMATION: This region may encompass 4-30 residues
<220> FEATURE:
<221> NAME/KEY: MOD_RES
<222> LOCATION: (1082)..(1085)
<223> OTHER INFORMATION: Any amino acid
<220> FEATURE:
<221> NAME/KEY: MISC_FEATURE
<222> LOCATION: (1082)..(1085)
<223> OTHER INFORMATION: This region may encompass 1-4 residues or this
      region may be absent in its entirety
<220> FEATURE:
<221> NAME/KEY: MOD_RES
<222> LOCATION: (1086)..(1090)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1091)..(1120)
<223> OTHER INFORMATION: Any amino acid
<220> FEATURE:
<221> NAME/KEY: MISC_FEATURE
<222> LOCATION: (1091)..(1120)
<223> OTHER INFORMATION: This region may encompass 4-30 residues
<220> FEATURE:
<221> NAME/KEY: MOD_RES
<222> LOCATION: (1122)..(1125)
<223> OTHER INFORMATION: Any amino acid
<220> FEATURE:
```

-continued

```
<221> NAME/KEY: MISC_FEATURE
<222> LOCATION: (1122)..(1125)
<223> OTHER INFORMATION: This region may encompass 1-4 residues or this
      region may be absent in its entirety
<220> FEATURE:
<221> NAME/KEY: MOD_RES
<222> LOCATION: (1126)..(1130)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1131)..(1160)
<223> OTHER INFORMATION: Any amino acid
<220> FEATURE:
<221> NAME/KEY: MISC_FEATURE
<222> LOCATION: (1131)..(1160)
<223> OTHER INFORMATION: This region may encompass 4-30 residues
<220> FEATURE:
<221> NAME/KEY: MOD_RES
<222> LOCATION: (1162)..(1165)
<223> OTHER INFORMATION: Any amino acid
<220> FEATURE:
<221> NAME/KEY: MISC_FEATURE
<222> LOCATION: (1162)..(1165)
<223> OTHER INFORMATION: This region may encompass 1-4 residues or this
      region may be absent in its entirety
<220> FEATURE:
<221> NAME/KEY: MOD_RES
<222> LOCATION: (1166)..(1170)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1171)..(1200)
<223> OTHER INFORMATION: Any amino acid
<220> FEATURE:
<221> NAME/KEY: MISC_FEATURE
<222> LOCATION: (1171)..(1200)
<223> OTHER INFORMATION: This region may encompass 4-30 residues
<220> FEATURE:
<221> NAME/KEY: MOD_RES
<222> LOCATION: (1202)..(1205)
<223> OTHER INFORMATION: Any amino acid
<220> FEATURE:
<221> NAME/KEY: MISC_FEATURE
<222> LOCATION: (1202)..(1205)
<223> OTHER INFORMATION: This region may encompass 1-4 residues or this
      region may be absent in its entirety
<220> FEATURE:
<221> NAME/KEY: MOD_RES
<222> LOCATION: (1206)..(1210)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1211)..(1240)
<223> OTHER INFORMATION: Any amino acid
<220> FEATURE:
<221> NAME/KEY: MISC_FEATURE
<222> LOCATION: (1211)..(1240)
<223> OTHER INFORMATION: This region may encompass 4-30 residues
<220> FEATURE:
<221> NAME/KEY: MOD_RES
<222> LOCATION: (1242)..(1245)
<223> OTHER INFORMATION: Any amino acid
<220> FEATURE:
<221> NAME/KEY: MISC_FEATURE
<222> LOCATION: (1242)..(1245)
<223> OTHER INFORMATION: This region may encompass 1-4 residues or this
      region may be absent in its entirety
<220> FEATURE:
<221> NAME/KEY: MOD_RES
<222> LOCATION: (1246)..(1250)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1251)..(1280)
<223> OTHER INFORMATION: Any amino acid
```

```
<220> FEATURE:
<221> NAME/KEY: MISC_FEATURE
<222> LOCATION: (1251)..(1280)
<223> OTHER INFORMATION: This region may encompass 4-30 residues
<220> FEATURE:
<221> NAME/KEY: MOD_RES
<222> LOCATION: (1282)..(1285)
<223> OTHER INFORMATION: Any amino acid
<220> FEATURE:
<221> NAME/KEY: MISC_FEATURE
<222> LOCATION: (1282)..(1285)
<223> OTHER INFORMATION: This region may encompass 1-4 residues or this
      region may be absent in its entirety
<220> FEATURE:
<221> NAME/KEY: MOD_RES
<222> LOCATION: (1286)..(1290)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1291)..(1320)
<223> OTHER INFORMATION: Any amino acid
<220> FEATURE:
<221> NAME/KEY: MISC_FEATURE
<222> LOCATION: (1291)..(1320)
<223> OTHER INFORMATION: This region may encompass 4-30 residues
<220> FEATURE:
<221> NAME/KEY: MOD_RES
<222> LOCATION: (1322)..(1325)
<223> OTHER INFORMATION: Any amino acid
<220> FEATURE:
<221> NAME/KEY: MISC_FEATURE
<222> LOCATION: (1322)..(1325)
<223> OTHER INFORMATION: This region may encompass 1-4 residues or this
      region may be absent in its entirety
<220> FEATURE:
<221> NAME/KEY: MOD_RES
<222> LOCATION: (1326)..(1330)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1331)..(1360)
<223> OTHER INFORMATION: Any amino acid
<220> FEATURE:
<221> NAME/KEY: MISC_FEATURE
<222> LOCATION: (1331)..(1360)
<223> OTHER INFORMATION: This region may encompass 4-30 residues
<220> FEATURE:
<221> NAME/KEY: MOD_RES
<222> LOCATION: (1362)..(1365)
<223> OTHER INFORMATION: Any amino acid
<220> FEATURE:
<221> NAME/KEY: MISC_FEATURE
<222> LOCATION: (1362)..(1365)
<223> OTHER INFORMATION: This region may encompass 1-4 residues or this
      region may be absent in its entirety
<220> FEATURE:
<221> NAME/KEY: MOD_RES
<222> LOCATION: (1366)..(1370)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1371)..(1400)
<223> OTHER INFORMATION: Any amino acid
<220> FEATURE:
<221> NAME/KEY: MISC_FEATURE
<222> LOCATION: (1371)..(1400)
<223> OTHER INFORMATION: This region may encompass 4-30 residues
<220> FEATURE:
<221> NAME/KEY: MOD_RES
<222> LOCATION: (1402)..(1405)
<223> OTHER INFORMATION: Any amino acid
<220> FEATURE:
<221> NAME/KEY: MISC_FEATURE
<222> LOCATION: (1402)..(1405)
<223> OTHER INFORMATION: This region may encompass 1-4 residues or this
      region may be absent in its entirety
```

```
<220> FEATURE:
<221> NAME/KEY: MOD_RES
<222> LOCATION: (1406)..(1410)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1411)..(1440)
<223> OTHER INFORMATION: Any amino acid
<220> FEATURE:
<221> NAME/KEY: MISC_FEATURE
<222> LOCATION: (1411)..(1440)
<223> OTHER INFORMATION: This region may encompass 4-30 residues
<220> FEATURE:
<221> NAME/KEY: MOD_RES
<222> LOCATION: (1442)..(1445)
<223> OTHER INFORMATION: Any amino acid
<220> FEATURE:
<221> NAME/KEY: MISC_FEATURE
<222> LOCATION: (1442)..(1445)
<223> OTHER INFORMATION: This region may encompass 1-4 residues or this
      region may be absent in its entirety
<220> FEATURE:
<221> NAME/KEY: MOD_RES
<222> LOCATION: (1446)..(1450)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1451)..(1480)
<223> OTHER INFORMATION: Any amino acid
<220> FEATURE:
<221> NAME/KEY: MISC_FEATURE
<222> LOCATION: (1451)..(1480)
<223> OTHER INFORMATION: This region may encompass 4-30 residues
<220> FEATURE:
<221> NAME/KEY: MOD_RES
<222> LOCATION: (1482)..(1485)
<223> OTHER INFORMATION: Any amino acid
<220> FEATURE:
<221> NAME/KEY: MISC_FEATURE
<222> LOCATION: (1482)..(1485)
<223> OTHER INFORMATION: This region may encompass 1-4 residues or this
      region may be absent in its entirety
<220> FEATURE:
<221> NAME/KEY: MOD_RES
<222> LOCATION: (1486)..(1490)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1491)..(1520)
<223> OTHER INFORMATION: Any amino acid
<220> FEATURE:
<221> NAME/KEY: MISC_FEATURE
<222> LOCATION: (1491)..(1520)
<223> OTHER INFORMATION: This region may encompass 4-30 residues
<220> FEATURE:
<221> NAME/KEY: MOD_RES
<222> LOCATION: (1522)..(1525)
<223> OTHER INFORMATION: Any amino acid
<220> FEATURE:
<221> NAME/KEY: MISC_FEATURE
<222> LOCATION: (1522)..(1525)
<223> OTHER INFORMATION: This region may encompass 1-4 residues or this
      region may be absent in its entirety
<220> FEATURE:
<221> NAME/KEY: MOD_RES
<222> LOCATION: (1526)..(1530)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1531)..(1560)
<223> OTHER INFORMATION: Any amino acid
<220> FEATURE:
<221> NAME/KEY: MISC_FEATURE
<222> LOCATION: (1531)..(1560)
<223> OTHER INFORMATION: This region may encompass 4-30 residues
```

```
<220> FEATURE:
<221> NAME/KEY: MOD_RES
<222> LOCATION: (1562)..(1565)
<223> OTHER INFORMATION: Any amino acid
<220> FEATURE:
<221> NAME/KEY: MISC_FEATURE
<222> LOCATION: (1562)..(1565)
<223> OTHER INFORMATION: This region may encompass 1-4 residues or this
      region may be absent in its entirety
<220> FEATURE:
<221> NAME/KEY: MOD_RES
<222> LOCATION: (1566)..(1570)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1571)..(1600)
<223> OTHER INFORMATION: Any amino acid
<220> FEATURE:
<221> NAME/KEY: MISC_FEATURE
<222> LOCATION: (1571)..(1600)
<223> OTHER INFORMATION: This region may encompass 4-30 residues
<220> FEATURE:
<221> NAME/KEY: MOD_RES
<222> LOCATION: (1602)..(1605)
<223> OTHER INFORMATION: Any amino acid
<220> FEATURE:
<221> NAME/KEY: MISC_FEATURE
<222> LOCATION: (1602)..(1605)
<223> OTHER INFORMATION: This region may encompass 1-4 residues or this
      region may be absent in its entirety
<220> FEATURE:
<221> NAME/KEY: MOD_RES
<222> LOCATION: (1606)..(1610)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1611)..(1640)
<223> OTHER INFORMATION: Any amino acid
<220> FEATURE:
<221> NAME/KEY: MISC_FEATURE
<222> LOCATION: (1611)..(1640)
<223> OTHER INFORMATION: This region may encompass 4-30 residues
<220> FEATURE:
<221> NAME/KEY: MOD_RES
<222> LOCATION: (1642)..(1645)
<223> OTHER INFORMATION: Any amino acid
<220> FEATURE:
<221> NAME/KEY: MISC_FEATURE
<222> LOCATION: (1642)..(1645)
<223> OTHER INFORMATION: This region may encompass 1-4 residues or this
      region may be absent in its entirety
<220> FEATURE:
<221> NAME/KEY: MOD_RES
<222> LOCATION: (1646)..(1650)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1651)..(1680)
<223> OTHER INFORMATION: Any amino acid
<220> FEATURE:
<221> NAME/KEY: MISC_FEATURE
<222> LOCATION: (1651)..(1680)
<223> OTHER INFORMATION: This region may encompass 4-30 residues
<220> FEATURE:
<221> NAME/KEY: MOD_RES
<222> LOCATION: (1682)..(1685)
<223> OTHER INFORMATION: Any amino acid
<220> FEATURE:
<221> NAME/KEY: MISC_FEATURE
<222> LOCATION: (1682)..(1685)
<223> OTHER INFORMATION: This region may encompass 1-4 residues or this
      region may be absent in its entirety
<220> FEATURE:
<221> NAME/KEY: MOD_RES
<222> LOCATION: (1686)..(1690)
<223> OTHER INFORMATION: This region may encompass one of the following
```

```
          sequences: GQ, GN, RPG, RPGGQ, RPGGN, SSS, SKG, or SN
<220> FEATURE:
<221> NAME/KEY: MOD_RES
<222> LOCATION: (1691)..(1720)
<223> OTHER INFORMATION: Any amino acid
<220> FEATURE:
<221> NAME/KEY: MISC_FEATURE
<222> LOCATION: (1691)..(1720)
<223> OTHER INFORMATION: This region may encompass 4-30 residues
<220> FEATURE:
<221> NAME/KEY: MOD_RES
<222> LOCATION: (1722)..(1725)
<223> OTHER INFORMATION: Any amino acid
<220> FEATURE:
<221> NAME/KEY: MISC_FEATURE
<222> LOCATION: (1722)..(1725)
<223> OTHER INFORMATION: This region may encompass 1-4 residues or this
          region may be absent in its entirety
<220> FEATURE:
<221> NAME/KEY: MOD_RES
<222> LOCATION: (1726)..(1730)
<223> OTHER INFORMATION: This region may encompass one of the following
          sequences: GQ, GN, RPG, RPGGQ, RPGGN, SSS, SKG, or SN
<220> FEATURE:
<221> NAME/KEY: MOD_RES
<222> LOCATION: (1731)..(1760)
<223> OTHER INFORMATION: Any amino acid
<220> FEATURE:
<221> NAME/KEY: MISC_FEATURE
<222> LOCATION: (1731)..(1760)
<223> OTHER INFORMATION: This region may encompass 4-30 residues
<220> FEATURE:
<221> NAME/KEY: MOD_RES
<222> LOCATION: (1762)..(1765)
<223> OTHER INFORMATION: Any amino acid
<220> FEATURE:
<221> NAME/KEY: MISC_FEATURE
<222> LOCATION: (1762)..(1765)
<223> OTHER INFORMATION: This region may encompass 1-4 residues or this
          region may be absent in its entirety
<220> FEATURE:
<221> NAME/KEY: MOD_RES
<222> LOCATION: (1766)..(1770)
<223> OTHER INFORMATION: This region may encompass one of the following
          sequences: GQ, GN, RPG, RPGGQ, RPGGN, SSS, SKG, or SN
<220> FEATURE:
<221> NAME/KEY: MOD_RES
<222> LOCATION: (1771)..(1800)
<223> OTHER INFORMATION: Any amino acid
<220> FEATURE:
<221> NAME/KEY: MISC_FEATURE
<222> LOCATION: (1771)..(1800)
<223> OTHER INFORMATION: This region may encompass 4-30 residues
<220> FEATURE:
<221> NAME/KEY: MOD_RES
<222> LOCATION: (1802)..(1805)
<223> OTHER INFORMATION: Any amino acid
<220> FEATURE:
<221> NAME/KEY: MISC_FEATURE
<222> LOCATION: (1802)..(1805)
<223> OTHER INFORMATION: This region may encompass 1-4 residues or this
          region may be absent in its entirety
<220> FEATURE:
<221> NAME/KEY: MOD_RES
<222> LOCATION: (1806)..(1810)
<223> OTHER INFORMATION: This region may encompass one of the following
          sequences: GQ, GN, RPG, RPGGQ, RPGGN, SSS, SKG, or SN
<220> FEATURE:
<221> NAME/KEY: MOD_RES
<222> LOCATION: (1811)..(1840)
<223> OTHER INFORMATION: Any amino acid
<220> FEATURE:
<221> NAME/KEY: MISC_FEATURE
<222> LOCATION: (1811)..(1840)
<223> OTHER INFORMATION: This region may encompass 4-30 residues
<220> FEATURE:
<221> NAME/KEY: MOD_RES
<222> LOCATION: (1842)..(1845)
<223> OTHER INFORMATION: Any amino acid
```

-continued

```
<220> FEATURE:
<221> NAME/KEY: MISC_FEATURE
<222> LOCATION: (1842)..(1845)
<223> OTHER INFORMATION: This region may encompass 1-4 residues or this
      region may be absent in its entirety
<220> FEATURE:
<221> NAME/KEY: MOD_RES
<222> LOCATION: (1846)..(1850)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1851)..(1880)
<223> OTHER INFORMATION: Any amino acid
<220> FEATURE:
<221> NAME/KEY: MISC_FEATURE
<222> LOCATION: (1851)..(1880)
<223> OTHER INFORMATION: This region may encompass 4-30 residues
<220> FEATURE:
<221> NAME/KEY: MOD_RES
<222> LOCATION: (1882)..(1885)
<223> OTHER INFORMATION: Any amino acid
<220> FEATURE:
<221> NAME/KEY: MISC_FEATURE
<222> LOCATION: (1882)..(1885)
<223> OTHER INFORMATION: This region may encompass 1-4 residues or this
      region may be absent in its entirety
<220> FEATURE:
<221> NAME/KEY: MOD_RES
<222> LOCATION: (1886)..(1890)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1891)..(1920)
<223> OTHER INFORMATION: Any amino acid
<220> FEATURE:
<221> NAME/KEY: MISC_FEATURE
<222> LOCATION: (1891)..(1920)
<223> OTHER INFORMATION: This region may encompass 4-30 residues
<220> FEATURE:
<221> NAME/KEY: MOD_RES
<222> LOCATION: (1922)..(1925)
<223> OTHER INFORMATION: Any amino acid
<220> FEATURE:
<221> NAME/KEY: MISC_FEATURE
<222> LOCATION: (1922)..(1925)
<223> OTHER INFORMATION: This region may encompass 1-4 residues or this
      region may be absent in its entirety
<220> FEATURE:
<221> NAME/KEY: MOD_RES
<222> LOCATION: (1926)..(1930)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1931)..(1960)
<223> OTHER INFORMATION: Any amino acid
<220> FEATURE:
<221> NAME/KEY: MISC_FEATURE
<222> LOCATION: (1931)..(1960)
<223> OTHER INFORMATION: This region may encompass 4-30 residues
<220> FEATURE:
<221> NAME/KEY: MOD_RES
<222> LOCATION: (1962)..(1965)
<223> OTHER INFORMATION: Any amino acid
<220> FEATURE:
<221> NAME/KEY: MISC_FEATURE
<222> LOCATION: (1962)..(1965)
<223> OTHER INFORMATION: This region may encompass 1-4 residues or this
      region may be absent in its entirety
<220> FEATURE:
<221> NAME/KEY: MOD_RES
<222> LOCATION: (1966)..(1970)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (1971)..(2000)
```

```
<223> OTHER INFORMATION: Any amino acid
<220> FEATURE:
<221> NAME/KEY: MISC_FEATURE
<222> LOCATION: (1971)..(2000)
<223> OTHER INFORMATION: This region may encompass 4-30 residues
<220> FEATURE:
<221> NAME/KEY: MOD_RES
<222> LOCATION: (2002)..(2005)
<223> OTHER INFORMATION: Any amino acid
<220> FEATURE:
<221> NAME/KEY: MISC_FEATURE
<222> LOCATION: (2002)..(2005)
<223> OTHER INFORMATION: This region may encompass 1-4 residues or this
      region may be absent in its entirety
<220> FEATURE:
<221> NAME/KEY: MOD_RES
<222> LOCATION: (2006)..(2010)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2011)..(2040)
<223> OTHER INFORMATION: Any amino acid
<220> FEATURE:
<221> NAME/KEY: MISC_FEATURE
<222> LOCATION: (2011)..(2040)
<223> OTHER INFORMATION: This region may encompass 4-30 residues
<220> FEATURE:
<221> NAME/KEY: MOD_RES
<222> LOCATION: (2042)..(2045)
<223> OTHER INFORMATION: Any amino acid
<220> FEATURE:
<221> NAME/KEY: MISC_FEATURE
<222> LOCATION: (2042)..(2045)
<223> OTHER INFORMATION: This region may encompass 1-4 residues or this
      region may be absent in its entirety
<220> FEATURE:
<221> NAME/KEY: MOD_RES
<222> LOCATION: (2046)..(2050)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2051)..(2080)
<223> OTHER INFORMATION: Any amino acid
<220> FEATURE:
<221> NAME/KEY: MISC_FEATURE
<222> LOCATION: (2051)..(2080)
<223> OTHER INFORMATION: This region may encompass 4-30 residues
<220> FEATURE:
<221> NAME/KEY: MOD_RES
<222> LOCATION: (2082)..(2085)
<223> OTHER INFORMATION: Any amino acid
<220> FEATURE:
<221> NAME/KEY: MISC_FEATURE
<222> LOCATION: (2082)..(2085)
<223> OTHER INFORMATION: This region may encompass 1-4 residues or this
      region may be absent in its entirety
<220> FEATURE:
<221> NAME/KEY: MOD_RES
<222> LOCATION: (2086)..(2090)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2091)..(2120)
<223> OTHER INFORMATION: Any amino acid
<220> FEATURE:
<221> NAME/KEY: MISC_FEATURE
<222> LOCATION: (2091)..(2120)
<223> OTHER INFORMATION: This region may encompass 4-30 residues
<220> FEATURE:
<221> NAME/KEY: MOD_RES
<222> LOCATION: (2122)..(2125)
<223> OTHER INFORMATION: Any amino acid
<220> FEATURE:
<221> NAME/KEY: MISC_FEATURE
<222> LOCATION: (2122)..(2125)
<223> OTHER INFORMATION: This region may encompass 1-4 residues or this
```

```
      region may be absent in its entirety
<220> FEATURE:
<221> NAME/KEY: MOD_RES
<222> LOCATION: (2126)..(2130)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2131)..(2160)
<223> OTHER INFORMATION: Any amino acid
<220> FEATURE:
<221> NAME/KEY: MISC_FEATURE
<222> LOCATION: (2131)..(2160)
<223> OTHER INFORMATION: This region may encompass 4-30 residues
<220> FEATURE:
<221> NAME/KEY: MOD_RES
<222> LOCATION: (2162)..(2165)
<223> OTHER INFORMATION: Any amino acid
<220> FEATURE:
<221> NAME/KEY: MISC_FEATURE
<222> LOCATION: (2162)..(2165)
<223> OTHER INFORMATION: This region may encompass 1-4 residues or this
      region may be absent in its entirety
<220> FEATURE:
<221> NAME/KEY: MOD_RES
<222> LOCATION: (2166)..(2170)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2171)..(2200)
<223> OTHER INFORMATION: Any amino acid
<220> FEATURE:
<221> NAME/KEY: MISC_FEATURE
<222> LOCATION: (2171)..(2200)
<223> OTHER INFORMATION: This region may encompass 4-30 residues
<220> FEATURE:
<221> NAME/KEY: MOD_RES
<222> LOCATION: (2202)..(2205)
<223> OTHER INFORMATION: Any amino acid
<220> FEATURE:
<221> NAME/KEY: MISC_FEATURE
<222> LOCATION: (2202)..(2205)
<223> OTHER INFORMATION: This region may encompass 1-4 residues or this
      region may be absent in its entirety
<220> FEATURE:
<221> NAME/KEY: MOD_RES
<222> LOCATION: (2206)..(2210)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2211)..(2240)
<223> OTHER INFORMATION: Any amino acid
<220> FEATURE:
<221> NAME/KEY: MISC_FEATURE
<222> LOCATION: (2211)..(2240)
<223> OTHER INFORMATION: This region may encompass 4-30 residues
<220> FEATURE:
<221> NAME/KEY: MOD_RES
<222> LOCATION: (2242)..(2245)
<223> OTHER INFORMATION: Any amino acid
<220> FEATURE:
<221> NAME/KEY: MISC_FEATURE
<222> LOCATION: (2242)..(2245)
<223> OTHER INFORMATION: This region may encompass 1-4 residues or this
      region may be absent in its entirety
<220> FEATURE:
<221> NAME/KEY: MOD_RES
<222> LOCATION: (2246)..(2250)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2251)..(2280)
<223> OTHER INFORMATION: Any amino acid
<220> FEATURE:
<221> NAME/KEY: MISC_FEATURE
<222> LOCATION: (2251)..(2280)
```

```
<223> OTHER INFORMATION: This region may encompass 4-30 residues
<220> FEATURE:
<221> NAME/KEY: MOD_RES
<222> LOCATION: (2282)..(2285)
<223> OTHER INFORMATION: Any amino acid
<220> FEATURE:
<221> NAME/KEY: MISC_FEATURE
<222> LOCATION: (2282)..(2285)
<223> OTHER INFORMATION: This region may encompass 1-4 residues or this
      region may be absent in its entirety
<220> FEATURE:
<221> NAME/KEY: MOD_RES
<222> LOCATION: (2286)..(2290)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2291)..(2320)
<223> OTHER INFORMATION: Any amino acid
<220> FEATURE:
<221> NAME/KEY: MISC_FEATURE
<222> LOCATION: (2291)..(2320)
<223> OTHER INFORMATION: This region may encompass 4-30 residues
<220> FEATURE:
<221> NAME/KEY: MOD_RES
<222> LOCATION: (2322)..(2325)
<223> OTHER INFORMATION: Any amino acid
<220> FEATURE:
<221> NAME/KEY: MISC_FEATURE
<222> LOCATION: (2322)..(2325)
<223> OTHER INFORMATION: This region may encompass 1-4 residues or this
      region may be absent in its entirety
<220> FEATURE:
<221> NAME/KEY: MOD_RES
<222> LOCATION: (2326)..(2330)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2331)..(2360)
<223> OTHER INFORMATION: Any amino acid
<220> FEATURE:
<221> NAME/KEY: MISC_FEATURE
<222> LOCATION: (2331)..(2360)
<223> OTHER INFORMATION: This region may encompass 4-30 residues
<220> FEATURE:
<221> NAME/KEY: MOD_RES
<222> LOCATION: (2362)..(2365)
<223> OTHER INFORMATION: Any amino acid
<220> FEATURE:
<221> NAME/KEY: MISC_FEATURE
<222> LOCATION: (2362)..(2365)
<223> OTHER INFORMATION: This region may encompass 1-4 residues or this
      region may be absent in its entirety
<220> FEATURE:
<221> NAME/KEY: MOD_RES
<222> LOCATION: (2366)..(2370)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2371)..(2400)
<223> OTHER INFORMATION: Any amino acid
<220> FEATURE:
<221> NAME/KEY: MISC_FEATURE
<222> LOCATION: (2371)..(2400)
<223> OTHER INFORMATION: This region may encompass 4-30 residues
<220> FEATURE:
<221> NAME/KEY: MOD_RES
<222> LOCATION: (2402)..(2405)
<223> OTHER INFORMATION: Any amino acid
<220> FEATURE:
<221> NAME/KEY: MISC_FEATURE
<222> LOCATION: (2402)..(2405)
<223> OTHER INFORMATION: This region may encompass 1-4 residues or this
      region may be absent in its entirety
<220> FEATURE:
<221> NAME/KEY: MOD_RES
<222> LOCATION: (2406)..(2410)
```

```
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2411)..(2440)
<223> OTHER INFORMATION: Any amino acid
<220> FEATURE:
<221> NAME/KEY: MISC_FEATURE
<222> LOCATION: (2411)..(2440)
<223> OTHER INFORMATION: This region may encompass 4-30 residues
<220> FEATURE:
<221> NAME/KEY: MOD_RES
<222> LOCATION: (2442)..(2445)
<223> OTHER INFORMATION: Any amino acid
<220> FEATURE:
<221> NAME/KEY: MISC_FEATURE
<222> LOCATION: (2442)..(2445)
<223> OTHER INFORMATION: This region may encompass 1-4 residues or this
      region may be absent in its entirety
<220> FEATURE:
<221> NAME/KEY: MOD_RES
<222> LOCATION: (2446)..(2450)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2451)..(2480)
<223> OTHER INFORMATION: Any amino acid
<220> FEATURE:
<221> NAME/KEY: MISC_FEATURE
<222> LOCATION: (2451)..(2480)
<223> OTHER INFORMATION: This region may encompass 4-30 residues
<220> FEATURE:
<221> NAME/KEY: MOD_RES
<222> LOCATION: (2482)..(2485)
<223> OTHER INFORMATION: Any amino acid
<220> FEATURE:
<221> NAME/KEY: MISC_FEATURE
<222> LOCATION: (2482)..(2485)
<223> OTHER INFORMATION: This region may encompass 1-4 residues or this
      region may be absent in its entirety
<220> FEATURE:
<221> NAME/KEY: MOD_RES
<222> LOCATION: (2486)..(2490)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2491)..(2520)
<223> OTHER INFORMATION: Any amino acid
<220> FEATURE:
<221> NAME/KEY: MISC_FEATURE
<222> LOCATION: (2491)..(2520)
<223> OTHER INFORMATION: This region may encompass 4-30 residues
<220> FEATURE:
<221> NAME/KEY: MOD_RES
<222> LOCATION: (2522)..(2525)
<223> OTHER INFORMATION: Any amino acid
<220> FEATURE:
<221> NAME/KEY: MISC_FEATURE
<222> LOCATION: (2522)..(2525)
<223> OTHER INFORMATION: This region may encompass 1-4 residues or this
      region may be absent in its entirety
<220> FEATURE:
<221> NAME/KEY: MOD_RES
<222> LOCATION: (2526)..(2530)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2531)..(2560)
<223> OTHER INFORMATION: Any amino acid
<220> FEATURE:
<221> NAME/KEY: MISC_FEATURE
<222> LOCATION: (2531)..(2560)
<223> OTHER INFORMATION: This region may encompass 4-30 residues
<220> FEATURE:
<221> NAME/KEY: MOD_RES
<222> LOCATION: (2562)..(2565)
```

```
<223> OTHER INFORMATION: Any amino acid
<220> FEATURE:
<221> NAME/KEY: MISC_FEATURE
<222> LOCATION: (2562)..(2565)
<223> OTHER INFORMATION: This region may encompass 1-4 residues or this
      region may be absent in its entirety
<220> FEATURE:
<221> NAME/KEY: MOD_RES
<222> LOCATION: (2566)..(2570)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2571)..(2600)
<223> OTHER INFORMATION: Any amino acid
<220> FEATURE:
<221> NAME/KEY: MISC_FEATURE
<222> LOCATION: (2571)..(2600)
<223> OTHER INFORMATION: This region may encompass 4-30 residues
<220> FEATURE:
<221> NAME/KEY: MOD_RES
<222> LOCATION: (2602)..(2605)
<223> OTHER INFORMATION: Any amino acid
<220> FEATURE:
<221> NAME/KEY: MISC_FEATURE
<222> LOCATION: (2602)..(2605)
<223> OTHER INFORMATION: This region may encompass 1-4 residues or this
      region may be absent in its entirety
<220> FEATURE:
<221> NAME/KEY: MOD_RES
<222> LOCATION: (2606)..(2610)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2611)..(2640)
<223> OTHER INFORMATION: Any amino acid
<220> FEATURE:
<221> NAME/KEY: MISC_FEATURE
<222> LOCATION: (2611)..(2640)
<223> OTHER INFORMATION: This region may encompass 4-30 residues
<220> FEATURE:
<221> NAME/KEY: MOD_RES
<222> LOCATION: (2642)..(2645)
<223> OTHER INFORMATION: Any amino acid
<220> FEATURE:
<221> NAME/KEY: MISC_FEATURE
<222> LOCATION: (2642)..(2645)
<223> OTHER INFORMATION: This region may encompass 1-4 residues or this
      region may be absent in its entirety
<220> FEATURE:
<221> NAME/KEY: MOD_RES
<222> LOCATION: (2646)..(2650)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2651)..(2680)
<223> OTHER INFORMATION: Any amino acid
<220> FEATURE:
<221> NAME/KEY: MISC_FEATURE
<222> LOCATION: (2651)..(2680)
<223> OTHER INFORMATION: This region may encompass 4-30 residues
<220> FEATURE:
<221> NAME/KEY: MOD_RES
<222> LOCATION: (2682)..(2685)
<223> OTHER INFORMATION: Any amino acid
<220> FEATURE:
<221> NAME/KEY: MISC_FEATURE
<222> LOCATION: (2682)..(2685)
<223> OTHER INFORMATION: This region may encompass 1-4 residues or this
      region may be absent in its entirety
<220> FEATURE:
<221> NAME/KEY: MOD_RES
<222> LOCATION: (2686)..(2690)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
```

```
<222> LOCATION: (2691)..(2720)
<223> OTHER INFORMATION: Any amino acid
<220> FEATURE:
<221> NAME/KEY: MISC_FEATURE
<222> LOCATION: (2691)..(2720)
<223> OTHER INFORMATION: This region may encompass 4-30 residues
<220> FEATURE:
<221> NAME/KEY: MOD_RES
<222> LOCATION: (2722)..(2725)
<223> OTHER INFORMATION: Any amino acid
<220> FEATURE:
<221> NAME/KEY: MISC_FEATURE
<222> LOCATION: (2722)..(2725)
<223> OTHER INFORMATION: This region may encompass 1-4 residues or this
      region may be absent in its entirety
<220> FEATURE:
<221> NAME/KEY: MOD_RES
<222> LOCATION: (2726)..(2730)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2731)..(2760)
<223> OTHER INFORMATION: Any amino acid
<220> FEATURE:
<221> NAME/KEY: MISC_FEATURE
<222> LOCATION: (2731)..(2760)
<223> OTHER INFORMATION: This region may encompass 4-30 residues
<220> FEATURE:
<221> NAME/KEY: MOD_RES
<222> LOCATION: (2762)..(2765)
<223> OTHER INFORMATION: Any amino acid
<220> FEATURE:
<221> NAME/KEY: MISC_FEATURE
<222> LOCATION: (2762)..(2765)
<223> OTHER INFORMATION: This region may encompass 1-4 residues or this
      region may be absent in its entirety
<220> FEATURE:
<221> NAME/KEY: MOD_RES
<222> LOCATION: (2766)..(2770)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2771)..(2800)
<223> OTHER INFORMATION: Any amino acid
<220> FEATURE:
<221> NAME/KEY: MISC_FEATURE
<222> LOCATION: (2771)..(2800)
<223> OTHER INFORMATION: This region may encompass 4-30 residues
<220> FEATURE:
<221> NAME/KEY: MOD_RES
<222> LOCATION: (2802)..(2805)
<223> OTHER INFORMATION: Any amino acid
<220> FEATURE:
<221> NAME/KEY: MISC_FEATURE
<222> LOCATION: (2802)..(2805)
<223> OTHER INFORMATION: This region may encompass 1-4 residues or this
      region may be absent in its entirety
<220> FEATURE:
<221> NAME/KEY: MOD_RES
<222> LOCATION: (2806)..(2810)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2811)..(2840)
<223> OTHER INFORMATION: Any amino acid
<220> FEATURE:
<221> NAME/KEY: MISC_FEATURE
<222> LOCATION: (2811)..(2840)
<223> OTHER INFORMATION: This region may encompass 4-30 residues
<220> FEATURE:
<221> NAME/KEY: MOD_RES
<222> LOCATION: (2842)..(2845)
<223> OTHER INFORMATION: Any amino acid
<220> FEATURE:
<221> NAME/KEY: MISC_FEATURE
<222> LOCATION: (2842)..(2845)
```

```
<223> OTHER INFORMATION: This region may encompass 1-4 residues or this
      region may be absent in its entirety
<220> FEATURE:
<221> NAME/KEY: MOD_RES
<222> LOCATION: (2846)..(2850)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2851)..(2880)
<223> OTHER INFORMATION: Any amino acid
<220> FEATURE:
<221> NAME/KEY: MISC_FEATURE
<222> LOCATION: (2851)..(2880)
<223> OTHER INFORMATION: This region may encompass 4-30 residues
<220> FEATURE:
<221> NAME/KEY: MOD_RES
<222> LOCATION: (2882)..(2885)
<223> OTHER INFORMATION: Any amino acid
<220> FEATURE:
<221> NAME/KEY: MISC_FEATURE
<222> LOCATION: (2882)..(2885)
<223> OTHER INFORMATION: This region may encompass 1-4 residues or this
      region may be absent in its entirety
<220> FEATURE:
<221> NAME/KEY: MOD_RES
<222> LOCATION: (2886)..(2890)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2891)..(2920)
<223> OTHER INFORMATION: Any amino acid
<220> FEATURE:
<221> NAME/KEY: MISC_FEATURE
<222> LOCATION: (2891)..(2920)
<223> OTHER INFORMATION: This region may encompass 4-30 residues
<220> FEATURE:
<221> NAME/KEY: MOD_RES
<222> LOCATION: (2922)..(2925)
<223> OTHER INFORMATION: Any amino acid
<220> FEATURE:
<221> NAME/KEY: MISC_FEATURE
<222> LOCATION: (2922)..(2925)
<223> OTHER INFORMATION: This region may encompass 1-4 residues or this
      region may be absent in its entirety
<220> FEATURE:
<221> NAME/KEY: MOD_RES
<222> LOCATION: (2926)..(2930)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2931)..(2960)
<223> OTHER INFORMATION: Any amino acid
<220> FEATURE:
<221> NAME/KEY: MISC_FEATURE
<222> LOCATION: (2931)..(2960)
<223> OTHER INFORMATION: This region may encompass 4-30 residues
<220> FEATURE:
<221> NAME/KEY: MOD_RES
<222> LOCATION: (2962)..(2965)
<223> OTHER INFORMATION: Any amino acid
<220> FEATURE:
<221> NAME/KEY: MISC_FEATURE
<222> LOCATION: (2962)..(2965)
<223> OTHER INFORMATION: This region may encompass 1-4 residues or this
      region may be absent in its entirety
<220> FEATURE:
<221> NAME/KEY: MOD_RES
<222> LOCATION: (2966)..(2970)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (2971)..(3000)
<223> OTHER INFORMATION: Any amino acid
<220> FEATURE:
<221> NAME/KEY: MISC_FEATURE
```

```
<222> LOCATION: (2971)..(3000)
<223> OTHER INFORMATION: This region may encompass 4-30 residues
<220> FEATURE:
<221> NAME/KEY: MOD_RES
<222> LOCATION: (3002)..(3005)
<223> OTHER INFORMATION: Any amino acid
<220> FEATURE:
<221> NAME/KEY: MISC_FEATURE
<222> LOCATION: (3002)..(3005)
<223> OTHER INFORMATION: This region may encompass 1-4 residues or this
      region may be absent in its entirety
<220> FEATURE:
<221> NAME/KEY: MOD_RES
<222> LOCATION: (3006)..(3010)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3011)..(3040)
<223> OTHER INFORMATION: Any amino acid
<220> FEATURE:
<221> NAME/KEY: MISC_FEATURE
<222> LOCATION: (3011)..(3040)
<223> OTHER INFORMATION: This region may encompass 4-30 residues
<220> FEATURE:
<221> NAME/KEY: MOD_RES
<222> LOCATION: (3042)..(3045)
<223> OTHER INFORMATION: Any amino acid
<220> FEATURE:
<221> NAME/KEY: MISC_FEATURE
<222> LOCATION: (3042)..(3045)
<223> OTHER INFORMATION: This region may encompass 1-4 residues or this
      region may be absent in its entirety
<220> FEATURE:
<221> NAME/KEY: MOD_RES
<222> LOCATION: (3046)..(3050)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3051)..(3080)
<223> OTHER INFORMATION: Any amino acid
<220> FEATURE:
<221> NAME/KEY: MISC_FEATURE
<222> LOCATION: (3051)..(3080)
<223> OTHER INFORMATION: This region may encompass 4-30 residues
<220> FEATURE:
<221> NAME/KEY: MOD_RES
<222> LOCATION: (3082)..(3085)
<223> OTHER INFORMATION: Any amino acid
<220> FEATURE:
<221> NAME/KEY: MISC_FEATURE
<222> LOCATION: (3082)..(3085)
<223> OTHER INFORMATION: This region may encompass 1-4 residues or this
      region may be absent in its entirety
<220> FEATURE:
<221> NAME/KEY: MOD_RES
<222> LOCATION: (3086)..(3090)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3091)..(3120)
<223> OTHER INFORMATION: Any amino acid
<220> FEATURE:
<221> NAME/KEY: MISC_FEATURE
<222> LOCATION: (3091)..(3120)
<223> OTHER INFORMATION: This region may encompass 4-30 residues
<220> FEATURE:
<221> NAME/KEY: MOD_RES
<222> LOCATION: (3122)..(3125)
<223> OTHER INFORMATION: Any amino acid
<220> FEATURE:
<221> NAME/KEY: MISC_FEATURE
<222> LOCATION: (3122)..(3125)
<223> OTHER INFORMATION: This region may encompass 1-4 residues or this
      region may be absent in its entirety
<220> FEATURE:
<221> NAME/KEY: MOD_RES
```

```
<222> LOCATION: (3126)..(3130)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3131)..(3160)
<223> OTHER INFORMATION: Any amino acid
<220> FEATURE:
<221> NAME/KEY: MISC_FEATURE
<222> LOCATION: (3131)..(3160)
<223> OTHER INFORMATION: This region may encompass 4-30 residues
<220> FEATURE:
<221> NAME/KEY: MOD_RES
<222> LOCATION: (3162)..(3165)
<223> OTHER INFORMATION: Any amino acid
<220> FEATURE:
<221> NAME/KEY: MISC_FEATURE
<222> LOCATION: (3162)..(3165)
<223> OTHER INFORMATION: This region may encompass 1-4 residues or this
      region may be absent in its entirety
<220> FEATURE:
<221> NAME/KEY: MOD_RES
<222> LOCATION: (3166)..(3170)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3171)..(3200)
<223> OTHER INFORMATION: Any amino acid
<220> FEATURE:
<221> NAME/KEY: MISC_FEATURE
<222> LOCATION: (3171)..(3200)
<223> OTHER INFORMATION: This region may encompass 4-30 residues
<220> FEATURE:
<221> NAME/KEY: MOD_RES
<222> LOCATION: (3202)..(3205)
<223> OTHER INFORMATION: Any amino acid
<220> FEATURE:
<221> NAME/KEY: MISC_FEATURE
<222> LOCATION: (3202)..(3205)
<223> OTHER INFORMATION: This region may encompass 1-4 residues or this
      region may be absent in its entirety
<220> FEATURE:
<221> NAME/KEY: MOD_RES
<222> LOCATION: (3206)..(3210)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3211)..(3240)
<223> OTHER INFORMATION: Any amino acid
<220> FEATURE:
<221> NAME/KEY: MISC_FEATURE
<222> LOCATION: (3211)..(3240)
<223> OTHER INFORMATION: This region may encompass 4-30 residues
<220> FEATURE:
<221> NAME/KEY: MOD_RES
<222> LOCATION: (3242)..(3245)
<223> OTHER INFORMATION: Any amino acid
<220> FEATURE:
<221> NAME/KEY: MISC_FEATURE
<222> LOCATION: (3242)..(3245)
<223> OTHER INFORMATION: This region may encompass 1-4 residues or this
      region may be absent in its entirety
<220> FEATURE:
<221> NAME/KEY: MOD_RES
<222> LOCATION: (3246)..(3250)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3251)..(3280)
<223> OTHER INFORMATION: Any amino acid
<220> FEATURE:
<221> NAME/KEY: MISC_FEATURE
<222> LOCATION: (3251)..(3280)
<223> OTHER INFORMATION: This region may encompass 4-30 residues
<220> FEATURE:
<221> NAME/KEY: MOD_RES
```

```
<222> LOCATION: (3282)..(3285)
<223> OTHER INFORMATION: Any amino acid
<220> FEATURE:
<221> NAME/KEY: MISC_FEATURE
<222> LOCATION: (3282)..(3285)
<223> OTHER INFORMATION: This region may encompass 1-4 residues or this
      region may be absent in its entirety
<220> FEATURE:
<221> NAME/KEY: MOD_RES
<222> LOCATION: (3286)..(3290)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3291)..(3320)
<223> OTHER INFORMATION: Any amino acid
<220> FEATURE:
<221> NAME/KEY: MISC_FEATURE
<222> LOCATION: (3291)..(3320)
<223> OTHER INFORMATION: This region may encompass 4-30 residues
<220> FEATURE:
<221> NAME/KEY: MOD_RES
<222> LOCATION: (3322)..(3325)
<223> OTHER INFORMATION: Any amino acid
<220> FEATURE:
<221> NAME/KEY: MISC_FEATURE
<222> LOCATION: (3322)..(3325)
<223> OTHER INFORMATION: This region may encompass 1-4 residues or this
      region may be absent in its entirety
<220> FEATURE:
<221> NAME/KEY: MOD_RES
<222> LOCATION: (3326)..(3330)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3331)..(3360)
<223> OTHER INFORMATION: Any amino acid
<220> FEATURE:
<221> NAME/KEY: MISC_FEATURE
<222> LOCATION: (3331)..(3360)
<223> OTHER INFORMATION: This region may encompass 4-30 residues
<220> FEATURE:
<221> NAME/KEY: MOD_RES
<222> LOCATION: (3362)..(3365)
<223> OTHER INFORMATION: Any amino acid
<220> FEATURE:
<221> NAME/KEY: MISC_FEATURE
<222> LOCATION: (3362)..(3365)
<223> OTHER INFORMATION: This region may encompass 1-4 residues or this
      region may be absent in its entirety
<220> FEATURE:
<221> NAME/KEY: MOD_RES
<222> LOCATION: (3366)..(3370)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3371)..(3400)
<223> OTHER INFORMATION: Any amino acid
<220> FEATURE:
<221> NAME/KEY: MISC_FEATURE
<222> LOCATION: (3371)..(3400)
<223> OTHER INFORMATION: This region may encompass 4-30 residues
<220> FEATURE:
<221> NAME/KEY: MOD_RES
<222> LOCATION: (3402)..(3405)
<223> OTHER INFORMATION: Any amino acid
<220> FEATURE:
<221> NAME/KEY: MISC_FEATURE
<222> LOCATION: (3402)..(3405)
<223> OTHER INFORMATION: This region may encompass 1-4 residues or this
      region may be absent in its entirety
<220> FEATURE:
<221> NAME/KEY: MOD_RES
<222> LOCATION: (3406)..(3410)
<223> OTHER INFORMATION: This region may encompass one of the following
      sequences: GQ, GN, RPG, RPGGQ, RPGGN, SSS, SKG, or SN
<220> FEATURE:
```

```
<221> NAME/KEY: MOD_RES
<222> LOCATION: (3411)..(3440)
<223> OTHER INFORMATION: Any amino acid
<220> FEATURE:
<221> NAME/KEY: MISC_FEATURE
<222> LOCATION: (3411)..(3440)
<223> OTHER INFORMATION: This region may encompass 4-30 residues
<220> FEATURE:
<221> NAME/KEY: MOD_RES
<222> LOCATION: (3442)..(3445)
<223> OTHER INFORMATION: Any amino acid
<220> FEATURE:
<221> NAME/KEY: MISC_FEATURE
<222> LOCATION: (3442)..(3445)
<223> OTHER INFORMATION: This region may encompass 1-4 residues or this
      region may be absent in its entirety
<220> FEATURE:
<221> NAME/KEY: MOD_RES
<222> LOCATION: (3446)..(3450)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3451)..(3480)
<223> OTHER INFORMATION: Any amino acid
<220> FEATURE:
<221> NAME/KEY: MISC_FEATURE
<222> LOCATION: (3451)..(3480)
<223> OTHER INFORMATION: This region may encompass 4-30 residues
<220> FEATURE:
<221> NAME/KEY: MOD_RES
<222> LOCATION: (3482)..(3485)
<223> OTHER INFORMATION: Any amino acid
<220> FEATURE:
<221> NAME/KEY: MISC_FEATURE
<222> LOCATION: (3482)..(3485)
<223> OTHER INFORMATION: This region may encompass 1-4 residues or this
      region may be absent in its entirety
<220> FEATURE:
<221> NAME/KEY: MOD_RES
<222> LOCATION: (3486)..(3490)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3491)..(3520)
<223> OTHER INFORMATION: Any amino acid
<220> FEATURE:
<221> NAME/KEY: MISC_FEATURE
<222> LOCATION: (3491)..(3520)
<223> OTHER INFORMATION: This region may encompass 4-30 residues
<220> FEATURE:
<221> NAME/KEY: MOD_RES
<222> LOCATION: (3522)..(3525)
<223> OTHER INFORMATION: Any amino acid
<220> FEATURE:
<221> NAME/KEY: MISC_FEATURE
<222> LOCATION: (3522)..(3525)
<223> OTHER INFORMATION: This region may encompass 1-4 residues or this
      region may be absent in its entirety
<220> FEATURE:
<221> NAME/KEY: MOD_RES
<222> LOCATION: (3526)..(3530)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3531)..(3560)
<223> OTHER INFORMATION: Any amino acid
<220> FEATURE:
<221> NAME/KEY: MISC_FEATURE
<222> LOCATION: (3531)..(3560)
<223> OTHER INFORMATION: This region may encompass 4-30 residues
<220> FEATURE:
<221> NAME/KEY: MOD_RES
<222> LOCATION: (3562)..(3565)
<223> OTHER INFORMATION: Any amino acid
<220> FEATURE:
<221> NAME/KEY: MISC_FEATURE
```

```
<222> LOCATION: (3562)..(3565)
<223> OTHER INFORMATION: This region may encompass 1-4 residues or this
      region may be absent in its entirety
<220> FEATURE:
<221> NAME/KEY: MOD_RES
<222> LOCATION: (3566)..(3570)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3571)..(3600)
<223> OTHER INFORMATION: Any amino acid
<220> FEATURE:
<221> NAME/KEY: MISC_FEATURE
<222> LOCATION: (3571)..(3600)
<223> OTHER INFORMATION: This region may encompass 4-30 residues
<220> FEATURE:
<221> NAME/KEY: MOD_RES
<222> LOCATION: (3602)..(3605)
<223> OTHER INFORMATION: Any amino acid
<220> FEATURE:
<221> NAME/KEY: MISC_FEATURE
<222> LOCATION: (3602)..(3605)
<223> OTHER INFORMATION: This region may encompass 1-4 residues or this
      region may be absent in its entirety
<220> FEATURE:
<221> NAME/KEY: MOD_RES
<222> LOCATION: (3606)..(3610)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3611)..(3640)
<223> OTHER INFORMATION: Any amino acid
<220> FEATURE:
<221> NAME/KEY: MISC_FEATURE
<222> LOCATION: (3611)..(3640)
<223> OTHER INFORMATION: This region may encompass 4-30 residues
<220> FEATURE:
<221> NAME/KEY: MOD_RES
<222> LOCATION: (3642)..(3645)
<223> OTHER INFORMATION: Any amino acid
<220> FEATURE:
<221> NAME/KEY: MISC_FEATURE
<222> LOCATION: (3642)..(3645)
<223> OTHER INFORMATION: This region may encompass 1-4 residues or this
      region may be absent in its entirety
<220> FEATURE:
<221> NAME/KEY: MOD_RES
<222> LOCATION: (3646)..(3650)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3651)..(3680)
<223> OTHER INFORMATION: Any amino acid
<220> FEATURE:
<221> NAME/KEY: MISC_FEATURE
<222> LOCATION: (3651)..(3680)
<223> OTHER INFORMATION: This region may encompass 4-30 residues
<220> FEATURE:
<221> NAME/KEY: MOD_RES
<222> LOCATION: (3682)..(3685)
<223> OTHER INFORMATION: Any amino acid
<220> FEATURE:
<221> NAME/KEY: MISC_FEATURE
<222> LOCATION: (3682)..(3685)
<223> OTHER INFORMATION: This region may encompass 1-4 residues or this
      region may be absent in its entirety
<220> FEATURE:
<221> NAME/KEY: MOD_RES
<222> LOCATION: (3686)..(3690)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3691)..(3720)
<223> OTHER INFORMATION: Any amino acid
<220> FEATURE:
```

```
<221> NAME/KEY: MISC_FEATURE
<222> LOCATION: (3691)..(3720)
<223> OTHER INFORMATION: This region may encompass 4-30 residues
<220> FEATURE:
<221> NAME/KEY: MOD_RES
<222> LOCATION: (3722)..(3725)
<223> OTHER INFORMATION: Any amino acid
<220> FEATURE:
<221> NAME/KEY: MISC_FEATURE
<222> LOCATION: (3722)..(3725)
<223> OTHER INFORMATION: This region may encompass 1-4 residues or this
      region may be absent in its entirety
<220> FEATURE:
<221> NAME/KEY: MOD_RES
<222> LOCATION: (3726)..(3730)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3731)..(3760)
<223> OTHER INFORMATION: Any amino acid
<220> FEATURE:
<221> NAME/KEY: MISC_FEATURE
<222> LOCATION: (3731)..(3760)
<223> OTHER INFORMATION: This region may encompass 4-30 residues
<220> FEATURE:
<221> NAME/KEY: MOD_RES
<222> LOCATION: (3762)..(3765)
<223> OTHER INFORMATION: Any amino acid
<220> FEATURE:
<221> NAME/KEY: MISC_FEATURE
<222> LOCATION: (3762)..(3765)
<223> OTHER INFORMATION: This region may encompass 1-4 residues or this
      region may be absent in its entirety
<220> FEATURE:
<221> NAME/KEY: MOD_RES
<222> LOCATION: (3766)..(3770)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3771)..(3800)
<223> OTHER INFORMATION: Any amino acid
<220> FEATURE:
<221> NAME/KEY: MISC_FEATURE
<222> LOCATION: (3771)..(3800)
<223> OTHER INFORMATION: This region may encompass 4-30 residues
<220> FEATURE:
<221> NAME/KEY: MOD_RES
<222> LOCATION: (3802)..(3805)
<223> OTHER INFORMATION: Any amino acid
<220> FEATURE:
<221> NAME/KEY: MISC_FEATURE
<222> LOCATION: (3802)..(3805)
<223> OTHER INFORMATION: This region may encompass 1-4 residues or this
      region may be absent in its entirety
<220> FEATURE:
<221> NAME/KEY: MOD_RES
<222> LOCATION: (3806)..(3810)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3811)..(3840)
<223> OTHER INFORMATION: Any amino acid
<220> FEATURE:
<221> NAME/KEY: MISC_FEATURE
<222> LOCATION: (3811)..(3840)
<223> OTHER INFORMATION: This region may encompass 4-30 residues
<220> FEATURE:
<221> NAME/KEY: MOD_RES
<222> LOCATION: (3842)..(3845)
<223> OTHER INFORMATION: Any amino acid
<220> FEATURE:
<221> NAME/KEY: MISC_FEATURE
<222> LOCATION: (3842)..(3845)
<223> OTHER INFORMATION: This region may encompass 1-4 residues or this
      region may be absent in its entirety
<220> FEATURE:
```

```
<221> NAME/KEY: MOD_RES
<222> LOCATION: (3846)..(3850)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3851)..(3880)
<223> OTHER INFORMATION: Any amino acid
<220> FEATURE:
<221> NAME/KEY: MISC_FEATURE
<222> LOCATION: (3851)..(3880)
<223> OTHER INFORMATION: This region may encompass 4-30 residues
<220> FEATURE:
<221> NAME/KEY: MOD_RES
<222> LOCATION: (3882)..(3885)
<223> OTHER INFORMATION: Any amino acid
<220> FEATURE:
<221> NAME/KEY: MISC_FEATURE
<222> LOCATION: (3882)..(3885)
<223> OTHER INFORMATION: This region may encompass 1-4 residues or this
      region may be absent in its entirety
<220> FEATURE:
<221> NAME/KEY: MOD_RES
<222> LOCATION: (3886)..(3890)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3891)..(3920)
<223> OTHER INFORMATION: Any amino acid
<220> FEATURE:
<221> NAME/KEY: MISC_FEATURE
<222> LOCATION: (3891)..(3920)
<223> OTHER INFORMATION: This region may encompass 4-30 residues
<220> FEATURE:
<221> NAME/KEY: MOD_RES
<222> LOCATION: (3922)..(3925)
<223> OTHER INFORMATION: Any amino acid
<220> FEATURE:
<221> NAME/KEY: MISC_FEATURE
<222> LOCATION: (3922)..(3925)
<223> OTHER INFORMATION: This region may encompass 1-4 residues or this
      region may be absent in its entirety
<220> FEATURE:
<221> NAME/KEY: MOD_RES
<222> LOCATION: (3926)..(3930)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3931)..(3960)
<223> OTHER INFORMATION: Any amino acid
<220> FEATURE:
<221> NAME/KEY: MISC_FEATURE
<222> LOCATION: (3931)..(3960)
<223> OTHER INFORMATION: This region may encompass 4-30 residues
<220> FEATURE:
<221> NAME/KEY: MOD_RES
<222> LOCATION: (3962)..(3965)
<223> OTHER INFORMATION: Any amino acid
<220> FEATURE:
<221> NAME/KEY: MISC_FEATURE
<222> LOCATION: (3962)..(3965)
<223> OTHER INFORMATION: This region may encompass 1-4 residues or this
      region may be absent in its entirety
<220> FEATURE:
<221> NAME/KEY: MOD_RES
<222> LOCATION: (3966)..(3970)
<223> OTHER INFORMATION: This region may encompass one of the following
      sequences: GQ, GN, RPG, RPGGQ, RPGGN, SSS, SKG, or SN
<220> FEATURE:
<221> NAME/KEY: MOD_RES
<222> LOCATION: (3971)..(4000)
<223> OTHER INFORMATION: Any amino acid
<220> FEATURE:
<221> NAME/KEY: MISC_FEATURE
<222> LOCATION: (3971)..(4000)
<223> OTHER INFORMATION: This region may encompass 4-30 residues
<220> FEATURE:
```

<223> OTHER INFORMATION: See specification as filed for detailed
      description of substitutions and preferred embodiments

<400> SEQUENCE: 65

Tyr Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Tyr Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Tyr Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Tyr Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Tyr Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Tyr Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Tyr Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Tyr Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Tyr Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Tyr Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Tyr Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Tyr Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa
465                 470                 475                 480

Tyr Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Tyr Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa
545                 550                 555                 560

Tyr Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Tyr Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa
            610                 615                 620

Xaa Xaa Xaa Xaa Xaa Xaa Xaa Xaa Xaa Xaa Xaa Xaa Xaa Xaa Xaa
625                 630                 635                 640

Tyr Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Tyr Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa
705                 710                 715                 720

Tyr Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Tyr Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa Xaa
785                 790                 795                 800

Tyr Xaa Xaa Xaa Xaa Xaa Xaa Xaa Xaa Xaa Xaa Xaa Xaa Xaa Xaa
            805                 810                 815

```
Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Tyr Xaa Xaa Xaa Xaa Xaa Xaa
            835                 840                 845

Xaa Xaa Xaa Xaa Xaa Xaa Xaa Xaa Xaa Xaa Xaa Xaa Xaa Xaa Xaa
            850                 855                 860

Xaa Xaa Xaa Xaa Xaa Xaa Xaa Xaa Xaa Xaa Xaa Xaa Xaa Xaa Xaa
865                 870                 875                 880

Tyr Xaa Xaa Xaa Xaa Xaa Xaa Xaa Xaa Xaa Xaa Xaa Xaa Xaa Xaa
            885                 890                 895

Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Tyr Xaa Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
            930                 935                 940

Xaa Xaa Xaa Xaa Xaa Xaa Xaa Xaa Xaa Xaa Xaa Xaa Xaa Xaa Xaa
945                 950                 955                 960

Tyr Xaa Xaa Xaa Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Tyr Xaa Xaa Xaa Xaa Xaa Xaa Xaa
            995                 1000                1005

Xaa Xaa Xaa Xaa Xaa Xaa Xaa Xaa Xaa Xaa Xaa Xaa Xaa Xaa Xaa
            1010                1015                1020

Xaa Xaa Xaa Xaa Xaa Xaa Xaa Xaa Xaa Xaa Xaa Xaa Xaa Xaa Xaa
            1025                1030                1035

Xaa Xaa Tyr Xaa Xaa Xaa Xaa Xaa Xaa Xaa Xaa Xaa Xaa Xaa Xaa
            1040                1045                1050

Xaa Xaa Xaa Xaa Xaa Xaa Xaa Xaa Xaa Xaa Xaa Xaa Xaa Xaa Xaa
            1055                1060                1065

Xaa Xaa Xaa Xaa Xaa Xaa Xaa Xaa Xaa Xaa Xaa Xaa Tyr Xaa Xaa
            1070                1075                1080

Xaa Xaa Xaa Xaa Xaa Xaa Xaa Xaa Xaa Xaa Xaa Xaa Xaa Xaa Xaa
            1085                1090                1095

Xaa Xaa Xaa Xaa Xaa Xaa Xaa Xaa Xaa Xaa Xaa Xaa Xaa Xaa Xaa
            1100                1105                1110

Xaa Xaa Xaa Xaa Xaa Xaa Xaa Tyr Xaa Xaa Xaa Xaa Xaa Xaa Xaa
            1115                1120                1125

Xaa Xaa Xaa Xaa Xaa Xaa Xaa Xaa Xaa Xaa Xaa Xaa Xaa Xaa Xaa
            1130                1135                1140

Xaa Xaa Xaa Xaa Xaa Xaa Xaa Xaa Xaa Xaa Xaa Xaa Xaa Xaa Xaa
            1145                1150                1155

Xaa Xaa Tyr Xaa Xaa Xaa Xaa Xaa Xaa Xaa Xaa Xaa Xaa Xaa Xaa
            1160                1165                1170

Xaa Xaa Xaa Xaa Xaa Xaa Xaa Xaa Xaa Xaa Xaa Xaa Xaa Xaa Xaa
            1175                1180                1185

Xaa Xaa Xaa Xaa Xaa Xaa Xaa Xaa Xaa Xaa Xaa Xaa Tyr Xaa Xaa
            1190                1195                1200

Xaa Xaa Xaa Xaa Xaa Xaa Xaa Xaa Xaa Xaa Xaa Xaa Xaa Xaa Xaa
            1205                1210                1215

Xaa Xaa Xaa Xaa Xaa Xaa Xaa Xaa Xaa Xaa Xaa Xaa Xaa Xaa Xaa
```

-continued

```
            1220                1225                1230

Xaa Xaa Xaa Xaa Xaa Xaa Xaa  Tyr Xaa Xaa Xaa  Xaa Xaa Xaa
            1235                1240                1245

Xaa Xaa Xaa Xaa Xaa Xaa Xaa  Xaa Xaa Xaa Xaa  Xaa Xaa Xaa
            1250                1255                1260

Xaa Xaa Xaa Xaa Xaa Xaa Xaa  Xaa Xaa Xaa Xaa  Xaa Xaa Xaa
            1265                1270                1275

Xaa Xaa Tyr Xaa Xaa Xaa Xaa  Xaa Xaa Xaa Xaa  Xaa Xaa Xaa
            1280                1285                1290

Xaa Xaa Xaa Xaa Xaa Xaa Xaa  Xaa Xaa Xaa Xaa  Xaa Xaa Xaa
            1295                1300                1305

Xaa Xaa Xaa Xaa Xaa Xaa Xaa  Xaa Xaa Xaa Xaa  Tyr Xaa Xaa
            1310                1315                1320

Xaa Xaa Xaa Xaa Xaa Xaa Xaa  Xaa Xaa Xaa Xaa  Xaa Xaa Xaa
            1325                1330                1335

Xaa Xaa Xaa Xaa Xaa Xaa Xaa  Xaa Xaa Xaa Xaa  Xaa Xaa Xaa
            1340                1345                1350

Xaa Xaa Xaa Xaa Xaa Xaa Xaa  Tyr Xaa Xaa Xaa  Xaa Xaa Xaa
            1355                1360                1365

Xaa Xaa Xaa Xaa Xaa Xaa Xaa  Xaa Xaa Xaa Xaa  Xaa Xaa Xaa
            1370                1375                1380

Xaa Xaa Xaa Xaa Xaa Xaa Xaa  Xaa Xaa Xaa Xaa  Xaa Xaa Xaa
            1385                1390                1395

Xaa Xaa Tyr Xaa Xaa Xaa Xaa  Xaa Xaa Xaa Xaa  Xaa Xaa Xaa
            1400                1405                1410

Xaa Xaa Xaa Xaa Xaa Xaa Xaa  Xaa Xaa Xaa Xaa  Xaa Xaa Xaa
            1415                1420                1425

Xaa Xaa Xaa Xaa Xaa Xaa Xaa  Xaa Xaa Xaa Xaa  Tyr Xaa Xaa
            1430                1435                1440

Xaa Xaa Xaa Xaa Xaa Xaa Xaa  Xaa Xaa Xaa Xaa  Xaa Xaa Xaa
            1445                1450                1455

Xaa Xaa Xaa Xaa Xaa Xaa Xaa  Xaa Xaa Xaa Xaa  Xaa Xaa Xaa
            1460                1465                1470

Xaa Xaa Xaa Xaa Xaa Xaa Xaa  Tyr Xaa Xaa Xaa  Xaa Xaa Xaa
            1475                1480                1485

Xaa Xaa Xaa Xaa Xaa Xaa Xaa  Xaa Xaa Xaa Xaa  Xaa Xaa Xaa
            1490                1495                1500

Xaa Xaa Xaa Xaa Xaa Xaa Xaa  Xaa Xaa Xaa Xaa  Xaa Xaa Xaa
            1505                1510                1515

Xaa Xaa Tyr Xaa Xaa Xaa Xaa  Xaa Xaa Xaa Xaa  Xaa Xaa Xaa
            1520                1525                1530

Xaa Xaa Xaa Xaa Xaa Xaa Xaa  Xaa Xaa Xaa Xaa  Xaa Xaa Xaa
            1535                1540                1545

Xaa Xaa Xaa Xaa Xaa Xaa Xaa  Xaa Xaa Xaa Xaa  Tyr Xaa Xaa
            1550                1555                1560

Xaa Xaa Xaa Xaa Xaa Xaa Xaa  Xaa Xaa Xaa Xaa  Xaa Xaa Xaa
            1565                1570                1575

Xaa Xaa Xaa Xaa Xaa Xaa Xaa  Xaa Xaa Xaa Xaa  Xaa Xaa Xaa
            1580                1585                1590

Xaa Xaa Xaa Xaa Xaa Xaa Xaa  Tyr Xaa Xaa Xaa  Xaa Xaa Xaa
            1595                1600                1605

Xaa Xaa Xaa Xaa Xaa Xaa Xaa  Xaa Xaa Xaa Xaa  Xaa Xaa Xaa
            1610                1615                1620
```

```
Xaa Xaa Xaa Xaa Xaa Xaa Xaa  Xaa Xaa Xaa Xaa Xaa  Xaa Xaa Xaa
    1625                1630                 1635

Xaa Xaa Tyr Xaa Xaa Xaa Xaa  Xaa Xaa Xaa Xaa Xaa  Xaa Xaa Xaa
    1640                1645                 1650

Xaa Xaa Xaa Xaa Xaa Xaa Xaa  Xaa Xaa Xaa Xaa Xaa  Xaa Xaa Xaa
    1655                1660                 1665

Xaa Xaa Xaa Xaa Xaa Xaa Xaa  Xaa Xaa Xaa Xaa Xaa  Tyr Xaa Xaa
    1670                1675                 1680

Xaa Xaa Xaa Xaa Xaa Xaa Xaa  Xaa Xaa Xaa Xaa Xaa  Xaa Xaa Xaa
    1685                1690                 1695

Xaa Xaa Xaa Xaa Xaa Xaa Xaa  Xaa Xaa Xaa Xaa Xaa  Xaa Xaa Xaa
    1700                1705                 1710

Xaa Xaa Xaa Xaa Xaa Xaa Xaa  Tyr Xaa Xaa Xaa Xaa  Xaa Xaa Xaa
    1715                1720                 1725

Xaa Xaa Xaa Xaa Xaa Xaa Xaa  Xaa Xaa Xaa Xaa Xaa  Xaa Xaa Xaa
    1730                1735                 1740

Xaa Xaa Xaa Xaa Xaa Xaa Xaa  Xaa Xaa Xaa Xaa Xaa  Xaa Xaa Xaa
    1745                1750                 1755

Xaa Xaa Tyr Xaa Xaa Xaa Xaa  Xaa Xaa Xaa Xaa Xaa  Xaa Xaa Xaa
    1760                1765                 1770

Xaa Xaa Xaa Xaa Xaa Xaa Xaa  Xaa Xaa Xaa Xaa Xaa  Xaa Xaa Xaa
    1775                1780                 1785

Xaa Xaa Xaa Xaa Xaa Xaa Xaa  Xaa Xaa Xaa Xaa Xaa  Tyr Xaa Xaa
    1790                1795                 1800

Xaa Xaa Xaa Xaa Xaa Xaa Xaa  Xaa Xaa Xaa Xaa Xaa  Xaa Xaa Xaa
    1805                1810                 1815

Xaa Xaa Xaa Xaa Xaa Xaa Xaa  Xaa Xaa Xaa Xaa Xaa  Xaa Xaa Xaa
    1820                1825                 1830

Xaa Xaa Xaa Xaa Xaa Xaa Xaa  Tyr Xaa Xaa Xaa Xaa  Xaa Xaa Xaa
    1835                1840                 1845

Xaa Xaa Xaa Xaa Xaa Xaa Xaa  Xaa Xaa Xaa Xaa Xaa  Xaa Xaa Xaa
    1850                1855                 1860

Xaa Xaa Xaa Xaa Xaa Xaa Xaa  Xaa Xaa Xaa Xaa Xaa  Xaa Xaa Xaa
    1865                1870                 1875

Xaa Xaa Tyr Xaa Xaa Xaa Xaa  Xaa Xaa Xaa Xaa Xaa  Xaa Xaa Xaa
    1880                1885                 1890

Xaa Xaa Xaa Xaa Xaa Xaa Xaa  Xaa Xaa Xaa Xaa Xaa  Xaa Xaa Xaa
    1895                1900                 1905

Xaa Xaa Xaa Xaa Xaa Xaa Xaa  Xaa Xaa Xaa Xaa Xaa  Tyr Xaa Xaa
    1910                1915                 1920

Xaa Xaa Xaa Xaa Xaa Xaa Xaa  Xaa Xaa Xaa Xaa Xaa  Xaa Xaa Xaa
    1925                1930                 1935

Xaa Xaa Xaa Xaa Xaa Xaa Xaa  Xaa Xaa Xaa Xaa Xaa  Xaa Xaa Xaa
    1940                1945                 1950

Xaa Xaa Xaa Xaa Xaa Xaa Xaa  Tyr Xaa Xaa Xaa Xaa  Xaa Xaa Xaa
    1955                1960                 1965

Xaa Xaa Xaa Xaa Xaa Xaa Xaa  Xaa Xaa Xaa Xaa Xaa  Xaa Xaa Xaa
    1970                1975                 1980

Xaa Xaa Xaa Xaa Xaa Xaa Xaa  Xaa Xaa Xaa Xaa Xaa  Xaa Xaa Xaa
    1985                1990                 1995

Xaa Xaa Tyr Xaa Xaa Xaa Xaa  Xaa Xaa Xaa Xaa Xaa  Xaa Xaa Xaa
    2000                2005                 2010
```

-continued

```
Xaa Xaa Xaa Xaa Xaa Xaa Xaa  Xaa Xaa Xaa Xaa Xaa  Xaa Xaa Xaa
    2015                 2020                 2025

Xaa Xaa Xaa Xaa Xaa Xaa Xaa  Xaa Xaa Xaa Xaa Xaa  Tyr Xaa Xaa
    2030                 2035                 2040

Xaa Xaa Xaa Xaa Xaa Xaa Xaa  Xaa Xaa Xaa Xaa Xaa  Xaa Xaa Xaa
    2045                 2050                 2055

Xaa Xaa Xaa Xaa Xaa Xaa Xaa  Xaa Xaa Xaa Xaa Xaa  Xaa Xaa Xaa
    2060                 2065                 2070

Xaa Xaa Xaa Xaa Xaa Xaa Xaa  Tyr Xaa Xaa Xaa Xaa  Xaa Xaa Xaa
    2075                 2080                 2085

Xaa Xaa Xaa Xaa Xaa Xaa Xaa  Xaa Xaa Xaa Xaa Xaa  Xaa Xaa Xaa
    2090                 2095                 2100

Xaa Xaa Xaa Xaa Xaa Xaa Xaa  Xaa Xaa Xaa Xaa Xaa  Xaa Xaa Xaa
    2105                 2110                 2115

Xaa Xaa Tyr Xaa Xaa Xaa Xaa  Xaa Xaa Xaa Xaa Xaa  Xaa Xaa Xaa
    2120                 2125                 2130

Xaa Xaa Xaa Xaa Xaa Xaa Xaa  Xaa Xaa Xaa Xaa Xaa  Xaa Xaa Xaa
    2135                 2140                 2145

Xaa Xaa Xaa Xaa Xaa Xaa Xaa  Xaa Xaa Xaa Xaa Xaa  Tyr Xaa Xaa
    2150                 2155                 2160

Xaa Xaa Xaa Xaa Xaa Xaa Xaa  Xaa Xaa Xaa Xaa Xaa  Xaa Xaa Xaa
    2165                 2170                 2175

Xaa Xaa Xaa Xaa Xaa Xaa Xaa  Xaa Xaa Xaa Xaa Xaa  Xaa Xaa Xaa
    2180                 2185                 2190

Xaa Xaa Xaa Xaa Xaa Xaa Xaa  Tyr Xaa Xaa Xaa Xaa  Xaa Xaa Xaa
    2195                 2200                 2205

Xaa Xaa Xaa Xaa Xaa Xaa Xaa  Xaa Xaa Xaa Xaa Xaa  Xaa Xaa Xaa
    2210                 2215                 2220

Xaa Xaa Xaa Xaa Xaa Xaa Xaa  Xaa Xaa Xaa Xaa Xaa  Xaa Xaa Xaa
    2225                 2230                 2235

Xaa Xaa Tyr Xaa Xaa Xaa Xaa  Xaa Xaa Xaa Xaa Xaa  Xaa Xaa Xaa
    2240                 2245                 2250

Xaa Xaa Xaa Xaa Xaa Xaa Xaa  Xaa Xaa Xaa Xaa Xaa  Xaa Xaa Xaa
    2255                 2260                 2265

Xaa Xaa Xaa Xaa Xaa Xaa Xaa  Xaa Xaa Xaa Xaa Xaa  Tyr Xaa Xaa
    2270                 2275                 2280

Xaa Xaa Xaa Xaa Xaa Xaa Xaa  Xaa Xaa Xaa Xaa Xaa  Xaa Xaa Xaa
    2285                 2290                 2295

Xaa Xaa Xaa Xaa Xaa Xaa Xaa  Xaa Xaa Xaa Xaa Xaa  Xaa Xaa Xaa
    2300                 2305                 2310

Xaa Xaa Xaa Xaa Xaa Xaa Xaa  Tyr Xaa Xaa Xaa Xaa  Xaa Xaa Xaa
    2315                 2320                 2325

Xaa Xaa Xaa Xaa Xaa Xaa Xaa  Xaa Xaa Xaa Xaa Xaa  Xaa Xaa Xaa
    2330                 2335                 2340

Xaa Xaa Xaa Xaa Xaa Xaa Xaa  Xaa Xaa Xaa Xaa Xaa  Xaa Xaa Xaa
    2345                 2350                 2355

Xaa Xaa Tyr Xaa Xaa Xaa Xaa  Xaa Xaa Xaa Xaa Xaa  Xaa Xaa Xaa
    2360                 2365                 2370

Xaa Xaa Xaa Xaa Xaa Xaa Xaa  Xaa Xaa Xaa Xaa Xaa  Xaa Xaa Xaa
    2375                 2380                 2385

Xaa Xaa Xaa Xaa Xaa Xaa Xaa  Xaa Xaa Xaa Xaa Xaa  Tyr Xaa Xaa
    2390                 2395                 2400

Xaa Xaa  Xaa Xaa Xaa Xaa Xaa  Xaa Xaa Xaa Xaa Xaa  Xaa Xaa Xaa
```

-continued

```
                2405                2410                2415

Xaa Xaa Xaa Xaa Xaa Xaa Xaa  Xaa Xaa Xaa Xaa Xaa  Xaa Xaa Xaa
                2420                2425                2430

Xaa Xaa Xaa Xaa Xaa Xaa Xaa  Tyr Xaa Xaa Xaa Xaa  Xaa Xaa Xaa
                2435                2440                2445

Xaa Xaa Xaa Xaa Xaa Xaa Xaa  Xaa Xaa Xaa Xaa Xaa  Xaa Xaa Xaa
                2450                2455                2460

Xaa Xaa Xaa Xaa Xaa Xaa Xaa  Xaa Xaa Xaa Xaa Xaa  Xaa Xaa Xaa
                2465                2470                2475

Xaa Xaa Tyr Xaa Xaa Xaa Xaa  Xaa Xaa Xaa Xaa Xaa  Xaa Xaa Xaa
                2480                2485                2490

Xaa Xaa Xaa Xaa Xaa Xaa Xaa  Xaa Xaa Xaa Xaa Xaa  Xaa Xaa Xaa
                2495                2500                2505

Xaa Xaa Xaa Xaa Xaa Xaa Xaa  Xaa Xaa Xaa Xaa Xaa  Tyr Xaa Xaa
                2510                2515                2520

Xaa Xaa Xaa Xaa Xaa Xaa Xaa  Xaa Xaa Xaa Xaa Xaa  Xaa Xaa Xaa
                2525                2530                2535

Xaa Xaa Xaa Xaa Xaa Xaa Xaa  Xaa Xaa Xaa Xaa Xaa  Xaa Xaa Xaa
                2540                2545                2550

Xaa Xaa Xaa Xaa Xaa Xaa Xaa  Tyr Xaa Xaa Xaa Xaa  Xaa Xaa Xaa
                2555                2560                2565

Xaa Xaa Xaa Xaa Xaa Xaa Xaa  Xaa Xaa Xaa Xaa Xaa  Xaa Xaa Xaa
                2570                2575                2580

Xaa Xaa Xaa Xaa Xaa Xaa Xaa  Xaa Xaa Xaa Xaa Xaa  Xaa Xaa Xaa
                2585                2590                2595

Xaa Xaa Tyr Xaa Xaa Xaa Xaa  Xaa Xaa Xaa Xaa Xaa  Xaa Xaa Xaa
                2600                2605                2610

Xaa Xaa Xaa Xaa Xaa Xaa Xaa  Xaa Xaa Xaa Xaa Xaa  Xaa Xaa Xaa
                2615                2620                2625

Xaa Xaa Xaa Xaa Xaa Xaa Xaa  Xaa Xaa Xaa Xaa Xaa  Tyr Xaa Xaa
                2630                2635                2640

Xaa Xaa Xaa Xaa Xaa Xaa Xaa  Xaa Xaa Xaa Xaa Xaa  Xaa Xaa Xaa
                2645                2650                2655

Xaa Xaa Xaa Xaa Xaa Xaa Xaa  Xaa Xaa Xaa Xaa Xaa  Xaa Xaa Xaa
                2660                2665                2670

Xaa Xaa Xaa Xaa Xaa Xaa Xaa  Tyr Xaa Xaa Xaa Xaa  Xaa Xaa Xaa
                2675                2680                2685

Xaa Xaa Xaa Xaa Xaa Xaa Xaa  Xaa Xaa Xaa Xaa Xaa  Xaa Xaa Xaa
                2690                2695                2700

Xaa Xaa Xaa Xaa Xaa Xaa Xaa  Xaa Xaa Xaa Xaa Xaa  Xaa Xaa Xaa
                2705                2710                2715

Xaa Xaa Tyr Xaa Xaa Xaa Xaa  Xaa Xaa Xaa Xaa Xaa  Xaa Xaa Xaa
                2720                2725                2730

Xaa Xaa Xaa Xaa Xaa Xaa Xaa  Xaa Xaa Xaa Xaa Xaa  Xaa Xaa Xaa
                2735                2740                2745

Xaa Xaa Xaa Xaa Xaa Xaa Xaa  Xaa Xaa Xaa Xaa Xaa  Tyr Xaa Xaa
                2750                2755                2760

Xaa Xaa Xaa Xaa Xaa Xaa Xaa  Xaa Xaa Xaa Xaa Xaa  Xaa Xaa Xaa
                2765                2770                2775

Xaa Xaa Xaa Xaa Xaa Xaa Xaa  Xaa Xaa Xaa Xaa Xaa  Xaa Xaa Xaa
                2780                2785                2790

Xaa Xaa Xaa Xaa Xaa Xaa Xaa  Tyr Xaa Xaa Xaa Xaa  Xaa Xaa Xaa
                2795                2800                2805
```

Xaa Xaa Xaa Xaa Xaa Xaa Xaa Xaa Xaa Xaa Xaa Xaa Xaa Xaa
    2810            2815            2820

Xaa Xaa Xaa Xaa Xaa Xaa Xaa Xaa Xaa Xaa Xaa Xaa Xaa Xaa
2825            2830            2835

Xaa Xaa Tyr Xaa Xaa Xaa Xaa Xaa Xaa Xaa Xaa Xaa Xaa Xaa
2840            2845            2850

Xaa Xaa Xaa Xaa Xaa Xaa Xaa Xaa Xaa Xaa Xaa Xaa Xaa Xaa
2855            2860            2865

Xaa Xaa Xaa Xaa Xaa Xaa Xaa Xaa Xaa Xaa Xaa Tyr Xaa Xaa
    2870            2875            2880

Xaa Xaa Xaa Xaa Xaa Xaa Xaa Xaa Xaa Xaa Xaa Xaa Xaa Xaa
2885            2890            2895

Xaa Xaa Xaa Xaa Xaa Xaa Xaa Xaa Xaa Xaa Xaa Xaa Xaa Xaa
2900            2905            2910

Xaa Xaa Xaa Xaa Xaa Xaa Xaa Tyr Xaa Xaa Xaa Xaa Xaa Xaa
2915            2920            2925

Xaa Xaa Xaa Xaa Xaa Xaa Xaa Xaa Xaa Xaa Xaa Xaa Xaa Xaa
2930            2935            2940

Xaa Xaa Xaa Xaa Xaa Xaa Xaa Xaa Xaa Xaa Xaa Xaa Xaa Xaa
2945            2950            2955

Xaa Xaa Tyr Xaa Xaa Xaa Xaa Xaa Xaa Xaa Xaa Xaa Xaa Xaa
2960            2965            2970

Xaa Xaa Xaa Xaa Xaa Xaa Xaa Xaa Xaa Xaa Xaa Xaa Xaa Xaa
2975            2980            2985

Xaa Xaa Xaa Xaa Xaa Xaa Xaa Xaa Xaa Xaa Xaa Tyr Xaa Xaa
2990            2995            3000

Xaa Xaa Xaa Xaa Xaa Xaa Xaa Xaa Xaa Xaa Xaa Xaa Xaa Xaa
3005            3010            3015

Xaa Xaa Xaa Xaa Xaa Xaa Xaa Xaa Xaa Xaa Xaa Xaa Xaa Xaa
3020            3025            3030

Xaa Xaa Xaa Xaa Xaa Xaa Xaa Tyr Xaa Xaa Xaa Xaa Xaa Xaa
3035            3040            3045

Xaa Xaa Xaa Xaa Xaa Xaa Xaa Xaa Xaa Xaa Xaa Xaa Xaa Xaa
3050            3055            3060

Xaa Xaa Xaa Xaa Xaa Xaa Xaa Xaa Xaa Xaa Xaa Xaa Xaa Xaa
3065            3070            3075

Xaa Xaa Tyr Xaa Xaa Xaa Xaa Xaa Xaa Xaa Xaa Xaa Xaa Xaa
3080            3085            3090

Xaa Xaa Xaa Xaa Xaa Xaa Xaa Xaa Xaa Xaa Xaa Xaa Xaa Xaa
3095            3100            3105

Xaa Xaa Xaa Xaa Xaa Xaa Xaa Xaa Xaa Xaa Xaa Tyr Xaa Xaa
3110            3115            3120

Xaa Xaa Xaa Xaa Xaa Xaa Xaa Xaa Xaa Xaa Xaa Xaa Xaa Xaa
3125            3130            3135

Xaa Xaa Xaa Xaa Xaa Xaa Xaa Xaa Xaa Xaa Xaa Xaa Xaa Xaa
3140            3145            3150

Xaa Xaa Xaa Xaa Xaa Xaa Xaa Tyr Xaa Xaa Xaa Xaa Xaa Xaa
3155            3160            3165

Xaa Xaa Xaa Xaa Xaa Xaa Xaa Xaa Xaa Xaa Xaa Xaa Xaa Xaa
3170            3175            3180

Xaa Xaa Xaa Xaa Xaa Xaa Xaa Xaa Xaa Xaa Xaa Xaa Xaa Xaa
3185            3190            3195

```
Xaa Xaa Tyr Xaa Xaa Xaa Xaa  Xaa Xaa Xaa Xaa  Xaa Xaa Xaa
3200            3205                3210

Xaa Xaa Xaa Xaa Xaa Xaa Xaa  Xaa Xaa Xaa Xaa  Xaa Xaa Xaa
3215            3220                3225

Xaa Xaa Xaa Xaa Xaa Xaa Xaa  Xaa Xaa Xaa Xaa  Tyr Xaa Xaa
3230            3235                3240

Xaa Xaa Xaa Xaa Xaa Xaa Xaa  Xaa Xaa Xaa Xaa  Xaa Xaa Xaa
3245            3250                3255

Xaa Xaa Xaa Xaa Xaa Xaa Xaa  Xaa Xaa Xaa Xaa  Xaa Xaa Xaa
3260            3265                3270

Xaa Xaa Xaa Xaa Xaa Xaa Xaa  Tyr Xaa Xaa Xaa  Xaa Xaa Xaa
3275            3280                3285

Xaa Xaa Xaa Xaa Xaa Xaa Xaa  Xaa Xaa Xaa Xaa  Xaa Xaa Xaa
3290            3295                3300

Xaa Xaa Xaa Xaa Xaa Xaa Xaa  Xaa Xaa Xaa Xaa  Xaa Xaa Xaa
3305            3310                3315

Xaa Xaa Tyr Xaa Xaa Xaa Xaa  Xaa Xaa Xaa Xaa  Xaa Xaa Xaa
3320            3325                3330

Xaa Xaa Xaa Xaa Xaa Xaa Xaa  Xaa Xaa Xaa Xaa  Xaa Xaa Xaa
3335            3340                3345

Xaa Xaa Xaa Xaa Xaa Xaa Xaa  Xaa Xaa Xaa Xaa  Tyr Xaa Xaa
3350            3355                3360

Xaa Xaa Xaa Xaa Xaa Xaa Xaa  Xaa Xaa Xaa Xaa  Xaa Xaa Xaa
3365            3370                3375

Xaa Xaa Xaa Xaa Xaa Xaa Xaa  Xaa Xaa Xaa Xaa  Xaa Xaa Xaa
3380            3385                3390

Xaa Xaa Xaa Xaa Xaa Xaa Xaa  Tyr Xaa Xaa Xaa  Xaa Xaa Xaa
3395            3400                3405

Xaa Xaa Xaa Xaa Xaa Xaa Xaa  Xaa Xaa Xaa Xaa  Xaa Xaa Xaa
3410            3415                3420

Xaa Xaa Xaa Xaa Xaa Xaa Xaa  Xaa Xaa Xaa Xaa  Xaa Xaa Xaa
3425            3430                3435

Xaa Xaa Tyr Xaa Xaa Xaa Xaa  Xaa Xaa Xaa Xaa  Xaa Xaa Xaa
3440            3445                3450

Xaa Xaa Xaa Xaa Xaa Xaa Xaa  Xaa Xaa Xaa Xaa  Xaa Xaa Xaa
3455            3460                3465

Xaa Xaa Xaa Xaa Xaa Xaa Xaa  Xaa Xaa Xaa Xaa  Tyr Xaa Xaa
3470            3475                3480

Xaa Xaa Xaa Xaa Xaa Xaa Xaa  Xaa Xaa Xaa Xaa  Xaa Xaa Xaa
3485            3490                3495

Xaa Xaa Xaa Xaa Xaa Xaa Xaa  Xaa Xaa Xaa Xaa  Xaa Xaa Xaa
3500            3505                3510

Xaa Xaa Xaa Xaa Xaa Xaa Xaa  Tyr Xaa Xaa Xaa  Xaa Xaa Xaa
3515            3520                3525

Xaa Xaa Xaa Xaa Xaa Xaa Xaa  Xaa Xaa Xaa Xaa  Xaa Xaa Xaa
3530            3535                3540

Xaa Xaa Xaa Xaa Xaa Xaa Xaa  Xaa Xaa Xaa Xaa  Xaa Xaa Xaa
3545            3550                3555

Xaa Xaa Tyr Xaa Xaa Xaa Xaa  Xaa Xaa Xaa Xaa  Xaa Xaa Xaa
3560            3565                3570

Xaa Xaa Xaa Xaa Xaa Xaa Xaa  Xaa Xaa Xaa Xaa  Xaa Xaa Xaa
3575            3580                3585

Xaa Xaa Xaa Xaa Xaa Xaa Xaa  Xaa Xaa Xaa Xaa  Tyr Xaa Xaa
```

-continued

Xaa Xaa Xaa Xaa Xaa Xaa Xaa Xaa Xaa Xaa Xaa Xaa Xaa Xaa Xaa
                3590                3595                3600

Xaa Xaa Xaa Xaa Xaa Xaa Xaa Xaa Xaa Xaa Xaa Xaa Xaa Xaa Xaa
                3605                3610                3615

Xaa Xaa Xaa Xaa Xaa Xaa Xaa Xaa Xaa Xaa Xaa Xaa Xaa Xaa Xaa
                3620                3625                3630

Xaa Xaa Xaa Xaa Xaa Xaa Xaa Tyr Xaa Xaa Xaa Xaa Xaa Xaa Xaa
                3635                3640                3645

Xaa Xaa Xaa Xaa Xaa Xaa Xaa Xaa Xaa Xaa Xaa Xaa Xaa Xaa Xaa
                3650                3655                3660

Xaa Xaa Xaa Xaa Xaa Xaa Xaa Xaa Xaa Xaa Xaa Xaa Xaa Xaa Xaa
                3665                3670                3675

Xaa Xaa Tyr Xaa Xaa Xaa Xaa Xaa Xaa Xaa Xaa Xaa Xaa Xaa Xaa
                3680                3685                3690

Xaa Xaa Xaa Xaa Xaa Xaa Xaa Xaa Xaa Xaa Xaa Xaa Xaa Xaa Xaa
                3695                3700                3705

Xaa Xaa Xaa Xaa Xaa Xaa Xaa Xaa Xaa Xaa Xaa Xaa Tyr Xaa Xaa
                3710                3715                3720

Xaa Xaa Xaa Xaa Xaa Xaa Xaa Xaa Xaa Xaa Xaa Xaa Xaa Xaa Xaa
                3725                3730                3735

Xaa Xaa Xaa Xaa Xaa Xaa Xaa Xaa Xaa Xaa Xaa Xaa Xaa Xaa Xaa
                3740                3745                3750

Xaa Xaa Xaa Xaa Xaa Xaa Xaa Tyr Xaa Xaa Xaa Xaa Xaa Xaa Xaa
                3755                3760                3765

Xaa Xaa Xaa Xaa Xaa Xaa Xaa Xaa Xaa Xaa Xaa Xaa Xaa Xaa Xaa
                3770                3775                3780

Xaa Xaa Xaa Xaa Xaa Xaa Xaa Xaa Xaa Xaa Xaa Xaa Xaa Xaa Xaa
                3785                3790                3795

Xaa Xaa Tyr Xaa Xaa Xaa Xaa Xaa Xaa Xaa Xaa Xaa Xaa Xaa Xaa
                3800                3805                3810

Xaa Xaa Xaa Xaa Xaa Xaa Xaa Xaa Xaa Xaa Xaa Xaa Xaa Xaa Xaa
                3815                3820                3825

Xaa Xaa Xaa Xaa Xaa Xaa Xaa Xaa Xaa Xaa Xaa Xaa Tyr Xaa Xaa
                3830                3835                3840

Xaa Xaa Xaa Xaa Xaa Xaa Xaa Xaa Xaa Xaa Xaa Xaa Xaa Xaa Xaa
                3845                3850                3855

Xaa Xaa Xaa Xaa Xaa Xaa Xaa Xaa Xaa Xaa Xaa Xaa Xaa Xaa Xaa
                3860                3865                3870

Xaa Xaa Xaa Xaa Xaa Xaa Xaa Tyr Xaa Xaa Xaa Xaa Xaa Xaa Xaa
                3875                3880                3885

Xaa Xaa Xaa Xaa Xaa Xaa Xaa Xaa Xaa Xaa Xaa Xaa Xaa Xaa Xaa
                3890                3895                3900

Xaa Xaa Xaa Xaa Xaa Xaa Xaa Xaa Xaa Xaa Xaa Xaa Xaa Xaa Xaa
                3905                3910                3915

Xaa Xaa Tyr Xaa Xaa Xaa Xaa Xaa Xaa Xaa Xaa Xaa Xaa Xaa Xaa
                3920                3925                3930

Xaa Xaa Xaa Xaa Xaa Xaa Xaa Xaa Xaa Xaa Xaa Xaa Xaa Xaa Xaa
                3935                3940                3945

Xaa Xaa Xaa Xaa Xaa Xaa Xaa Xaa Xaa Xaa Xaa Xaa Tyr Xaa Xaa
                3950                3955                3960

Xaa Xaa Xaa Xaa Xaa Xaa Xaa Xaa Xaa Xaa Xaa Xaa Xaa Xaa Xaa
                3965                3970                3975

-continued

```
Xaa Xaa  Xaa Xaa Xaa Xaa Xaa  Xaa Xaa Xaa Xaa Xaa  Xaa Xaa Xaa
    3980              3985              3990

Xaa Xaa  Xaa Xaa Xaa Xaa Xaa
    3995              4000
```